(12) United States Patent
Corry et al.

(10) Patent No.: US 8,318,450 B2
(45) Date of Patent: Nov. 27, 2012

(54) OPTICALLY-DETECTABLE ENZYME SUBSTRATES AND THEIR METHOD OF USE

(75) Inventors: Schuyler Corry, Eugene, OR (US); William Downey, Eugene, OR (US); Brian Filanoski, Spokane Valley, WA (US); Kyle Gee, Springfield, OR (US); Lawrence Greenfield, Eugene, OR (US); James Hirsch, Springfield, OR (US); Iain Johnson, Eugene, OR (US); Aleksey Rukavishnikov, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/166,627

(22) Filed: Jun. 22, 2011

(65) Prior Publication Data

US 2012/0040380 A1    Feb. 16, 2012

Related U.S. Application Data

(63) Continuation of application No. 12/099,085, filed on Apr. 7, 2008, now abandoned, which is a continuation of application No. 11/040,924, filed on Jan. 21, 2005, now abandoned.

(60) Provisional application No. 60/538,357, filed on Jan. 21, 2004.

(51) Int. Cl.
    *C12Q 1/34* (2006.01)
(52) U.S. Cl. .......................... 435/18; 435/227; 435/231
(58) Field of Classification Search .................. 435/18, 435/227, 231
    See application file for complete search history.

(56) References Cited

U.S. PATENT DOCUMENTS

| | | |
|---|---|---|
| 4,074,047 A | 2/1978 | Foxton et al. |
| 4,486,586 A | 12/1984 | Narita et al. |
| 4,520,110 A | 5/1985 | Stryer et al. |
| 4,542,104 A | 9/1985 | Stryer et al. |
| 4,603,209 A | 7/1986 | Tsien et al. |
| 4,711,955 A | 12/1987 | Ward et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,945,171 A | 7/1990 | Haugland et al. |
| 5,024,939 A | 6/1991 | Gorman |
| 5,047,519 A | 9/1991 | Hobbs et al. |
| 5,055,556 A | 10/1991 | Stryer et al. |
| 5,075,298 A | 12/1991 | Aszodi et al. |
| 5,126,444 A | 6/1992 | Acton et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,338,843 A | 8/1994 | Quante et al. |
| 5,352,803 A | 10/1994 | Mattingly |
| 5,362,628 A | 11/1994 | Haugland et al. |
| 5,371,220 A | 12/1994 | Boucherot et al. |
| 5,405,975 A | 4/1995 | Kuhn et al. |
| 5,433,896 A | 7/1995 | Kang et al. |
| 5,442,045 A | 8/1995 | Haugland et al. |
| 5,451,343 A | 9/1995 | Neckers et al. |
| 5,453,517 A | 9/1995 | Kuhn et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,541,318 A | 7/1996 | Aszodi et al. |
| 5,569,587 A | 10/1996 | Waggoner |
| 5,569,766 A | 10/1996 | Waggoner et al. |
| 5,573,904 A | 11/1996 | Mattingly |
| 5,627,027 A | 5/1997 | Waggoner |
| 5,656,544 A | 8/1997 | Bergendahl |
| 5,696,157 A | 12/1997 | Wang et al. |
| 5,714,327 A | 2/1998 | Houthoff et al. |
| 5,741,657 A | 4/1998 | Tsien et al. |
| 5,766,891 A | 6/1998 | Shuman |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |

(Continued)

FOREIGN PATENT DOCUMENTS

EP    0553741    8/2000

(Continued)

OTHER PUBLICATIONS

Ambler, R. P., "The structure of B-lactamases", *Series B, Philosophical Transactions of the Royal Society of London*, vol. 289, Series B, Biological Sciences, The Royal Society Publishing, 1980 ; pp. 321-331.

Andersen, Anni H. et al., "Studies of the Topoisomerase II-mediated Cleavage and Religation AT 1 Reactions by Use of a Suicidal Double-stranded DNA Substrate" *The Journal of Biological Chemistry*, vol. 266, No. 14, The American Society for Biochemistry and Molecular Biology, Inc, May 15, 1991 ; pp. 9203-9210.

Berger, et al., "Structure of DNA topoisomerases", *Biochimica et Biophysica Acta*, vol. 1400, No. 1-3, Oct. 1, 1998 ; pp. 3-18.

Bonner, et al., "m5 Muscarinic Acetylcholine Receptor Genes", *Neuron*, vol. 1, 1988 ; pp. 403-410.

(Continued)

*Primary Examiner* — Susan Hanley

(57) ABSTRACT

The present invention relates to compounds that are substrates for an enzyme, and upon reaction with the enzyme provide a detectable response, such as an optically detectable response. In particular, the compounds have utility in detecting the presence of a β-lactamase in a sample. In addition to the compounds, methods are disclosed for analyzing a sample for the presence of a β-lactmase, for example, as an indicator of expression of a nucleic acid sequence including a sequence coding for a β-lactmase. Kits are disclosed that include the disclosed compounds and additional components, for example, cells, antibodies, a β-lactmase or instructions for using the components in an assay.

4 Claims, 12 Drawing Sheets

U.S. PATENT DOCUMENTS

| | | | |
|---|---|---|---|
| 5,863,727 | A | 1/1999 | Lee et al. |
| 5,888,732 | A | 3/1999 | Hartley et al. |
| 5,945,526 | A | 8/1999 | Lee et al. |
| 5,948,484 | A | 9/1999 | Gudimenko et al. |
| 5,955,604 | A | 9/1999 | Tsien et al. |
| 6,008,378 | A | 12/1999 | Tsien et al. |
| 6,008,379 | A | 12/1999 | Benson et al. |
| 6,017,712 | A | 1/2000 | Lee et al. |
| 6,031,094 | A | 2/2000 | Tsien et al. |
| 6,048,982 | A | 4/2000 | Waggoner et al. |
| 6,080,852 | A | 6/2000 | Lee et al. |
| 6,111,116 | A | 8/2000 | Benson et al. |
| 6,130,101 | A | 10/2000 | Mao et al. |
| 6,140,494 | A | 10/2000 | Hamilton et al. |
| 6,143,557 | A | 11/2000 | Hartley et al. |
| 6,162,931 | A | 12/2000 | Gee et al. |
| 6,171,861 | B1 | 1/2001 | Hartley et al. |
| 6,184,379 | B1 | 2/2001 | Josel et al. |
| 6,190,894 | B1 | 2/2001 | Thornfeldt et al. |
| 6,197,223 | B1 | 3/2001 | Weaver et al. |
| 6,200,762 | B1 | 3/2001 | Zlokarnic et al. |
| 6,221,606 | B1 | 4/2001 | Benson et al. |
| 6,270,969 | B1 | 8/2001 | Hartley et al. |
| 6,277,608 | B1 | 8/2001 | Hartley et al. |
| 6,277,620 | B1 | 8/2001 | Gwynn et al. |
| 6,291,162 | B1 | 9/2001 | Tsien et al. |
| 6,335,440 | B1 | 1/2002 | Lee et al. |
| 6,339,392 | B1 | 1/2002 | Ashihara et al. |
| 6,348,599 | B1 | 2/2002 | Cummins et al. |
| 6,358,684 | B1 | 3/2002 | Lee |
| 6,372,445 | B1 | 4/2002 | Davis et al. |
| 6,399,392 | B1 | 6/2002 | Haugland et al. |
| 6,403,807 | B1 | 6/2002 | Singh et al. |
| 6,472,205 | B1 | 10/2002 | Tsien et al. |
| 6,486,612 | B2 | 11/2002 | Fujimura et al. |
| 6,664,047 | B1 | 12/2003 | Haugland et al. |
| 6,716,979 | B2 | 4/2004 | Diwu et al. |
| 6,846,612 | B2 | 1/2005 | Deshpande |
| 6,964,861 | B1 | 11/2005 | Gerard et al. |
| 6,974,873 | B2 | 12/2005 | Leung et al. |
| 7,244,560 | B2 | 7/2007 | Chestnut et al. |
| 7,393,632 | B2 | 7/2008 | Cheo et al. |
| 7,396,926 | B2 | 7/2008 | Tsien et al. |
| 2003/0003526 | A1 | 1/2003 | Tsien et al. |
| 2005/0118669 | A1 | 6/2005 | Tsien et al. |
| 2006/0014230 | A1 | 1/2006 | Murata |
| 2006/0046173 | A1 | 3/2006 | Sakai et al. |
| 2007/0020715 | A1* | 1/2007 | Tsien et al. ............ 435/18 |
| 2009/0047692 | A1 | 2/2009 | Corry et al. |
| 2009/0131394 | A1 | 5/2009 | Sutton et al. |
| 2009/0275065 | A1 | 11/2009 | Xing et al. |
| 2011/0020240 | A1 | 1/2011 | Cirillo et al. |

FOREIGN PATENT DOCUMENTS

| | | |
|---|---|---|
| WO | WO-95/16099 | 11/1995 |
| WO | WO-98/12372 | 3/1998 |

OTHER PUBLICATIONS

Bouizar, Zhor et al., "Purification and Characterization of Calcitonin Receptors in Rat Kidney Membranes by Covalent Cross-Linking Techniques,", *Eur. J. Biochem*, vol. 155, No. 1, 1986 ; pp. 141-147.

Brinkley, Michael , "A Brief Survey of Methods for Preparing Protein Conjugates with Dyes, Haptens, and Cross-Linking Reagents", *Bioconjugate Chemistry*, vol. 3, Issue 1, Jan.-Feb. 1992 ; pp. 2-13.

Bush, Karen et al., "A functional classification scheme for [beta]—lactamases and its correlation with molecular structure.", *Antimicrobial Agents and Chemotherapy*, vol. 39, No. 6, American Society for Microbiology, Jun. 1995 ; pp. 1211-1233.

Caron, et al., "Appendix II: Alignment of primary sequences of DNA topoisomerases", *Advances in Pharmacology*, vol. 29 B, 1994; pp. 271-297.

Chasin, "Effect of Gamma Rays at the Dihydrofolate Reductase Locus: Deletions and Inversions", *Cell. Molec. Genet*, vol. 12, 1986 ; pp. 555-556.

Cheng, et al., "Conservation of structure and mechanism between eukaryotic topoisomerase I and site-specific recombinases", *Cell*, vol. 92, No. 6, Mar. 20, 1998 ; pp. 841-850.

Digate, Russell J. et al., "Molecular Cloning and DNA Sequence Analysis of *Escherichia coli* topB, the Gene Encoding Topoisomerase III", *The Journal of Biological Chemistry*, vol. 264, No. 30, The American society for Biochemistry and Molecular Biology, Inc., Oct. 25, 1989 ; pp. 17924-17930.

Eggertsson, Gudmundur et al., "Transfer Ribonucleic Acid-Mediated Suppression of Termination Codons in *Escherichia coli*", *Microbiological Reviews*, vol. 52, No. 3, American Society for Microbiology, Sep. 1988 ; pp. 354-374.

Engelberg-Kulka, Hanna et al., "Ch 60: Suppression of Termination Codons", *Escherichia Coli and Samonella Cellular and Molecular Biology*, Second Edition, vol. 1, No. 2, Ch. 60 American Society for Microbiology, 1996 ; pp. 909-921.

Farina, et al., "Palladium Catalysis in Cephalosporin Chemistry: General Methodology for the Synthesis of Cephem Side Chains", *J. Org. Chem.*, vol. 55, No. 23, 1990 ; pp. 5833-5847 pgs.

Ghysen, "The D-Alanyl-D-Alanine-Cleaving Peptidases and B-Lactamases. Structure and Mechanism.", *Prospect Biotechnol*, vol. 128, 1987 ; pp. 67-95.

Gupta, et al., "Eukaryotic DNA Topoisomerases I", *Biochmica et Biophysica Acta*, vol. 1262, 1994 ; pp. 271-297.

Hanai, Ryo et al., "Human TOP3: A single-copy gene encoding DNA topoisomerase III", *Proceedings of the National Academy of Sciences (PNAS)*, vol. 93, The National Academy of Sciences, Apr. 1996 ; pp. 3653-3657.

Haugland, Richard P., "Molecular Probes Handbook of Fluorescent Probes and Research Products", *Sixth Edition*, 1996 ; pp. 13-15.

Haugland, Richard P., "Molecular Probes Handbook of Fluorescent Probes and Research Products", *Ninth Edition, CD ROM, Table of Contents*, Molecular Probes, Inc., 2002 ; pp. 1-6.

Joshi, Saroj et al., "ATP Synthase Complex from Bovine Heart Mitochondria", *J. Biol. Chem.*, vol. 265, No. 24, 1990 ; pp. 14518-14525.

Kim, Raymond A. et al., "Molecular Cloning and DNA Sequence Analysis of *Escherichia coli* topB, the Gene Encoding Topoisomerase III", *The Journal of Biological Chemistry*, vol. 267, 1992 ; pp. 17178-17185.

Landy, "Mechanistic and structural complexity in the site-specific recombination pathways of Int and FLP.", *Current Opinion in Genetics and Development*, vol. 3, No. 5, Oct. 1993 ; pp. 699-707.

Li, Zhiyu et al., "The traE Gene of Plasmid RP4 Encodes a Homologue of *Escherichia coli* DNA Topoisomerase III", *The Journal of Biological Chemistry*, vol. 272, No. 31, The American Society for Biochemistry and Molecular Biology, Inc., Aug. 1, 1997 ; pp. 19582-19587.

Mottagui-Tabar, Salim , "Quantitative analysis of in vivo ribosomal events at UGA and UAG stop codons", *Nucleic Acids Research*, vol. 26, No. 11, Oxford University Press, 1998 ; pp. 2789-2796.

Nunes-Duby, Simone E. et al., "Half-att Site Substrates Reveal the Homology Independence and Minimal Protein Requirements for Productive Synapsis in .lamda. Excisive Recombination", *Cell*, vol. 59, Oct. 6, 1989, 197-206.

Osborne, Neal F. et al., "The Chemistry of 4-Mercaptoazetidin-2-ones. Part 3. Synthesis of 6-Phenoxyacetamido-2-alklidenepenam-3-carboxylic Acids", *Journal of the Chemical Society, Perkin Transactions 1*, vol. 1, 1982 ; pp. 1429-1433.

Roca, Joaquim et al., "The capture of a DNA double helix by an ATP-dependent protein clamp: A key step in DNA transport by type II DNA topoisomerases.", *Cell*, vol. 71, Cell Press, Nov. 27, 1992 ; pp. 833-840.

Sandler, Stanley R. et al., "Organic Functional Group Preparations", *New York: Academic Press*, vol. 3, 1972 ; pp. 5-7.

Sauer, "Site-specific recombination: developments and applications", *Current Opinion in Biotechnology*, vol. 5, No. 5, Oct. 1994 ; pp. 521-527.

Sekiguchi, Joann et al., "Requirements for noncovalent binding of vaccina topoisomerase I to duplex DNA", *Nucleic Acids Research*, vol. 22, No. 24, Oxford University Press, Dec. 11, 1994 ; pp. 5360-5365.

Shuman, "Novel approach to molecular cloning and polynucleotide synthesis using vaccinia DNA Topoisomerase", *The Journal of Biological Chemistry*, vol. 269, No. 51,, Dec. 23, 1994 ; pp. 32678-32684.

Shuman, "Vaccinia virus DNA topoisomerase: a model eukaryotic type IB enzyme", *Biochimica et Biophysica Acta*, vol. 1400, No. 1-3, Oct. 1, 1998 ; pp. 321-337.

Shuman, Stewart, "Site-specific interaction of Vaccinia Virus Topoisomerase I with Duplex DNA.Minimal DNA Substrate for Strand Cleavage In Vitro", *Journal of Biological Chemistry*, vol. 266, No. 17, The American Society for Biochemistry and Molecular Biology, Inc., Jun. 15, 1991 ; pp. 11372-11379.

Smith, Temple F. et al., "Comparison of Biosequences", *Advances in Applied Mathematics*, vol. 2, Academic Press, Inc., 1981 ; pp. 482-489.

Stillman, et al., "Replication and Supercoiling of Simian Virus 40 DNA in Cell Extracts from Human Cells", *Mol. Cell Biol.*, vol. 5 ; pp. 2051-2060, 1985.

Wang, James C. et al., "DNA Topoisomerases: Why So Many?", *The Journal of Biological Chemistry*, vol. 266, No. 11, Apr. 15, 1991 ; pp. 6659-6662.

Wilson, Tina M. et al., "Cloning and Characterization of *Drosophila* Topoisomerase IIIβ", *The Journal of Biological Chemistry*, vol. 275, No. 3, Jan. 21, 2000 ; pp. 1533-1540.

Zarling, David A. et al., "Mapping of Lymphocyte Surface Polypeptide Antigens by Chemical Cross-Linking with BSOCOES", *Journal of Immunology*, vol. 124, No. 2, 1980 ; pp. 913-920.

Zhang, Hong L. et al., "*Escherichia coli* DNA Topoisomerase III is a Site-specific DNA Binding Protein That Binds Asymmetrically to Its Cleavage Site.", *The Journal of Biological Chemistry*, vol. 270, No. 40, The American Society for Biochemistry and Molecular Biology, Inc., Oct. 6, 1995 ; pp. 23700-23705.

\* cited by examiner

OPTICALLY-DETECTABLE ENZYME SUBSTRATES AND THEIR METHOD OF USE

CROSS-REFERENCE TO RELATED APPLICATIONS

The present application is a continuation of U.S. patent application Ser. No. 12/099,085, filed on Apr. 7, 2008, now abandoned, which is a continuation of U.S. patent application Ser. No. 11/040,924, filed Jan. 21, 2005, now abandoned, which claims the benefit of U.S. Provisional Patent Application Ser. No. 60/538,357, filed Jan. 21, 2004, the contents of which are hereby incorporated herein by reference in their entirety.

INTRODUCTION

1. Field of the Invention

This disclosure relates to enzyme substrates that exhibit a detectable response following a reaction catalyzed by an enzyme. Particular embodiments concern substrates that provide detectable optical responses (such as fluorescence changes) when contacted with a β-lactamase [and/or a related enzymes]. The substrates are useful in a variety of fields, including immunology, diagnostics, drug discovery and molecular biology.

2. Background of the Invention

An important mechanism of microbial resistance to β-lactam antibiotics is the production of enzymes known as β-lactamases or cephalosporinases. These enzymes hydrolytically cleave β-lactam antibiotics such as penicillins and cephalosporins. This type of resistance can be transferred horizontally by plasmids that are capable of rapidly spreading the resistance, not only to other members of the same strain of bacteria, but even to other species of bacteria.

In one classification scheme, β-lactamases are organized into four molecular classes (A, B, C and D) based on their amino acid sequences. Class A enzymes have a molecular weight of about 29 kDa and preferentially hydrolyze penicillins. Examples of class A enzymes include RTEM and the β-lactamase of *Staphylococcus aureus*. Class B enzymes include metalloenzymes that have a broader substrate profile than the other classes of β-lactamases. Class C enzymes have molecular weights of approximately 39 kDa and include the chromosomal cephalosporinases of gram-negative bacteria, which are responsible for the resistance of gram-negative bacteria to a variety of both traditional and newly designed antibiotics. In addition, class C enzymes also include the lactamase of P99 *Enterobacter cloacae*, which is responsible for making this *Enterobacter* species one of the most widely spread bacterial agents in United States hospitals. The recently recognized class D enzymes are serine hydrolases, which exhibit a unique substrate profile.

The spread of antibiotic resistance conferred by expression of β-lactamases in bacteria threatens the ability to treat bacterial infections. Therefore, both the detection of β-lactamase activity and the development of β-lactamase inhibitors are top priorities for pharmaceutical companies.

β-lactamase enzymes also are an important component of various assays used for detecting gene expression and measuring gene regulation by various substances. For example, a number of commercially available nucleic acid expression vectors include nucleic acid sequences that code for a β-lactamase. In these vectors, the β-lactamase coding sequence is coupled to a nucleic acid sequence of interest, and β-lactamase activity is used as a measure of the expression level of the sequence of interest. β-lactamase-based detection of expression is especially useful for detecting nucleic acid expression in mammalian cells since mammalian cells do not contain endogenous β-lactamase activity.

An additional component of a β-lactamase assay is a substrate for the enzyme that undergoes a detectable response when acted upon by the enzyme. One method that has been utilized for detecting β-lactamase activity uses pairs of fluorescent donor and quencher dyes coupled to a cephalosporin ring system. In the intact substrate, the close proximity and optical characteristics of the dyes result in fluorescence resonance energy transfer (FRET) between an excited donor dye and the acceptor dye, thereby masking the fluorescence of the donor dye. Cleavage of the β-lactam portion of the cephalosporin ring by a β-lactamase initiates a reaction that allows the donor and quencher dyes to separate by a distance that reduces or eliminates FRET. Once separated, quenching of the donor dye's fluorescence is relieved and the donor dye's fluorescence may be detected as an indicator of β-lactamase activity. FRET-based β-lactamase substrates for detection of β-lactamase activity are disclosed, for example, in U.S. Pat. No. 5,741,657.

Since β-lactamase enzymes differ in their specificity, a need still exists for additional detectable β-lactamase substrates. Furthermore, since β-lactamase enzymes are increasingly being used as reporters in gene regulation assays, a need also exists for β-lactamase substrates that are more readily incorporated into living cells than large FRET-based substrates. The disclosed β-lactamase substrates provide new options for additional, sensitive assays of β-lactamase activity that can be used to exploit differential substrate specificities of β-lactamases.

SUMMARY OF THE INVENTION

Compounds which are useful for detecting a β-lactamase are disclosed. The disclosed compounds have the general formula:

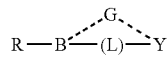

where B is a β-lactamase substrate moiety ("substrate moiety"), Y is a first dye moiety, R is a group of one or more atoms that can include a second, optional dye moiety. G and L are optional linking moieties. Cleavage of the substrate moiety by a β-lactamase generates a detectable optical response that may be used to detect the presence of β-lactamase activity (and a β-lactamase) in a sample. In particular embodiments, a detectable optical response is provided when cleavage of the substrate moiety generates a free phenolic, thiophenolic or amine group on the dye moiety, thereby generating a detectable response, for example, a detectable optical response such as a change in fluorescence of the dye moiety. In some embodiments, the disclosed compounds further include a reactive group, a carrier molecule or a targeting molecule. In still other embodiments, the disclosed compounds are bonded to a solid support.

In another aspect, methods are described in which the disclosed compounds are used to detect the presence and/or quantify amounts of a β-lactamase (or activity) in a sample. In these methods, β-lactamase activity is detected by detecting an optical response of a disclosed compound. The detected optical response is a measure of amounts/activity of the β-lactmase present in the sample. In some embodiments, a β-lactamase is detected (and/or quantified) by contacting a sample with a disclosed compound and a change in a fluorescence property of a dye moiety of the compound is measured. Changes in sample fluorescence are optionally detected in real time [using desired time increments including, for example, nanosecond, microsecond, millisecond, second or minute(s) time increments] to provide kinetic information about the β-lactamase's catalytic activity and/or the rate at which a β-lactamase is produced in the sample.

In yet another aspect, kits including the disclosed compounds are provided. Particularly disclosed kits further include one or more of the following: nucleic acid expression vectors including a nucleic acid sequence coding for a β-lactamase, antibodies conjugated to a β-lactamase and instructions for using the disclosed compounds to detect β-lactamase activity (and thus a β-lactamase) in a sample. Additional aspects and advantages will be apparent from the detailed description that follows.

DETAILED DESCRIPTION OF THE INVENTION

Figure 1:
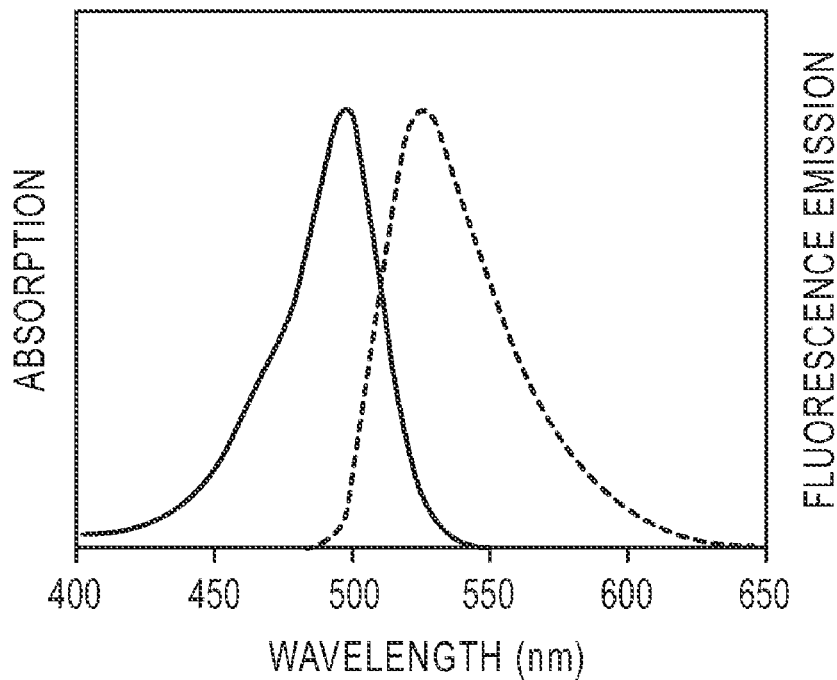
FIG. 1: Shows normalized absorption and fluorescence emission spectra of Compound 108 after reaction with the β-lactamase enzyme.

In order to facilitate an understanding of the embodiments presented, the following abbreviations, terms, explanations and examples are provided. Although methods and materials similar or equivalent to those described herein can be used in practice, suitable methods and materials are described below. The specifically described materials, methods, and examples are illustrative only and not intended to be limiting.

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a present compound" includes a plurality of compounds and reference to "a β-lactamase substrate" includes a plurality of ions and the like.

Unless defined otherwise, all technical and scientific terms used herein have the same meaning as commonly understood by one of ordinary skill in the art to which this invention is related. The following terms are defined for purposes of the invention as described herein.

The symbol $\sim\!\sim$, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent and are intended to be included in the scope of the disclosed compounds and methods.

Certain disclosed compounds are chiral molecules, some embodiments of which possess one or more asymmetrically bonded atoms, particularly carbon atoms (optical or chiral centers), double bonds and/or planes of asymmetry. Individual isomers (such as individual enantiomers, diastereomers and geometric isomers), racemates, optically-active mixtures of enantiomers and/or diastereomers, and mixtures of geometric isomers are also included as part of the disclosure.

The disclosed compounds may be prepared as a single isomer (such as a single enantiomer, single cis-trans isomer, single positional isomer, or single diastereomer) or as a mixture of isomers. In one embodiment, the compounds are prepared substantially as a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either retain the stereochemistry at a chiral center unchanged or result in its complete or partial inversion. Alternatively, the final product or intermediates along the synthetic route can be resolved into a single stereoisomer. Techniques for inverting or leaving a particular chiral center unchanged, and those for resolving mixtures of stereoisomers are well known in the art, and it is well within the ability of one of skill in the art to choose appropriate methods for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The disclosed compounds and the components used in the disclosed methods and/or included in the disclosed kits also may contain non-naturally occurring proportions of atomic isotopes at one or more of the atoms that constitute such compounds and components. For example, the compounds and components may be radio-labeled with radioactive isotopes, such as for example tritium ($^3$H), iodine-125 ($^{125}$I) or carbon-14 ($^{14}$C). Alternatively, or in addition to radio-labeling, the compounds and components may be labeled with stable isotopes such as $^{13}$C, $^2$H, $^{18}$O and $^{15}$N. All isotopic variations of the compounds and components are contemplated herein. For example, the compounds and components may include both radioactive and stable isotopes in non-naturally occurring proportions.

Where substituent groups are specified by their conventional chemical formulae, written from left to right, they equally encompass the chemically identical substituents, which would result from writing the structure from right to left (for example, —CH$_2$O— is equivalent to —OCH$_2$—).

As used herein, the term "radical" is synonymous with the term "group" and is not intended to mean, unless otherwise stated, a group of atoms bearing an unpaired electron.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus or position of the alkane radical. The "acyl group" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (that is C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (for example, methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom, for example, O, N, Si, P or S, Nitrogen, phosphorous and sulfur atoms are optionally oxidized, and the nitrogen heteroatom is optionally quaternized. The heteroatom(s) such as O, N, P, S and Si also may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means an aromatic compound, and unless otherwise stated, a polyunsaturated, aromatic moiety that can be a single ring or multiple rings (for example, from 1 to 3 rings), which are fused together or linked covalently. The term "heteroaryl" refers to aryl groups (or rings) that contain from at least one heteroatom (such as from 1 to 4) which are a member selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (such as in aryloxy, arylthioxy or arylalkyl) includes both aryl and heteroaryl rings as defined above. Thus, the term "arylalkyl" is meant to include those radicals in which an aryl group is attached to an alkyl group (such as benzyl, phenethyl, pyridylmethyl and the like) including those alkyl groups in which a carbon atom (such as a methylene group) has been replaced by, for example, an oxygen atom (for example, phenoxymethyl, 2-pyridyloxymethyl, 3-(1-naphthyloxy)propyl, and the like).

Each of the above terms (for example, "alkyl," "heteroalkyl," "aryl" and "heteroaryl") includes both substituted and unsubstituted forms of the indicated radical. Substituents that can occupy one or more positions for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen (—F, —Cl, —Br, and —I), —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R"' and R"" each independently refer to hydrogen, substituted or unsubstituted heteroalkyl, substituted aryl (such as aryl substituted with 1-3 halogens) or unsubstituted aryl, substituted or unsubstituted alkyl, alkoxy or thioalkoxy groups, or arylalkyl groups. When a compound includes more than one R group, unless otherwise stated, each of the R groups is independently selected as are each of the R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen (—F, —Cl, —Br and —I), —OR', =O, =NR', =N—OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and in particular embodiments R', R", R"' and R"" are independently selected from hydrogen, substituted or unsubstituted alkyl, substituted or unsubstituted heteroalkyl, substituted or unsubstituted aryl and substituted or unsubstituted heteroaryl. When a compound of the disclosed embodiments includes more than one R group, unless otherwise stated, each of the R groups is independently selected as are each R', R", R'" and R"" groups when more than one of these groups is present.

Two of the substituents on adjacent atoms of the aryl or heteroaryl ring optionally may be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring optionally may be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed optionally may be replaced with a double bond. Alternatively, two of the substituents on adjacent atoms of the aryl or heteroaryl ring optionally may be replaced with a substituent of the formula —(CRR')$_s$—Z—(CR"R'")$_d$—, where s and d are independently integers of from 0 to 3, and Z is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl.

As used herein, the term "heteroatom" includes oxygen (O), nitrogen (N), sulfur (S), phosphorus (P) and silicon (Si).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and anionic counterions such as biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "detectable response" as used herein refers to an occurrence of, or a change in, a signal that is directly or indirectly detectable (observable) either by visual observation or by instrumentation. Typically, the detectable response is a detectable response in an optical property ("detectable optical response") such as a change in the wavelength distribution patterns or intensity of absorbance or fluorescence or a change in light scatter, fluorescence lifetime, fluorescence polarization, or a combination of such parameters in a sample.

The term "dye" refers to a compound that absorbs and/or emits light to produce a detectable optical response or reacts with a second molecule to produce a compound that absorbs and/or emits light to produce a detectable optical response. "Dyes" include colored, fluorescent and non-fluorescent compounds that include, without limitation, pigments, fluorophores, chemiluminescent compounds, quenchers (including collisional and electronic), luminescent compounds and chromophores. "Dyes" also include colorogenic and fluorogenic compounds and compositions.

Fluorescence refers to light that is re-emitted by a molecule following absorption of energy, such light as light energy, by the molecule. A photon that is re-emitted as fluorescence typically has a lower energy than the photon(s) that is (are) initially absorbed.

The term "non-fluorescent" is a relative term since virtually all compounds will exhibit some detectable fluorescence. In some embodiments, a non-fluorescent compound is a compound that emits less fluorescence than a compound to which it is compared. In other embodiments, a non-fluorescent compound has a fluorescence quantum yield below 0.1, for example, below 0.01, below 0.001 or below 0.001.

The term "quencher" refers to a compound or moiety that absorbs energy from an excited donor compound or moiety. A quencher may absorb the fluorescent photons emitted by a donor compound, thereby masking the donor compound's fluorescence. In some embodiments, the quencher receives energy from an excited donor compound by fluorescence resonance energy transfer (FRET). Alternatively, the quencher may receive energy from the donor in the form of heat or an electron. Quenchers include collisional and electronic quenchers. In particular embodiments, a quencher absorbs 30% or greater, 50% or greater, 70% or greater, or 90% or greater of the fluorescence photons emitted by a dye product or dye moiety.

The term "FRET-pair" refers to a pair of dye molecules where one of the dye molecules absorbs light (the acceptor or quencher dye) at a wavelength at which the other emits light (the donor dye) and the two dyes are spatially separated by a distance that permits energy transfer with the disclose embodiments generally being within about 100 angstroms, such as within about 50, 20 or 10 angstroms of each other (for example, because they are bonded to the same substrate moiety). Excitation of the donor dye leads to excitation of the acceptor dye through the FRET mechanism, and a lower level of fluorescence is observed from the donor dye. The dependence of FRET efficiency on the distance between the dyes, the quantum yield of the donor dye, the fluorescence lifetime of the donor dye, and the overlap of the donor's emission spectrum and the acceptor's absorption spectrum is well known and is discussed in detail in U.S. Pat. No. 5,955,604, which is incorporated by reference herein. In some embodiments, a FRET-pair is substantially non-fluorescent, for example, when FRET is very efficient (such as greater than about 90%, 95% or 99%) and the acceptor dye is substantially non-fluorescent (for example, because it dissipates the excitation energy it receives from the donor to its surroundings, such as to a solvent). A FRET-pair also can be substantially non-fluorescent because the donor and acceptor dyes stack due to hydrophobic interactions, creating a non-fluorescent "dark complex." In other embodiments, the FRET-pair exhibits fluorescence from the donor and/or acceptor dye. For example, substantially only acceptor dye fluorescence may be observed from a FRET-pair where FRET is very efficient and the acceptor dye is fluorescent. If FRET is less efficient (such as between 10% and 90% efficient) and both the donor and acceptor dyes are fluorescent, fluorescence is observed at wavelengths characteristic of both the donor and acceptor. When the FRET-pair is attached to a substrate moiety, cleavage of the substrate moiety, such as by a β-lactamase, can lead to separation of the dyes in the FRET-pair, thereby relieving the quenching (to whatever extent it is present). Relief of quenching can lead, for example, to an increase in the fluorescence intensity and the fluorescence lifetime of the donor dye. Examples of combinations of dyes that are suitable for use as a FRET-pair, and methods for measuring FRET in a sample are provided in U.S. Pat. No. 5,955,604, which is incorporated by reference herein. Xanthene dyes that are particularly suited for use as an acceptor (quencher) in a FRET-pair are disclosed in U.S. Pat. No. 6,399,392, which discloses nitrogen-substituted xanthenes that are substituted by one or more aromatic or heteroaromatic quenching moieties, and exhibit little or no observable fluorescence. In one example, FRET is measured by ratioing the donor and acceptor dye fluorescence intensities and/or lifetimes at one or more wavelengths. In embodiments of the disclosed compounds that include a FRET-pair, monitoring of the amount of FRET can be used as a measure of enzymatic activity, particularly the β-lacatamase activity, in a sample. Typically, the amount of FRET is reduced over time as the compound is cleaved.

The term non-FRET-pair refers to a pair of dye moieties that do not substantially transfer energy between each other by the FRET mechanism, and thus there is no substantial affect on the fluorescence properties of the dyes when they are in close proximity, such as within 100 angstroms of each other. In some embodiments, a non-FRET-pair exhibits FRET with an efficiency (calculated or measured) of less than about 10%, 5%, 1% or 0.1%.

The term "β-lactam moiety", as used herein, refers to a compound which comprises a β-lactam ring structure. Examples of compounds that include the beta-lactam moiety include clavulanic acid, penicillanic acid, and cephalosporanic acid. The β-lactam structure is:

The term "buffer" as used herein refers to a system that acts to minimize the change in acidity or basicity of the solution against addition or depletion of chemical substances.

The term "carbonyl" as used herein refers to the functional group —(C=O)—. However, it will be appreciated that this group may be replaced with other well-known groups that have similar electronic and/or steric character, such as thiocarbonyl (—(C=S)—); sulfinyl (—S(O)—); sulfonyl (—SO$_2$)—), phosphonyl (—PO$_2$—).

The term "carboxy" or "carboxyl" refers to the group —R' (COOR) where R' is alkyl, substituted alkyl, aryl, substituted aryl, arylalkyl, substituted arylalkyl, heteroaryl, or substituted heteroaryl. R is hydrogen, a salt or —CH$_2$OC(O)CH$_3$.

The term "colored" refers to a composition (or compound) that absorbs light, such as light with wavelengths between about 260 nm and about 1200 nm, likely between about 300 nm and about 1000 nm and typically between about 400 nm and 750 nm. Generally, colored compositions and compounds may be detected visually or using a spectrophotometer, such as a UV-Vis or UV-Vis-NIR spectrophotometer. The term "colorogenic" refers to a composition that generates a colored composition or a colored composition that exhibits a change in its absorption spectrum upon interacting with another substance, for example, upon binding to a biological compound or metal ion, upon reaction with another molecule or upon metabolism by an enzyme.

The term "fluorophore" refers to a compound, a portion of a compound or a composition that exhibits fluorescence. The term "fluorogenic" refers to a compound or composition that becomes fluorescent or demonstrates a change in its fluorescence (such as an increase or decrease in fluorescence intensity or a change in its fluorescence spectrum) upon interacting with another substance, for example, upon binding to a biological compound or metal ion, upon reaction with another molecule or upon metabolism by an enzyme. Fluorophores may be substituted to alter their solubility, spectral properties and/or physical properties. Numerous fluorophores and fluorogenic compounds and compositions are known to those skilled in the art and include, but are not limited to benzofurans, quinolines, quinazolines, quinazolinones, indoles, benzazoles, indodicarbocyanines, borapolyazaindacenes and xanthenes, with the latter including fluoresceins, rhodamines and rhodols as well as other fluorophores described in Haugland, *Molecular Probes, Inc. Handbook of Fluorescent Probes and Research Chemicals*, (9$^{th}$ ed., including the CD-ROM, September 2002).

The term "carrier molecule" as used herein refers to a biological or non-biological component to which a disclosed compound is associated, typically bonded (such as covalently bonded). Such components include, but are not limited to, an amino acid, a peptide, a protein (such as an antiobody or a binding fragment thereof, such as a Fab fragment thereof), a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "cell permeable" as used herein refers to compounds of the present invention that are able to cross the cell membrane of live cells. Lipophilc groups that are covalently attached to the present compounds facilitate this permeability and live cell entry. Once inside the cells, the lipophilic groups are hydrolyzed resulting in charged molecules that are well retained in living cells. Particularly useful lipophilic groups include acetoxymethyl (AM) ester and acetate esters wherein once inside the cells the groups are cleaved by nonspecific esterases resulting in charged molecules.

The term "complex" as used herein refers to the association of two or more molecules, usually by non-covalent bonding.

The term "directly detectable" as used herein refers to the presence of a detectable label or the signal generated from a detectable label that is immediately detectable by observation, instrumentation, or film without requiring chemical modifications or additional substances. For example, a fluorophore produces a directly detectable response.

The term "kit" as used herein refers to a packaged set of related components, typically one or more compounds or compositions.

The term "linker" or "L" as used herein refers to a bond or one or more atoms that effectively couple two molecules or moieties together. More specifically, "linker" or "L" refers to a single covalent bond or a series of stable covalent bonds incorporating 1-30 non-hydrogen atoms selected from the group consisting of C, N, O, S and P that covalently attach the present β-lactamase substrate compounds to another moiety such as a chemically reactive group, fluorphore, quencher or a conjugated substance including biological and non-biological substances. Exemplary linking members include a moiety that includes —C(O)NH—, —C(O)O—, —NH—, —S—, —O—, and the like. A "cleavable linker" is a linker whereby its coupling of two molecules or moieties can be disrupted. Particular embodiments of disclosed cleavable linkers have one or more covalent bonds that can be broken by the result of a reaction or condition. For example, an ester in a molecule is a linker that can be cleaved by a reagent, e.g. sodium hydroxide, resulting in a carboxylate-containing fragment and a hydroxyl-containing product, or by an enzyme, for example, a hydrolase. In some embodiments, the linker includes a —C(O)O—, —C(S)O—, C(O)S—, or —C(S)S— group.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues and/or peptide bonds are an artificial chemical analogue of a corresponding naturally occurring amino acid or peptide bond, as well as to naturally occurring amino acid polymers.

The term "reactive group" as used herein refers to a group that is capable of reacting with another species, such as an atom or chemical group to form a covalent bond, that is, a group that is covalently reactive under suitable reaction conditions, and generally represents a point of attachment for another substance, for example, a carrier molecule or a substrate. For example, the reactive group on a disclosed compound is a moiety, such as carboxylic acid or succinimidyl ester, on the compounds that can chemically react with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amines, amides, cyanates, isocyanates, thiocyanates, isothiocyanates, hydrazines, hydrazones, hydrazides, diazo groups, diazonium groups, nitro groups, nitriles, mercaptans, sulfides, disulfides, sulfoxides, sulfones, sulfonic acid groups, sulfinic acid groups, acetals, ketals, anhydrides, sulfates, sulfenic acid groups isonitriles, amidines, imides, imidates, nitrones, hydroxylamines, oximes, hydroxamic acid groups thiohydroxamic acid groups, allenes, ortho esters, sulfites, enamines, ynamines, ureas, pseudoureas, semicarbazides, carbodiimides, carbamates, imines, azides, azo groups, azoxy groups, and nitroso groups. Reactive functional groups also include those used to prepare bioconjugates, for example, N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations,* Academic Press, San Diego, 1989).

The term "sample" as used herein refers to any material that may contain a β-lactamase or a nucleotide sequence coding for a β-lactamase, or to a material to which a β-lactamase or a nucleotide sequence coding for a β-lactamase is added. Typically, the sample is a live cell or a fluid, such as a biological fluid, that further includes endogenous host cell proteins, nucleic acid polymers, nucleotides, oligonucleotides proteins or peptides, and also may include a buffer solution. The sample may be in a fluid dispersion, such as an aqueous solution, a cell culture (viable or otherwise) or immobilized on a solid or semi solid surface such as a polyacrylamide gel, membrane blot or on a microarray.

As used herein, the term "β-lactamase" denotes a protein capable of catalyzing cleavage of a β-lactamase substrate such as a β-lactam containing molecule (such as a β-lactam antibiotic) or derivative thereof, a clavulanic acid or derivative thereof, an aceturate or derivative thereof, a benzofuranone or derivative thereof, a benzopyranone or a derivative thereof or a malonamate or a derivative thereof. In an exemplary embodiment, the β-lactamase is an enzyme which catalyzes the hydrolysis of the β-lactam ring of a β-lactam antibiotic. In another exemplary embodiment, the β-lactamase is microbial. In yet another exemplary embodiment, the β-lactamase is a serine β-lactamase. In still another exemplary embodiment, the β-lactamase is a zinc β-lactamase. The terms "class A", "class B", "class C", and "class D" β-lactamase are understood by those skilled in the art and are described in Waley, *The Chemistry of β-Lactamase,* Page Ed., Chapman & Hall, London, (1992) 198-228. In yet another exemplary embodiment, the β-lactamase is class C β-lactamase of *Enterobacter cloacae* P99 (hereinafter P99 β-lactamase), or class A β-lactamase of the TEM-2 plasmid (hereinafter TEM β-lactamase). In certain embodiments, a β-lactamase is a portion of a β-lactamase enzyme, such as a catalytic portion of a β-lactamase enzyme. In other embodiments, the β-lactamase is a fusion protein including a β-lactamase or a portion thereof, such as a catalytic portion thereof. The term β-lactamase also is meant to include conservative and functional variants of a β-lactamase. Moreover, the term is meant to include variants of a β-lactamase that exhibits a substrate specificity that differs due to one or more amino acid substitutions, particularly one or more amino acid substitutions in the catalytic region of the β-lactamase.

One skilled in the art will recognize that individual substitutions, deletions or additions which alter, add or delete a single amino acid or a small percentage of amino acids (typically less than 5%, more typically less than 1%) in an encoded sequence are "conservative substitutions" or "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

Aliphatic: Glycine (G), Alanine (A), Valine (V), Leucine (L), Isoleucine (I);
Aromatic: Phenylalanine (F), Tyrosine (Y), Tryptophan (W);
Sulfur-containing: Methionine (M), Cysteine (C);
Basic: Arginine (R), Lysine (K), Histidine (H);
Acidic: Aspartic acid (D), Glutamic acid (E), Asparagine (N), Glutamine (Q).
See also, Creighton, *Proteins,* W. H. Freeman and Company, 1984, for additional groupings of amino acids. In addition, individual substitutions, deletions or additions which alter, add or delete a single amino acid or a small percentage of amino acids in an encoded sequence are also "conservative variations." Variants of a peptide are typically characterized by possession of at least 50% sequence identity counted over the full length alignment with the amino acid sequence of the peptide using the NCBI Blast 2.0, gapped blastp set to default parameters. For comparisons of amino acid sequences of greater than 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap1 penalties). Proteins with even greater similarity to the reference sequences will show increasing percentage of identities when assessed by this method, such as at least 60%, at least 65%, at least 75%, at least 80%, at least 90%, or 95%, or 98%, or 99% sequence identity. When less than the entire sequence is being compared for sequence identity (for example, sequence identity of catalytic portions of a β-lactamase), homologs and variants will typically possess at least 75% sequence identity over short windows of 10-20 amino acids, and may possess sequence identifies of at least 85% or at least 90%, or 95%, or 98%, or 99% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

As used herein, the term "β-lactamase conjugate" refers to a "β-lactamase enzyme", as disclosed above, that has been covalently attached to a carrier molecule or solid support such as an antibody or streptavidin.

As used herein, the term "β-lactamase inhibitor" is used to identify a compound that inhibits a β-lactamase activity. Inhibiting β-lactamase activity means reducing the catalytic activity, such as the observed catalytic activity, of a class A, B, C, or class D β-lactamase, or other β-lactamase, for example, with a 50% inhibition concentration ($IC_{50}$) below 100 micrograms/mL, below 30 micrograms/mL or below 10 micrograms/mL.

In some embodiments, the β-lactamase inhibitor is also capable of acting as an antibiotic, for example, by inhibiting bacterial cell-wall cross-linking enzymes. Thus, the term β-lactamase inhibitor is intended to encompass such dual-acting inhibitors. In certain preferred embodiments, the β-lactamase inhibitor is capable of inhibiting D-alanyl-D-alanine-carboxy-peptidases/transpeptidases (hereinafter DD-peptidases). The term "DD-peptidase" is used in its usual sense to denote penicillin-binding proteins involved in bacterial cell wall biosynthesis (e.g., Ghysen, Prospect. Biotechnol., 128:67-95 (1987)). In certain particularly preferred embodiments, the D-alanyl-D-alanine-carboxy-peptidases/transpeptidase inhibited is the *Streptomyces* R61 DD-peptidase.

"rt", as used herein, refers to room temperature.

A "lipophilic moiety" as used herein, refers to a molecule or a portion of a molecule that confers hydrophobicity to a second molecule. In general, hydrophobicity may be conferred by a non-polar group of atoms, for example, substituted or unsubstituted alkyl groups containing six or more carbons. Such alkyl groups can include heteroatoms. Examples of hydrophobic groups include long chain fatty acids (such as dodecanoyl) long chain fatty alcohols (such as octanol), and phospholipids. One skilled in the art will recognize that lipophilicity may be conferred to a molecule by adding to it a single, large and non polar group of atoms (such as a a phospholipid), or by converting one or more polar groups on a molecule to less polar groups. For example, polar hydroxyl groups, carboxylic acid groups, and amine groups may be reacted to form esters or amides. Lipophilic moieties further include "hydrolase-cleavable moieties" such as esters and amides that are added to a molecule to increase its lipophilicity, but which may be removed by a hydrolase (other than a β-lactamase), such as by an endogenous lipase or esterase. For example, where a disclosed compound does not readily enter a cell because it is too polar to cross a cell membrane the molecule may be reacted to convert polar groups to non-polar hydrolase-cleavable moieties, which facilitate movement of the compound across the cell membrane into the interior of the cell. Once in the interior of the cell, endogenous hydrolases remove the non-polar hydrolase-cleavable moieties and thereby trap the compound in the interior of the cell.

A "targeting moiety", as used herein, refers to species that will selectively localize in a particular tissue or region of the body or a cell. Localization of the targeting moiety may be mediated, for example, by specific recognition of molecular determinants, molecular size of the targeting agent or conjugate, ionic interactions or hydrophobic interactions. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like. In some embodiments, a targeting moiety binds specifically to another substance, for example, a protein, a nucleic acid, a cell or a cell component, such as an organelle. As used herein, a targeting moiety such as an antibody, or antigen-binding fragment thereof, is said to "bind specifically" if it reacts at a detectable level (within, for example, an ELISA) with a substance, such as a protein, and does not react detectably with unrelated substances, such as other peptides, polypeptides, nucleic acids and proteins, under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In particular embodiments, two compounds are said to "bind specifically" when the binding constant for complex formation exceeds about $10^2$ L/mol, for example, exceeds $10^3$ L/mol, or exceeds $10^4$ L/mol, or greater. The binding constant may be determined using methods well known in the art.

"Localize," as used herein, means to accumulate in, or be restricted to, a specific or limited area.

The Compounds

In general, for ease of understanding the present invention, the β-lactamase substrate compounds and corresponding substituents will first be described in detail, followed by the β-lactamase conjugates, the methods in which the substrates and conjugates find uses, which is followed by exemplified methods of use and synthesis of certain novel compounds that are particularly advantageous for use with the methods of the present invention.

Compounds are provided that are useful for the detection of β-lactamase activity. The disclosed compounds include colored, colorogenic, fluorescent and fluorogenic compounds that produce a detectable optical response (for example, an increase, decrease or wavelength shift in absorption and/or fluorescence) when contacted with a β-lactamase. The compounds include a dye moiety effectively coupled to, such as covalently bonded to, a β-lactamase substrate moiety, such as a cephalosporin, a benzofuranone, a benzopyranone, an aceturate, a malonamate or a clavulanic acid moiety. The β-lactamase substrate moiety ("substrate moiety") is a group of atoms in which at least one bond is cleaved when contacted by a β-lactamase. Cleavage of the substrate moiety of the disclosed compounds by a β-lactamase provides a detectable response, such as a detectable optical response, of the dye moiety, which either remains connected to the cleaved substrate moiety or separates from the cleaved substrate moiety. In some embodiments, cleavage of the substrate generates a free phenol (phenolate), thiophenol (thiophenolate) or amine group on the dye moiety, thereby causing a change in the electronic structure of the dye moiety that provides a detectable optical change, such as a change in fluorescence. In particular embodiments, cleavage of the substrate moiety generates a free phenol or phenolate group on the dye moiety, and alters the fluorescence of the dye moiety.

Certain embodiments of the disclosed compounds have the general formula:

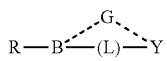

where B is a β-lactamase substrate moiety ("substrate moiety"), Y is a first dye moiety, R is one or more atoms that can include a second dye moiety, and also can be selected to confer β-lactamase enzyme specificity to the compound. B also can further include a second dye moiety. G is first optional linking moiety. If G is present, B and G are bonded to the first dye moiety at different atoms. A second optional linker, L, can be present between B and Y when G is absent.

The substrate moiety can be cleaved by a β-lactamase to generate a detectable optical response of the first and/or second dye moiety (if present). When G is absent, the first dye moiety Y is released from the substrate moiety B following cleavage of the substrate moiety by a β-lactamase. When G is absent, R or B includes a second dye moiety, and B is not a cephalosporin ring system, the first and second dye moieties can be a donor and acceptor dye moiety pair selected for fluorescence resonance energy transfer (a FRET-pair). In such FRET embodiments, cleavage of the substrate moiety allows the first and second dye moieties to move apart, thereby relieving or eliminating the quenching of the donor dye moiety's fluorescence by the acceptor dye moiety. One or more of R, B, G and Y may further include a reactive group, a lipophilic moiety, a hydrolase cleavable moiety or a targeting moiety.

In some embodiments, when the compound is contacted with a β-lactamase, the substrate moiety B undergoes an enzyme-catalyzed reaction that severs a bond between the substrate moiety and the dye moiety to generate a free amine, phenol (phenolate) or thiophenol (thiophenolate) group on the first dye moiety. Generation of the free amine, phenol (phenolate) or thiophenol (thiophenolate) group on the first dye moiety induces a detectable optical response. Detection of an optical response in a sample that is contacted with a disclosed compound indicates β-lactamase activity (and the presence a β-lactamase) in the sample.

If G is present, the substrate moiety and the first dye moiety remain bonded following the enzyme-catalyzed reaction. If G is absent, the substrate moiety and the first dye moiety are no longer bonded following the enzyme-catalyzed reaction. In particular embodiments, the optically detectable response catalyzed by a β-lactamase includes a change in a fluorescence characteristic of the first dye moiety (for example, a change in the dye's fluorescence quantum yield and/or fluorescence spectrum).

In other embodiments, cleavage of the substrate moiety does not generate a free amine, phenol (phenolate) or thiophenol (thiophenolate) group on the dye moiety, but nonetheless generates a detectable response, such as a detectable optical response.

In some embodiments, the disclosed compounds have the structure:

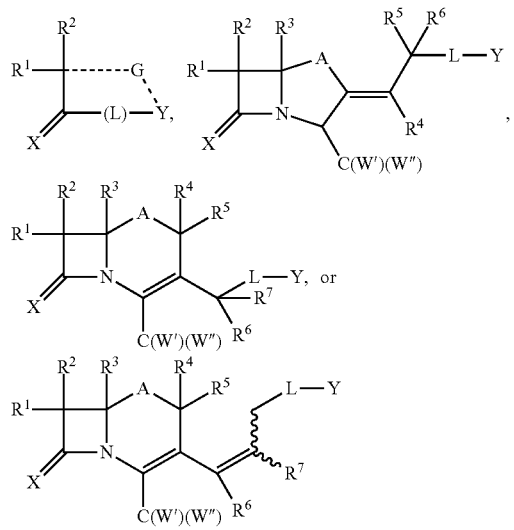

where $R_1$ is H,

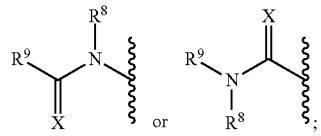

A is S, O, SO, $SO_2$ or $CH_2$; G is a first optional linker that can be nothing (absent), a bond, or —$CH_2$—; If A and/or G is —$CH_2$—, either or both of the hydrogens of the methylene group can be replaced by an alkyl, heteroalkyl, aryl or heteroaryl group; X is O, S or NH; L is a second optional linker that can be present if G is absent from the structure; $R^2$ through $R^8$ are independently H, substituted or unsubstituted alkyl or heteroalkyl, or substituted or unsubstituted aryl or heteroaryl; $R^9$ is

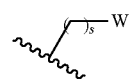

in which W is substituted or unsubstituted alkyl or heteroalkyl, substituted or unsubstituted aryl, substituted or unsubstituted aryloxy, substituted or unsubstituted heteroaryl, or CN, and s is an integer from 0 to 5; W' and W" are independently H, substituted or unsubstituted alkyl or heteroalkyl, substituted or unsubstituted aryl or heteroaryl, (=O), (=NH), $OR^{10}$, $NHR^{11}$, or halogen; $R_{10}$ is H, substituted or unsubstituted alkyl or heteroalkyl, or substituted or unsubstituted aryl or heteroaryl; $R^{11}$ is H, substituted or unsubstituted alkyl, substituted or unsubstituted heteroalkyl, substituted or unsubstituted aryl or heteroaryl or $OR^{12}$; $R^{12}$ is H, substituted or unsubstituted alkyl, and substituted or unsubstituted heteroalkyl or substituted or unsubstituted aryl or heteroaryl; and Y is a first dye moiety. W, W' W" may or may not be quenchers of fluorescence emitted by the first dye moiety. In some embodiments, at least one of W, W', and W" includes a second dye moiety and either the second dye moiety is a quencher of fluorescence of the first dye moiety or the first dye moiety is a quencher of fluorescence of the second dye moiety. In particular embodiments, the compound is other than a cephalosporin having an $R^9$ group that is benzyl, 2-thienylmethyl or cyanomethyl.

In particular embodiments, $R^9$ is:

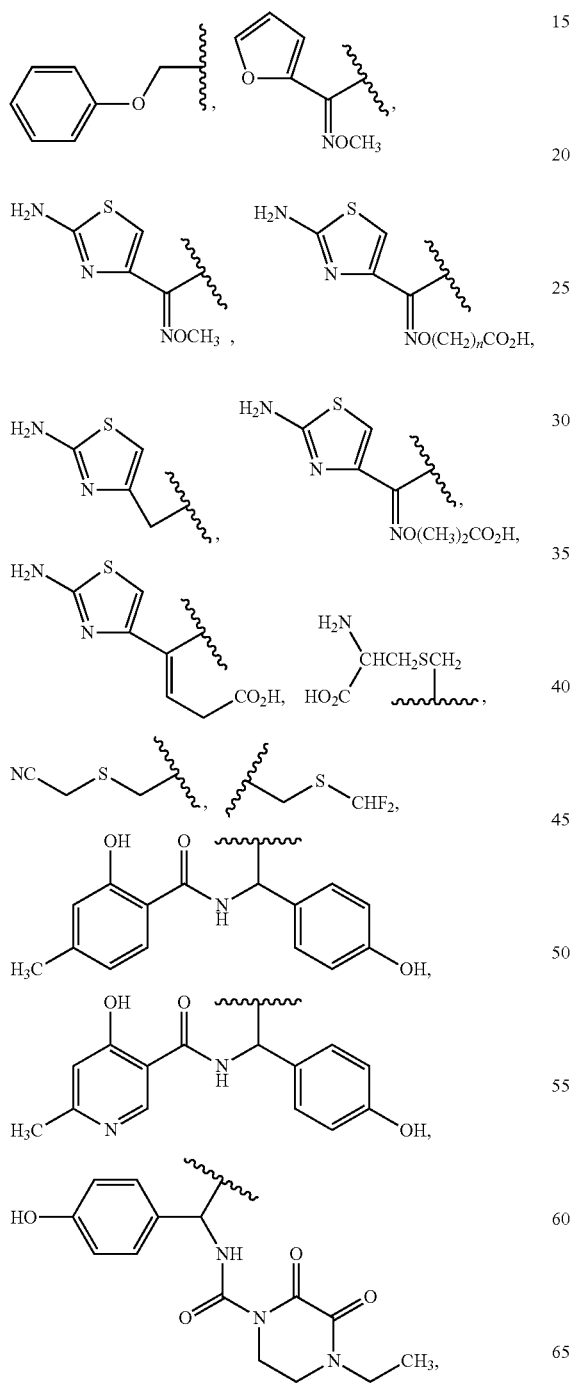

-continued

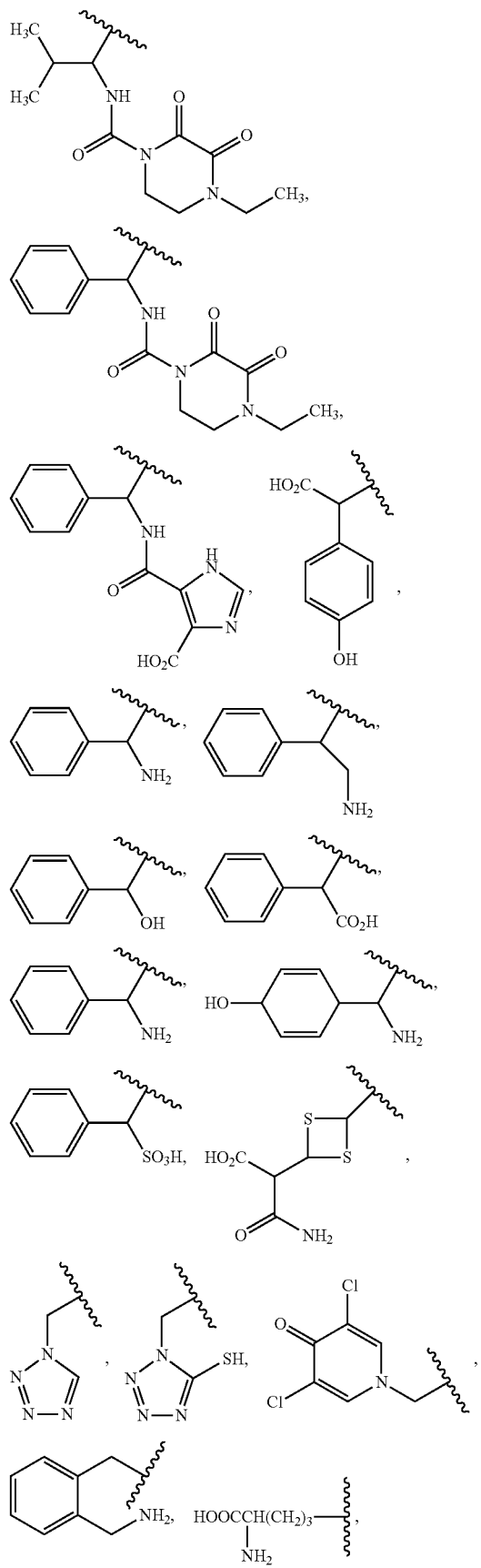

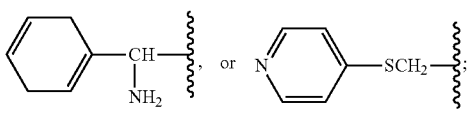

where the symbol n is an integer selected from 1 to 8. In other particular embodiments, $R^9$ is other than benzyl, 2-thienylmethyl or cyanomethyl.

In an exemplary embodiment, the disclosed compound is a cephalosporin derivative (a cephalosporin) and has the formula:

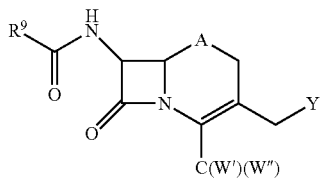

in which A is S, O, SO, $SO_2$ or $CH_2$. One of Y and $R^9$ includes a dye moiety, an the other has the formula:

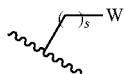

in which W is substituted or unsubstituted alkyl, substituted or unsubstituted heteroaklyl, substituted or unsubstituted aryl, substituted or unsubstituted aryloxy, substituted or unsubstituted heteroaryl, or CN. The symbol s represents an integer selected from 0 to 5. The symbols W' and W" are independently H, substituted or unsubstituted alkyl, (=O), (=NH), $OR^{10}$, $NHR^{11}$, or halogen. In this embodiment, W, W', and W" are not quenchers of the fluorescence emitted by the dye moiety, nor is the first dye moiety a quencher of fluorosecence emitted by W, W' or W" if one or more of these groups includes a fluorescent dye moiety. Thus, for example, non-FRET pairs are possible in this embodiment. $R_{10}$ is a member selected from H, substituted or unsubstituted alkyl, and substituted or unsubstituted heteroalkyl. $R^{11}$ is a member selected from H, substituted or unsubstituted alkyl, substituted or unsubstituted heteroalkyl, and $OR^{12}$. $R^{12}$ is a member selected from H, substituted or unsubstituted alkyl, and substituted or unsubstituted heteroalkyl. In some particular embodiments, $R^9$ is one of those groups specifically listed above for $R^9$, and in other particular embodiments, $R^9$ is other than benzyl, 2-thienylmethyl or cyanomethyl.

In some embodiments, Y is a dye moiety and $R^9$ is

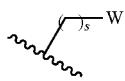

in which W is substituted or unsubstituted alkyl, substituted or unsubstituted heteroaklyl, substituted or unsubstituted aryl, substituted or unsubstituted aryloxy, substituted or unsubstituted heteroaryl, or CN. The symbol s represents an integer selected from 0 to 5. W, W', and W" are not quenchers of the fluorescence emitted by the dye moiety, nor is the first dye moiety a quencher of fluorosecence emitted by W, W' or W" if one or more of these groups includes a fluorescent dye moiety. Thus, for example, non-FRET pairs are possible in this embodiment. In yet another exemplary embodiment, $R^9$ is substituted or unsubstituted benzyl, substituted or unsubstituted 5-membered heteroaryl, or CN. In still another exemplary embodiment, A is a member selected from S and SO. In another exemplary embodiment, W' is (=O) and W" is (OH). In yet another embodiment, $R^9$ is

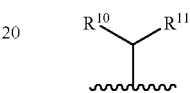

in which $R^{10}$ and $R^{11}$ are independently H, —OH, —$NH_2$, substituted or unsubstituted $C_1$-$C_{18}$ alkyl, substituted or unsubstituted $C_1$-$C_{18}$ heteroalkyl, substituted or unsubstituted $C_1$-$C_{18}$ cycloalkyl, substituted or unsubstituted $C_1$-$C_{18}$ heterocycloalkyl, substituted or unsubstituted $C_1$-$C_{18}$ aryl, or substituted or unsubstituted $C_1$-$C_{18}$ heteroaryl. $R^9$ also can be any of the particular $R^9$ groups recited above. In some embodiments, $R^9$ is other than benzyl, 2-thienylmethyl or cyanomethyl. Particular structural embodiments of such compounds are provided below:

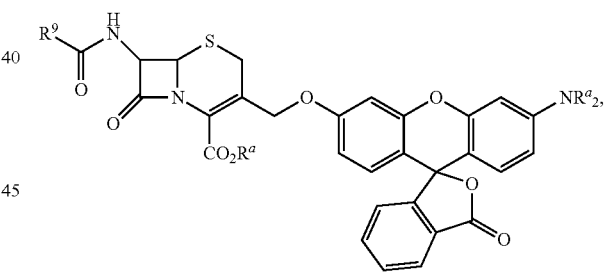

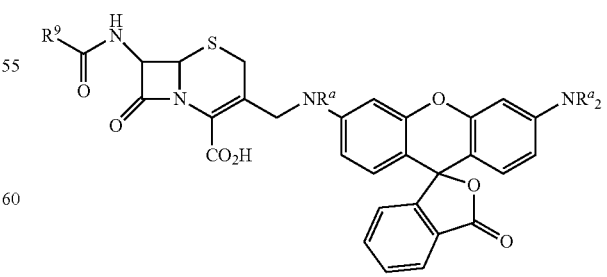

where $R^9$ and each $R^a$ group is independently H, substituted or unsubstituted alkyl or heteroalkyl, or substituted or unsubstituted aryl or heteroaryl.

In more particular embodiments, the compound is:
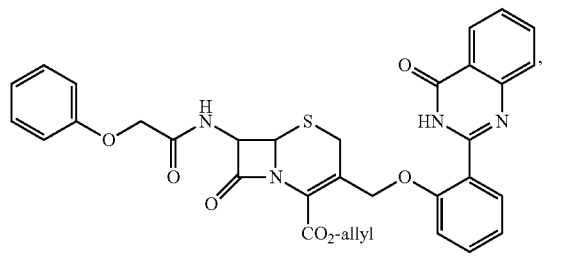
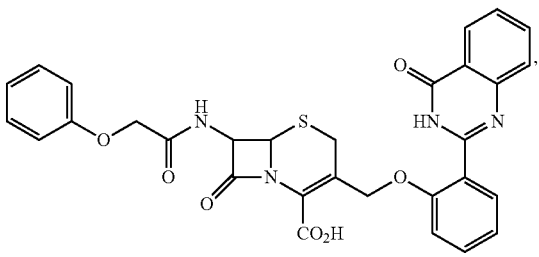
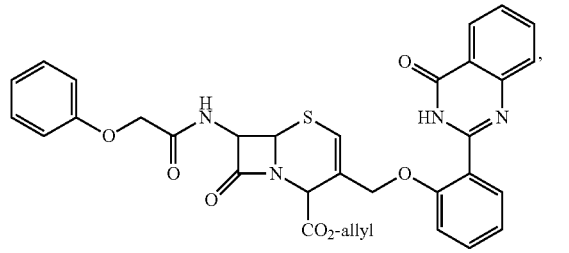
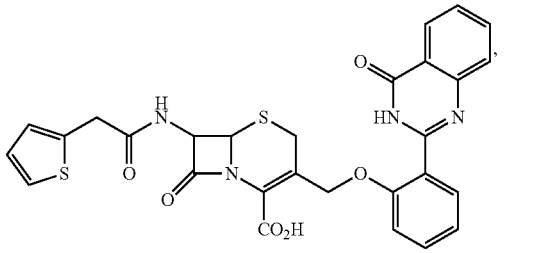
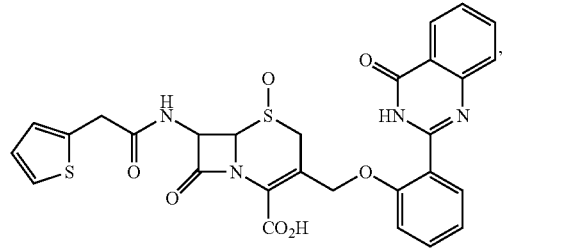
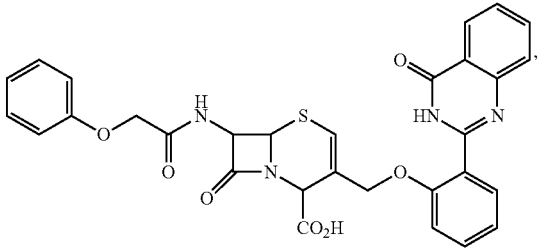
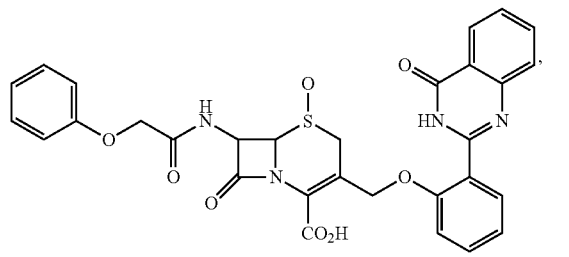
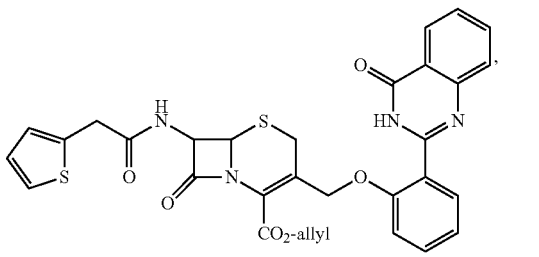
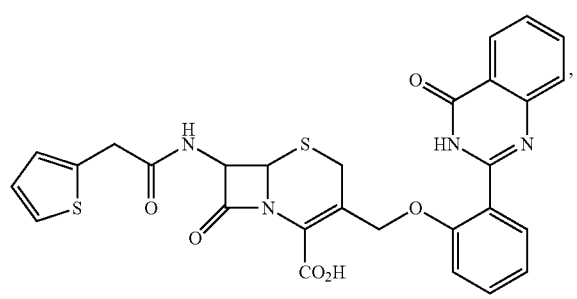
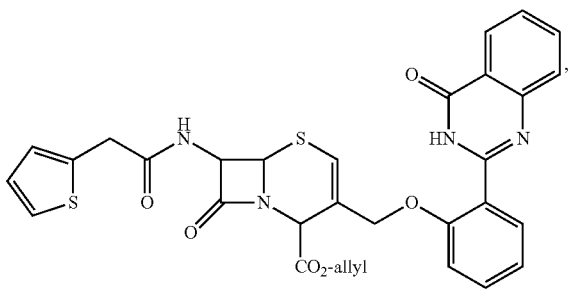
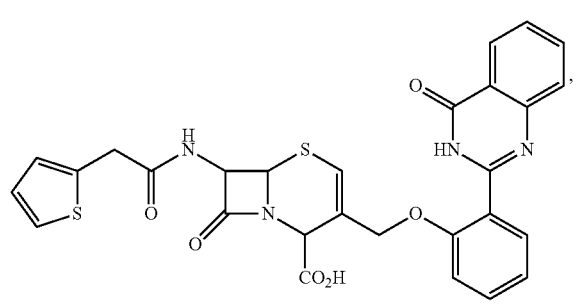
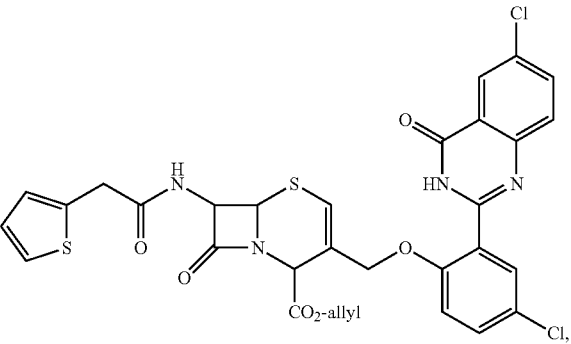

-continued
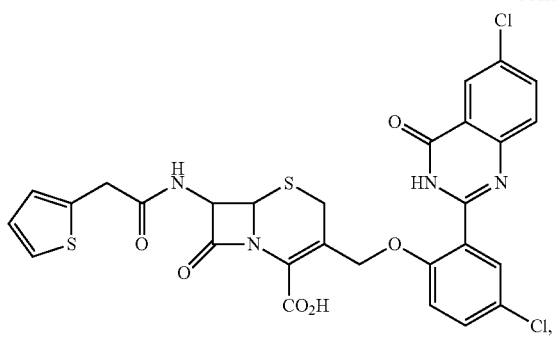
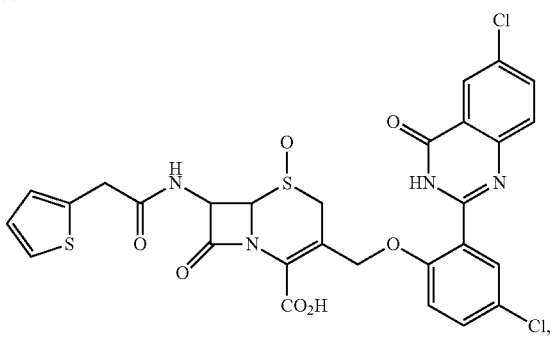
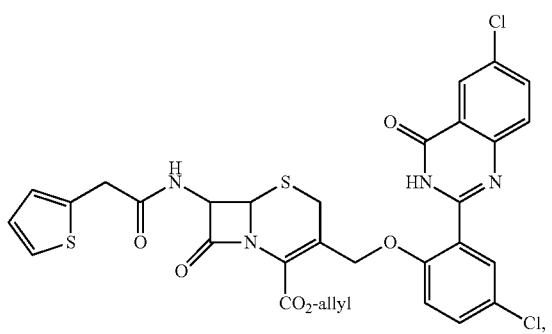
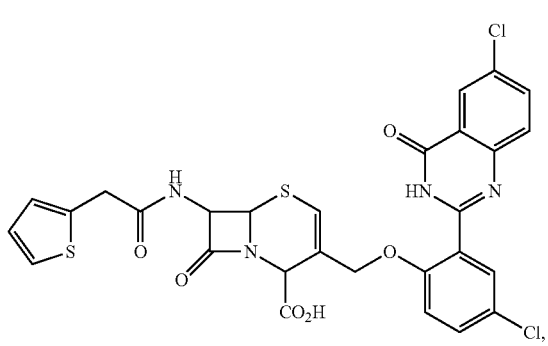
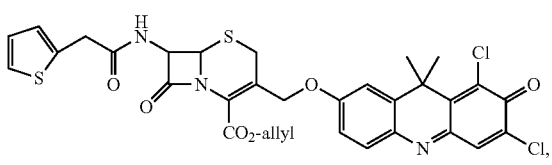
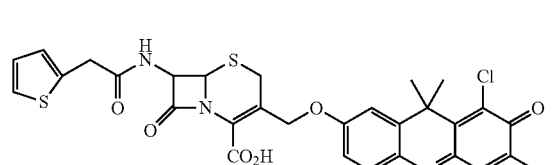
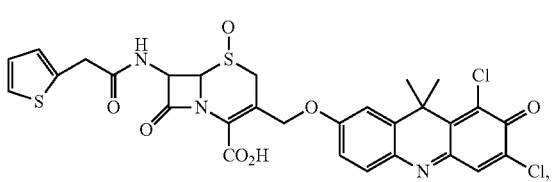
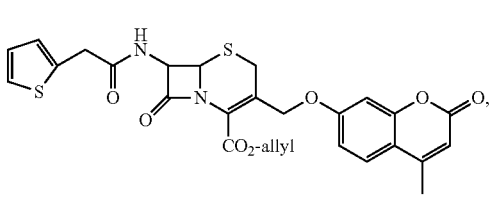
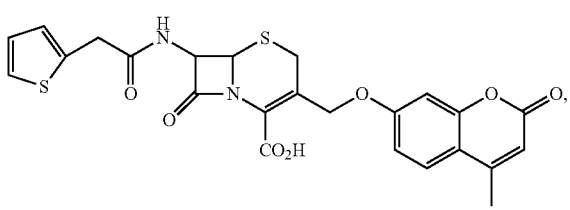
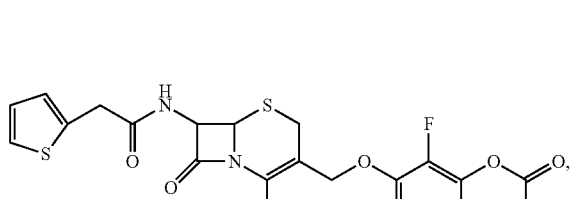
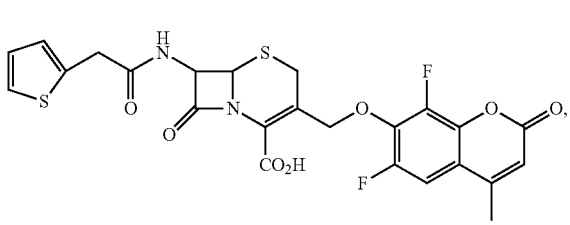
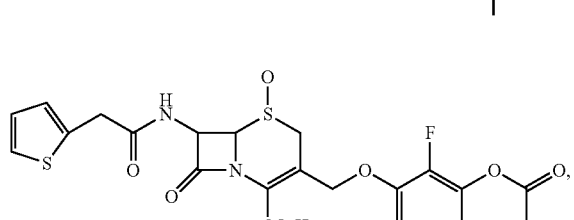

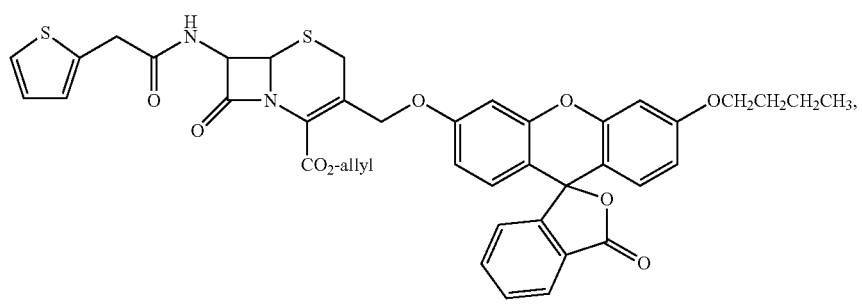
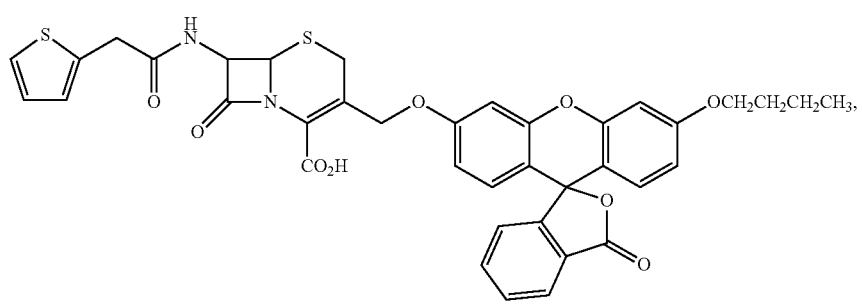
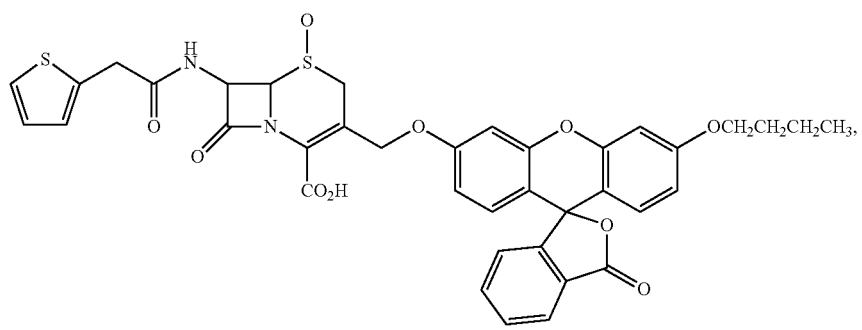
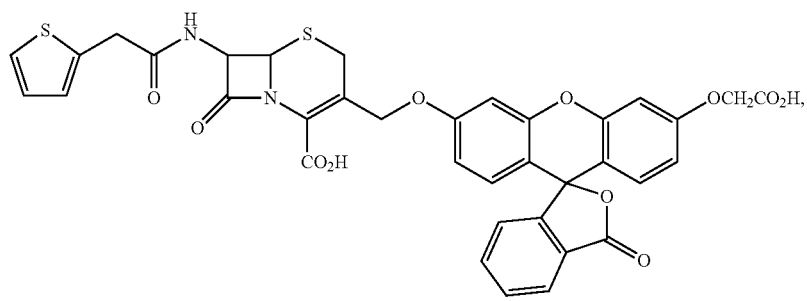
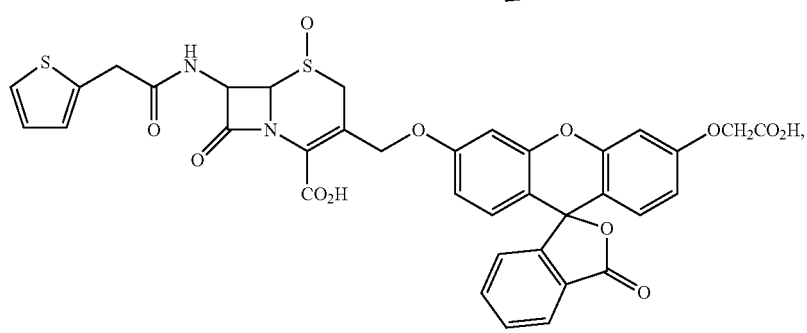

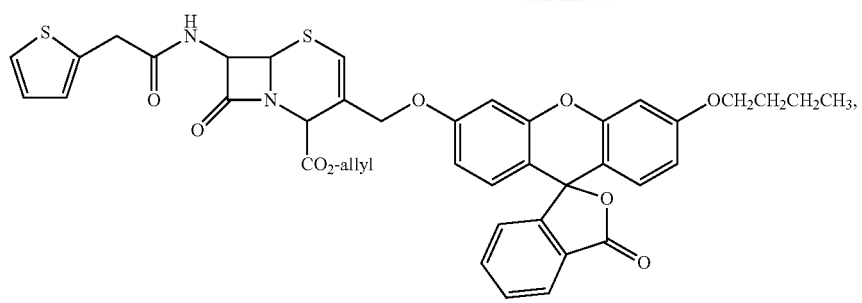
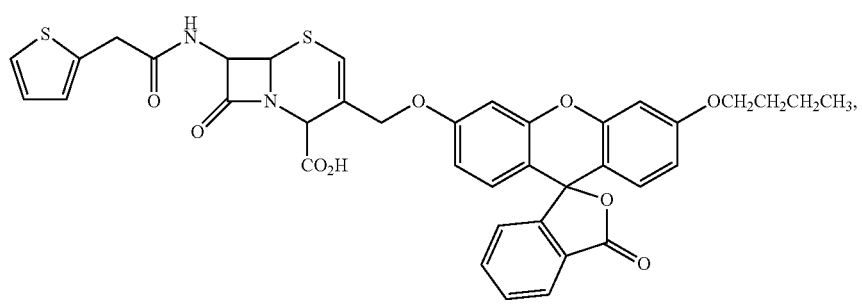
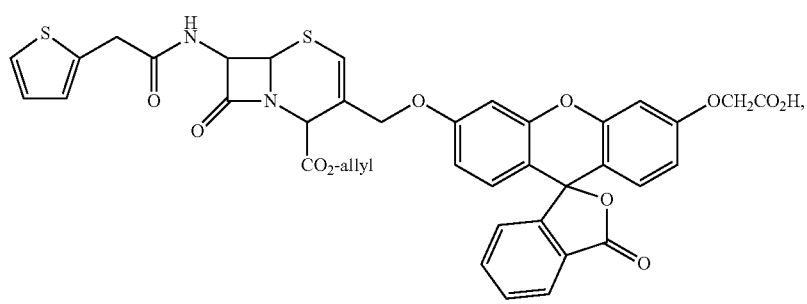
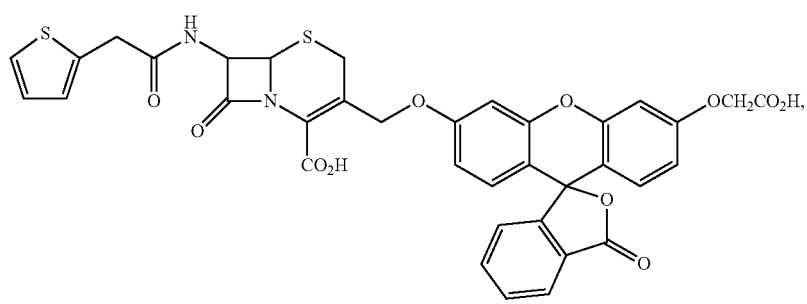
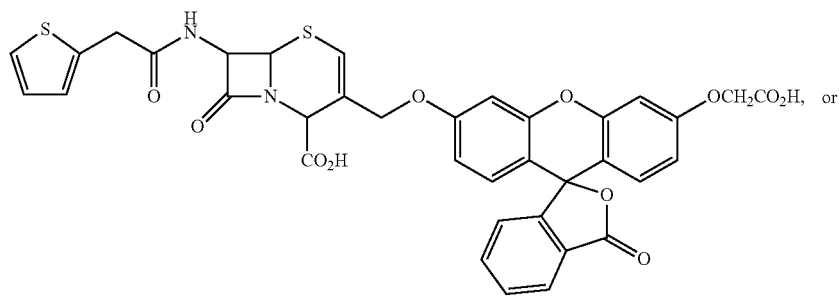

-continued

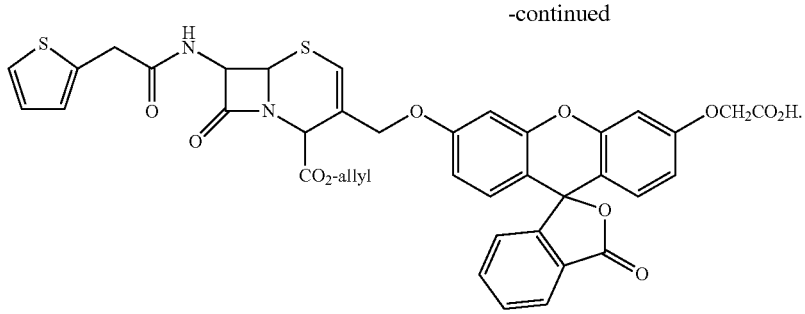

In some embodiments, one dye moiety is bonded to two substrate moieties. The two substrate moieties that are bonded to the single dye moiety can be the same or different. For example, the two substrate moieties bonded to the single dye moiety can independently be a cephalosporin, a clavulanate, an aceturate, a malonamate, benzofuranone or benzopyranone as disclosed herein, or a simple β-lactam ring substrate moiety as disclosed in U.S. Pat. No. 6,031,094. In some embodiments, at least one of the two substrate moieties bonded to the single dye moiety is other than cephalosporin substrate moieties. In other embodiments the two substrate moieties are, for example, two clavulanates, two aceturates, two malonamates, two benzofuranones, two benzopyranones, a clavulanate and a cephalosporin, a clavulanate and an aceturate, a clavulanate and a malonamate, a clavulanate and a benzofuranone, a clavulanate and a benzopyranone, a clavulanate and a simple β-lactam ring substrate moiety, an aceturate and a cephalosporin, an aceturate and a malonamate, an aceturate and a benzofuranone, an aceturate and a benzopyranone, an aceturate and a simple β-lactam ring substrate moiety, a malonamate and a cephalosporin, a malonamate and a benzofuranone, a malonamate and a benzopyranone, a malonamate and a simple β-lactam ring substrate moiety, a benzofuranone and a cephalosporin, a benzofuranone and a benzopyranone, a benzofuranone and a simple β-lactam ring substrate moiety, a benzopyranone and a cephalosporin, or a benzopyranone and a simple β-lactam ring substrate moiety. A detectable optical change can occur upon cleavage of either or both of the substrate moieties. For example, one substrate moiety can be specifically cleaved by one β-lactamase and the other substrate moiety can be specifically cleaved by another, different β-lactamase. Thus, a first detectable optical response can occur in the presence of one of the β-lactamases, a second detectable response can occur in the presence of the other β-lactamase, and a third detectable optical response can occur in the presence of both β-lactamases. In particular embodiments, cleavage of two substrate moiety bonded to a single dye moiety generates at least one phenol (phenolate), thiophenol (thiophenolate) or amine groups on the dye moiety. In a more particular embodiment, the compound has the formula:

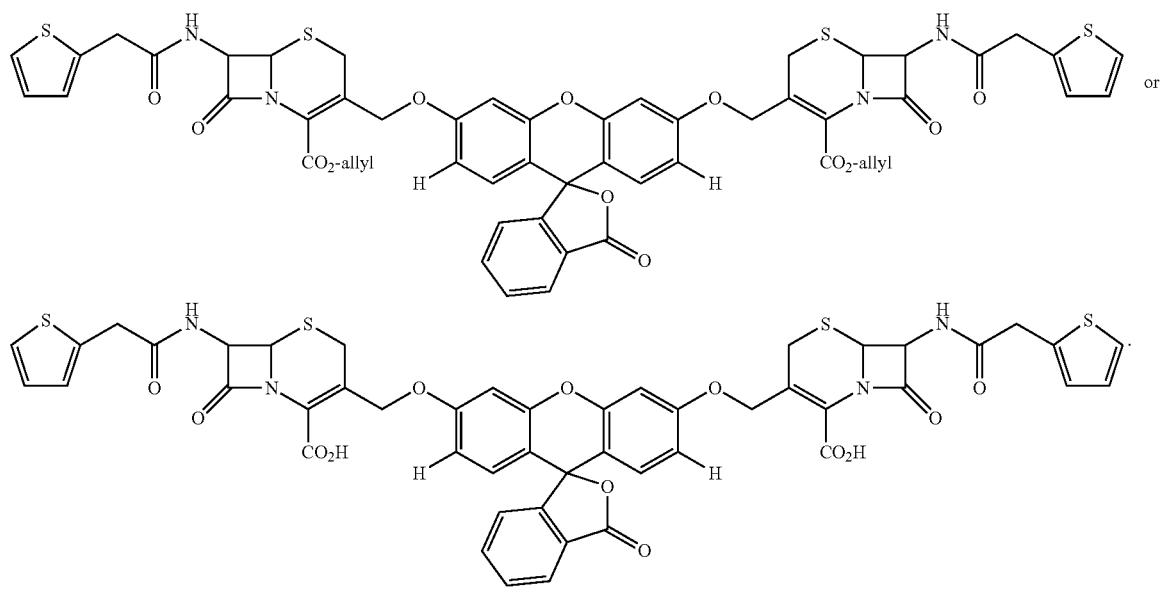

In another exemplary embodiment, the compound is a clavulanic acid derivative (a clavulanate) and has the formula:

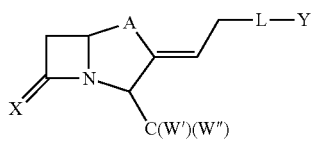

in which Y is a first dye moiety. L is an optional linker moiety (for example, —OC(O)—, —OC(S)—, —SC(O)—, or —SC (S)—). A is S, O, SO, SO$_2$, or CH$_2$. X is O, S or NH. W' and W" are independently H, substituted or unsubstituted alkyl, (=O), (=NH), OR$^{13}$, NHR$^{14}$, or halogen. In this embodiment, W' and W" may or may not be quenchers of the fluorescence emitted by the first dye moiety. If at least one of W' and W" includes a second dye moiety, the first dye moiety may or may not be a quencher of fluorescence of the second dye moiety and vice versa. R$^{13}$ is a member selected from H, substituted or unsubstituted alkyl, and substituted or unsubstituted heteroalkyl. R$^{14}$ is a member selected from H, substituted or unsubstituted alkyl, substituted or unsubstituted heteroalkyl, and OR$^{15}$. R$^{15}$ is a member selected from H, substituted or unsubstituted alkyl, and substituted or unsubstituted heteroalkyl. In a particular embodiment, X and A are O. In another particular embodiment, W' is (=O) and W" is (OH). In other particular embodiments, the compound is:

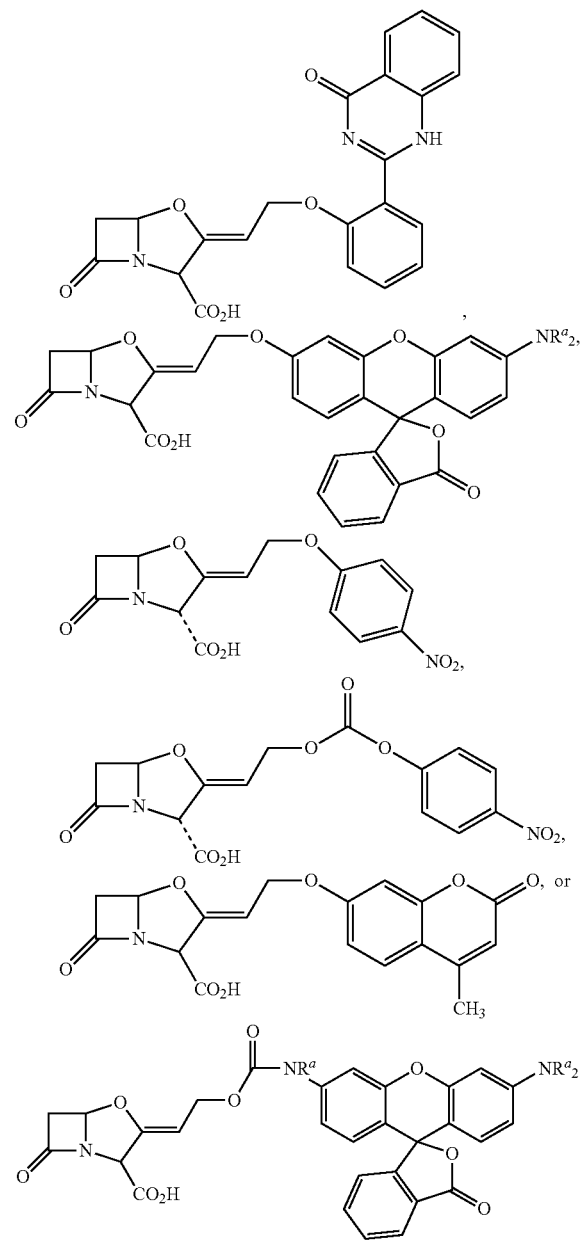

where each R$^a$ group is independently H, substituted or unsubstituted alkyl, substituted or unsubstituted heteroaklyl, substituted or unsubstituted aryl, or substituted or unsubstituted heteroaryl. The dye moiety can be further substituted as described below.

In another exemplary embodiment, the compound is an aceturate derivative (an aceturate), a malonamate derivative (a malonamate), a benzofuranone derivative (a benzofuranone) or a benzopyranone derivative (a benzopyranone) and has the formula:

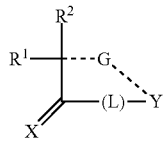

where R$^1$ is,

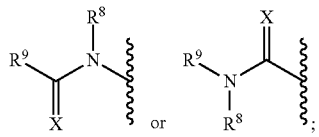

X is O, S or NH, Y is a first dye moiety, G is a first optional linker moiety that can be absent, a bond or —CH$_2$—. If G is a bond or —CH$_2$—, it is attached to a different atom on Y than where Y is bonded to the remainder of the molecule. R$^2$, R$^8$ and R$^9$ are independently H, substituted or unsubstituted alkyl, substituted or unsubstituted heteroaklyl, substituted or unsubstituted aryl, substituted or unsubstituted aryloxy, or substituted or unsubstituted heteroaryl. One or more of R$^2$, R$^8$ and R$^9$ can include a second dye moiety. If G is absent, the first and second dye moieties can comprise a FRET-pair. Also, if G is absent, a second optional linker L [for example, —OC(O)—, —OC(S)—, —SC(O)—, or —SC(S)—] can be present between dye moiety Y and the remainder of the molecule.

In some embodiments, the compound is a malonamate derivative (a malonamate) with the structure:

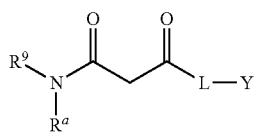

where Y is a first dye moiety. L is an optional linker moiety [for example, —OC(O)—, —OC(S)—, —SC(O)—, or —SC(S)—]. R$^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic R$^9$ groups described above. R$^a$ is H, substituted or unsubstituted alkyl, substituted or unsubstituted heteroaklyl, substituted or unsubstituted aryl, substituted or unsubstituted aryloxy, or substituted or unsubstituted heteroaryl. In some particular embodiments, at least one of R$^9$ and R$^a$ includes a second dye moiety, and in more particular embodiments the first and second dye moieties can be a FRET-pair. In other particular embodiments, the compound has the structure:

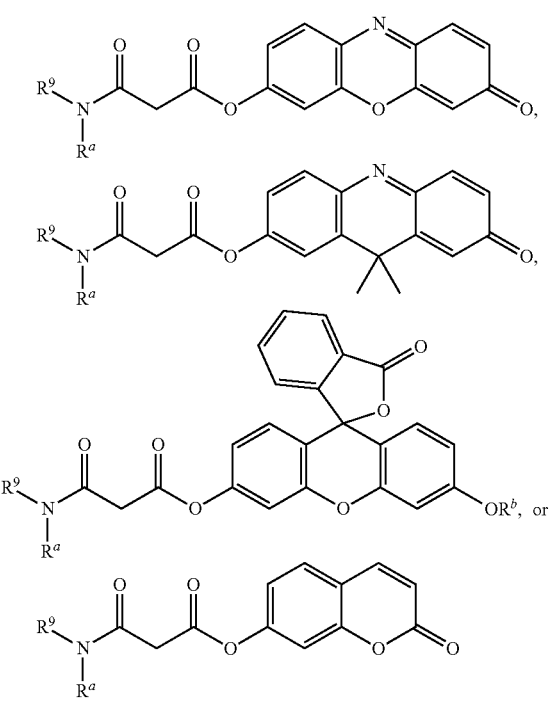

where $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ and $R^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. In some particular embodiments, at least one of $R^9$ and $R^a$ includes a second dye moiety, and in more particular embodiments the first and second dye moieties can be a FRET-pair. The first and/or second dye moieties can be further substituted as described below.

In a more particular embodiment, the compound has a coumarin dye moiety, the compound having the formula:

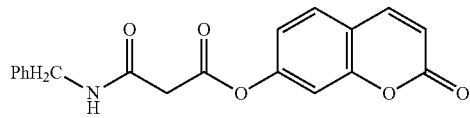

where the coumarin dye moiety may be further substituted as described below.

In other exemplary embodiments, the compound is an aceturate derivative (an aceturate) with the structure:

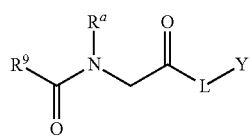

where Y is a first dye moiety. L is an optional linker moiety [for example, —OC(O)—, —OC(S)—, —SC(O)—, or —SC(S)—]. $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ is H, substituted or unsubstituted alkyl, substituted or unsubstituted heteroaklyl, substituted or unsubstituted aryl, substituted or unsubstituted aryloxy, or substituted or unsubstituted heteroaryl. In some particular embodiments, at least one of $R^9$ and $R^a$ includes a second dye moiety, and in more particular embodiments the first and second dye moieties can be a FRET-pair.

In particular embodiments, the compound has the formula:

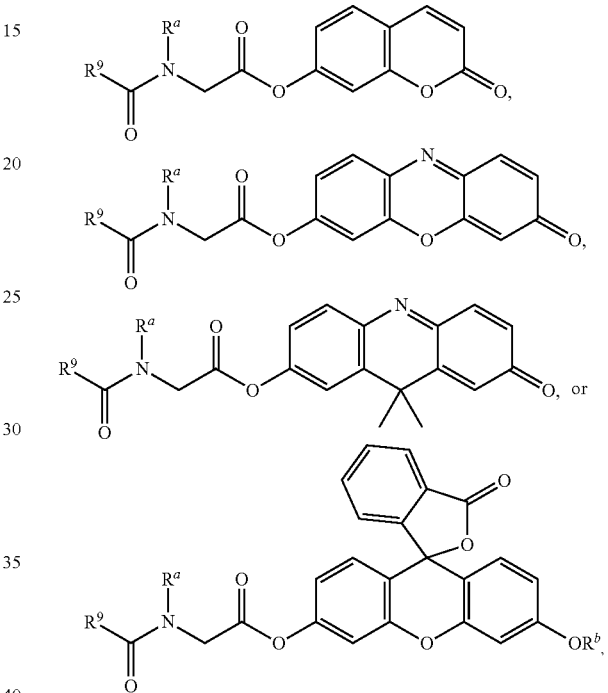

where $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ and $R^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. In some particular embodiments, at least one of $R^9$ and $R^a$ is a second dye moiety, and in more particular embodiments the first and second dye moieties can be a FRET-pair. The first and/or second dye moieties can be further substituted as described below.

In a more particular embodiment the compound has the structure:

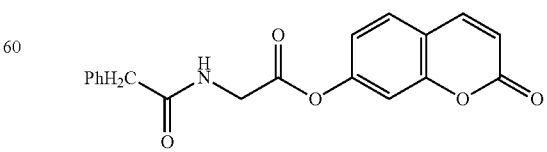

where the dye moiety can be further substituted as described below.

In another exemplary embodiment, the compound is a benzofuranone (G=a bond) derivative (a benzofuranone) and has the structure:

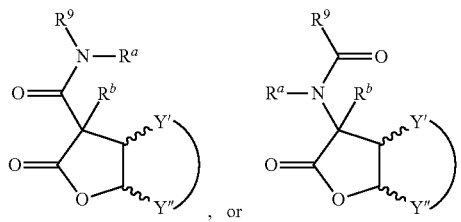, or where $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ and $R^b$ are independently H, substituted or unsubstituted alkyl, substituted or unsubstituted heteroaklyl, substituted or unsubstituted aryl, substituted or unsubstituted aryloxy, or substituted or unsubstituted heteroaryl; and Y' and Y" are connections to an aryl or heteroaryl ring of the remainder of the dye moiety, which is fused to the five-membered ring shown. For example, in particular embodiments, the compound has the structure:

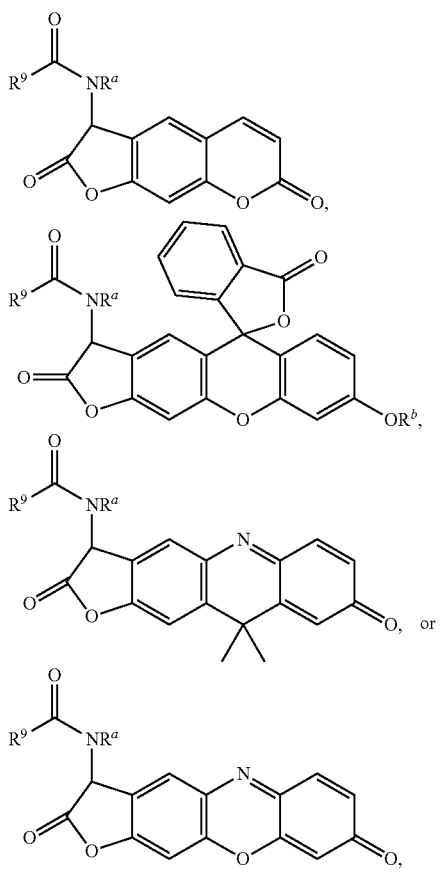

where $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ and $R^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. The dye moiety can be further substituted as described below.

In other particular embodiments, the compound has the structure:

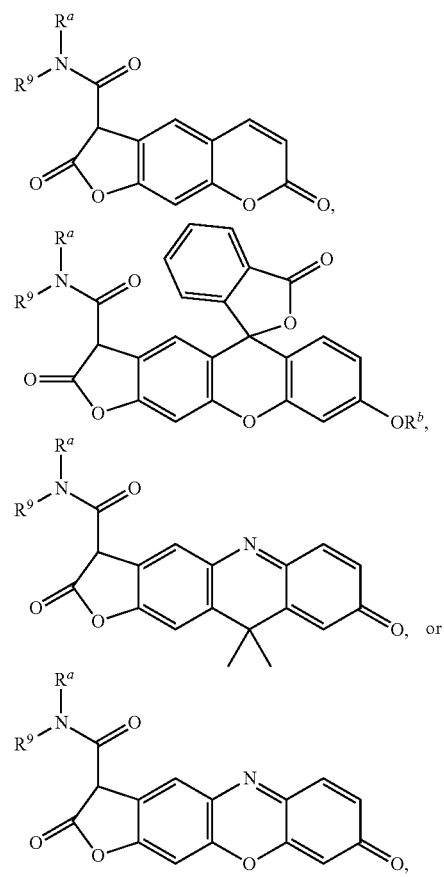

where $R^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic $R^9$ groups described above. $R^a$ and $R^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. The dye moiety can be further substituted as described below.

In more particular embodiments, the compound has the structure:

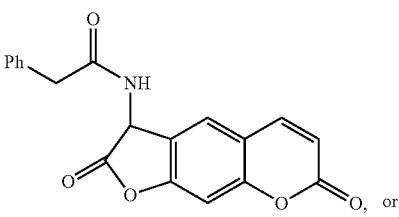

-continued

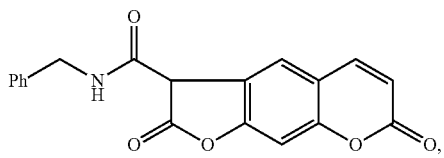

where the dye moiety can be further substituted as described below.

In yet another exemplary embodiment, the compound is a benzopyranone (G=—CH$_2$—) derivative (a benzopyranone) and has the structure:

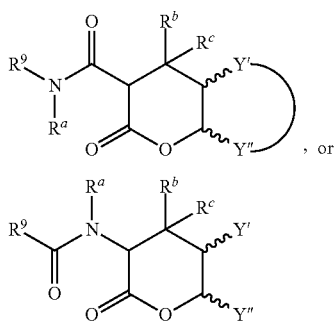

where R$^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic R$^9$ groups described above. R$^a$, R$^b$ and R$^c$ are independently H, substituted or unsubstituted alkyl, substituted or unsubstituted heteroaklyl, substituted or unsubstituted aryl, substituted or unsubstituted aryloxy, or substituted or unsubstituted heteroaryl; and Y' and Y'' are connections to an aryl or heteroaryl ring of the remainder of the dye moiety which is fused to the six-membered ring shown. For example, in particular embodiments, the compound has the structure:

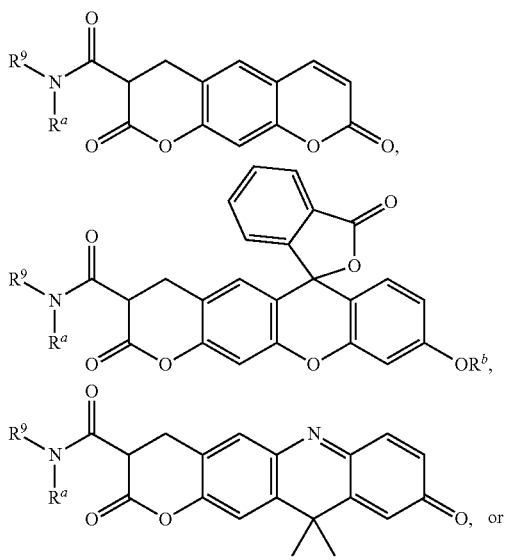

-continued

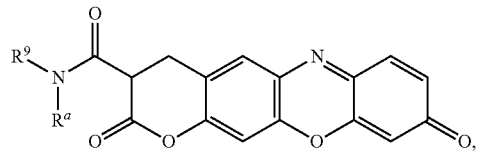

where R$^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic R$^9$ groups described above. R$^a$ and R$^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. The dye moiety can be further substituted as described below.

In other particular embodiments, the compound has the structure:

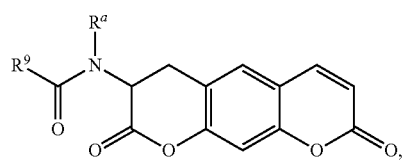

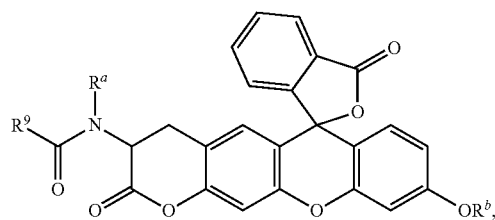

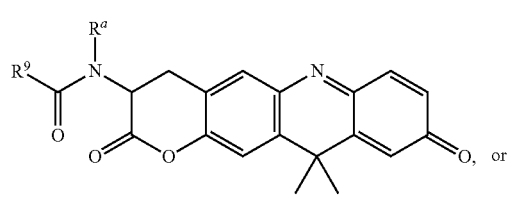

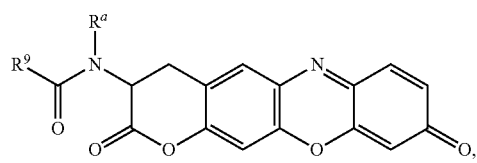

where R$^9$ is H, substituted or unsubstituted alkyl, substituted or unsubstituted heteroaklyl, substituted or unsubstituted aryl, substituted or unsubstituted aryloxy, or substituted or unsubstituted heteroaryl, and can be any of the specific or sub-generic R$^9$ groups described above. R$^a$ and R$^b$ are independently H, substituted or unsubstituted alkyl, substituted or unsubstituted heteroaklyl, substituted or unsubstituted aryl, substituted or unsubstituted aryloxy, or substituted or unsubstituted heteroaryl. The dye moiety can be further substituted as described below.

In more particular embodiments, the compound has the structure:

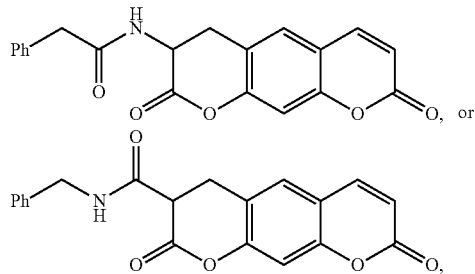

where the dye moiety can be further substituted as described below.

Reporter Molecule Moiety

In an exemplary embodiment, the present compounds confer a detectable signal, directly or indirectly, to the sample comprising a β-lactamase enzyme, wherein they are covalently bonded to a reporter molecule. This results in the ability to detect, monitor and quantitate β-lactmase enzyme in a sample.

The present reporter molecules can be any reporter molecule known to one skilled in the art and when the reporter molecule is either covalently linked to a metal-chelating moiety or comprises part of the metal-chelating moiety wherein no linker is present, forms a metal ion binding compound of the present invention that is useful for the detection of lead, mercury and/or cadmium ions. Reporter molecules include, without limitation, a dye, (chromophore or fluorophore), a fluorescent protein, a phosphorescent dye, a tandem dye (energy transfer pair), a microparticle, a hapten, an enzyme and a radioisotope. Preferred reporter molecules include dyes (both chromophores and fluorophores), fluorescent proteins, haptens, and enzymes. When the reporter molecule is a chromophore the β-lactamase substrates compounds are chromogenic substrates, or more preferably, the reporter molecule is a fluorophore, resulting in a compound that is a fluorescent or fluorogenic indicator for β-lactamase activity.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon cleavage by a β-lactamase enzyme is a change in fluorescence intensity that is greater than approximately 10-fold relative to the same compound in the absence of the enzyme, more preferably greater than 50-fold, and most preferably more that 100-fold. In another aspect, the detectable optical response upon cleavage by a β-lactamase enzyme is a shift in either the maximal excitation or emission wavelength or both that is greater than about 20 nm, more preferably greater than about 30 nm.

A dye of the present invention is any chemical moiety that exhibits an absorption maximum beyond 280 nm, and when covalently linked to the β-lactamase substrate of the present invention, or shares atoms with the β-lactamase substrate, forms a fluorescent or fluorogenic β-lactamase substrate. As described below in more detail, the covalent linkage can be a single covalent bond or a combination of stable chemical bonds. The covalent linkage binding the dye to the β-lacamase substrate moiety is typically a single covalent bond or a substituted alkyl chain that incorporates 1-20 nonhydrogen atoms selected from the group consisting of C, N, O, S and P.

A variety of dye moieties and combinations of dye moieties can be effectively coupled, such as covalently bonded, to the β-lactamase substrate moiety in order to provide a substrate that is capable of reacting with a β-lactamase to provide a detectable response, such as a detectable optical response, upon reaction with a β-lactamase. Dye moieties include luminophores, chromophores, fluorophores and moieties that react with a second compound to generate a luminophore, chromphore or fluorophore. In some embodiments, FRET-pairs of dyes are added to the disclosed compounds. In other embodiments, the dye moiety is joined to a substrate moiety through an amine, hydroxyl or thiol group on an aryl ring or heteroaryl ring of the dye moiety, so that when the substrate moiety is cleaved by a β-lactamase, a phenol (phenolate), thiophenol (thiophenolate) or amine group is generated on the dye moiety.

Exemplary dye moieties include, for example, a pyrene, an anthracene, a naphthalene, an acridine, a stilbene, an indole or benzindole, an oxazole or benzoxazole, a thiazole, a benzothiazole, a 4-amino-7-nitrobenz-2-oxa-1,3-diazole (NBD), a cyanine (including such compounds disclosed in U.S. patent application Ser. Nos. 09/968,401 and 09/969,853, and U.S. Pat. Nos. 6,403,807 and 6,348,599, all of which are incorporated by reference herein), a carbocyanine (including such compounds disclosed in U.S. patent application Ser. No. 09/557,275, and in U.S. Pat. Nos. 5,486,616; 5,268,486; 5,569,587; 5,569,766; 5,627,027 and 6,048,982; all of which are incorporated by reference herein), a carbostyryl, a porphyrin, a salicylate, an anthranilate, an azulene, a perylene, a pyridine, a quinoline, a quinone, a borapolyazaindacene (including such compounds disclosed in U.S. Pat. Nos. 4,774,339; 5,187,288; 5,248,782; 5,274,113 and 5,433,896, all of which are incorporated by reference herein), a xanthene (including any such compounds disclosed in U.S. Pat. Nos. 6,162,931; 6,130,101; 6,229,055; 6,339,392; 5,451,343 6,221,606; 6,358,684; 6,008,379; 6,111,116; 6,184,379; 6,017,712; 6,080,852; and 5,847,162 and U.S. patent application Ser. No. 09/922,333; all of which are incorporated by reference herein) an oxazine or a benzoxazine, a carbazine (including any such compounds disclosed in U.S. Pat. No. 4,810,636, which is incorporated by reference herein), a phenalenone, a coumarin (including an such compounds disclosed in U.S. Pat. Nos. 5,696,157; 5,459,276; 5,501,980 and 5,830,912; all of which are incorporated by reference herein), a benzofuran (including any such compounds disclosed in U.S. Pat. Nos. 4,603,209 and 4,849,362; both of which are incorporated by reference herein) and benzphenalenone (including any such compounds disclosed in U.S. Pat. No. 4,812, 409) and derivatives thereof. As used herein, oxazines include resorufins (including any such compounds disclosed in U.S. Pat. No. 5,242,805, which is incorporated by reference herein), aminooxazinones, diaminooxazines, and their benzo-substituted analogs. Any such dyes are optionally substituted at one or more positions (such as at a position occupied by a hydrogen in a parent ring structure that is characteristic of the class of dyes) with a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on dyes known in the art. In particular embodiments, the dyes are substituted at one or more positions with fluorine, chlorine, alkoxy (such as methoxy or ethoxy), carboxy (such as ester or amide groups), alkyl, aryl, or heteroaryl. In more particular embodiments, the dyes are substituted at one or more positions with fluorine, chlorine or alkoxy.

Where the dye is a xanthene, the dye is optionally a fluorescein, a rhodol (including any such compounds disclosed in U.S. Pat. Nos. 5,227,487 and 5,442,045, which are both incorporated by reference herein), a rhodamine (including any such compounds in U.S. Pat. Nos. 5,798,276 and 5,846,737, which are both incorporated by reference herein). As used herein, rhodamine and rhodol dyes include, among other derivatives, compounds that comprise xanthenes with saturated or unsaturated "julolidine" rings. As used herein, fluorescein includes benzo- or dibenzofluoresceins, seminaphthofluoresceins, and naphthofluoresceins. Similarly, as used herein, rhodol includes seminaphthorhodafluors (including any such compounds disclosed in U.S. Pat. No. 4,945,171, which is incorporated by reference herein).

In certain embodiments, the dye moiety is a benzofuran, a quinoline, a quinazolinone, a xanthene, an indole, a benzazole or a borapolyazaindacene. Particular xanthenes include julolidine-containing xanthenes, as well as fluoresceins, rhodols, rhodamines and rosamines. Xanthenes also include compounds that are substituted or unsubstituted on the carbon atom of the central ring of the xanthene, for example, with substituents typically found in such xanthene-based dyes such as phenyl and substituted-phenyl moieties.

In one aspect, the dye can have an absorption maximum at wavelengths longer than 480 nm. In a particularly useful embodiment, the dye moiety absorbs at or near 488 nm to 514 nm (particularly suitable for excitation by the output of the argon-ion laser excitation source) or near 546 nm (particularly suitable for excitation by a mercury arc lamp). As is the case for many dyes, such dyes can function as both chromophores and fluorophores that may be detected in both colorimetric and fluorescent assays.

Additional examples of suitable dyes are known (see, for example MOLECULAR PROBES HANDBOOK OF FLUORESCENT PROBES AND RESEARCH CHEMICALS, Ninth Ed., Richard P. Haugland, ed. (2002), in particular Chapters 1-3; BIOPROBES 26 (October 1997); BIOPROBES 27 (February 1998); BIOPROBES 28 (May 1998); BIOPROBES 29 (November 1998); and BIOPROBES 30 (January 1999). The spectral properties of dye moieties in solution or when conjugated to a selected substrate moiety are known or are readily measured using a spectrofluorometer. Still further examples of suitable dye moieties include those disclosed in U.S. Pat. No. 5,955,604 and in U.S. Patent Application Publication No. 2003/0003526A1, both of which are incorporated by reference herein. Dyes disclosed in U.S. Pat. No. 5,955,604 include coumarins and related dyes, xanthene dyes (including fluoresceins, rhodols, and rhodamines), resorufins, cyanine dyes, difluoroboradiazaindacene dyes, bimanes, acridines, isoindoles, dansyl dyes, aminophthalic hydrazides (luminal and isoluminol derivatives), aminophthalimides, aminonaphthalimides, aminobenzofurans, aminoquinolines, dicyanohdroquinones, indigo dyes, anthraquinone dyes, polymethine dyes, nitro dyes and their cyano derivatives, quinione dyes, dicyanovinyl and tricyanovinyl dyes, indoaniline dyes (ninhydrin derivatives), di- and tri-phenylmethane dyes, indamines, lanthanide metal chelates and porphyrins.

In an exemplary embodiment, the dye moiety is a substituted or unsubstituted coumarin, a substituted or unsubstituted borapolyazaindacene, a substituted or unsubstituted cyanine, a substituted or unsubstituted styryl, a substituted or unsubstituted 4-[5-(4-dimethylaminophenyl)-2-oxazolyl]phenyl, a substituted or unsubstituted fluorescein, a substituted or unsubstituted rhodamine, a substituted or unsubstituted rhodol, a substituted or unsubstituted oxazine, a substituted or unsubstituted acridinone, a substituted or unsubstituted napthofluorescein, or a substituted or unsubstituted oxoquinazoline.

In some embodiments the dye moiety has the structure:

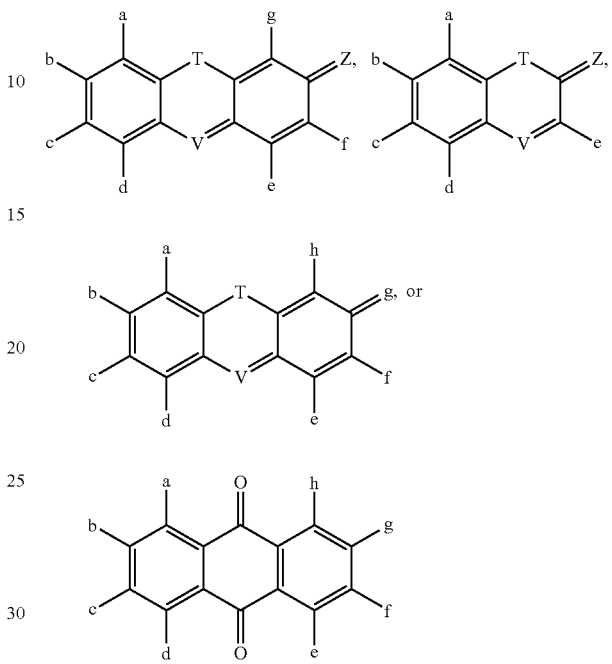

where T is O, S, $CR^s_2$ [such as $C(CH_3)_2$], or $NR^p$; V is N or $CR^s$; Z is O, S or $N^+R^pR^q$; a, b, c, d, e, f, g, and h are independently, a bond, H, —O—, —$NR^p$—, —OH, —$OR^t$, —$NR^pR^q$, —F, —Cl, —Br, —I, —$OOCR^s$, —$CO_2R^s$, -L-O—, -L-$NR^p$—, -L-S—; $R^p$, $R^q$ are independently H, substituted or unsubstituted alkyl or heteroalkyl, substituted or unsubstituted aryl or heteroaryl, or substituted or unsubstituted acyl; $R^s$, $R^t$ are independently H, substitituted or unsubstituted alkyl or heteroalkyl, or substituted or unsubstituted aryl or heteroaryl; and L is a linker.

In particular embodiments, the dye moiety is:

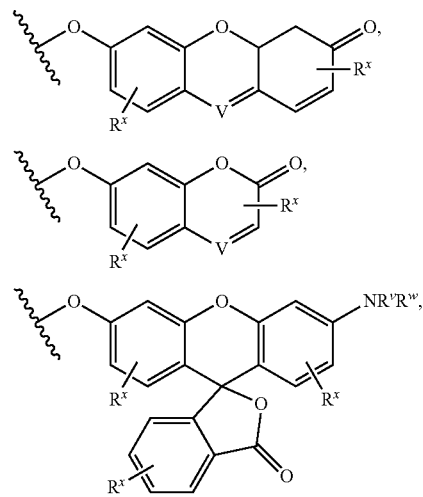

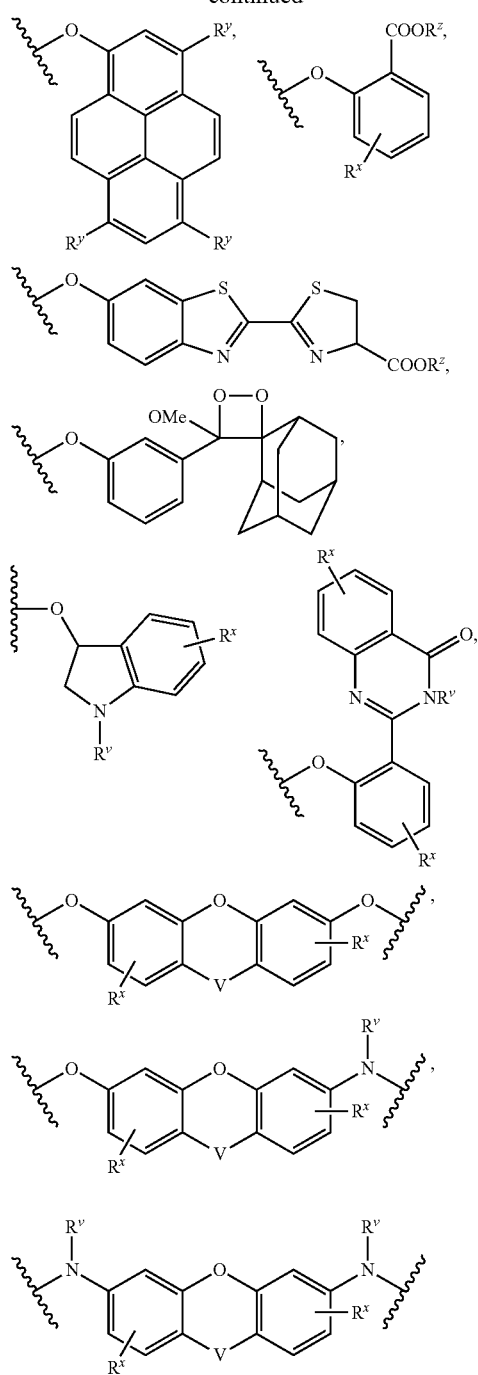

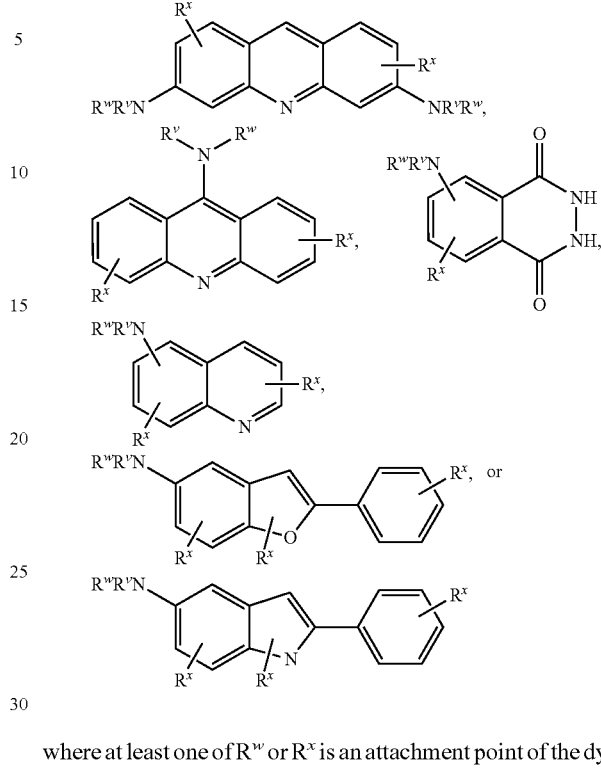

In other particular embodiments, the dye moiety is:

where at least one of $R^w$ or $R^x$ is an attachment point of the dye moiety to a substrate moiety or an attachment to a linker between the dye moiety and a substrate moiety. If other than an attachment point, $R^w$ is H, substituted or unsubstituted alkyl or heteroalkyl, substituted or unsubstituted aryl or heteroaryl, or substituted or unsubstituted acyl. If other than an attachment point, $R^x$ is one or more of H, substituted or unsubstituted alkyl or heteroalkyl, substituted or unsubstituted aryl or heteroaryl, or substituted or unsubstituted acyl, or halogen. $R^v$ is H, substituted or unsubstituted alkyl or heteroalkyl, substituted or unsubstituted aryl or heteroaryl, or substituted or unsubstituted acyl. In more particular embodiments, $R^x$ is H, halogen (F, Cl, Br or I), alkoxy (such as methoxy or ethoxy), or —C(O)OR$^z$, where $R^z$ is H, a metal ion (such as a physiologically acceptable metal ion, for example, Na$^+$ or K$^+$), or substituted or unsubstituted alkyl or heteroalkyl, substituted or unsubstituted aryl or heteroaryl.

In other embodiments, the dye moiety is a substituted or unsubstituted fluorescein, a substituted or unsubstituted oxoquinazoline, a substituted or unsubstituted difluoromethylcoumarin, and substituted or unsubstituted acridinone. In particular embodiments, the dye moiety is:

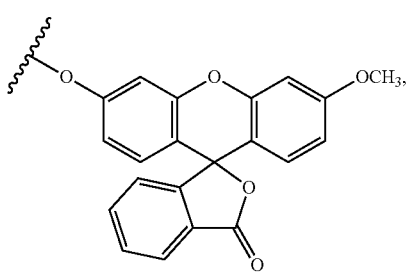

V is N or CR$^s$. $R^s$, $R^v$ and $R^w$ are independently H, substituted or unsubstituted alkyl or heteroalkyl, substituted or unsubstituted aryl or heteroaryl, or substituted or unsubstituted acyl. $R^x$ is one or more of H, substituted or unsubstituted alkyl or heteroalkyl, substituted or unsubstituted aryl or heteroaryl, or substituted or unsubstituted acyl, or halogen. $R^y$ is H, halogen, —SO$_3$H, or —SO$_3^-$. $R^z$ is H, a metal ion (such as a physiologically acceptable metal ion, for example, Na$^+$ or K$^+$), substituted or unsubstituted alkyl or heteroalkyl, or substituted or unsubstituted aryl or heteroaryl. In more particular embodiments, $R^x$ is H, halogen (F, Cl, Br or I), alkoxy (such as methoxy or ethoxy), or —C(O)OR$^z$.

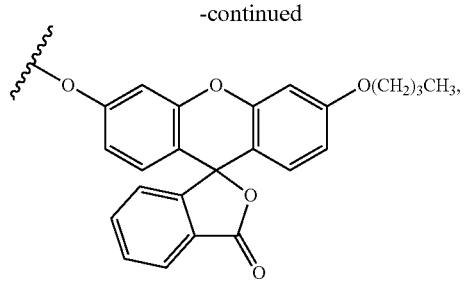
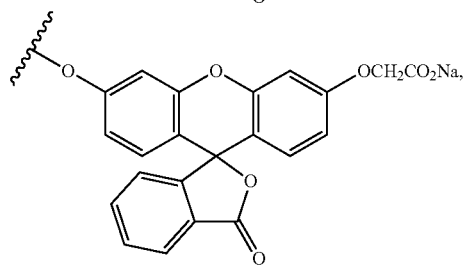
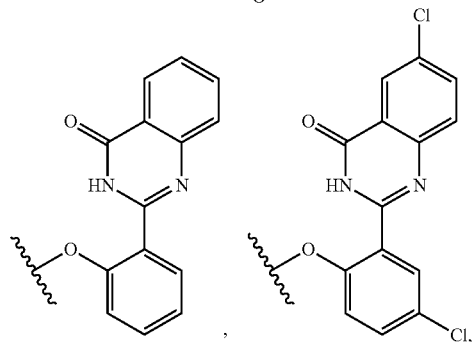
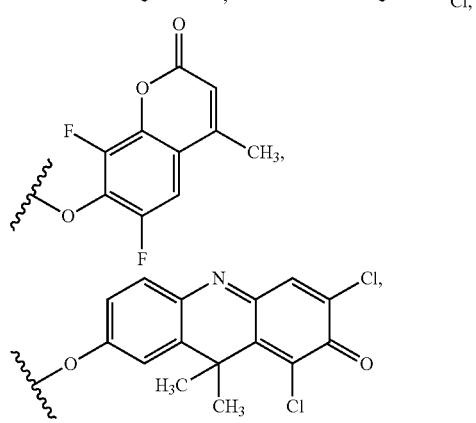
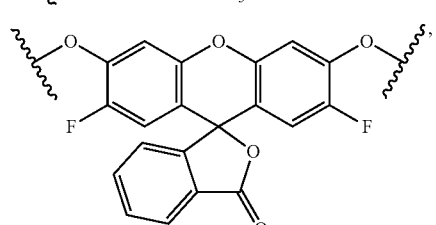
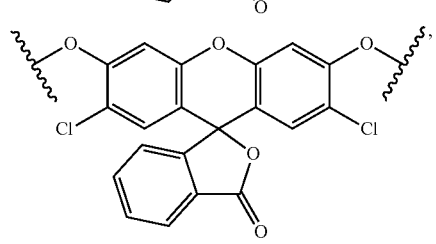
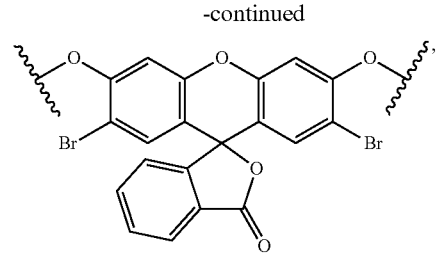
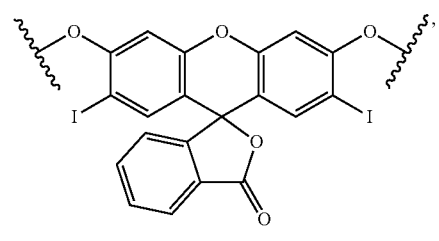
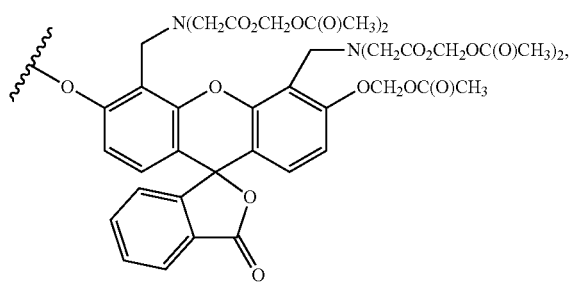
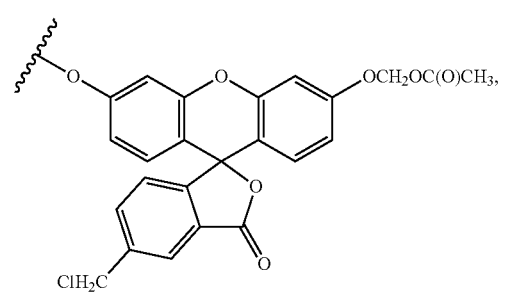
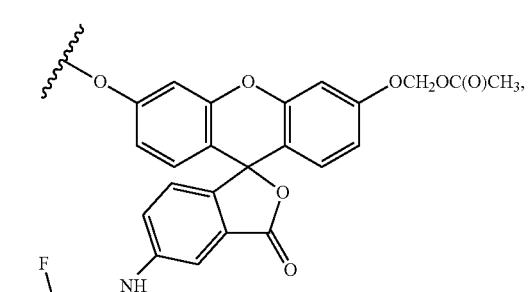

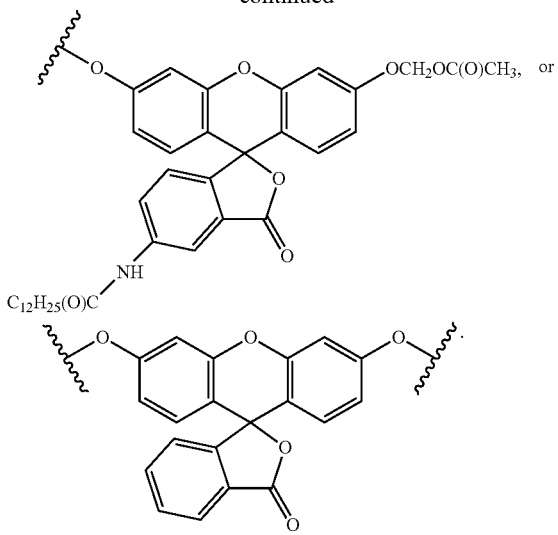

In another exemplary embodiment, the dye moiety further comprises a member selected from a lipophilic moiety, chloromethyl, pentafluorobenzyl, and a targeting moiety. In yet another exemplary embodiment, the dye moiety is a member selected from substituted or unsubstituted aminofluorescein, substituted or unsubstituted aminorhodamine, and substituted or unsubstituted aminorhodol. In still another exemplary embodiment, the dye moiety is

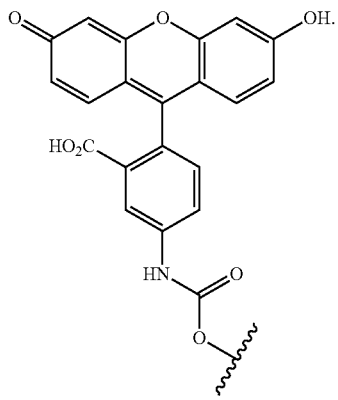

Fluorescent proteins also find use as labels for the β-lactamase substrates of the present invention. Examples of fluorescent proteins include green fluorescent protein (GFP) and the phycobiliproteins and the derivatives thereof. The fluorescent proteins, especially phycobiliproteins, are particularly useful for creating tandem dye-reporter molecules. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target heavy metal ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, solid supports and Reporter molecule (as described above), comprise a linker that is used to covalently attach the substituents to any of the moieties of the present compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. This description of the linker also applies to the reporter molecules, as disclosed above. The linker may also be substituted to alter the physical properties of the reporter moiety or chelating moiety, such as spectral properties of the dye. Examples of L include substituted or unsubstituted polyalkylene, arylene, alkylarylene, arylenealkyl, or arylthio moieties.

The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —(CH$_2$)$_d$(CONH(CH$_2$)$_e$)$_z$— or where d is an integer from 0-5, e is an integer from 1-5 and z is 0 or 1. In a further embodiment, the linker is or incorporates the formula —O—(CH$_2$)—. In yet another embodiment, the linker is or incorporates a phenylene or a 2-carboxy-substituted phenylene.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect the compounds comprise a dye moiety, a substrate moiety, and a reactive group moiety.

The reactive group can, for example, be bound to the compounds at $R^9$, W, W', W'', A, or Y. In another exemplary embodiment, the reactive group can be bound to the compounds at $R^9$ or Y. In another exemplary embodiment, the reactive group can be bound to the compounds at $R^9$. In yet another exemplary embodiment, the reactive group can be bound to the compounds at A, W', W'', or Y. In another exemplary embodiment, the reactive group can be bound to the compounds at W' or W''. In another exemplary embodiment, the reactive group can be bound to the compounds at Y. In another exemplary embodiment, the reactive group can be bound to the compounds at A.

In an exemplary embodiment, the compounds further comprise a reactive group that is acrylamide, an activated ester of a carboxylic acid, an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine, a hydrazide, an imido ester, an isocyanate, an isothiocyanate, a maleimide, a phosphoramidite, a reactive platinum complex, a sulfonyl halide, a thiol group, or a photoactivatable group.

The pro-reactive groups are synthesized during the formation of the monomer moieties and carrier molecule and solid support containing compounds to provide chemically reactive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |

TABLE 1-continued

Examples of some routes to useful covalent linkages

| Electrophilic Group | Nucleophilic Group | Resulting Covalent Linkage |
| --- | --- | --- |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. Exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. The carrier molecule can, for example, be bound to the compounds at $R^9$, W, W', W'', A, or Y. In another exemplary embodiment, the carrier molecule can be bound to the compounds at $R^9$ or Y. In another exemplary embodiment, the carrier molecule can be bound to the compounds at $R^9$. In yet another exemplary embodiment, the carrier molecule can be bound to the compounds at A, W', W'', or Y. In another exemplary embodiment, the carrier molecule can be bound to the compounds at W' or W''. In another exemplary embodiment, the carrier molecule can be bound to the compounds at Y. In another exemplary embodiment, the carrier molecule can be bound to the compounds at A.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In an exemplary embodiment, the carrier molecule comprises a specific binding pair member wherein the present compounds are conjugated to a specific binding pair member and are used to detect a heavy metal ion in close proximity to the complimentary member of the specific binding pair. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |

TABLE 2-continued

Representative Specific Binding Pairs

| | |
|---|---|
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization In an exemplary embodiment, the compounds of the invention are covalently bonded to a solid support. The solid support may be attached to the compound either through the β-lactam moiety, or through the dye moiety, or through the reactive group, if present, or through a carrier molecule, if present. Even if a reactive group and/or a carrier molecule are present, the solid support may be attached through the β-lactam moiety or the dye moiety. In another exemplary embodiment, at least one member selected from $R^9$, W, W', W'', A, and Y includes a solid support or is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

While it has been stressed that a wide range of components can be used to make the heavy metal-binding compounds it should also be understood that the individual selection of components to make a particularly useful heavy metal-binding compound for detection purposes requires an understanding of the reporter molecules, carrier molecules, reactive group, solid supports, the linkers, the metal chelating moiety and how certain combinations, and substituents function to selectively bind to physiological concentrations of heavy metal ions in the presence of physiological concentrations of calcium ions or other non-target metal ions.

Preparation of Conjugates

Conjugates of components (carrier molecules or solid supports), e.g., drugs, peptides, toxins, nucleotides, phospholipids and other organic molecules are prepared by organic synthesis methods using the reactive dyes, are generally prepared by means well recognized in the art (Haugland, MOLECULAR PROBES HANDBOOK, supra, 2002). Conjugation to form a covalent bond may consist of simply mixing the reactive compounds of the present invention in a suitable solvent in which both the reactive compound and the substance to be conjugated are soluble. The reaction preferably proceeds spontaneously without added reagents at room temperature or below. For those reactive dyes that are photoactivated, conjugation is facilitated by illumination of the reaction mixture to activate the reactive dye. Chemical modification of water-insoluble substances, so that a desired dye-conjugate may be prepared, is preferably performed in an aprotic solvent such as dimethylformamide (DMF), dimethylsulfoxide (DMSO), acetone, ethyl acetate, toluene, or chloroform.

Preparation of peptide or protein conjugates typically comprises first dissolving the protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the present compound are added to the protein, the conjugate is chromatographically purified to separate unconjugated compound and the compound-protein conjugate is tested in its desired application.

Following addition of the reactive compound to the component solution, the mixture may be incubated for a suitable period (typically about 1 hour at room temperature to several hours on ice), the excess unreacted compound is removed by gel filtration, dialysis, HPLC, adsorption on an ion exchange or hydrophobic polymer or other suitable means. The conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of substitution is determined from the long wavelength absorption of the compound-protein conjugate by using the extinction coefficient of the un-reacted compound at its long wavelength absorption peak, the unmodified protein's absorption peak in the ultraviolet and by correcting the UV absorption of the conjugate for absorption by the compound in the UV.

Conjugates of polymers, including biopolymers and other higher molecular weight polymers are typically prepared by means well recognized in the art (for example, Brinkley et al., Bioconjugate Chem., 3: 2 (1992)). In these embodiments, a single type of reactive site may be available, as is typical for polysaccharides or multiple types of reactive sites (e.g. amines, thiols, alcohols, phenols) may be available, as is typical for proteins. Selectivity of labeling is best obtained by selection of an appropriate reactive compound. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of the compound is typically used, relative to the expected degree of compound substitution. Any residual, un-reacted compound or hydrolysis product is typically removed by dialysis, chromatography or precipitation. Presence of residual, unconjugated compound can be detected by thin layer chromatography using a solvent that elutes the compound away from its conjugate. In all cases it is usually preferred that the reagents be kept as concentrated as practical so as to obtain adequate rates of conjugation.

In an exemplary embodiment, the conjugate is associated with an additional substance that binds either to the compound or the component (reporter molecule, carrier molecule, solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

Synthesis

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention; it is not intended to define the scope of reactions or reaction sequences that are useful in preparing the compounds of the present invention.

a) Exemplary Synthesis of Cephalosporin-Containing Compounds

In Schemes 1-8, a general preparatory synthesis for the cephalosporin-containing compounds of the invention is presented.

Scheme 1

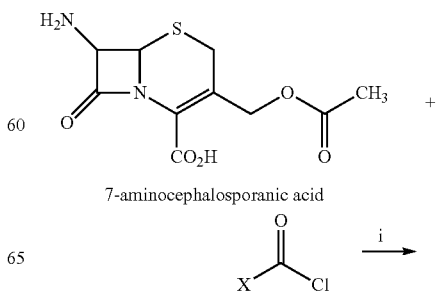

7-aminocephalosporanic acid

Scheme 1

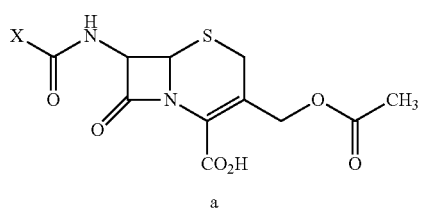

a

In Scheme 1, 7-aminocephalosporanic acid is reacted with a substituted acyl chloride in order to produce a (reaction i).

Scheme 2

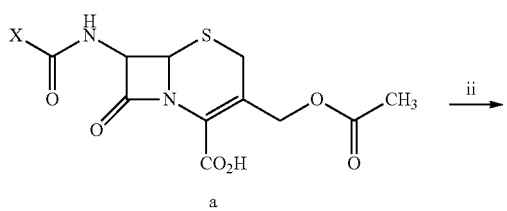

a

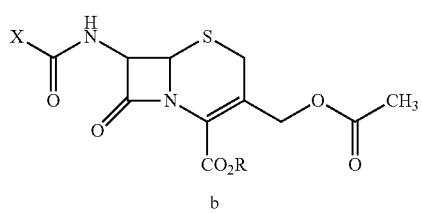

b

In Scheme 2, the carboxylate in a is protected to yield b. Examples of protecting groups include allyl, benzhydryl, and t-butyl ester (reaction ii).

Scheme 3

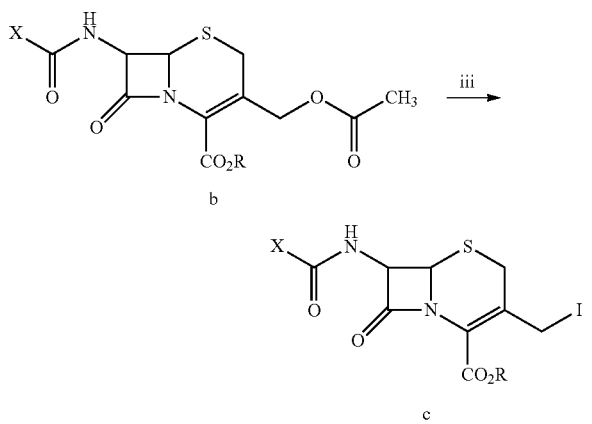

In Scheme 3, the acetate moiety in b is cleaved to afford the electrophilic iodide c, commonly using reagents such as trimethylsilyl iodide (reaction iii).

Scheme 4

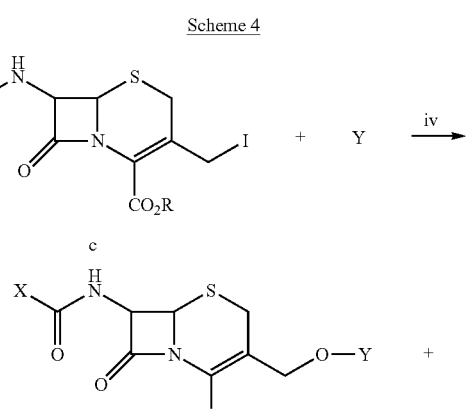

In Scheme 4, reaction of the iodide with the hydroxyl group of a dye compound, mediated by a mild base such as potassium carbonate or sodium methoxide, affords, for example, a non-fluorescent or weakly fluorescent ether d. (reaction iv). In an exemplary embodiment, this reaction affords two products, d and e, instead of a single product, d. Examples of reactions which produce both d and e include those involving fluorescein or an oxoquinazoline as the dye moiety.

Scheme 5

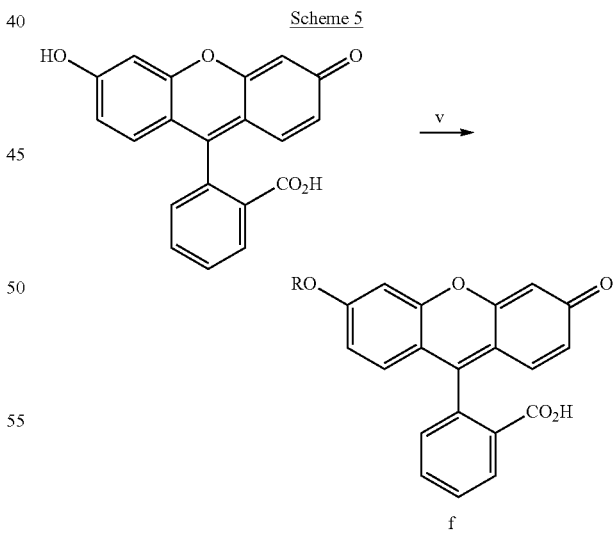

When fluorescein is the dye, the fluorescein can optionally be substituted before the addition reaction in Scheme 4. In an exemplary embodiment, R is the optionally substituted moiety, and it comprises substituted and unsubstituted alkyl. Thus, in Scheme 5, when Y is fluorescein, the fluorescein can be substituted to yield f (reaction v).

Scheme 6

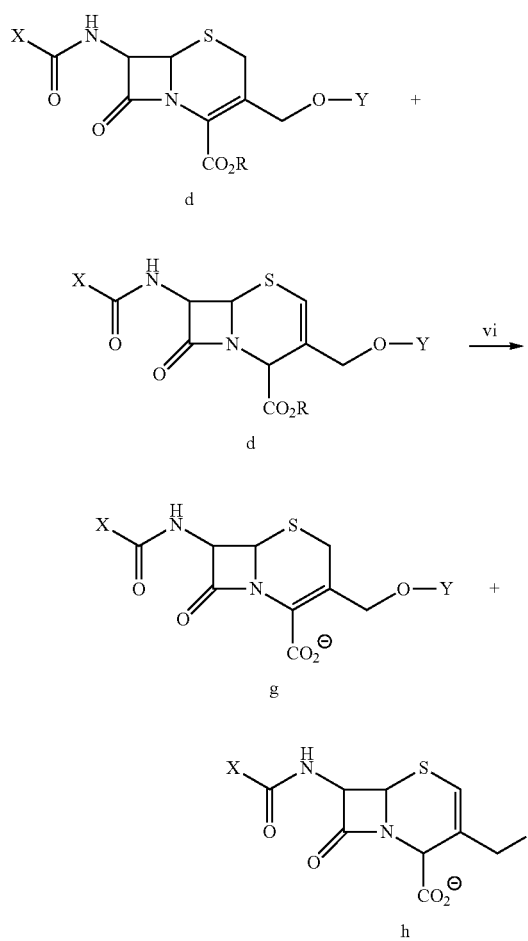

In Scheme 6, the protecting group R is removed to afford the β-lactamase substrate g (reaction vi). In an exemplary embodiment, this reaction affords two products, g and h, instead of a single product, g. Examples of reactions which produce both g and h include those involving fluorescein or an oxoquinazoline as the dye moiety.

Scheme 7

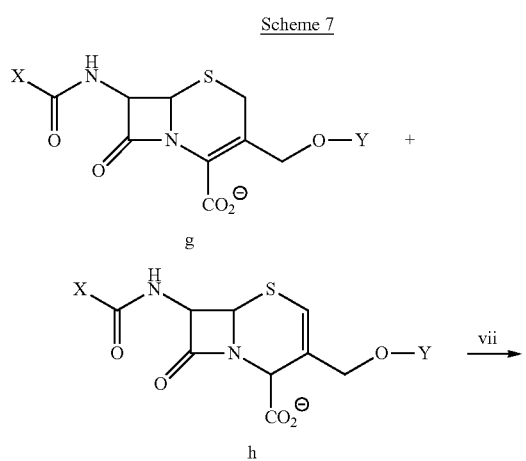

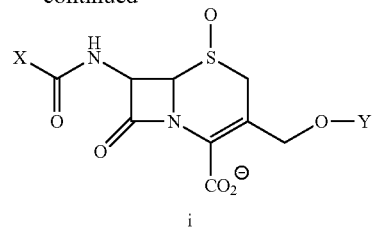

In optional Scheme 7, the sulfide g can be oxidized, commonly using 3-chloroperbenzoic acid, to yield the sulfoxide i (reaction vii). In an exemplary embodiment, a mixture of sulfides g and h can be oxidized, commonly using 3-chloroperbenzoic acid, to yield one sulfoxide, i.

Scheme 8

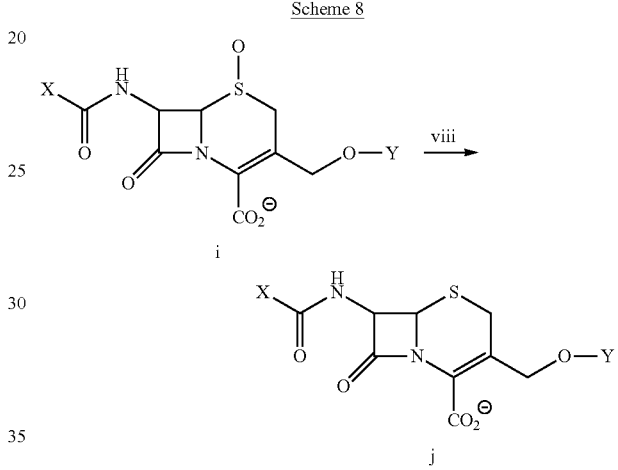

In optional Scheme 8, the sulfoxide i can be reduced, commonly using a tin derivative, to yield the sulfide j (reaction viii). This synthetic step is performed in order to convert isomer h into isomer g.

b) Exemplary Synthesis of Clavulanic Acid-Containing Compounds

In Schemes 9-13, a general preparatory synthesis for the clavulanic acid-containing compounds of the invention is presented.

Scheme 9

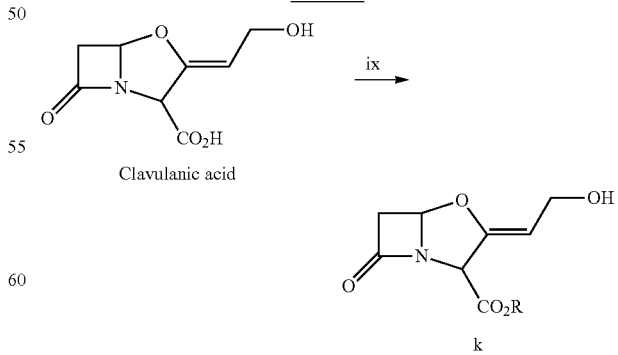

In Scheme 9, the carboxylate in clavulanic acid is esterified to produce k (reaction ix). In an exemplary embodiment, the ester formed includes allyl, benzhydryl or t-butyl ester.

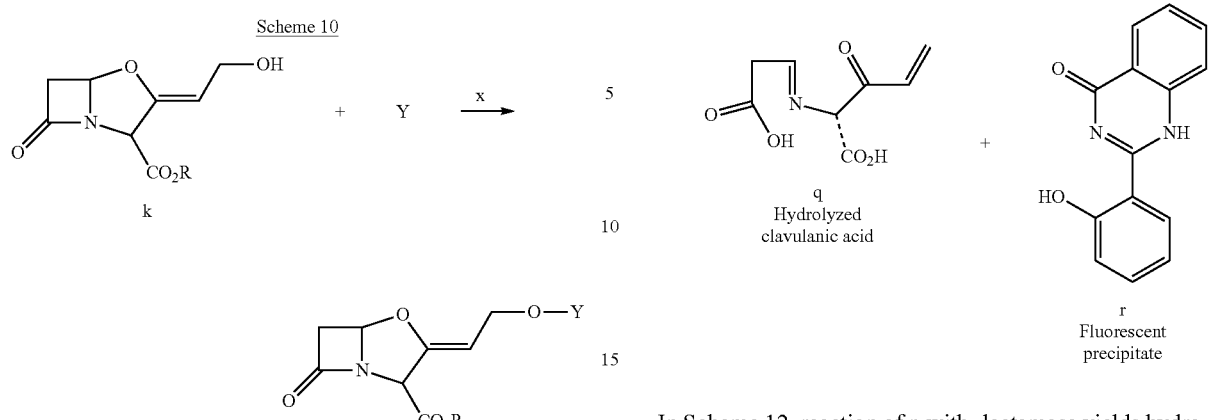

In Scheme 10, k is coupled with the hydroxyl group of a dye under standard Mitsunobu reaction conditions to afford l (reaction x).

In Scheme 11, removal of the protecting group R from l yields the -lactamase substrate m (reaction xi).

In Scheme 12, reaction of p with -lactamase yields hydrolyzed clavulanic acid and a fluorescent precipitate (reaction xiii).

c) Exemplary Synthesis of Malonamate and Phenaceturate Compounds

In scheme 13, a malonamate s is coulpled with a phenol-bearing dye moiety to provide, for example, a colorogenic or fluorogenic malonamate t. Reaction xv employs any one of a number of coupling protocols, for example, carbodiimide mediated esterification catalyzed, for example, by DCC, DIC, or EDCI. Additional agents for esterification include phosphonium salts, such as PyBop and the like, and uronium salts, such as HBTU, HATU, TFFH and the like.

In scheme 14, an optionally protected aceturate u (protected shown, for example, protected with BOC) is reacted with a phenol-bearing dye to provide, for example, a colorogenic or fluorogenic aceturate v. In reaction xvi, the protected aceturate is coupled to the dye using, for example, DCC. In the second step, the product is deprotected (if protecting group present) using, for example, TFA.

Scheme 15

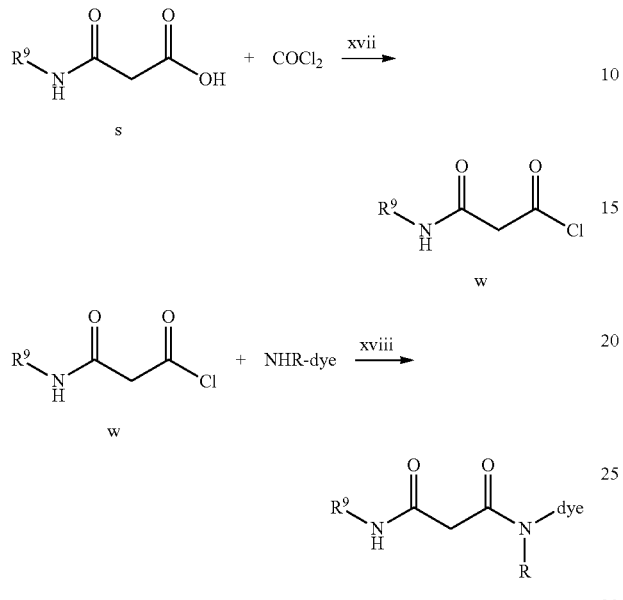

In scheme 15, a malonamate is first reacted (reaction xvii) to form acyl chloride w, for example, with COCl$_2$. The acyl chloride w is then reacted (reaction xviii) with an amine-bearing dye to provide, for example, a colorogenic or fluorogenic malonamate.

Scheme 16

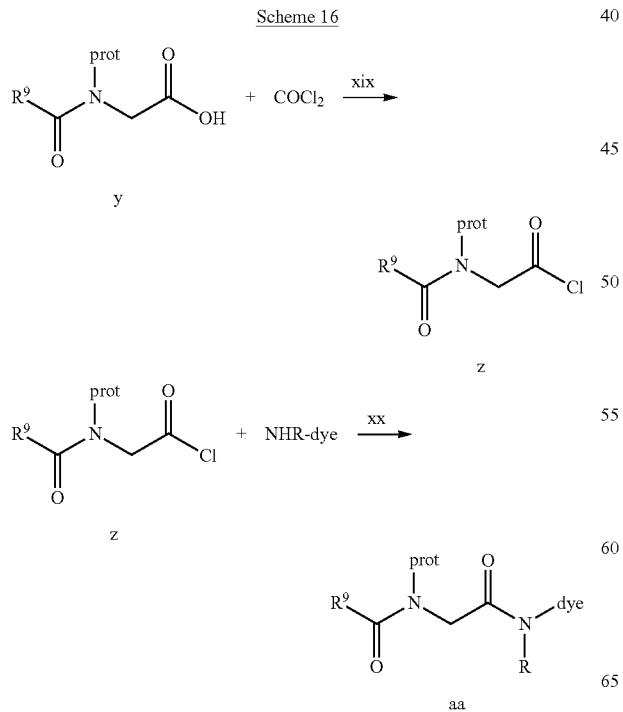

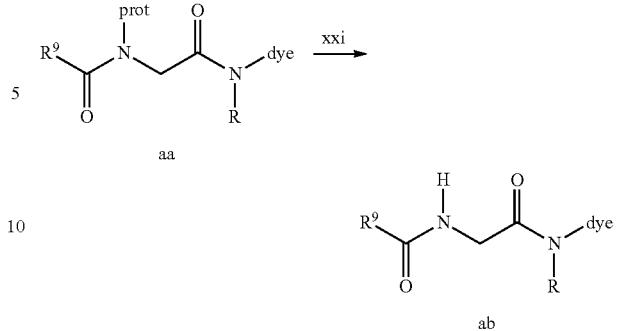

In scheme 16, an optionally protected aceturate (protected shown) is first reacted (reaction xix) to form acyl chloride z, for example, by reaction with COCl$_2$. The acyl chloride z is then reacted (reaction xvii) with an amine-bearing dye to provide aa, which can then be deprotected (if protecting group present), for example, with TFA, to provide a colorogenic or fluorogenic aceturate ab.

d) Exemplary Synthesis of Benzofuranone Compounds

Scheme 17

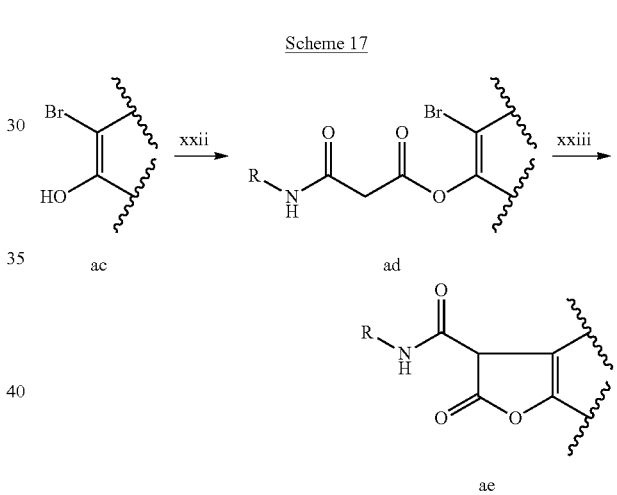

In scheme 17, a dye bearing adjacent hydroxyl and halogen (bromine shown) groups (ac) is esterified (reaction xxii) with an N-substituted malonamic acid (where R=substituted or unsubstituted alkyl or heteroakyl, or substituted or unsubstituted aryl or heteroaryl) in the presence of a coupling reagent (such as DCC) to provide a compound of formula ad. Compound ad is then cyclized in reaction xxiii to provide compound ae, which can be a colorogenic or fluorogenic benzofuranone.

Scheme 18

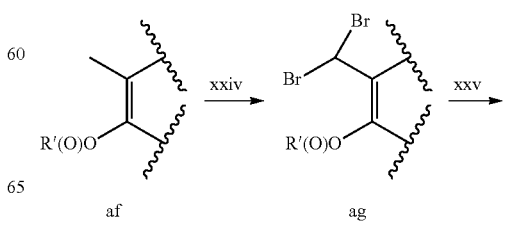

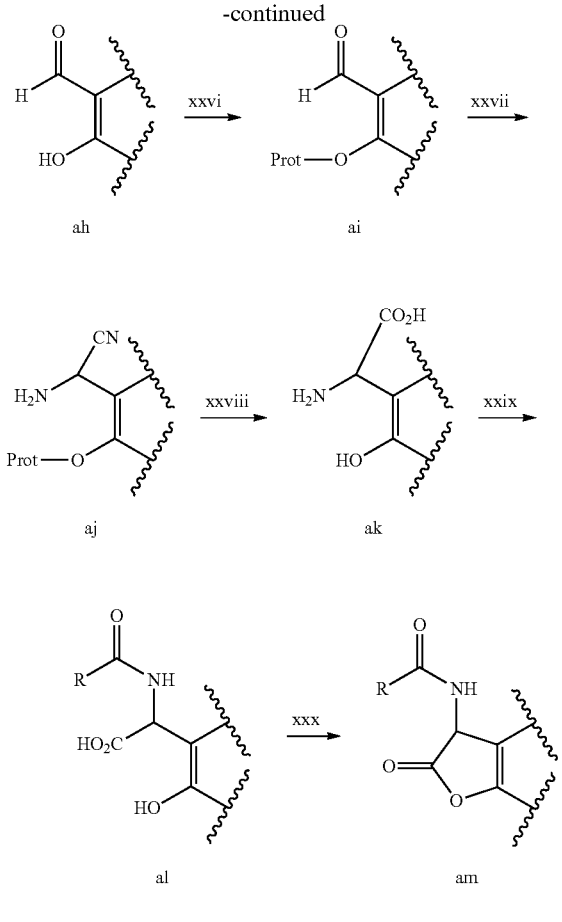

e) Exemplary Synthesis of Benzopyranone Compounds

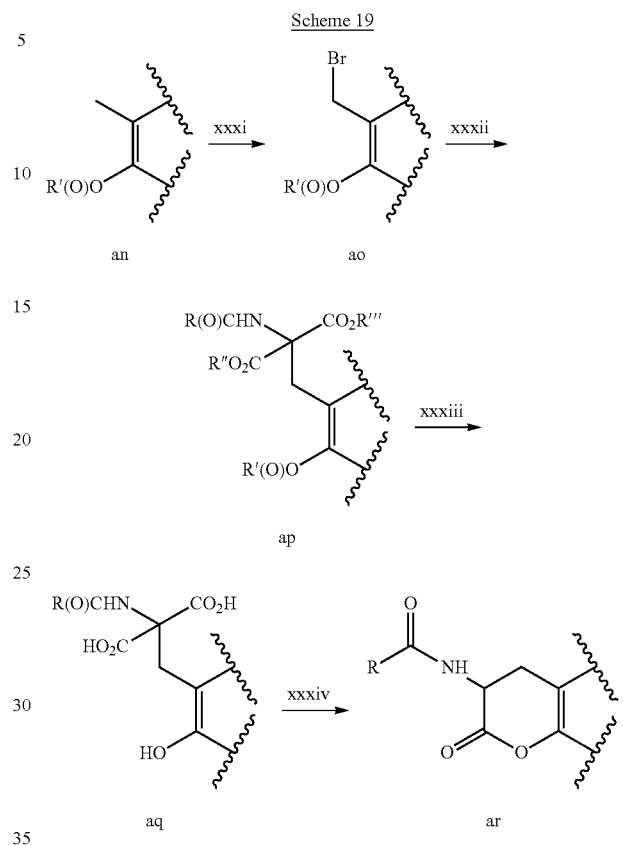

In scheme 18, a dye bearing adjacent methyl and ester groups of (R'=substituted or unsubstituted alkyl or heteroakyl, or substituted or unsubstituted aryl or heteroaryl) is halogenated (reaction xxiv, employing, for example, 2 equivalents of NBS) to provide a dye compound ag with adjacent dihalomethyl (dibromomethyl shown) and ester groups. In reaction xxv, the dihalomethyl group is converted to an aldehyde group and the ester group is cleaved to provide a hydroxyl group (for example, with sodium carbonate in ethanol/water). The product of reaction xxv is a dye bearing adjacent hydroxyl and aldehyde groups (compound ah). The hydroxyl group on compound ah is then protected (reaction xxvi), for example, by reaction with an alkyl or aryl halide (such as with benzyl bromide in potassium carbonate/DMF) to provide a dye moiety bearing adjacent aldehyde and ether groups (compound ai). The aldehyde group on compound ai is then reacted (reaction xxvii) to provide an amino-cyanomethyl group (such as with a solution of NaCN, $NH_4Cl$, and $NH_3$ in MeOH) as shown in compound aj. The cyano group bonded to the methyl group is then converted to a carboxylic acid group and the ether group is converted back to a hydroxyl group (deprotection) to provide compound ak (reaction xxviii, employing, for example, HCl). Next, compound ak is reacted (reaction xxix) with an acyl halide [R—C(O)-halide, such as R—C(O)—Cl, where R=substituted or unsubstituted alkyl or heteroakyl, or substituted or unsubstituted aryl or heteroaryl] to provide a compound of formula al, which is then cyclized (reaction xxx) to provide a benzofuranone compound am, which can be a colorogenic or fluorogenic benzofuranone.

In scheme 19, a dye compound an bearing adjacent methyl and ester groups (where R'=substituted or unsubstituted alkyl or heteroakyl, or substituted or unsubstituted aryl or heteroaryl) is halogenated (reaction xxxi), for example with 1 equivalent of NBS, to provide a dye compound of formula ao having adjacent ester and halomethyl groups (bromomethyl shown). The dye compound of formula ao is then reacted (reaction xxxii) with an N-substituted amidomalonate diester in the presence of an alkali or alkaline earth hydride such as NaH to provide compound ap (where R" and R'" can be substituted or unsubstituted alkyl or heteroakyl, or substituted or unsubstituted aryl or heteroaryl, for example, diethyl-benzamidomalonate). The ester groups are converted to carboxylic acid and hydroxyl groups in reaction xxxiii to provide compound aq, which is cyclized in reaction xxxiv to provide a benzopyranone compound ar, which may, for example, be a colorogenic or fluorogenic benzopyranone compound.

Scheme 20

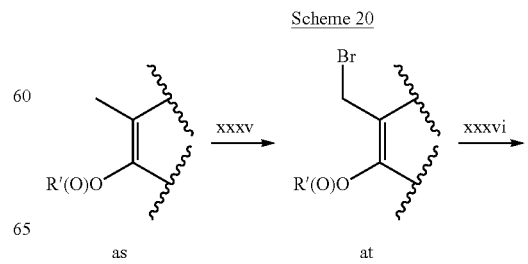

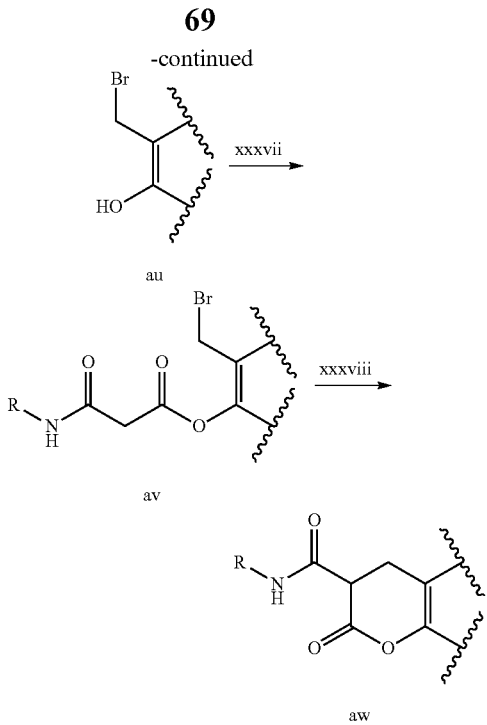

In scheme 20, a dye bearing adjacent methyl and ester groups (compound as, where R'=substituted or unsubstituted alkyl or heteroakyl, or substituted or unsubstituted aryl or heteroaryl) is halogenated (bromine shown) in reaction xxxv, for example, with 1 equivalent NBS, to generate a dye (at) bearing adjacent halomethyl (bromomethyl shown) and ester groups. In reaction xxxvi, the ester is cleaved, for example, with sodium or potassium carbonate, to provide a dye (au) bearing adjacent halomethyl (bromomethyl shown) and hydroxyl groups. In reaction xxxvii, dye au is the coupled with an N-substituted malonamate (where R=substituted or unsubstituted alkyl or heteroakyl, or substituted or unsubstituted aryl or heteroaryl, for example, N-benzylmalonamate) in the presence of a coupling reagent (such as DCC) to provide a compound of formula av. Compound av is then cyclized in the presence of a mild base (such as potassium carbonate) to provide a benzopyranone compound of formula aw, which can, for example, be a colorogenic or fluorogenic benzopyranone compound.

Methods of Use

In another aspect, methods of using the compounds described herein for a wide variety of chemical, biological and biochemical applications are disclosed.

Thus, in another aspect, the present invention provides a method for detecting the presence of β-lactamase activity in a sample. The method includes contacting the sample with at least one disclosed compound, for example, a disclosed cephalosporin, clavulanate, aceturate, malonamate, benzofuranone or benzopyranone.

In another aspect, the a method is provided for the determination of the presence of a β-lactamase in a sample. The method includes contacting the sample with a disclosed compound, which is substantially nonfluorescent. The compound is then incubated with the sample for a sufficient amount of time (for example, between 1 and 60 minutes, or longer) for the β-lactamase to react with the compound to produce a fluorescent product. The fluorescent product is illuminated with an appropriate wavelength and its fluorescence is detected, whereby the presence of the β-lactamase is deter-mined in the sample. In an exemplary embodiment, the method further comprises incubating the sample with an esterase, for example, to remove any hydrolase-cleavable moieties that are present.

In another aspect, a method is provided for the determination of the presence of β-lactamase in a sample. The method includes contacting the sample with a disclosed compound, which is fluorescent. The sample is then illuminated with an appropriate wavelength and the fluorescence intensity of the fluorescent compound is determined. The β-lactamase substrate is then incubated with the sample for a sufficient amount of time (for example, between 1 and 60 minutes) for the β-lactamase to react with the compound to produce a non-fluorescent product. The sample is illuminated with an appropriate wavelength and the difference in fluorescence intensity between the first and second measurements is determined. In an exemplary embodiment, the method further comprises incubating the sample with an esterase.

In yet another aspect, a method is provided for the determination of the presence of β-lactamase in a sample. The method includes contacting the sample with a fluorescent compound comprising a first β-lactam moiety and a first dye moiety, and a (relative) non-fluorescent compound comprising a second β-lactam moiety and a second dye moiety. The sample is illuminated with an appropriate wavelength(s) for determining the fluorescence intensity of the fluorescent compound (and the non-fluorescent compound, if it is not substantially non-fluorescent). The fluorescent and non-fluorescent compounds are incubated with the sample for a sufficient amount of time for the β-lactamase to cleave the first and second compounds, for example, to produce a non-fluorescent (relative) product from the fluorescent compound and a fluorescent (relative) product from the non-fluorescent compound. The sample is illuminated with an appropriate wavelength(s) for determining the fluorescence intensity of the products.

In another aspect, a method is provided for localizing a fluorescent dye product in an environment comprising an aqueous solution and a β-lactamase. In this method, the environment is contacted with a disclosed fluorogenic compound. Next, the environment is incubated for a sufficient amount of time for the β-lactamase to cleave the substrate moiety, thereby producing a fluorescent dye product which is insoluble in the aqueous solution, and thereby localizing the fluorescent dye product in the environment. In an exemplary embodiment, the environment is either a biological cell or a cell-free environment. In another exemplary embodiment, the environment is a either an interior of a cell, an interior of a cell organelle, or an exterior of a cell.

In another aspect, the invention provides a method of localizing a fluorescent dye product on the exterior of a cell, in which the exterior comprises a β-lactamase and is surrounded by an aqueous solution. This method includes contacting the exterior with a disclosed fluorogenic compound. The exterior is incubated for a sufficient amount of time for the β-lactamase to cleave the compound, and produce a fluorescent dye product which is insoluble in the aqueous solution and thereby localized on the cell exterior.

In another aspect, a method of detecting a protein or target antigen is disclosed. This method includes contacting the protein with a primary antibody that binds specifically to the protein. The primary antibody is contacted with a secondary antibody that binds specifically to the primary antibody, wherein the secondary antibody includes a β-lactamase. The secondary antibody is contacted with a disclosed compound. The sample is incubated for a sufficient amount of time for the β-lactamase to cleave the compound, and produce a detectable optical response, which is used to detect the presence of the protein. If, for example, the detectable optical response includes production of an insoluble dye product, the location of the protein in the sample may be determined by visual or electronic inspection (such as with a fluorescence microscope, optionally including a CCD camera).

In another aspect, the invention provides a method of detecting a protein in a sample immobilized on a gel. This method includes subjecting the sample to an electrophoretic separation. Next, the protein is transferred from the gel to a polymer sheet. Next, the protein on the polymer sheet is contacted with a primary antibody. Then the primary antibody is contacted with a secondary antibody that comprises a β-lactamase. Then the protein on the polymer sheet with the primary and secondary antibodies is contacted with a fluorogenic compound comprising a dye moiety and a β-lactam moiety. Finally, the product of this reaction is incubated for a sufficient amount of time for said β-lactamase to cleave the dye moiety from the β-lactam moiety. This produces a fluorescent dye product which is insoluble in an aqueous solution, and thereby enables the detection of the protein.

Compounds disclosed to include a reactive group or a carrier molecule are discussed in detail above and are equally applicable to the methods discussed herein.

In another exemplary embodiment, the present invention provides a method of detecting a β-lactamase in a sample by using an immobilized compound of the invention comprising a β-lactam moiety and a dye moiety. The method includes combining the sample with a compound of the invention covalently bonded to a solid support. The β-lactamase in the sample is then allowed to react and cleave the bond linking the β-lactam moiety and a dye moiety, thus producing a fluorescent dye product. In another exemplary embodiment, the method further comprises illuminating the fluorescent dye product with an appropriate wavelength so that the presence of the β-lactamase in the sample is determined and its concentration in the sample is optionally quantified.

In methods of detecting a β-lactamase by using an immobilized compound of the invention, the methods may further include, after forming the fluorescent product, rinsing the solid support to remove components of the sample other than the immobilized fluorescent product. In another exemplary embodiment, the methods may further provide, after forming the immobilized fluorescent product, detecting the immobilized fluorescent product. In a related embodiment, the immobilized fluorescent product is detected after rinsing the solid support.

In another exemplary embodiment, the present invention provides a method of detecting a β-lactamase in a sample by using an immobilized compound of the invention which is fluorescent and comprises a β-lactam moiety and a dye moiety. The method includes combining the sample with a compound of the invention covalently bonded to a solid support. In this method, the immobilized compound is illuminated with an appropriate wavelength in order to determine its fluorescence intensity. The β-lactamase in the sample is then allowed to react and cleave the bond linking the β-lactam moiety and the dye moiety, thus producing a non-fluorescent product. In another exemplary embodiment, the method further comprises illuminating the non-fluorescent product with an appropriate wavelength in order to determine the fluorescence intensity. Then, the first and second fluorescence intensities are compared in order to determine the presence, and optionally the concentration, of β-lactamase in the sample.

Solid supports covalently bonded to a compound of the invention are discussed in detail above and are equally applicable to the methods discussed herein. Likewise, carrier molecules covalently bonded to a compound of the invention are discussed in detail above and are equally applicable to the methods discussed herein.

Rinsing the solid support typically functions to remove residual, excess or unbound materials from the solid support other than the immobilized fluorescent product. Any appropriate solution or series of solutions may be used to rinse the solid support. Exemplary solvents useful in the present invention include both polar and non-polar solvents. Thus, any appropriate organic solvent or aqueous solution is useful in the methods of the current invention.

Solutions of the disclosed compounds may be prepared according to methods generally known in the art. The disclosed compounds are generally soluble in water and aqueous solutions having a pH greater than or equal to about 6. Stock solutions of pure compounds of the invention, however, may be dissolved in organic solvent before diluting into aqueous solution or buffer. Exemplary organic solvents include aprotic polar solvents such as DMSO, DMF, N-methylpyrrolidone, acetone, acetonitrile, dioxane, tetrahydrofuran and other nonhydroxylic, completely water-miscible solvents. In general, the amount of the disclosed compounds in solution is the minimum amount that will yield a detectable optical response in the presence of a particular enzyme, in a particular amount, within a reasonable time, and with minimal background signal. The exact concentration of compound of the invention to be used is dependent upon the experimental conditions and the desired results, and those skilled in the art can readily determine the optimal concentration to be used in a given application. The concentration typically ranges from nanomolar to micromolar. The optimal concentration is determined by systematic variation in compound concentration until satisfactory results are accomplished. The starting ranges are readily determined from methods known in the art for use of similar compounds under comparable conditions for the desired response.

For those compounds of the present invention that are substituted by lipophilic moieties, the compounds of the invention are optionally introduced into living cells by passive permeation through the cellular membranes. Less cell-permeant embodiments of the invention are optionally introduced into cells by pressure microinjection methods, scrape loading techniques (short mechanical disruption of the plasma membrane where the plasma membrane is peeled away from the cytoplasm, the compound is perfused through the sample and the plasma membrane is reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the compounds into the cellular cytoplasm.

Any suitable method of detection is useful in detecting fluorogenic or fluorescent compounds of the invention. In an exemplary embodiment, detection is achieved by illuminating the fluorogenic or fluorescent compounds at a wavelength selected to elicit a detectable optical response.

A detectable optical response means a change in, or occurrence of, a parameter in a test system that is capable of being perceived, either by direct observation or instrumentally. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample. The presence or absence of the optical response after the elapsed time is indicative of one or more characteristic of the sample. Comparison of the amount of the compound of the invention with a standard or expected response can be used to determine whether and to what degree a sample possesses the enzyme (and enzymatic activity) of interest.

In those embodiments in which a compound of the invention is covalently bonded to a carrier molecule that is a chelator of calcium, sodium, magnesium, potassium, or other biologically important metal ion, the amount of the compound that fluoresces functions as an indicator of the ion, which indicators are optionally further conjugated to a biological or plastic polymer according to methods known in the art; e.g., using fluorinated analogs of the compounds described in U.S. Pat. Nos. 5,453,517 and 5,405,975. Alternatively, the compound of the invention acts as a pH indicator at pH values within about 1.5 pH units of the individual dye's pKa. Typically the detectable optical response of the ion indicators is a change in fluorescence of the ion chelator.

Also disclosed are methods for detecting β-lactamase activity using the disclosed compounds, which include methods for detecting β-lactmase activity per se (such as for detecting antibiotic resistance in bacteria) and for detecting β-lactamase activity as a measure of another process that involves production of a β-lactamase (such as where a β-lactamase encoding nucleic acid is used as a reporter gene to measure expression of the nucleic acid). The methods may be practiced on both cell-free and cellular systems (e.g., intracellular detection). Examples of methods for detecting β-lactamase activity in which the presently disclosed compounds may be utilized as susbstrates for a β-lactamase include those methods disclosed in U.S. Pat. Nos. 5,955,604, 5,741,657, 6,031,094, 6,291,162, and 6,472,205.

As described in the above-referenced United States patents (such as, U.S. Pat. No. 6,472,205), cells to be assayed for β-lactamase activity may be contacted with a disclosed compound, for example, a fluorogenic compound. In the presence of a β-lactamase, the substrate is cleaved and a detectable optical response, such as a change in the fluorescence emission spectrum of the dye, is produced. If a β-lactamase is present in the sample, then the sample will exhibit increased or decreased fluorescence when contacted with a disclosed compound. Such fluorescence changes can be detected by exciting the sample with radiation of a first wavelength, which excites the dye moiety, which emits radiation of a second wavelength, which can be detected. The amount of the emission is measured, and compared to proper control or background values. The amount of emitted radiation that differs from the background and control levels, either increased or decreased, correlates with the amount or activity of the β-lactamase in the sample. Standard curves can be determined for quantitative measurements.

β-lactamase activity may be measured using the disclosed compounds by measuring any number of optical changes catalyzed by a β-lactamase. For example, cleavage of the substrate moiety of a disclosed compound by a β-lactamase may result in any of the following: (1) a shifting of the emission spectrum of the dye moiety (2) the compound is fluorescent and the product of the reaction with the β-lactamase is non-fluorescent, and (3) the compound is non-fluorescent and the product of the reaction with the β-lactamase is fluorescent.

In another aspect, a method is provided for determining whether a β-lactamase enzyme can cleave a disclosed compound. The method involves contacting the sample with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates that the beta-lactamase enzyme can cleave the compound and that the compound is a substrate for the β-lactamase enzyme.

In another aspect, a method for determining whether a sample contains beta-lactamase activity is provided. The method involves contacting the sample with a disclosed compound, exciting the sample with radiation of one or more wavelengths that are absorbed by the cleaved compound, and determining the degree of fluorescence emitted from the sample. A degree of fluorescence emitted from the sample that is greater than an expected degree indicates the presence of β-lactamase activity in the sample. One aspect of this method is for determining the amount of an enzyme in a sample by determining the degree of fluorescence emitted at a first and second time after contacting the sample with a compound of the present invention. The difference in the degree of fluorescence emitted from the sample at the first and second time is determined, and the difference reflects the amount of a beta-lactamase enzyme in the sample.

In another aspect, screening assays are presented for the use of the disclosed compounds and a host cell, such as a mammalian cell, transfected with at least one recombinant nucleic acid molecule encoding at least one protein having β-lactamase activity. Such recombinant nucleic acid molecules can include expression control sequences adapted for function in a eukaryotic cell, such as a vertebrate cell, operatively linked to a nucleotide sequence coding for the expression of a β-lactamase enzyme. Such recombinant nucleic acid molecules include the GeneBLAzer, LiveBLAzer and LyticBALzer constructs sold by Invitrogen (Carlsbad, Calif.).

In yet another aspect, methods are provided for determining the amount of beta-lactamase activity in a cell. This method involves contacting a sample including a host cell that is transfected with a recombinant nucleic acid molecule that includes a nucleic acid sequence coding for the expression of a beta-lactamase. The sample can comprise whole host cells, or an extract of the host cells, which is contacted with a compound of the present invention. The amount of compound cleaved is measured by measuring a detectable optical response, whereby the amount of substrate cleaved is related to the amount of beta-lactamase activity in the host cell.

In another aspect, a method for monitoring the expression of a gene operably linked to a set of expression control sequences is provided. The method involves providing a host cell transfected with a recombinant nucleic acid molecule, where the nucleic acid molecule comprises a set of expression control sequences operatively linked to nucleic acid sequences coding for the expression of a beta-lactamase enzyme, except if the host cell is a fungus, the beta-lactamase is a cytosolic beta-lactamase enzyme. A sample comprising the host cell, or an extract or conditioned medium produced therefrom or thereby, is contacted with a disclosed compound. The amount of compound cleaved is determined, wherein the amount of substrate cleaved is related to the amount of beta-lactamase activity in the host eukaryotic cell, which is related to the expression of the gene.

In another aspect, a method is provided for determining whether a test compound alters the expression of nucleic acid sequence operably linked to an expression control sequence(s). The method involves contacting a host cell transfected with a recombinant nucleic acid sequence, where the recombinant nucleic acid comprises an expression control sequence(s) operably linked to a nucleic acid sequence coding for a beta-lactamase. The host cell is contacted with the test compound, and the host cell is then contacted with a disclosed compound. The amount of the compound cleaved is then measured, whereby the amount of the compound cleaved is related to the amount of beta-lactamase activity in the cell. In addition, the amount of compound cleaved in the presence of the test compound can be compared to the amount of compound cleaved in the absence of the test compound to determine if the test compound alters expression regulated by the control sequence.

In another aspect, a method for clonal selection is provided, wherein cells that are presumably transfected with a recombinant nucleic acid molecule comprising a sequence coding for a β-lactamase are contacted with a disclosed compound. Those cells that are in fact transfected with the recombinant nucleic acid molecule will exhibit β-lactamase activity, which is detected by measuring the detectable optical change produced upon cleavage of the compound. Cells that exhibit β-lactamase activity, or greater than a predetermined level of β-lactamase activity may be selected, and propagated if desired. Selection of cells exhibiting β-lactamase activity can be accomplished using fluorescence activated cell sorting (FACS), using, for example, a Becton Dickinson FACS Vantage.

Another aspect is to use a beta-lactamase reporter gene and a compound of the present invention to screen test chemicals for biochemical activity. A cell transfected with a recombinant nucleic acid molecule that includes at least one expression control sequence operably linked to at least one nucleic acid sequence encoding for the expression of a beta-lactamase enzyme is contacted with the test chemical. The cell is contacted with a disclosed compound and the amount of the compound cleaved is measured. The amount of compound cleaved reflects the amount of beta-lactamase activity within the at least one cell, and reflects the biochemical activity of the test chemical. The amount of compound cleaved in the presence of the test chemical is compared to the amount of compound cleaved in the absence of the test chemical to determine if the test chemical increases, decreases or does not alter expression under control of the control sequence.

The interaction of a particular disclosed compound with a particular β-lactamase enzyme can be readily determined. In one embodiment, such a method involves contacting the sample with the compound, exciting at one or more wavelengths that are suitable for the cleaved compound, and determining the degree of fluorescence in the sample. A degree of fluorescence that is greater than an expected amount in the absence of beta-lactamase activity indicates that the particular beta-lactamase enzyme can cleave the particular compound. The amount of fluorescence expected can be determined using, for example, a control sample, or control values determined contemporaneously, prior to, or after a particular assay was performed. Such expected values can include a statistical analysis, such as a mean and standard deviation, to provide a chosen statistical confidence level. Both naturally occurring beta-lactamase enzymes and beta-lactamase enzymes prepared by mutagenesis can be tested with a particular disclosed compound.

Even if a particular compound is not cleaved by a particular β-lactamase, the particular compound may have value as an inhibitor of the β-lactamase enzyme. The ability of a compound to inhibit a beta-lactamase can be confirmed by comparing the amount of β-lactamase activity detected with the compound, compared to that detected with a compound that is a known to be cleaved by the β-lactamase. An amount of beta-lactamase activity less than expected indicates that the compound inhibits beta-lactamase activity. The expected level of activity can be determined using a proper control or historical values, or other methods known in the art.

Any of the above methods specifically disclosed, and other method that include the use of the disclosed compounds to detect β-lactamase activity may further include use of the methods described in U.S. Pat. No. 6,284,461 to increase the signal to noise ratio of the disclosed assays.

In addition, the disclosed compounds may be used to detect beta-lactamase activity in a wide variety of biologically important environments, such as human blood serum, the cytoplasm of cells and intracellular compartments, which can facilitate the measurement of periplasmic or secreted beta-lactamase enzyme. In addition, the presence (for example, in human serum, pus, urine, or other fluid, sample, or tissue) of bacteria resistant to beta-lactam antibiotics may be readily detected by using the disclosed compounds. Only in the presence of an active beta-lactamase enzyme is there a fluorescence spectrum that is characteristic of the cleaved compound. Such methods include contacting the environment with a disclosed compound and detecting any β-lactamase activity present by measuring the detectable optical change that occurs upon cleavage of the compound by a β-lactamase. Further, the expression of any target protein may be detected by fusing a gene encoding the target protein to a beta-lactamase gene, which can be localized by immunostaining or fluorescence or electron microscopy. For example, beta-lactamase fusion proteins can be detected in the lumen of organelles through the use of the substrates of the invention. In this instance, only subcellular compartments containing the fusion protein fluoresce at a wavelength characteristic of the cleaved substrate, whereas all others fluoresce at a wavelength characteristic of the intact molecule.

Illumination

A sample can be illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The disclosed compounds and their products and precursors may, at any time after or during an assay, be illuminated with a wavelength of light that results in a detectable optical response, and observed with a means for detecting the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device.

Sample Preparation

The end user will determine the choice of the sample and the way in which the sample is prepared. The sample includes, without limitation, any biological derived material that is thought to contain a β-lactamase. Alternatively, samples also include material in which a β-lactamase has been added.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons.

In many instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

In fluorescence experiments, the reaction is optionally quenched. Various quenching agents may be used, both physical and chemical. Conveniently, a small amount of a water-soluble solvent may be added, such as acetonitrile, DMSO, SDS, methanol, DMF, etc.

Kits

In another aspect, a kit is provided that includes one or more of the disclosed compounds. The kit also includes at least one additional component, for example, instructions for using the compound(s) in one or more methods, additional molecules (such as a β-lactamase, or a nucleic acid coding for a β-lactamase such as a vector having a β-lactamase sequence as a reporter), substances (such as a reaction buffer), or biological components (such as cells, or cell extracts). For example, cells (e.g., prokaryotic or eukaryotic cells) which contain β-lactamase activity and/or at least one β-lactamase substrate, as well as compositions and reaction mixtures which contain such cells can be included in the kits. Cells may further include receptor and signaling molecules that regulate expression of nucleic acid sequences within the cell, either sequences found on vectors, or in the nucleus or mitochondria of the cells. Cells, compositions and reaction mixtures that include at least one of the disclosed compounds are also part of the disclosure, regardless of whether or not they are part of a "kit" per se.

In some embodiments, the kit includes a solid support covalently bonded to a disclosed compound and instructions for detecting a β-lactamase in a sample with the solid support. In other embodiments, the kit includes a disclosed compound that includes a reactive group, a solid support and instructions which specify how to immobilize the compound on the solid support and how, after forming the immobilized compound, to detect a β-lactamase. Alternatively, the kit includes a solid support bearing reactive groups that can react with and immobilize a β-lactamase, and instructions that specify how to immobilize β-lactamases to the solid support and to detect such immobilized β-lactamases using one or more of the compounds of the disclosure. Methods of detecting immobilized β-lactamases are presented above.

In another aspect, the kit may include compositions for the quantitative determination of a β-lactamase in a sample. In an exemplary embodiment, the composition comprises a sample containing a known amount of a β-lactamase (such as a solution containing the known amount of β-lactamase or cells expressing known amounts of the β-lactmase) and a disclosed compound of the invention, wherein the compound reacts with a β-lactamase to produce a detectable optical response that is proportional to the amount of the β-lactamase in the sample, for example, an amount of a fluorescent product that is proportional to the amount of the β-lactmase in the sample.

β-lactamases that may be included in a kit according to the disclosure can be of any type, and include both naturally-occurring β-lactmases and non-naturally-occurring β-lactamases. β-lactamases are classified based on amino acid and nucleotide sequence (Ambler, R. P., *Phil. Trans. R. Soc. Lond.* [Ser.B.] 289: 321-331 (1980)) into classes A-D. Class A β-lactamases possess a serine in the active site and have an approximate weight of 29 kd. This class contains the plasmid-mediated TEM β-lactamases such as the RTEM enzyme of pBR322. Class B β-lactamases have an active-site zinc bound to a cysteine residue. Class C enzymes have an active site serine and a molecular weight of approximately 39 kd, but have no amino acid homology to the class A enzymes. Class D enzymes also contain an active site serine. Representative examples of each class are provided in Tables 1-4 along with the accession numbers that may be used to retrieve the sequences from the indicated databases. The sequences of the enzymes in Tables 1-4 are specifically incorporated herein by reference, and any of these β-lactamases, or nucleic acids which encode these β-lactamases, which have suitable characteristics (for example, they cleave at least one of the disclosed compounds or other fluorogenic and colorogenic compounds known in the art) for the particular application may be used in the practice of the invention.

TABLE 3

Exemplary Class A β-lactamases

| Class A β-lactamase and Source | Accession No. | Database |
|---|---|---|
| *Bacteroides fragilis* CS30 | L13472 | GenBank |
| *Bacteroides uniformis* WAL-7088 | P30898 | SWISS-PROT |
| PER-1, *P. aeruginosa* RNL-1 | P37321 | SWISS-PROT |
| *Bacteroides vulgatus* CLA341 | P30899 | SWISS-PROT |
| OHIO-1, *Enterobacter cloacae* | P18251 | SWISS-PROT |
| SHV-1, *K. pneumoniae* | P23982 | SWISS-PROT |
| LEN-1, *K. pneumoniae* LEN-1 | P05192 | SWISS-PROT |
| TEM-1, *E. coli* | P00810 | SWISS-PROT |
| *Proteus mirabilis* GN179 | P30897 | SWISS-PROT |
| PSE-4, *P. aeruginosa* Dalgleish | P16897 | SWISS-PROT |
| *Rhodopseudomonas capsulatus* SP108 | P14171 | SWISS-PROT |
| NMC, *E. cloacae* NOR-1 | P52663 | SWISS-PROT |
| Sme-1, *Serratia marcescens* S6 | P52682 | SWISS-PROT |
| OXY-2, *Klebsiella oxytoca* D488 | P23954 | SWISS-PROT |
| *K. oxytoca* E23004/SL781/SL7811 | P22391 | SWISS-PROT |
| *S. typhimurium* CAS-5 | X92507 | GenBank |
| MEN-1, *E. coli* MEN | P28585 | SWISS-PROT |
| *Serratia fonticola* CUV | P80545 | SWISS-PROT |
| *Citrobacter diversus* ULA27 | P22390 | SWISS-PROT |
| *Proteus vulgaris* 5E78-1 | P52664 | SWISS-PROT |
| *Burkholderia cepacia* 249 | U85041 | GenBank |
| *Yersinia enterocolitica* serotype O:3/Y-56 | Q01166 | SWISS-PROT |
| *M. tuberculosis* H37RV | Q10670 | SWISS-PROT |

TABLE 3-continued

Exemplary Class A β-lactamases

| Class A β-lactamase and Source | Accession No. | Database |
|---|---|---|
| S. clavuligerus NRRL 3585 | Z54190 | GenBank |
| III, Bacillus cereus 569/H | P06548 | SWISS-PROT |
| B. licheniformis 749/C | P00808 | SWISS-PROT |
| I, Bacillus mycoides NI10R | P28018 | SWISS-PROT |
| I, B. cereus 569/H/9 | P00809 | SWISS-PROT |
| I, B. cereus 5/B | P10424 | SWISS-PROT |
| B. subtilis 168/6GM | P39824 | SWISS-PROT |
| 2, Streptomyces cacaoi DSM40057 | P14560 | SWISS-PROT |
| Streptomyces badius DSM40139 | P35391 | SWISS-PROT |
| Actinomadura sp. strain R39 | X53650 | GenBank |
| Nocardia lactamdurans LC411 | Q06316 | SWISS-PROT |
| S. cacaoi KCC S0352 | Q03680 | SWISS-PROT |
| ROB-1, H. influenzae F990/LNPB51/ serotype A1 | P33949 | SWISS-PROT |
| Streptomyces fradiae DSM40063 | P35392 | SWISS-PROT |
| Streptomyces lavendulae DSM2014 | P35393 | SWISS-PROT |
| Streptomyces albus G | P14559 | SWISS-PROT |
| S. lavendulae KCCS0263 | D12693 | GenBank |
| Streptomyces aureofaciens | P10509 | SWISS-PROT |
| Streptomyces cellulosae KCCS0127 | Q06650 | SWISS-PROT |
| Mycobacterium fortuitum | L25634 | GenBank |
| S. aureus PC1/SK456/NCTC9789 | P00807 | SWISS-PROT |
| BRO-1, Moraxella catarrhalis | Z54181 | GenBank; |
| ATCC 53879 | Q59514 | SWISS-PROT |

TABLE 4

Exemplary Class B β-lactamases

| Class B β-lactamase and Source | Accession No. | Database |
|---|---|---|
| II, B. cereus 569/H | P04190 | SWISS-PROT |
| II, Bacillus sp. 170 | P10425 | SWISS-PROT |
| II, B. cereus 5/B/6 | P14488 | SWISS-PROT |
| Chryseobacterium meningosepticum CCUG4310 | X96858 | GenBank |
| IMP-1, S. marcescens AK9373/TN9106 | P52699 | SWISS-PROT |
| B. fragilis TAL3636/TAL2480 | P25910 | SWISS-PROT |
| Aeromonas hydrophila AE036 | P26918 | SWISS-PROT |
| L1, Xanthomonas maltophilia IID 1275 | P52700 | SWISS-PROT |

TABLE 5

Exemplary Class C β-lactamases

| Class C β-lactamase and Source | Accession No. | Database |
|---|---|---|
| Citrobacter freundii OS60/GN346 | P05193 | SWISS-PROT |
| E. coli K-12/MG1655 | P00811 | SWISS-PROT |
| P99, E. cloacae P99/Q908R/MHN1 | P05364 | SWISS-PROT |
| Y. enterocolitica IP97/serotype O:5B | P45460 | SWISS-PROT |
| Morganella morganii SLM01 | Y10283 | GenBank |
| A. sobria 163a | X80277 | GenBank |
| FOX-3, K. oxytoca 1731 | Y11068 | GenBank |
| K. pneumoniae NU2936 | D13304 | GenBank |
| P. aeruginosa PAO1 | P24735 | SWISS-PROT |
| S. marcescens SR50 | P18539 | SWISS-PROT |
| Psychrobacter immobilis A5 | X83586 | GenBank |

TABLE 6

Exemplary Class D β-lactamases

| Class D β-lactamase and Source | Accession No. | Database |
|---|---|---|
| OXA-18, Pseudomonas aeruginosa Mus | U85514 | GenBank |
| OXA-9, Klebsiella pneumoniae | P22070 | SWISS-PROT |
| Aeromonas sobria AER 14 | X80276 | GenBank |
| OXA-1, Escherichia coli K10-35 | P13661 | SWISS-PROT |
| OXA-7, E. coli 7181 | P35695 | SWISS-PROT |
| OXA-11, P. aeruginosa ABD | Q06778 | SWISS-PROT |
| OXA-5, P. aeruginosa 76072601 | Q00982 | SWISS-PROT |
| LCR-1, P. aeruginosa 2293E | Q00983 | SWISS-PROT |
| OXA-2, Salmonella typhimurium type 1A | P05191 | SWISS-PROT |

For additional β-lactamases and a more detailed description of substrate specificities of β-lactamases, consult Bush et al. (1995) *Antimicrob. Agents Chemother.* 39:1211-1233.

Those skilled in the art will appreciate that the polypeptides having β-lactamase activity disclosed herein may be altered by for example, mutating, deleting, and/or adding one or more amino acids and may still be used in the practice of the invention so long as the polypeptide retains detectable β-lactamase activity toward at least one disclosed compound. An example of a suitably altered polypeptide having β-lactamase activity is one from which a signal peptide sequence has been deleted and/or altered such that the polypeptide is retained in the cytosol of prokaryotic and/or eukaryotic cells. The amino acid sequence of one such polypeptide is provided in SEQ ID NO:1. In many eukaryotic cells, the signal peptide of bacterial β-lactamases is functional, which function rests in the enzyme being exported from the cells. In instances where this is desirable a functional signal peptide may be associated with the enzyme. In instances where it is desirable that the β-lactamases remain intracellular for at least a period of time, the signal peptide may be deleted or rendered otherwise non-functional.

One skilled in the art will appreciate that the sequence in SEQ ID NO:1 may be modified and still be within the scope of the disclosure. For example, the Gly-His sequence of the polypeptide in Table 3 (amino acids 2-3) can be changed to an Asp.

Any number of nucleic acid molecules (e.g., vectors) may be used to practice the disclosed methods, and thus may be part of the disclosed kits. In many instances, such nucleic acid molecules will encode a polypeptide having β-lactamase activity. In appropriate instances, nucleic acids which encode polypeptides having β-lactamase activity will be operable connected to nucleic acid segments with promoter activity (e.g., an activity associated with a regulatable promoter, such an inducible promoter or a repressible promoter, or a constitutive promoter). Thus, in particular aspects, the invention includes methods for detecting the presence of a polypeptide with β-lactamase activity. In many instances, this polypeptide will be expressed from a nucleic acid molecule which encodes a polypeptide having β-lactamase activity.

As indicated above, nucleic acids which may be used to practice the disclosed methods include vectors. Such vectors, which may be included in the disclosed kits may contain a nucleic acid sequence that encodes a polypeptide having β-lactamase activity, wherein the nucleic acid segment is located between cloning sites (e.g., is flanked by cloning sites). The nucleic acid segment which encodes a polypeptide having β-lactamase activity in such vectors may also have a cloning site on one end (e.g., a cloning site may be present on both ends or on only one end). Vectors such as these may be used for any number of purposes.

For example, such vectors may be used to clone nucleic acid sequences which are then screened for promoter activity (see, for example, U.S. Patent Application Nos. 60/482,504 filed Jun. 26, 2003, 60/487,301 filed Jul. 16, 2003, and 60/511,634 filed Oct. 17, 2003, the entire disclosures of which are incorporated herein by reference). A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g., the human actin promoter). Suitable expression vectors for use in practicing the present invention include, for example, vectors such as pSVL and pMSG (Pharmacia, Uppsala, Sweden), pRSV-cat (ATCC 37152), pSV2dhfr (ATCC 37146) and pBC12MI (ATCC 67109).

Cloning sites present in nucleic acid molecules can include multiple cloning sites (for example, a nucleic acid segment of 15 nucleotides or less which contains at least four sites which are recognized by one or more restriction endonucleases), recombination sites and topoisomerase recognition sequences. Thus, nucleic acid molecules include those which contain at least one cloning site.

A used herein, the phrase "recombination site" refers to a recognition sequence on a nucleic acid molecule that participates in an integration/recombination reaction by recombination proteins, and the disclosed kits may contain vectors having any known or later discovered recombination site. Recombination sites are discrete sections or segments of nucleic acid on the participating nucleic acid molecules that are recognized and bound by a site-specific recombination protein during the initial stages of integration or recombination. For example, the recombination site for Cre recombinase is loxP, which is a 34 base pair sequence comprised of two 13 base pair inverted repeats (serving as the recombinase binding sites) flanking an 8 base pair core sequence [see FIG. 1 of Sauer, B., *Curr. Opin. Biotech.* 5:521-527 (1994)]. Other examples of recombination sites include the attB, attP, attL, and attR sequences described in U.S. provisional patent applications 60/136,744, filed May 28, 1999, and 60/188,000, filed Mar. 9, 2000, and in co-pending U.S. patent application Ser. No. 09/517,466 all of which are specifically incorporated herein by reference—and mutants, fragments, variants and derivatives thereof, which are recognized by the recombination protein λ Int and by the auxiliary proteins integration host factor (IHF), FIS and excisionase (Xis) [see Landy, *Curr. Opin. Biotech.* 3:699-707 (1993)].

Recombination sites may be added to molecules by any number of known methods. For example, recombination sites can be added to nucleic acid molecules by blunt end ligation, PCR performed with fully or partially random primers, or inserting the nucleic acid molecules into a vector using a restriction site flanked by recombination sites.

As used herein, the term "topoisomerase recognition site" or "topoisomerase site" means a defined nucleotide sequence that is recognized and bound by a site specific topoisomerase. For example, the nucleotide sequence 5'-(C/T)CCTT-3' (SEQ ID NO:2) is a topoisomerase recognition site that is bound specifically by most poxvirus topoisomerases, including vaccinia virus DNA topoisomerase I, which then can cleave the strand after the 3'-most thymidine of the recognition site to produce a nucleotide sequence comprising 5'-(C/T)CCTT-PO$_4$-TOPO (SEQ ID NO:2), i.e., a complex of the topoisomerase covalently bound to the 3' phosphate through a tyrosine residue in the topoisomerase (see Shuman, *J. Biol. Chem.* 266:11372-11379, 1991; Sekiguchi and Shuman, *Nucl. Acids Res.* 22:5360-5365, 1994; each of which is incorporated herein by reference; see, also, U.S. Pat. No. 5,766,891; PCT/US95/16099; and PCT/US98/12372 also incorporated herein by reference). In comparison, the nucleotide sequence 5'-GCAACTT-3' (SEQ ID NO:3) is the topoisomerase recognition site for type IA *E. coli* topoisomerase III.

Recombination sites may be any nucleic acid that can serve as a substrate in a recombination reaction. Such recombination sites may be wild-type or naturally occurring recombination sites, or modified, variant, derivative, or mutant recombination sites. Examples of recombination sites for use in the invention include, but are not limited to, phage-lambda recombination sites (such as attP, attB, attL, and attR and mutants or derivatives thereof) and recombination sites from other bacteriophages such as phi80, P22, P2, 186, P4 and P1 (including lox sites such as loxP and loxP511).

Recombination proteins and mutant, modified, variant, or derivative recombination sites include those described in U.S. Pat. Nos. 5,888,732, 6,143,557, 6,171,861, 6,270,969, and 6,277,608 and in U.S. application Ser. No. 09/438,358, filed Nov. 12, 1999, which are specifically incorporated herein by reference. Mutated att sites (e.g., attB 1-10, attP 1-10, attR 1-10 and attL 1-10) are described in U.S. application Ser. Nos. 09/517,466, filed Mar. 2, 2000, and 09/732,914, filed Dec. 11, 2000 (published as US 2002/0007051-A1) the disclosures of which are specifically incorporated herein by reference in their entirety. Other suitable recombination sites and proteins are those associated with the GATEWAY® Cloning Technology systems available from Invitrogen Corporation, Carlsbad, Calif., and are described in the associated product literature, the entire disclosures of all of which are specifically incorporated herein by reference in their entireties.

Recombination sites that may be present include att sites. The 15 bp core region of the wild-type att site (GCTTTTT-TAT ACTAA (SEQ ID NO: 4)), which is identical in all wild-type att sites, may be mutated in one or more positions. Engineered att sites that specifically recombine with other engineered att sites can be constructed by altering nucleotides in and near the 7 base pair overlap region, bases 6-12, of the core region. Thus, recombination sites suitable for use in the methods, molecules, compositions, and vectors of the invention include, but are not limited to, those with insertions, deletions or substitutions of one, two, three, four, or more nucleotide bases within the 15 base pair core region (see U.S. Pat. Nos. 5,888,732 and 6,277,608, which describe the core region in further detail, and the disclosures of which are incorporated herein by reference in their entireties). Recombination sites suitable also include those with insertions, deletions or substitutions of one, two, three, four, or more nucleotide bases within the 15 base pair core region that are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

As a practical matter, whether any particular nucleic acid molecule is at least 50%, 60%, 70%, 75%, 80%, 85%, 90%, 95%, 96%, 97%, 98% or 99% identical to, for instance, a given recombination site nucleotide sequence or portion thereof can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments. Alternatively, such determinations may be accomplished using the BESTFIT program (Wisconsin Sequence Analysis Package, Genetics Computer Group, University Research Park, 575 Science Drive, Madison, Wis. 53711), which employs a local homology algorithm (Smith and Waterman, *Advances in Applied Mathematics* 2: 482-489 (1981)) to find the best segment of homology between two sequences. When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed. Computer programs such as those discussed above may also be used to determine percent identity and homology between two proteins at the amino acid level.

Analogously, the core regions in attB1, attP1, attL1 and attR1 are identical to one another, as are the core regions in attB2, attP2, attL2 and attR2. Nucleic acid molecules suitable for use with the invention also include those comprising insertions, deletions or substitutions of one, two, three, four, or more nucleotides within the seven base pair overlap region (TTTATAC (SEQ ID NO:5), bases 6-12 in the core region). The overlap region is defined by the cut sites for the integrase protein and is the region where strand exchange takes place. Examples of such mutants, fragments, variants and derivatives include, but are not limited to, nucleic acid molecules in which (1) the thymine at position 1 of the seven by overlap region has been deleted or substituted with a guanine, cytosine, or adenine; (2) the thymine at position 2 of the seven by overlap region has been deleted or substituted with a guanine, cytosine, or adenine; (3) the thymine at position 3 of the seven by overlap region has been deleted or substituted with a guanine, cytosine, or adenine; (4) the adenine at position 4 of the seven by overlap region has been deleted or substituted with a guanine, cytosine, or thymine; (5) the thymine at position 5 of the seven by overlap region has been deleted or substituted with a guanine, cytosine, or adenine; (6) the adenine at position 6 of the seven by overlap region has been deleted or substituted with a guanine, cytosine, or thymine; and (7) the cytosine at position 7 of the seven by overlap region has been deleted or substituted with a guanine, thymine, or adenine; or any combination of one or more (e.g., two, three, four, five, etc.) such deletions and/or substitutions within this seven by overlap region. The nucleotide sequences of representative seven base pair core regions are set out below.

Altered att sites have been constructed that demonstrate that (1) substitutions made within the first three positions of the seven base pair overlap (TTTATAC; SEQ ID NO:6) strongly affect the specificity of recombination, (2) substitutions made in the last four positions (TTTATAC; SEQ ID NO:6) only partially alter recombination specificity, and (3) nucleotide substitutions outside of the seven by overlap, but elsewhere within the 15 base pair core region, do not affect specificity of recombination but do influence the efficiency of recombination. Thus, nucleic acid molecules and methods of the invention include those comprising or employing one, two, three, four, five, six, eight, ten, or more recombination sites which affect recombination specificity, particularly one or more (e.g., one, two, three, four, five, six, eight, ten, twenty, thirty, forty, fifty, etc.) different recombination sites that may correspond substantially to the seven base pair overlap within the 15 base pair core region, having one or more mutations that affect recombination specificity. Such molecules may comprise a consensus sequence such as NNNATAC (SEQ ID NO:7) wherein "N" refers to any nucleotide (i.e., may be A, G, T/U or C, or an analogue or derivative thereof).

In particular embodiments, if one of the first three nucleotides in the consensus sequence is a T/U, then at least one of the other two of the first three nucleotides is not a T/U.

The core sequence of each att site (attB, attP, attL and attR) can be divided into functional units consisting of integrase binding sites, integrase cleavage sites and sequences that determine specificity. Specificity determinants are defined by the first three positions following the integrase top strand cleavage site. These three positions are shown with underlining in the following reference sequence: CAACTTTTT-TATAC AAAGTTG (SEQ ID NO:8). Modification of these three positions (64 possible combinations) can be used to generate att sites that recombine with high specificity with other att sites having the same sequence for the first three nucleotides of the seven base pair overlap region. The possible combinations of first three nucleotides of the overlap region are shown in Table 7.

TABLE 7

Modifications of the First Three Nucleotides of the att Site Seven Base Pair Overlap Region that Alter Recombination Specificity.

| AAA | CAA | GAA | TAA |
| AAC | CAC | GAC | TAC |
| AAG | CAG | GAG | TAG |
| AAT | CAT | GAT | TAT |
| ACA | CCA | GCA | TCA |
| ACC | CCC | GCC | TCC |
| ACG | CCG | GCG | TCG |
| ACT | CCT | GCT | TCT |
| AGA | CGA | GGA | TGA |
| AGC | CGC | GGC | TGC |
| AGG | CGG | GGG | TGG |
| AGT | CGT | GGT | TGT |
| ATA | CTA | GTA | TTA |
| ATC | CTC | GTC | TTC |
| ATG | CTG | GTG | TTG |
| ATT | CTT | GTT | TTT |

Representative examples of suitable seven base pair att site overlap regions of the vectors are shown in Table 8. The invention further includes nucleic acid molecules comprising one or more (e.g., one, two, three, four, five, six, eight, ten, twenty, thirty, forty, fifty, etc.) nucleotides sequences set out in Table 8. Thus, for example, in one aspect, the invention provides nucleic acid molecules comprising the nucleotide sequence GAAATAC (SEQ ID NO:9), GATATAC (SEQ ID NO:10), ACAATAC (SEQ ID NO:11), or TGCATAC (SEQ ID NO:12).

TABLE 8

Representative Examples of Seven Base Pair att Site Overlap Regions Suitable for use in the recombination sites of the Invention.

| Sequence | SEQ ID NO: |
|---|---|
| AAAATAC | 13 |
| AACATAC | 14 |
| AAGATAC | 15 |
| AATATAC | 16 |
| ACAATAC | 17 |
| ACCATAC | 18 |

TABLE 8-continued

Representative Examples of Seven Base Pair att Site Overlap Regions Suitable for use in the recombination sites of the Invention.

| Sequence | SEQ ID NO: |
|---|---|
| ACGATAC | 19 |
| ACTATAC | 20 |
| AGAATAC | 21 |
| AGCATAC | 22 |
| AGGATAC | 23 |
| AGTATAC | 24 |
| ATAATAC | 25 |
| ATCATAC | 26 |
| ATGATAC | 27 |
| ATTATAC | 28 |
| CAAATAC | 29 |
| CACATAC | 30 |
| CAGATAC | 31 |
| CATATAC | 32 |
| CCAATAC | 33 |
| CCCATAC | 34 |
| CCGATAC | 35 |
| CCTATAC | 36 |
| CGAATAC | 37 |
| CGCATAC | 38 |
| CGGATAC | 39 |
| CGTATAC | 40 |
| CTAATAC | 41 |
| CTCATAC | 42 |
| CTGATAC | 43 |
| CTTATAC | 44 |
| GAAATAC | 45 |
| GACATAC | 46 |
| GAGATAC | 47 |
| GATATAC | 48 |
| GCAATAC | 49 |
| GCCATAC | 50 |
| GCGATAC | 51 |
| GCTATAC | 52 |
| GGAATAC | 53 |
| GGCATAC | 54 |
| GGGATAC | 55 |
| GGTATAC | 56 |
| GTAATAC | 57 |
| GTCATAC | 58 |
| GTGATAC | 59 |
| GTTATAC | 60 |
| TAAATAC | 61 |
| TACATAC | 62 |
| TAGATAC | 63 |
| TATATAC | 64 |
| TCAATAC | 65 |
| TCCATAC | 66 |
| TCGATAC | 67 |
| TCTATAC | 68 |
| TGAATAC | 69 |
| TGCATAC | 70 |
| TGGATAC | 71 |
| TGTATAC | 72 |
| TTAATAC | 73 |
| TTCATAC | 74 |
| TTGATAC | 75 |
| TTTATAC | 76 |

As noted above, alterations of nucleotides located 3' to the three base pair region discussed above can also affect recombination specificity. For example, alterations within the last four positions of the seven base pair overlap can also affect recombination specificity.

For example, mutated att sites that may be included in the vectors of the kits include attB1 (AGCCTGCTTT TTTGTA-CAAA CTTGT (SEQ ID NO:77)), attP1 (TACAGGTCAC TAATACCATC TAAGTAGTTG ATTCATAGTG ACTG-GATATG TTGTGTTTTA CAGTATTATG TAGTCTGTTT TTTATGCAAA ATCTAATTTA ATATATTGAT ATT-TATATCA TTTTACGTTT CTCGTTCAGC TTTTTTGTAC AAAGTTGGCA TTATAAAAAA GCATTGCTCA TCAATTTGTT GCAACGAACA GGTCACTATC AGT-CAAAATA AAATCATTAT TTG (SEQ ID NO:78)), attL1 (CAAATAATGA TTTTATTTTG ACTGATAGTG ACCT-GTTCGT TGCAACAAAT TGATAAGCAA TGCTTTTTTA TAATGCCAAC TTTGTACAAA AAAG-CAGGCT (SEQ ID NO:79)), and attR1 (ACAAGTTTGT ACAAAAAAGC TGAACGAGAA ACGTAAAATG ATATAAATAT CAATATATTA AATTAGATTT TGCAT-AAAAA ACAGACTACA TAATACTGTA AAACACAACA TATCCAGTCA CTATG (SEQ ID NO:80)). Table 9 provides the sequences of the regions surrounding the core region for the wild type att sites (attB0, P0, R0, and L0) as well as a variety of other suitable recombination sites. Those skilled in the art will appreciated that the remainder of the site may be the same as the corresponding site (B, P, L, or R) listed above.

TABLE 9

| | Nucleotide sequences of att sites. | |
|---|---|---|
| attB0 | AGCCTGCTTT TTTATACTAA CTTGAGC | (SEQ ID NO: 81) |
| attP0 | GTTCAGCTTT TTTATACTAA GTTGGCA | (SEQ ID NO: 82) |
| attL0 | AGCCTGCTTT TTTATACTAA GTTGGCA | (SEQ ID NO: 83) |
| attR0 | GTTCAGCTTT TTTATACTAA CTTGAGC | (SEQ ID NO: 84) |
| attB1 | AGCCTGCTTT TTTGTACAAA CTTGT | (SEQ ID NO: 85) |
| attP1 | GTTCAGCTTT TTTGTACAAA GTTGGCA | (SEQ ID NO: 86) |
| attL1 | AGCCTGCTTT TTTGTACAAA GTTGGCA | (SEQ ID NO: 87) |
| attR1 | GTTCAGCTTT TTTGTACAAA CTTGT | (SEQ ID NO: 88) |
| attB2 | ACCCAGCTTT CTTGTACAAA GTGGT | (SEQ ID NO: 89) |
| attP2 | GTTCAGCTTT CTTGTACAAA GTTGGCA | (SEQ ID NO: 90) |
| attL2 | ACCCAGCTTT CTTGTACAAA GTTGGCA | (SEQ ID NO: 91) |
| attR2 | GTTCAGCTTT CTTGTACAAA GTGGT | (SEQ ID NO: 92) |
| attB5 | CAACTTTATT ATACAAAGTT GT | (SEQ ID NO: 93) |
| attP5 | GTTCAACTTT ATTATACAAA GTTGGCA | (SEQ ID NO: 94) |
| attL5 | CAACTTTATT ATACAAAGTT GGCA | (SEQ ID NO: 95) |
| attR5 | GTTCAACTTT ATTATACAAA GTTGT | (SEQ ID NO: 96) |
| attB11 | CAACTTTTCT ATACAAAGTT GT | (SEQ ID NO: 97) |
| attP11 | GTTCAACTTT TCTATACAAA GTTGGCA | (SEQ ID NO: 98) |
| attL11 | CAACTTTTCT ATACAAAGTT GGCA | (SEQ ID NO: 99) |
| attR11 | GTTCAACTTT TCTATACAAA GTTGT | (SEQ ID NO: 100) |
| attB17 | CAACTTTTGT ATACAAAGTT GT | (SEQ ID NO: 101) |
| attP17 | GTTCAACTTT TGTATACAAA GTTGGCA | (SEQ ID NO: 102) |
| attL17 | CAACTTTTGT ATACAAAGTT GGCA | (SEQ ID NO: 103) |
| attR17 | GTTCAACTTT TGTATACAAA GTTGT | (SEQ ID NO: 104) |
| attB19 | CAACTTTTTC GTACAAAGTT GT | (SEQ ID NO: 105) |
| attP19 | GTTCAACTTT TTCGTACAAA GTTGGCA | (SEQ ID NO: 106) |
| attL19 | CAACTTTTTC GTACAAAGTT GGCA | (SEQ ID NO: 107) |
| attR19 | GTTCAACTTT TTCGTACAAA GTTGT | (SEQ ID NO: 108) |
| attB20 | CAACTTTTTG GTACAAAGTT GT | (SEQ ID NO: 109) |
| attP20 | GTTCAACTTT TTGGTACAAA GTTGGCA | (SEQ ID NO: 110) |
| attL20 | CAACTTTTTG GTACAAAGTT GGCA | (SEQ ID NO: 111) |
| attR20 | GTTCAACTTT TTGGTACAAA GTTGT | (SEQ ID NO: 112) |
| attB21 | CAACTTTTTA ATACAAAGTT GT | (SEQ ID NO: 113) |
| attP21 | GTTCAACTTT TTAATACAAA GTTGGCA | (SEQ ID NO: 114) |
| attL21 | CAACTTTTTA ATACAAAGTT GGCA | (SEQ ID NO: 115) |
| attR21 | GTTCAACTTT TTAATACAAA GTTGT | (SEQ ID NO: 116) |

Other recombination sites having unique specificity (i.e., a first site will recombine with its corresponding site and will not substantially recombine with a second site having a different specificity) are known to those skilled in the art and may be included in the vectors. Corresponding recombination proteins for these systems may be used with the indicated recombination sites. Other systems providing recombination sites and recombination proteins include the FLP/FRT system from *Saccharomyces cerevisiae*, the resolvase family (e.g., yδ, TndX, TnpX, Tn3 resolvase, Hin, Hjc, Gin, SpCCE1, ParA, and Cin), and IS231 and other *Bacillus thuringiensis* transposable elements. Other suitable recombination systems include the XerC and XerD recombinases and the psi, dif and cer recombination sites in *E. coli*. Other suitable recombination sites may be found in U.S. Pat. No. 5,851,808 issued to Elledge and Liu which is specifically incorporated herein by reference.

Those skilled in the art can readily optimize the conditions for conducting the recombination reactions described herein without the use of undue experimentation, based on the guidance provided herein and available in the art (see, e.g., U.S. Pat. Nos. 5,888,732 and 6,277,608, which are specifically incorporated herein by reference in their entireties). Such guidance for performing recombination reactions with vectors of a kit may be included as part of instructions included in the kit.

In a typical recombination reaction from, about 50 ng to about 1000 ng of a second nucleic acid molecule may be contacted with a first nucleic acid molecule under suitable reaction conditions. Each nucleic acid molecule may be present in a molar ratio of from about 25:1 to about 1:25 first nucleic acid molecule:second nucleic acid molecule. In some embodiments, a first nucleic acid molecule may be present at a molar ratio of from about 10:1 to 1:10 first nucleic acid molecule:second nucleic acid molecule. In one embodiment, each nucleic acid molecule may be present at a molar ratio of about 1:1 first nucleic acid molecule:second nucleic acid molecule.

Typically, the nucleic acid molecules may be dissolved in an aqueous buffer and added to the reaction mixture. One suitable set of conditions is 4 µl CLONASE™ enzyme mixture (e.g., Invitrogen Corporation, Cat. Nos. 11791-019 and 11789-013), 4 µl 5× reaction buffer and nucleic acid and water to a final volume of 20 µl. This will typically result in the inclusion of about 200 ng of Int and about 80 ng of IHF in a 20 µl BP reaction and about 150 ng Int, about 25 ng IHF and about 30 ng Xis in a 20 µl LR reaction.

Proteins for conducting an LR reaction may be stored in a suitable buffer, for example, LR Storage Buffer, which may comprise about 50 mM Tris at about pH 7.5, about 50 mM NaCl, about 0.25 mM EDTA, about 2.5 mM Spermidine, and about 0.2 mg/ml BSA. When stored, proteins for an LR reaction may be stored at a concentration of about 37.5 ng/l INT, 10 ng/l IHF and 15 ng/l XIS. Proteins for conducting a BP reaction may be stored in a suitable buffer, for example, BP Storage Buffer, which may comprise about 25 mM Tris at about pH 7.5, about 22 mM NaCl, about 5 mM EDTA, about 5 mM Spermidine, about 1 mg/ml BSA, and about 0.0025% Triton X-100. When stored, proteins for an BP reaction may be stored at a concentration of about 37.5 ng/l INT and 20 ng/l IHF. One skilled in the art will recognize that enzymatic activity may vary in different preparations of enzymes. The amounts suggested above may be modified to adjust for the amount of activity in any specific preparation of enzymes.

A suitable 5× reaction buffer for conducting recombination reactions may comprise 100 mM Tris pH 7.5, 88 mM NaCl, 20 mM EDTA, 20 mM Spermidine, and 4 mg/ml BSA. Thus, in a recombination reaction, the final buffer concentrations may be 20 mM Tris pH 7.5, 17.6 mM NaCl, 4 mM EDTA, 4 mM Spermidine, and 0.8 mg/ml BSA. Those skilled in the art will appreciate that the final reaction mixture may incorporate additional components added with the reagents used to prepare the mixture, for example, a BP reaction may include 0.005% Triton X-100 incorporated from the BP CLONASE™.

In some embodiments, particularly those in which attL sites are to be recombined with attR sites, the final reaction mixture may include about 50 mM Tris HCl, pH 7.5, about 1 mM EDTA, about 1 mg/ml BSA, about 75 mM NaCl and about 7.5 mM spermidine in addition to recombination enzymes and the nucleic acids to be combined. In other embodiments, particularly those in which an attB site is to be recombined with an attP site, the final reaction mixture may include about 25 mM Tris HCl, pH 7.5, about 5 mM EDTA, about 1 mg/ml bovine serum albumin (BSA), about 22 mM NaCl, and about 5 mM spermidine.

In some embodiments, particularly those in which attL sites are to be recombined with attR sites, the final reaction mixture may include about 40 mM Tris HCl, pH 7.5, about 1 mM EDTA, about 1 mg/ml BSA, about 64 mM NaCl and about 8 mM spermidine in addition to recombination enzymes and the nucleic acids to be combined. One of skill in the art will appreciate that the reaction conditions may be varied somewhat without departing from the invention. For example, the pH of the reaction may be varied from about 7.0 to about 8.0; the concentration of buffer may be varied from about 25 mM to about 100 mM; the concentration of EDTA may be varied from about 0.5 mM to about 2 mM; the concentration of NaCl may be varied from about 25 mM to about 150 mM; and the concentration of BSA may be varied from 0.5 mg/ml to about 5 mg/ml. In other embodiments, particularly those in which an attB site is to be recombined with an attP site, the final reaction mixture may include about 25 mM Tris HCl, pH 7.5, about 5 mM EDTA, about 1 mg/ml bovine serum albumin (BSA), about 22 mM NaCl, about 5 mM spermidine and about 0.005% detergent (e.g., Triton X-100).

One or more topoisomerases may be used to generate a recombinant nucleic acid molecule comprising two or more nucleotide sequences, any one or more of which may comprise, for example, all or a portion of a nucleic acid sequence encoding a polypeptide having a detectable activity such as β-lactamase activity. Topoisomerases may be used in combination with recombinational cloning techniques described above. For example, a topoisomerase-mediated reaction may be used to attach one or more recombination sites to one or more nucleic acid segments. The segments may then be further manipulated and combined using, for example, recombinational cloning techniques.

A method for generating a double stranded recombinant nucleic acid molecule covalently linked in one strand can be performed by contacting a first nucleic acid molecule which has a site-specific topoisomerase recognition site (e.g., a type IA or a type II topoisomerase recognition site), or a cleavage product thereof, at a 5' or 3' terminus, with a second (or other) nucleic acid molecule, and optionally, a topoisomerase (e.g., a type IA, type IB, and/or type II topoisomerase), such that the second nucleotide sequence can be covalently attached to the first nucleotide sequence.

Generation of a double stranded recombinant nucleic acid molecule covalently linked in both strands can be performed, for example, by contacting a first nucleic acid molecule having a first end and a second end, wherein, at the first end or second end or both ends, the first nucleic acid molecule has a topoisomerase recognition site (or cleavage product thereof)

at or near the 5' or 3' terminus; at least a second nucleic acid molecule having a first end and a second end, wherein, at the first end or second end or both ends, the at least second double stranded nucleotide sequence has a topoisomerase recognition site (or cleavage product thereof) at or near a 5' or 3' terminus; and at least one site specific topoisomerase (e.g., a type IA and/or a type IB topoisomerase), under conditions such that all components are in contact and the topoisomerase can effect its activity. In one embodiment, the method is performed by contacting a first nucleic acid molecule and a second (or other) nucleic acid molecule, each of which has a topoisomerase recognition site in addition to viral sequences an/or sequences of interest, or a cleavage product thereof, at the 3' termini or at the 5' termini of two ends to be covalently linked. In another embodiment, the method is performed by contacting a first nucleic acid molecule having a topoisomerase recognition site, or cleavage product thereof, at the 5' terminus and the 3' terminus of at least one end, and a second (or other) nucleic acid molecule having a 3' hydroxyl group and a 5' hydroxyl group at the end to be linked to the end of the first nucleic acid molecule containing the recognition sites.

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a nucleic acid molecule. Cleavage of a nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a nucleic acid molecule by type IB topoisomerases generates a 3' phosphate and a 5' hydroxyl at the cleavage site, with the type IB topoisomerase covalently binding to the 3' terminus of a cleaved strand. As disclosed herein, type I and type II topoisomerases, as well as catalytic domains and mutant forms thereof, are useful for generating double stranded recombinant nucleic acid molecules covalently linked in both strands.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase III, human topoisomerase III, *Streptococcus pneumoniae* topoisomerase III, and the like, including other type IA topoisomerases (see Berger, *Biochim. Biophys. Acta* 1400: 3-18, 1998; DiGate and Marians, *J. Biol. Chem.* 264:17924-17930, 1989; Kim and Wang, *J. Biol. Chem.* 267:17178-17185, 1992; Wilson, et al., *J. Biol. Chem.* 275:1533-1540, 2000; Hanai, et al., *Proc. Natl. Acad. Sci., USA* 93:3653-3657, 1996, U.S. Pat. No. 6,277,620, each of which is incorporated herein by reference). *E. coli* topoisomerase III, which is a type IA topoisomerase that recognizes, binds to and cleaves the sequence 5'-GCAACTT-3', can be particularly useful (Zhang, et al., *J. Biol. Chem.* 270:23700-23705, 1995, which is incorporated herein by reference). A homolog, the traE protein of plasmid RP4, has been described by Li, et al., *J. Biol. Chem.* 272:19582-19587 (1997) and can also be used. A DNA-protein adduct is formed with the enzyme covalently binding to the 5'-thymidine residue, with cleavage occurring between the two thymidine residues.

Type IB topoisomerases include the nuclear type I topoisomerases present in all eukaryotic cells and those encoded by vaccinia and other cellular poxviruses (see Cheng, et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 298,:271-297, 1994; Gupta, et al., *Biochim. Biophys. Acta* 1262:1-14, 1995, each of which is incorporated herein by reference; see, also, Berger, supra, 1998). Viral type IB topoisomerases are exemplified by those produced by the vertebrate poxviruses (vaccinia, Shope fibroma virus, ORF virus, fowlpox virus, and molluscum contagiosum virus), and the insect poxvirus (*Amsacta moorei* entomopoxvirus) (see Shuman, *Biochim. Biophys. Acta* 1400:321-337, 1998; Petersen, et al., *Virology* 230:197-206, 1997; Shuman and Prescott, *Proc. Natl. Acad. Sci., USA* 84:7478-7482, 1987; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng, et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833-840, 1992; Wang, *J. Biol. Chem.* 266:6659-6662, 1991, each of which is incorporated herein by reference; Berger, supra, 1998;). Like the type IB topoisomerases, the type II topoisomerases have both cleaving and ligating activities. In addition, like type IB topoisomerase, substrate nucleic acid molecules can be prepared such that the type II topoisomerase can form a covalent linkage to one strand at a cleavage site. For example, calf thymus type II topoisomerase can cleave a substrate nucleic acid molecule containing a 5' recessed topoisomerase recognition site positioned three nucleotides from the 5' end, resulting in dissociation of the three nucleotide sequence 5' to the cleavage site and covalent binding the of the topoisomerase to the 5' terminus of the nucleic acid molecule (Andersen, et al., supra, 1991). Furthermore, upon contacting such a type II topoisomerase charged nucleic acid molecule with a second nucleotide sequence containing a 3' hydroxyl group, the type II topoisomerase can ligate the sequences together, and then is released from the recombinant nucleic acid molecule. As such, type II topoisomerases also are useful.

The various topoisomerases exhibit a range of sequence specificity, and any may be included in the disclosed kits, for example, as components of the expression system. For example, type II topoisomerases can bind to a variety of sequences, but cleave at a highly specific recognition site (see Andersen, et al., *J. Biol. Chem.* 266:9203-9210, 1991, which is incorporated herein by reference.). In comparison, the type IB topoisomerases include site specific topoisomerases, which bind to and cleave a specific nucleotide sequence ("topoisomerase recognition site"). Upon cleavage of a nucleic acid molecule by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end.

In particular embodiments, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type IB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5' overhang" or "5' overhanging sequence" is used herein to refer to a strand of a nucleic acid molecule that extends in a 5' direction beyond the terminus of the complementary strand of the nucleic acid molecule. Conveniently, a 5' overhang can be produced as a result of site specific cleavage of a nucleic acid molecule by a type IB topoisomerase.

In particular embodiments, the 3' termini of the ends of the nucleotide sequences to be linked by a type IA topoisomerase contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3' overhang" or "3' overhanging sequence" is used herein to refer to a strand of a nucleic acid molecule that extends in a 3' direction beyond the terminus of the complementary strand of the nucleic acid molecule. Conveniently, a 3' overhang can be produced upon cleavage by a type IA or type II topoisomerase.

The 3' or 5' overhanging sequences can have any sequence, though generally the sequences are selected such that they allow ligation of a predetermined end of one nucleic acid molecule to a predetermined end of a second nucleotide sequence according to a method of the invention. As such, while the 3' or 5' overhangs can be palindromic, they generally are not because nucleic acid molecules having palindromic overhangs can associate with each other, thus reducing the yield of a ds recombinant nucleic acid molecule covalently linked in both strands comprising two or more nucleic acid molecules in a predetermined orientation.

Any number of methods may be used to add topoisomerase cleavage sites to nucleic acid molecules and/or generate nucleic acid molecules to which topoisomerase is covalently bound. Examples of such methods are provided in U.S. Patent Publication No. 2003-0186233, the entire disclosure of which is incorporated herein by reference.

Mutant tRNA molecules that recognize what are ordinarily stop codons suppress the termination of translation of an mRNA molecule and are termed suppressor tRNAs, and also may be included in the disclosed kits. Three codons are used by both eukaryotes and prokaryotes to signal the end of gene. When transcribed into mRNA, the codons have the following sequences: UAG (amber), UGA (opal) and UAA (ochre). Under most circumstances, the cell does not contain any tRNA molecules that recognize these codons. Thus, when a ribosome translating an mRNA reaches one of these codons, the ribosome stalls and falls of the RNA, terminating translation of the mRNA. The release of the ribosome from the mRNA is mediated by specific factors (see S. Mottagui-Tabar, *Nucleic Acids Research* 26(11), 2789, 1998). A gene with an in-frame stop codon (TAA, TAG, or TGA) will ordinarily encode a protein with a native carboxy terminus. However, suppressor tRNAs can result in the insertion of amino acids and continuation of translation past stop codons.

A number of such suppressor tRNAs have been found. Examples include, but are not limited to, the supE, supP, supD, supF and supZ suppressors, which suppress the termination of translation of the amber stop codon, supB, gIT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. For a more detailed discussion of suppressor tRNAs, the reader may consult Eggertsson, et al., (1988) *Microbiological Review* 52(3):354-374, and Engleerg-Kukla, et al. (1996) in *Escherichia coli and Salmonella Cellular and Molecular Biology*, Chapter 60, pps 909-921, Neidhardt, et al. eds., ASM Press, Washington, D.C.

Mutations that enhance the efficiency of termination suppressors, i.e., increase the read through of the stop codon, have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Under ordinary circumstances, host cells would not be expected to be healthy if suppression of stop codons is too efficient. This is because of the thousands or tens of thousands of genes in a genome, a significant fraction will naturally have one of the three stop codons; complete read-through of these would result in a large number of aberrant proteins containing additional amino acids at their carboxy termini. If some level of suppressing tRNA is present, there is a race between the incorporation of the amino acid and the release of the ribosome. Higher levels of tRNA may lead to more read-through although other factors, such as the codon context, can influence the efficiency of suppression.

Organisms ordinarily have multiple genes for tRNAs. Combined with the redundancy of the genetic code (multiple codons for many of the amino acids), mutation of one tRNA gene to a suppressor tRNA status does not lead to high levels of suppression. The TAA stop codon is the strongest, and most difficult to suppress. The TGA is the weakest, and naturally (in *E. coli*) leaks to the extent of 3%. The TAG (amber) codon is relatively tight, with a read-through of ~1% without suppression. In addition, the amber codon can be suppressed with efficiencies on the order of 50% with naturally occurring suppressor mutants. Suppression in some organisms (e.g., *E. coli*) may be enhanced when the nucleotide following the stop codon is an adenosine. Thus, the present invention contemplates nucleic acid molecules having a stop codon followed by an adenosine (e.g., having the sequence TAGA, TAAA, and/or TGAA).

Cells which may used in the disclosed methods and may be included as a component of the disclosed kits include both prokaryotic and eukaryotic cells. Particular examples of cells, specifically mammalian cells include baby hamster kidney (BHK) cells (ATCC No. CCL10), mouse L cells (ATCC No. CCL1.3), Jurkats (ATCC No. TIB 152) and 153 DG44 cells (see, Chasin (1986) Cell. Molec. Genet. 12: 555) human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21) and COS-7 cells (ATCC No. CRL1651). Additional examples of mammalian host cells that could be used include, human Hela 293, and H9 cells, mouse NIH3T3 and C127 cells, Cos 1, Cos 7 and CV1, and quail QC1-3 cells.

Such cells can, for example, further include nucleic acid sequences that code for heterologous cell surface proteins and thus, are desirably readily and efficiently transfected with appropriate vectors. Particularly useful cells include Jurkat cells and HEK 293 cells, such as those described in U.S. Pat. No. 5,024,939 and by Stillman et al. (1985) Mol. Cell. Biol. 5: 2051-2060.

Exemplary proteins that may be expressed by cells include, but are not limited to, surface receptors and ion channels. Surface receptors include, but are not limited to, muscarinic receptors [for example, human M2 (GenBank accession #M16404), rat M3 (GenBank accession #M16407), human M4 (GenBank accession #M16405), and human M5 (Bonner, et al., 1988 Neuron 1, pp. 403-410)] and the like, neuronal nicotinic acetylcholine receptors, GABA receptors, glutamate receptors, adrenergic receptors, dopamine receptors, NGF receptors, and serotonin receptors. Ion channels include, calcium channels, potassium ion channels, sodium ion channels, chloride ion channels. Intracellular receptors may also be included in the cells, such as estrogen receptors, glucocorticoid receptors, androgen receptors, progesterone receptors, and mineralocorticoid receptor. In addition, transcription factors and kinases can also be present in the cells. In particular embodiments, the influence of compounds, such as toxins, on the receptors and other components of the cells are determined by their effect on expression of nucleic acid sequences under their control, which nucleic acid sequences also code for a peptide having β-lactamase activity.

A detailed description of the invention having been provided above, the following examples are given for the purpose of illustrating the invention and shall not be construed as being a limitation on the scope of the invention or claims.

EXAMPLES

The materials and methods of the present invention are further illustrated by the examples which follow. These examples are offered to illustrate, but not to limit, the claimed invention.

Example 1

7-phenoxyacetamidocephalosporanic acid (1)

Phenoxyacetic acid (0.50 g, 3.3 mmol) was dissolved in 5 mL of methylene chloride and the solution was cooled in an ice/water bath. $(COCl)_2$ was added to the solution followed by 3 drops of DMF. The reaction mixture was stirred for 20 min in the bath before the solvent was removed in vacuo. The residue was dissolved in toluene, which was removed in vacuo. The residue was then dissolved in 5 mL of dioxane and added dropwise to a stirred and ice/water bath-cooled mixture of 7-aminocephalosporanic acid (0.60 g, 2.2 mmol), 1 M $Et_3NH_2CO_3$ buffer (13.5 mL, 13.5 mmol) and dioxane (5 mL). After the reaction mixture was stirred overnight at rt, the solvent was removed in vacuo. The residue was dissolved in water, which was removed in vacuo. The residue was dissolved in chloroform and loaded onto a silica gel column. The resulting solution was eluted using chloroform:methanol: acetic acid (6:2:0.1). The product-containing fractions were concentrated. The residue was dissolved in toluene, which was removed in vacuo. The residue was dissolved in 50 mL of 10% HCl and extracted with ethyl acetate (3×30 mL). The combined extracts were washed with water (2×20 mL), brine (20 mL), and dried over sodium sulfate. After filtering, the solvent was removed in vacuo to yield 1 (0.676 g, 76%).

Example 2

Preparation of b: Compounds 2-3 a) Allyl 7β-(phenoxy)acetamido-3-(acetoxymethyl)-3-cephem-4-carboxylate (2)

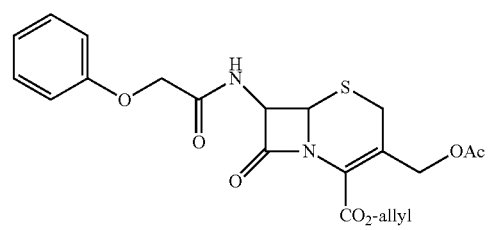

7-Phenoxyacetamidocephalosporanic acid 1 (0.676 g, 1.66 mmol) was dissolved in 20 mL of $CH_3CN$. i-$Pr_2NEt$ (0.38 mL, 2.2 mmol) and allyl bromide (0.16 mL, 1.8 mmol) were added to the reaction mixture, which was then stirred for 72 h at rt. The solvent was removed in vacuo, dissolved in 30 mL of 5% HCl, and extracted with ethyl acetate (3×30 mL). The combined extracts were washed with water (30 mL), brine (30 mL), and dried over sodium sulfate. After filtering, the solvent was removed in vacuo. The residue was dissolved in chloroform and loaded onto a silica gel column, which was eluted using chloroform:ethyl acetate (5:1). The eluate containing the desired product was then evaporated to yield 2 (0.334 g, 45%).

b) Allyl 7β-((2-thien-2-yl)acetamido)-3-(acetoxymethyl)-3-cephem-4-carboxylate (3)

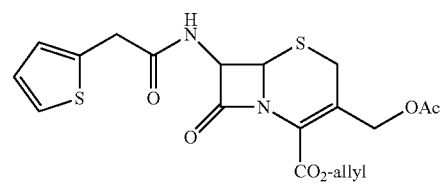

Compound 3 was prepared from cephalothin sodium salt (Sigma) according to the literature procedure of Jungheim et al., *J. Org. Chem.*, 57: 2334-2340 (1992).

Example 3

Preparation of c: Compounds 4-5 a) Allyl 7β-(phenoxy)acetamido)-3-(iodomethyl)-3-cephem-4-carboxylate (4)

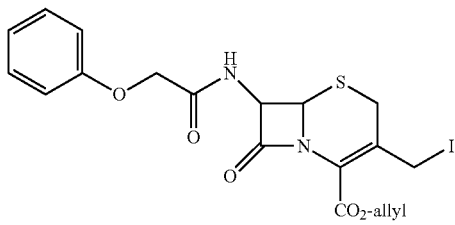

Compound 2 (0.288 g, 0.646 mmol) was dissolved in 5 mL of dry methylene chloride and the solution was cooled in an ice/water bath. Me₃SiI (0.20 mL, 1.4 mmol) was added to the cooled solution. The reaction mixture was stirred for 20 min in the cooled bath, then stirred for 40 min at rt and diluted with ethyl acetate (80 mL). The solution was washed with 10% sodium thiosulfate (2×30 mL), sat. sodium bicarbonate (2×30 mL), brine (30 mL), and dried over sodium sulfate. After filtering, the solvent was removed in vacuo to yield 4 (0.248 g, 75%).

b) Allyl 7β-((2-thien-2-yl)acetamido)-3-(iodomethyl)-3-cephem-4-carboxylate (5)

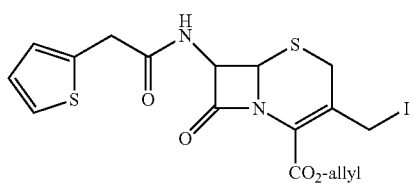

Compound 5 was prepared from 3 according to the literature procedure of Jungheim et al., *J. Org. Chem.*, 57: 2334-2340 (1992).

Example 4

Preparation of f: Compounds 6-8 a) Fluorescein 3-O-butyl ether, n-butyl ester (6)

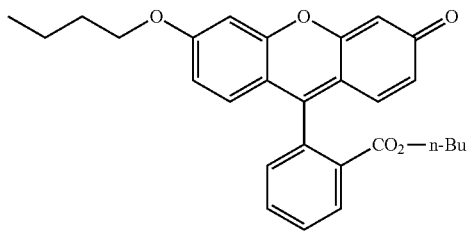

Fluorescein (2.0 g, 6.0 mmol) was dissolved in 50 mL of DMF. Powdered K₂CO₃ (2.0 g, 14 mmol) and bromobutane (6.4 mL, 60 mmol) were added to the solution and the mixture was stirred at 80° C. for 3 h. The solids were filtered off and washed with ethyl acetate. The ethyl acetate washings were then combined with the DMF solution and diluted with 150 mL of 10% HCl. An extraction was performed using ethyl acetate (3×40 mL). The combined ethyl acetate extracts were then washed with water (3×40 mL), brine (40 mL), and dried over sodium sulfate. After filtering, the solvent was removed in vacuo to yield 6 (2.23 g, 84%).

b) Fluorescein 3-O-butyl ether (7)

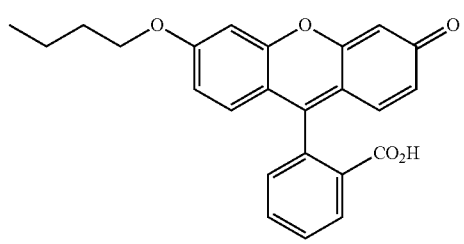

Compound 6 (2.23 g, 5.02 mmol) was dissolved in 100 mL of dioxane. 1 M aqueous KOH (30 mL, 30 mmol) was added and the mixture was stirred at rt for 6 h. The solution was diluted with 10% HCl (300 mL) and the product was extracted with ethyl acetate (4×80 mL). The combined extracts were washed with water (3×60 mL), brine (60 mL), and dried over sodium sulfate. After filtering, the solvent was removed in vacuo. The crude product was dissolved in chloroform and purified by silica gel column chromatography using chloroform:ethyl acetate (5:1) as an eluent. Evaporation of eluate provided 7 as an orange powder (1.0 g, 51%).

c) Fluorescein 3-O-acetic acid ether (8)

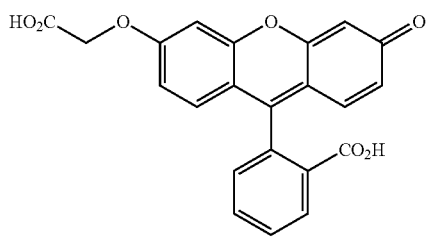

Fluorescein (3.00 g, 9.03 mmol) was dissolved in 30 mL of DMF. Powdered potassium carbonate (1.26 g, 9.13 mmol) and KI (0.30 g, 1.8 mmol) were added to the solution followed by the addition of allyl bromoacetate (1.05 mL, 9.04 mmol). The reaction mixture was stirred for 20 h at rt and then diluted with 10% HCl (50 mL). The reaction mixture was then extracted with ethyl acetate (3×30 mL). The combined ethyl acetate extracts were then washed with water (3×30 mL), brine (30 mL), and dried over sodium sulfate. After filtering, the solvent was removed in vacuo. The residue was dissolved in chloroform and loaded onto a silica gel column, which was eluted using chloroform:ethyl acetate (2:1). Evaporation of the eluate yielded 8 as an orange powder (0.64 g, 16%).

Example 5

Preparation of d and/or e: Compounds 9-22 a) Allyl 7β-(phenoxyacetamido)-3-(((2-(3H-quinazoline-4-one-2-yl)-phenyl)oxy)methyl)-3-cephem-4-carboxylate (9)

Allyl 7β-(phenoxyacetamido)-3-(((2-(3H-quinazoline-4-one-2-yl)-phenyl)oxy)methyl)-2-cephem-4-carboxylate (10)

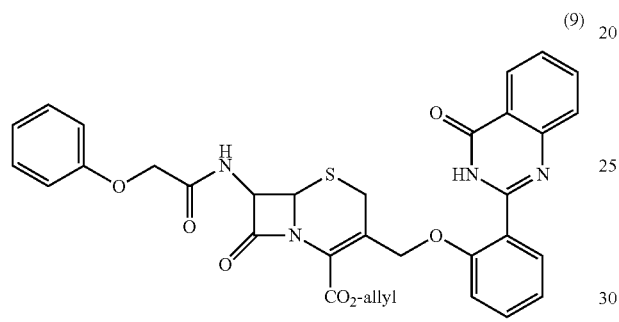

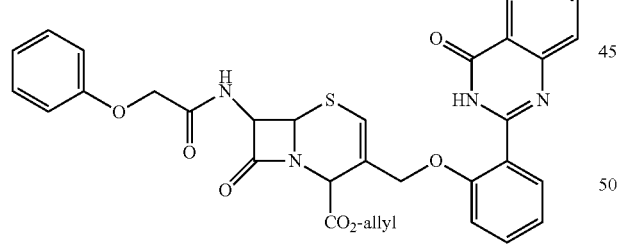

2-(2-Hydroxy-phenyl)-3H-quinazolin-4-one (0.150 g, 0.630 mmol) was suspended in 5 mL of DMF. Sodium methoxide in MeOH (25% solution, 0.11 mL, 0.48 mmol) was then added to the suspension. The suspension soon became clear and was then cooled using an ice/water bath. Compound 4 (0.248 g, 0.482 mmol) was dissolved in 3 mL of DMF and added dropwise to the oxoquinazolinone solution with stirring. The reaction mixture was stirred for 1.5 h at the bath temperature and then diluted with 10% HCl (50 mL). The reaction mixture was then extracted with ethyl acetate (30+ 3×20 mL). The combined ethyl acetate extracts were then washed with water (4×20 mL), brine (20 mL), and dried over sodium sulfate. After filtering, the solvent was removed in vacuo. The residue was suspended in chloroform and loaded onto a silica gel column, which was eluted using chloroform: ethyl acetate (5:1). Evaporation of the eluate yielded two separable isomers, 9 and 10 (0.075 g, 25%).

b) Allyl 7β-(2-(thien-2-yhacetamido)-3-(((2-(-3H-quinazoline-4-one-2-yl)-(phenyl)oxy)methyl)-3-cephem-4-carboxylate (11)

Allyl 7β-(2-(thien-2-yl)acetamido)-3-(((2-(-3H-quinazoline-4-one-2-yl)-(phenyl)oxy)methyl)-2-cephem-4-carboxylate (12)

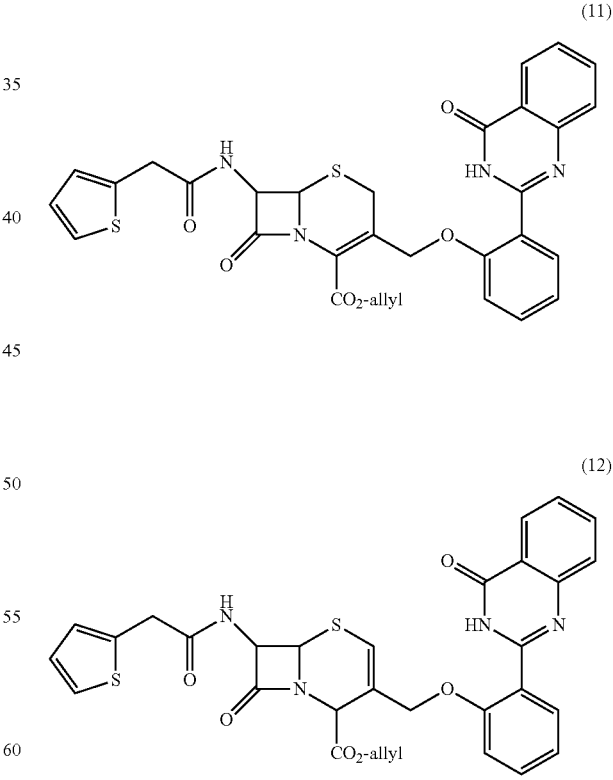

2-(2-Hydroxy-phenyl)-3H-quinazolin-4-one (2.64 g, 5.24 mmol) was suspended in 30 mL of DMF. Sodium methoxide in MeOH (25% solution, 0.12 mL, 0.525 mmol) was then added to the suspension. The suspension soon became clear and was then cooled using an ice/water bath. 5 (1.62 g, 6.81 mmol) was dissolved in 15 mL of DMF and added to the oxoquinazoline solution dropwise with stirring. The reaction mixture was stirred for 1.5 h at the bath temperature and then diluted with 10% HCl (150 mL). The reaction mixture was then extracted with ethyl acetate (4×40 mL). The combined ethyl acetate extracts were then washed with water (4×40 mL), brine (40 mL), and dried over sodium sulfate. After filtering, the solvent was removed in vacuo. The residue was suspended in chloroform and loaded onto a silica gel column. Less polar impurities were eluted with chloroform:ethyl acetate (10:1). The desired product was eluted with chloroform:ethyl acetate (5:1). Evaporation of the eluate yielded two separable isomers, 11 and 12 (1.54 g, 48%).

c) Allyl 7β-(2-(thien-2-yl)acetamido)-3-(((2-((6-chloro)-3H-quinazoline-4-one-2-yl)-(4-chlorophenyl)oxy)methyl)-3-cephem-4-carboxylate (13)

Allyl 7β-(2-(thien-2-yl)acetamido)-3-((2-((6-chloro)-3H-quinazoline-4-one-2-yl)-(4-chlorophenyloxy)methyl)-2-cephem-4-crboxylate (14)

3H-quinazolin-4-one (0.299 g, 0.973 mmol) was suspended in 5 mL of DMF. Sodium methoxide in MeOH (25% solution, 0.148 mL, 0.647 mmol) was then added to the suspension, which was stirred for 30 min. Compound 5 (0.327 g, 0.649 mmol) was dissolved in 4 mL of DMF and added to the above suspension. The reaction mixture was stirred for 2 h at rt, then diluted with 5% HCl (50 mL). The reaction mixture was then extracted with ethyl acetate (3×30 mL). The combined ethyl acetate extracts were then washed with brine (30 mL), and dried over sodium sulfate. After filtering, the solvent was removed in vacuo. The residue was mixed with chloroform (~20 mL) and loaded onto a silica gel column. Less polar impurities were eluted with chloroform:ethyl acetate (10:1). The desired product was eluted with chloroform:ethyl acetate (5:1). Evaporation of the eluate yielded two separable isomers, 13 and 14 (0.138 g, 31%).

d) Allyl 7β-(2-(thien-2-yl)acetamido)-3-((9H-(1,3-dichloro-9,9-dimethylacridin-2-one)-7-oxy)methyl)-3-cephem-4-carboxylate (15)

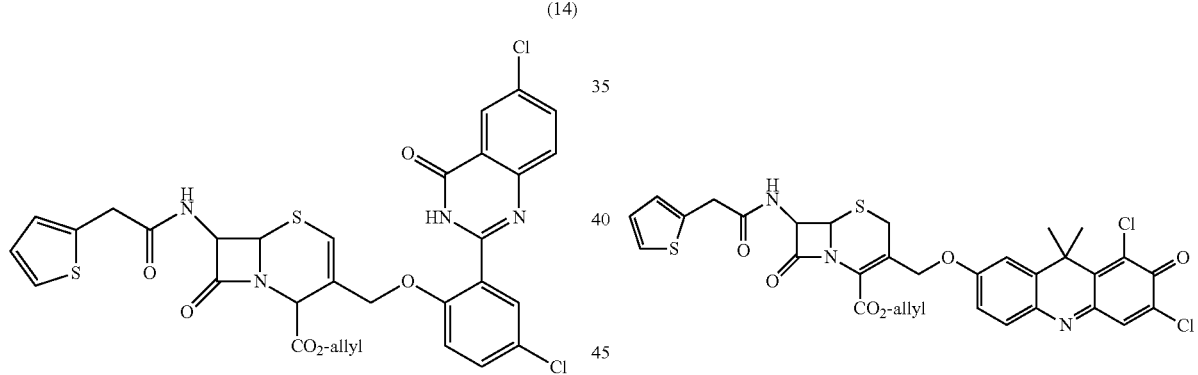

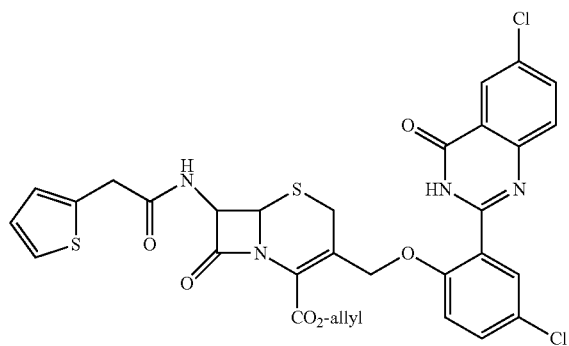

7-Hydroxy-9H-(1,3-dichloro-9,9-dimethylacridin-2-one) (0.361 g, 1.17 mmol) was suspended in 90 mL of acetone. Powdered $K_2CO_3$ (0.16 g, 1.16 mmol) was added to the suspension followed by addition of 5 (0.591 g, 1.17 mmol). The reaction mixture was stirred at rt for 4 h and concentrated in vacuo. The residue was mixed with 50 mL of 5% HCl and the solution was extracted with ethyl acetate (3×30 mL). The combined ethyl acetate extracts were washed with water (30 mL), brine (30 mL), and dried over sodium sulfate. After filtering, the solvent was removed in vacuo. The residue was suspended in chloroform and loaded onto a silica gel column, which was eluted using hexanes:ethyl acetate (4:3). Evaporation of the eluate yielded 15 as a brown wax (0.173 g, 22%).

e) Allyl 7β-(2-(thien-2-yl)acetamido)-3-(((4-methy-lumbelliferyl)-7-oxy)methyl)-3-cephem-4-carboxylate (16)

f) Allyl 7β-(2-(thien-2-yl)acetamido)-3-(((((6,8-difluoro)-4-methylumbelliferyl)-7-oxy)methyl)-3-cephem-4-carboxylate (17)

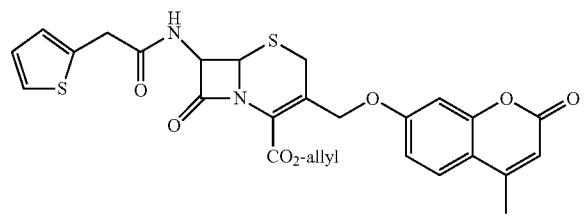

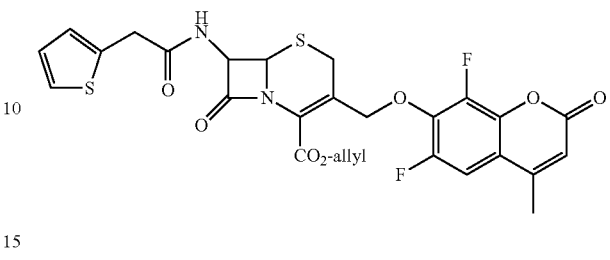

7-Hydroxy-4-methylcoumarin (0.212 g, 1.20 mmol) was dissolved in 3 mL of DMF. Sodium methoxide (25% solution in methanol, 0.206 mL, 0.901 mmol) was added to the solution and the mixture was cooled down using ice/water bath. 5 (0.303 g, 0.601 mmol) was added to the mixture as a solution in 3 mL of DMF. The reaction mixture was stirred at bath temperature for 1 h, and then diluted with 5% HCl (60 mL). The reaction mixture was then extracted with ethyl acetate (3×25 mL). The combined ethyl acetate extracts were washed with water (3×15 mL), brine (20 mL), and dried over sodium sulfate. After filtering, the solvent was removed in vacuo. The residue was dissolved in chloroform and loaded onto a silica gel column. Less polar impurities were eluted with hexanes:ethyl acetate (1:1). The desired product was eluted using hexanes:ethyl acetate (4:5). Evaporation of the eluate yielded 16 as a viscous oil (0.05 g, 15%).

6,8-Difluoro-7-hydroxy-4-methylcoumarin (0.209 g, 0.986 mmol) was dissolved in 3 mL of DMF and the solution was cooled in an ice/water bath. Sodium methoxide (25% in MeOH, 0.15 mL, 0.66 mmol) was added to the solution followed by addition of 5 (0.332 g, 0.659 mmol) dissolved in 3 mL of DMF. The reaction mixture was stirred for 1.5 h at bath temperature, and then diluted with 5% HCl (80 mL). The reaction mixture was then extracted with ethyl acetate (3×30 mL). The combined ethyl acetate extracts were washed with water (40 mL), brine (20 mL), and dried over sodium sulfate. After filtering, the solvent was removed in vacuo. The residue was dissolved in chloroform and loaded onto a silica gel column, which was eluted with chloroform:ethyl acetate (5:1). Evaporation of the eluate yielded 17 as a white powder (0.22 g, 57%).

g) Preparation of (18) and (19)

(18)

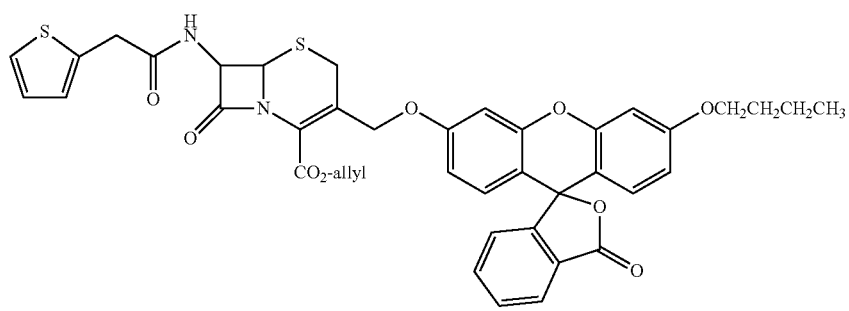

(19)

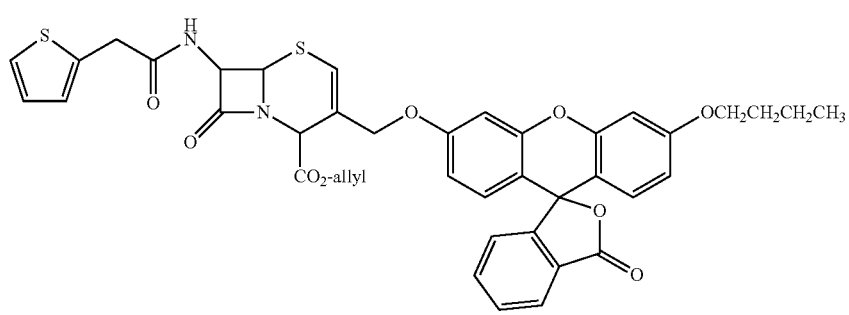

Compound 5 (0.33 g, 0.65 mmol) was dissolved in 10 mL of acetone. Butyl-fluorescein (0.25 g, 0.64 mmol) was added to the solution followed by addition of powdered potassium carbonate (0.09 g, 0.6 mmol). The mixture was stirred at rt for 2.5 h and diluted with 10% HCl (50 mL). The reaction mixture was then extracted with ethyl acetate (2×40 mL). The combined ethyl acetate extracts were washed with water (30 mL), brine (30 mL), and dried over sodium sulfate. After filtering, the solvent was removed in vacuo. The residue was dissolved in chloroform and loaded onto a silica gel column, which was eluted with chloroform:ethyl acetate (10:1). Evaporation of the eluate yielded two separable isomers, 18 and 19, as an orange powder (0.075 g, 15%).

h) Preparation of (20) and (21)

Compound 5 (0.744 g, 1.48 mmol) and O-alkylated fluorescein (0.423 g, 0.984 mmol) were dissolved in 15 mL of acetone. Powdered potassium carbonate (0.204 g, 1.48 mmol) was added to the solution and reaction mixture was stirred overnight at rt. The mixture was concentrated in vacuo, and the residue was mixed with 100 mL of ethyl acetate. An extraction was then performed with 1 M KOH solution (2×20 mL). The combined ethyl acetate extracts were washed with water (30 mL), brine (30 mL), and dried over sodium sulfate. After filtering, the solvent was removed in vacuo. The residue was dissolved in chloroform and loaded onto a silica gel column. Less polar impurities were eluted with chloroform:ethyl acetate (10:1). The desired product was eluted using chloroform:ethyl acetate (5:1). Evaporation of the eluate yielded two separable isomers, 20 and 21, as a yellow glass (0.231 g, 19%).

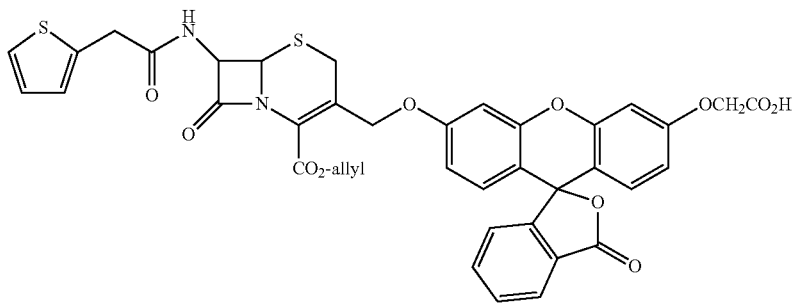

(20)

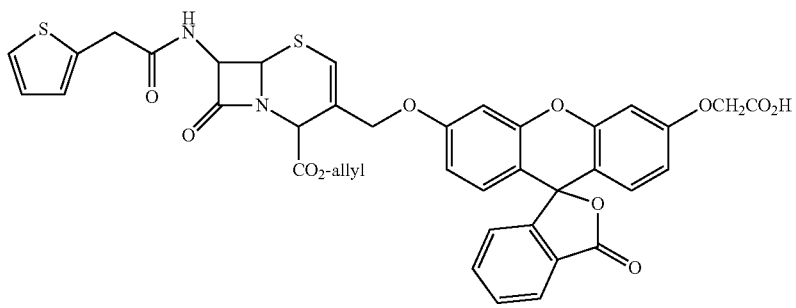

(21)

i) Preparation of (22)

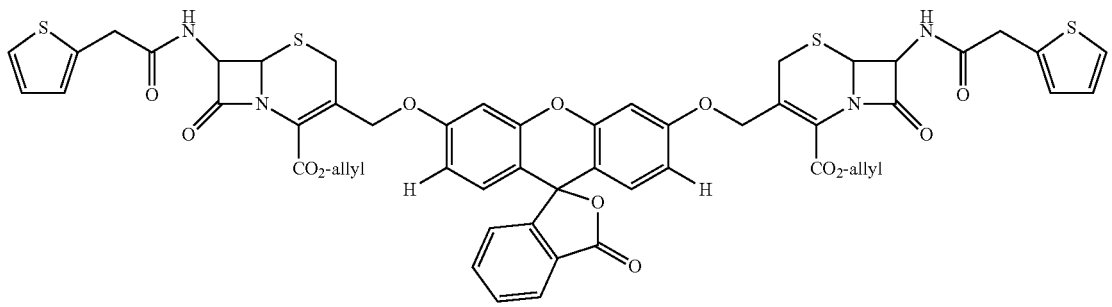

Fluorescein (0.20 g, 0.060 mmol) is dissolved in dioxane (20 mL), then diluted with toluene (50 mL). 5 (0.18 mmol) is added, followed by silver carbonate (0.20 mmol). The resulting mixture is heated at 50° C. for 48 h, then cooled and filtered. 22 is identified in the filtrate by TLC analysis (Rf 0.6, 5% MeOH/chloroform) as a non-fluorescent quenching spot, in contrast to fluorescing impurities. Compound 22 is purified by flash chromatography using methanol in chloroform to afford a pale yellow powder.

Example 6

Preparation of g and/or h: Compounds 23-36 a) 7β-(Phenoxyacetamido)-3-(((2-(3H-quinazoline-4-one-2-yl)-phenyl)oxy)methyl)-3-cephem-4-carboxylic acid (23)

7β-(Phenoxyacetamido)-3-(((2-(3H-quinazoline-4-one-2-yl)-phenyl)oxy)methyl)-2-cephem-4-carboxylic acid (24)

Compound 9 and 10 (0.071 g, 0.114 mmol) were dissolved in 5 mL of dry methylene chloride. Sodium 2-ethylhexanoate (0.019 g, 0.11 mmol) was dissolved in 2 mL of ethyl acetate. After these two solutions were mixed together, PPh$_3$ (0.01 g, 0.04 mmol) and Pd(PPh$_3$)$_4$ (0.01 g, 0.009 mmol) were added. The combined reaction mixture was stirred for 1.5 h at rt. AcOH (0.5 mL) was added to the solution and the reaction mixture was evaporated in vacuo. The residue was re-evaporated from toluene to yield two separable isomers, 23 and 24 (0.09 g). The crude product was used for the next step without any purification.

b) 7β-(2-(Thien-2-yl)acetamido)-3-(((2-(-3H-quinazoline-4-one-2-yl)-(phenyl)oxy)methyl)-3-cephem-4-carboxylic acid (25)

7β-(2-(Thien-2-yl)acetamido)-3-(((2-(-3H-quinazoline-4-one-2-yl)-(phenyl)oxy)methyl)-2-cephem-4-carboxylic acid (26)

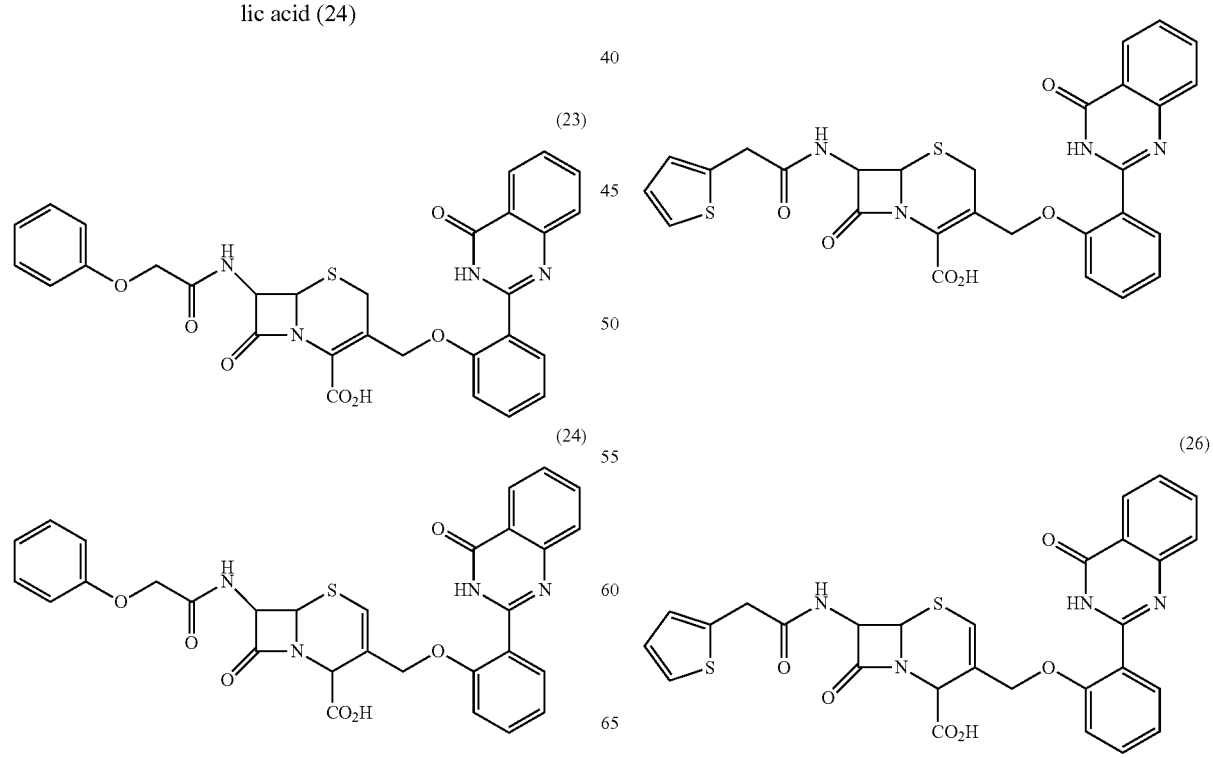

Compound 11 and 12 (1.54 g, 2.51 mmol) were dissolved in 150 mL of dry methylene chloride. Sodium 2-ethylhexanoate (0.417 g, 2.51 mmol) was dissolved in 50 mL of ethyl acetate. After these two solutions were mixed together, PPh$_3$ (0.05 g, 0.2 mmol) and Pd(PPh$_3$)$_4$ (0.05 g, 0.04 mmol) were added. The combined reaction mixture was stirred for 1.5 h at rt. AcOH (5 mL) was added to the solution and the reaction mixture was evaporated in vacuo. The residue was re-evaporated from toluene to yield two separable isomers, 25 and 26 (2.27 g). The crude product was used for the next reaction without purification.

c) 7β-(2-(Thien-2-yl)acetamido)-3-((2-((6-chloro)-3H-quinazoline-4-one-2-yl)-4-chlorophenyloxy)methyl)-3-cephem-4-carboxylic acid (27)

7β-(2-(Thien-2-yl)acetamido)-3-((2-((6-chloro)-3H-quinazoline-4-one-2-yl)-4-chlorophenyloxy)methyl)-2-cephem-4-carboxylic acid (28)

(27)

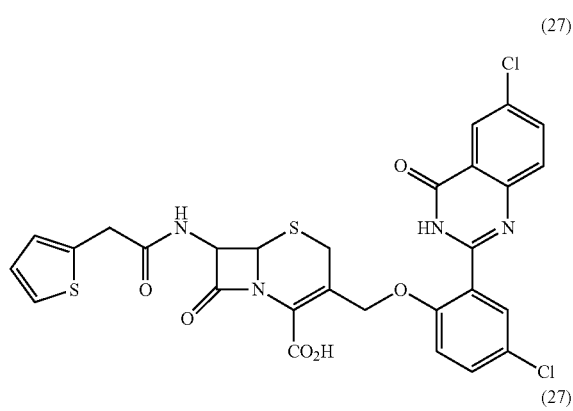

(27)

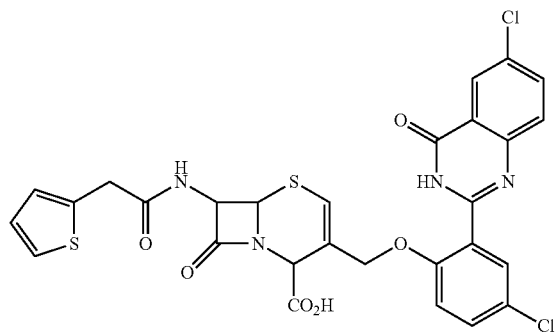

Compound 13 and 14 (0.133 g, 0.195 mmol) were dissolved in 4 mL of methylene chloride. PPh$_3$ (0.006 g, 0.02 mmol) and Pd(PPh$_3$)$_4$ (0.005 g, 0.004 mmol) were then added, followed by sodium 2-ethylhexanoate (0.036 g, 0.217 mmol) in 3 mL of ethyl acetate. The solution was stirred at rt for 1.5 h. During this period, a white precipitate formed. AcOH (0.5 mL) was added to the solution and the reaction mixture was evaporated in vacuo. The residue was re-evaporated from toluene to yield two separable isomers, 27 and 28 (0.170 g). The crude product was used for the next step without purification.

d) 7β-(2-(Thien-2-yl)acetamido)-3-((9H-(1,3-dichloro-9,9-dimethylacridin-2-one)-7-oxy)methyl)-3-cephem-4-carboxylic acid (29)

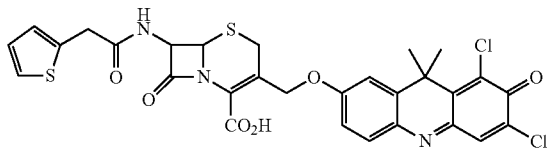

Compound 15 (0.173 g, 0.253 mmol) were dissolved in a mixture of 2 mL methylene chloride and 2 mL ethyl acetate. PPh$_3$ (0.005 g, 0.02 mmol) and Pd(PPh$_3$)$_4$ (0.005 g, 0.0043 mmol) were then added, followed by sodium 2-ethylhexanoate (0.042 g, 0.253 mmol) in 2 mL of ethyl acetate. The solution was stirred for 2 h at rt. During this period, a precipitate formed which was centrifuged, and separated from the supernatant. The solid was washed with methylene chloride and dried. After filtering, the solid was dissolved in chloroform and loaded onto a silica gel column. Less polar impurities were eluted with chloroform:methanol (10:1) mixture. The desired product was eluted using chloroform:methanol:acetic acid (20:3:0.5). The eluate was concentrated in vacuo, dissolved in toluene, and concentrated again. This residue was then dissolved in chloroform:methanol (10:1), filtered and evaporated to yield 29 (0.06 g, 36%).

$^1$H NMR (δ, CD$_3$OD): 1.88 (s, 6H), 3.84 (AB, J=15.2, 2H), 3.87 (AB, J=18.0, 2H), 4.77 (d, J=11.6, 1H), 4.98 (d, J=11.6, 1H), 5.13 (d, J=4.8, 1H), 5.74 (d, J=4.8, 1H), 6.47-6.55 (m, 2H), 6.67 (s, 1H), 6.81 (d, J=2.4, 1H), 6.96-7.00 (m, 2H), 7.30 (d, J=4.8, 1H).

e) 7β-(2-(Thien-2-yl)acetamido)-3-(((4-methylumbelliferyl)-7-oxy)methyl)-3-cephem-4-carboxylic acid (30)

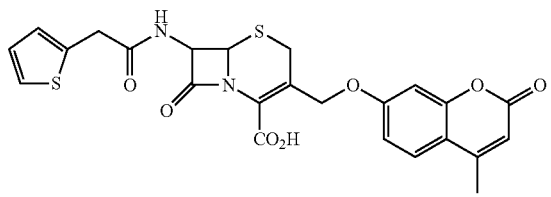

Compound 16 (0.05 g, 0.090 mmol) was dissolved in a mixture of 2 mL methylene chloride and 2 mL ethyl acetate. Sodium 2-ethylhexanoate (0.022 g, 0.13 mmol) was added to the solution followed by PPh$_3$ (0.005 g, 0.02 mmol) and Pd(PPh$_3$)$_4$ (0.005 g, 0.0043 mmol). The combined reaction mixture was stirred for 2 h at rt. During this period, a precipitate formed which was centrifuged, and separated from the supernatant. The solid was washed with ethyl acetate and dissolved in chloroform:methanol:acetic acid (50:10:0.5). The solution was loaded on prep. TLC plate, and the plate was developed using chloroform:methanol:acetic acid (50:10:0.5). The band of the product was separated, and the compound was dissolved in methanol. Evaporation of the methanol yielded 30 as a white powder (0.021 g, 45%).

LCMS: single peak, 511 [M–H$^+$], calculated for C$_{24}$H$_{20}$N$_2$O$_7$S$_2$: 512.

f) 7β-(2-(Thien-2-yl)acetamido)-3-((((6,8-difluoro)-4-methylumbelliferyl)-7-oxy)methyl)-3-cephem-4-carboxylic acid (31)

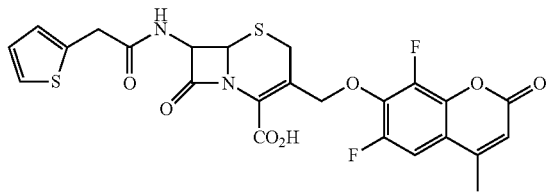

Compound 17 (0.22 g, 0.37 mmol) was dissolved in a mixture of 8 mL of methylene chloride. Sodium 2-ethylhexanoate (0.093 g, 0.56 mmol) was dissolved in 3 mL of ethyl acetate. After these two solutions were mixed together, PPh₃ (0.005 g, 0.02 mmol) and Pd(PPh₃)₄ (0.005 g, 0.0043 mmol) were added. The combined reaction mixture was stirred overnight at rt. The formed precipitate was separated, washed with ethyl acetate and dried to yield 31 as a white powder (0.19 g, 89%).

$^1$H NMR (δ, CD$_3$OD): 2.45 (s, 3H), 3.58 (d, J=17.6, 1H), 3.82 (d, J=17.6, 1H), 3.83 (AB, J=19.3, 2H), 5.04 (d, J=4.4, 1H), 5.06 (d, J=12.0, 1H), 7.41 (d, J=11.2, 1H), 5.31 (d, J=11.6, 1H), 5.67 (d, J=4.8, 1H), 6.36 (s, 1H), 6.98 (m, 2H), 7.28 (d, J=5.2, 1H). LCMS: single peak, 549 [M+H$^+$], calculated for C$_{24}$H$_{18}$N$_2$O$_7$F$_2$S$_2$: 548.

g) Preparation of (32) and (33)

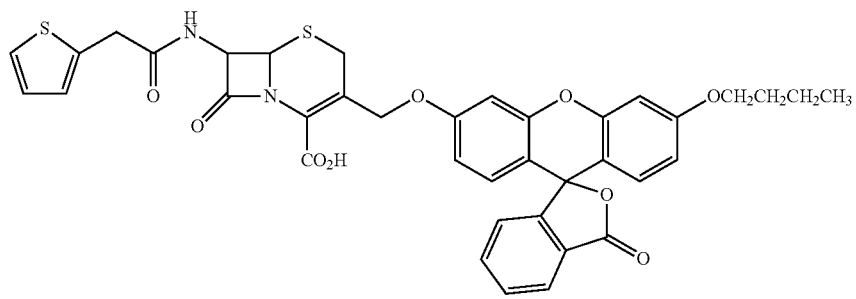

(32)

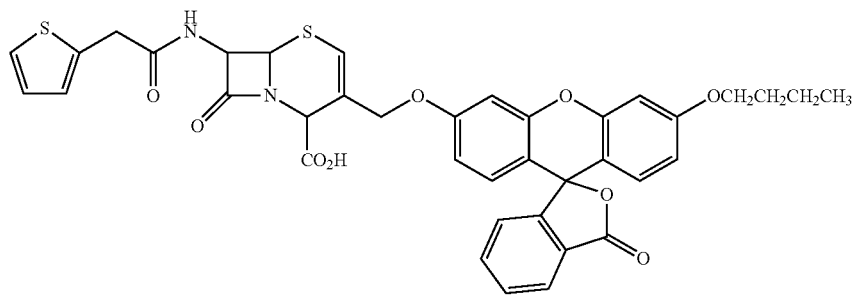

(33)

Compound 18 and 19 (0.075 g, 0.098 mmol) were dissolved in the mixture of 1 mL of methylene chloride and 1 mL of ethyl acetate. Sodium 2-ethylhexanoate (0.0163 g, 0.098 mmol) was added to the solution followed by PPh$_3$ (0.005 g, 0.02 mmol) and Pd(PPh$_3$)$_4$ (0.005 g, 0.0043 mmol). The combined reaction mixture was stirred for 2 h at rt. After that 0.5 mL of AcOH was added to the mixture and it was concentrated in vacuo. The residue was concentrated in vacuo, dissolved in toluene, and concentrated again. The crude product was dissolved in chloroform and loaded on a prep. TLC plate. The plate was developed using chloroform:methanol: acetic acid (50:10:0.5). The product was separated as a mixture of two isomers. The bands were separated from the plate, and the product was dissolved in methanol. After evaporation, dissolution in methanol, filtration, and evaporation, two separable isomers, 32 and 33 (0.024 g, 34%), was recovered.

h) Preparation of (34) and (35)

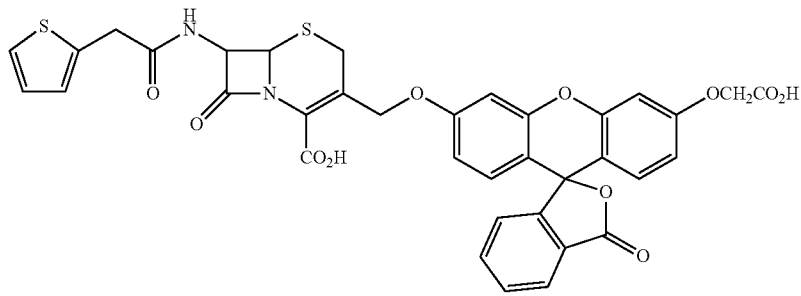

(34)

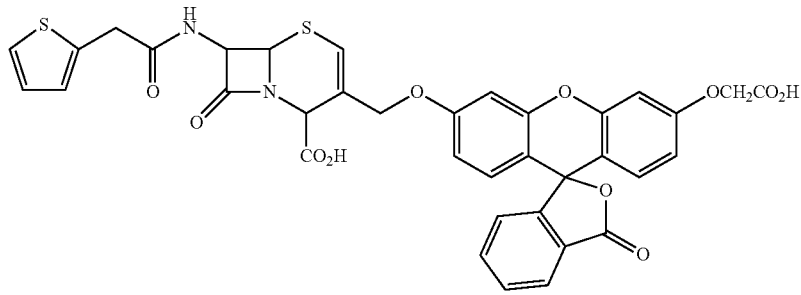

(35)

Compound 20 and 21 (0.120 g, 0.146 mmol) were dissolved in 3 mL of methylene chloride. PPh$_3$ (0.0046 g, 0.0175 mmol) and Pd(PPh$_3$)$_4$ (0.0033 g, 0.00285 mmol) were added to the solution followed by addition of sodium 2-ethylhexanoate (0.053 g, 0.319 mmol), dissolved in 3 mL of ethyl acetate. The reaction mixture was stirred for 2 h at rt. The formed yellow precipitate was separated, washed with methylene chloride and dried. The residue was re-dissolved in 6:2:0.4 chloroform-methanol-acetic acid mixture and the solution was loaded on prep. PLC plate. The plate was developed in 6:2:0.4 chloroform-methanol-acetic acid mixture. The band containing desired product was separated, compound was washed out of silica gel with methanol and solution was evaporated. The residue was re-dissolved in chloroform, filtered and evaporated to yield two separable isomers, 34 and 35, as a yellow powder (0.048 g, 44%).

$^1$H NMR (6, CD$_3$OD): 3.87 (2AB, J=15.6, 4H), 4.68 (br s, 2H), 4.75 (d, J=4.0, 1H), 4.84 (d, J=12.4, 1H), 5.40 (d, J=12.4, 1H), 5.86 (d, J=4.4, 1H), 6.50-7.30 (m, 10H), 7.72 (t, J=7.6, 1H), 7.79 (t, J=7.6, 1H), 8.02 (d, J=7.6, 1H). LCMS: single peak, 741 [M−H$^+$], calculated for C$_{36}$H$_{26}$N$_2$O$_{12}$S$_2$: 742.

i) Preparation of (36)

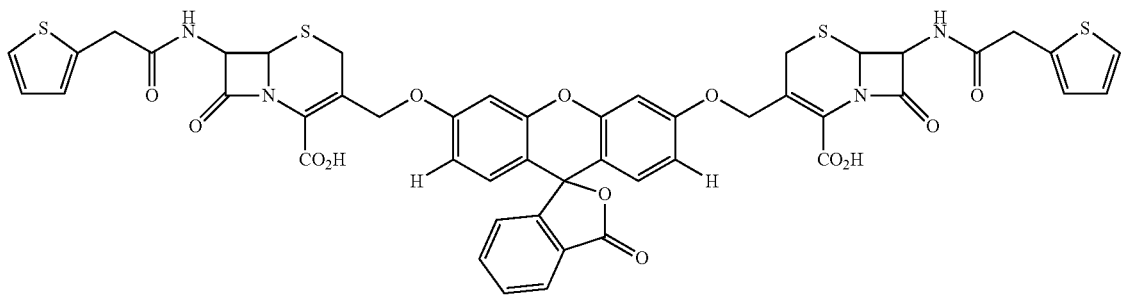

Compound 22 (0.01 mmol) is dissolved in dry dichloromethane (20 mL). Sodium 2-ethylhexanoate (0.02 mmol) is dissolved in 5 mL ethyl acetate. After these two solutions are mixed together, $PPh_3$ (0.002 mmol) and $Pd(PPh_3)_4$ (0.002 mmol) are added. The resulting solution is stirred at rt for 3 h, then acetic acid (2 mL) is added and the reaction mixture evaporated in vacuo to afford 36 as a pale yellow powder.

Example 7

Preparation of i: Compounds 37-43 a) 7β-(Phenoxyacetamido)-3-(((2-(3H-quinazoline-4-one-2-yl)-phenyl)oxy)methyl)-3-cephem-4-carboxylic acid 1β-sulfoxide (37)

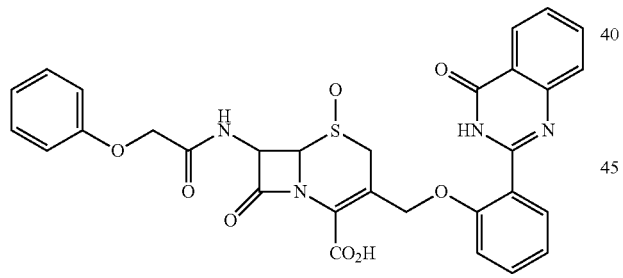

Compound 23 and 24 (0.09 g) were dissolved in 3 mL of methylene chloride and the solution was cooled in an ice/water bath. m-Chloroperoxybenzoic acid (77% in methylene chloride, 0.025 g, 0.11 mmol) was added to the above solution. The reaction mixture was stirred at the bath temperature for 30 min, and then concentrated in vacuo to ~2 mL. During concentration, a precipitate formed, which was then centrifuged, and separated from the supernatant. The solid was washed with 1 mL of methylene chloride and dried to yield a single product, 37, as a white powder (0.02 g).

$^1$H NMR (δ, $CD_3OD$): 3.50 (d, J=18.4, 1H), 3.98 (d, J=18.4, 1H), 4.65 (AB, 2H), 4.81 (d, J=4.8, 1H), 4.93 (d, J=11.6, 1H), 5.44 (d, J=11.6, 1H), 6.90-8.0 (m, 12H), 8.25 (d, J=8.0, 1H). LCMS: single peak, 555 [M-$CO_2$—H$^+$], calculated for $C_{30}H_{24}N_4O_8S$: 600.

b) 7β-(2-(Thien-2-yl)acetamido)-3-(((2-(-3H-quinazoline-4-one-2-yl)-(phenyl)oxy)methyl)-3-cephem-4-carboxylic acid 1β-sulfoxide (38)

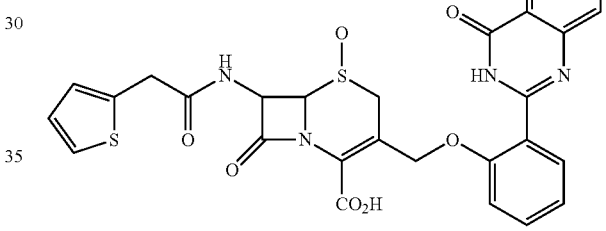

Compound 25 and 26 (2.27 g) were dissolved in 40 mL of methylene chloride and the solution was cooled with an ice/water bath. m-Chloroperoxybenzoic acid (77% in methylene chloride, 0.85 g, 3.79 mmol) was added dropwise to the above solution. The reaction mixture was stirred at the bath temperature for 30 min, and then concentrated in vacuo. During concentration, a precipitate formed, which was separated from the solution by filtration. The solid was washed with methylene chloride (3×10 mL) and dried to give the first crop of sulfoxide (~0.8 g). An organic solution was combined with the washings, which produced a white precipitate. The precipitate was filtered, washed with methylene chloride (3×5 mL) and dried to give a second crop of product (0.2 g). These two crops were similar by TLC and were combined to yield a single product, 38 (1.05 g).

$^1$H NMR (δ, $CD_3OD$): 3.46 (d, J=20.0, 1H), 3.86 (AB, J=16.0, 2H), 3.91 (d, J=20.0, 1H), 4.75 (d, J=4.8, 1H), 4.90 (d, J=11.6, 1H), 5.85 (d, J=11.6, 1H), 6.90-7.90 (m, 10H), 8.25 (d, J=8.0, 1H). LCMS: single peak, 545 [M-$CO_2$—H$^+$], calculated for $C_{28}H_{22}N_4O_7S_2$: 590.

c) 7β-(2-(Thien-2-yl)acetamido)-3-(((2-((6-chloro)-3H-quinazoline-4-one-2-yl)-(4-chlorophenyl)oxy)methyl)-3-cephem-4-carboxylic acid 1β-sulfoxide (39)

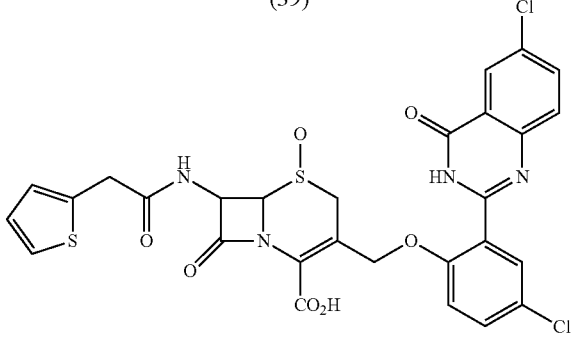

Compound 27 and 28 (0.170 g) were dissolved in a solution of methylene chloride (~15 mL) and methanol (~2 mL) which was cooled in an ice/water bath. m-Chloroperoxybenzoic acid was dissolved in 2 mL of methylene chloride and added to the above solution. The reaction mixture was stirred at the bath temperature for 1.5 h. During this period, a precipitate formed, which was separated, washed with methylene chloride and dried to give the first crop of product. An organic solution was combined with the washings. After evaporation, the residue was mixed with 10 mL of methylene chloride. A white precipitate formed, which was separated from the solution, washed with methylene chloride, and dried to give a second crop of product. These two crops were similar by TLC and were combined to yield a single product, 39 (0.07 g).

$^1$H NMR (δ, DMSO-$d_6$): 3.28 (d, J=18.0, 1H), 3.78 (d, J=18, 1H), 3.84 (AB, J=15.6, 2H), 4.70 (d, J=3.6, 1H), 4.80 (d, J=11.2, 1H), 5.33 (d, J=10.9, 1H), 5.58 (br s, 1H), 6.90-8.20 (m, 9H). LCMS: single peak, 615 [M-$CO_2$—H$^+$], calculated for $C_{28}H_{20}N_4O_7S_2Cl_2$: 660.

d) 7β-(2-(Thien-2-yl)acetamido)-3-((9H-(1,3-dichloro-9,9-dimethylacridin-2-one)-7-oxy)methyl)-3-cephem-4-carboxylic acid 1β-sulfoxide (40)

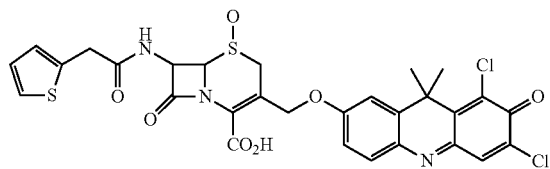

Compound 29 (0.10 g, 0.20 mmol) was dissolved in 4 mL methylene chloride and the solution was cooled in an ice/water batch. m-Chloroperbenzoic acid (77% in 4 mL methylene chloride, 0.075 g, 0.33 mmol) was added to the above solution. The reaction mixture was stirred at bath temperature for 30 min, then concentrated in vacuo to a volume of 2 mL. During the concentration a precipitate formed, which was isolated by centrifugation, separated from the supernatant, washed with 1 mL cold methylene chloride, and dried to yield 40 as a brown solid (0.02 g).

e) 7β-(2-(Thien-2-yl)acetamido)-3-((((6,8-difluoro)-4-methylumbelliferyl)-7-oxy)methyl)-3-cephem-4-carboxylic acid 1β-sulfoxide (41)

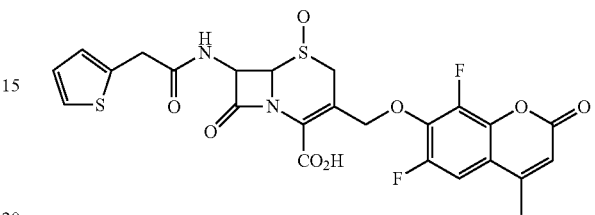

Compound 30 (0.047 g, 0.083 mmol) was dissolved in 20 mL of water. The solution was acidified with 3 mL of 10% HCl and the acid was extracted with methylene chloride (4×20 mL). The combined extracts were washed with brine (20 mL), and dried over sodium sulfate. After filtering, the solution was concentrated down to ~20 mL. The solution was then cooled in an ice/water bath, and m-chloroperoxybenzoic acid (77% in methylene chloride, 0.0185 g, 0.0825 mmol) and added. The reaction mixture was stirred at the bath temperature for 30 min. During this period, a precipitate formed, which was separated, washed with methylene chloride (~1.5 mL) and dried to yield 41 as a white powder (0.040 g, 86%).

$^1$H NMR (δ, DMSO-$d_6$): 2.40 (s, 3H), 3.69 (d, J=18.4, 1H), 3.86 (AB, J=15.2, 2H), 4.92 (d, J=3.6, 1H), 4.96 (d, J=12.4, 1H), 5.44 (d, J=12.4, 1H), 5.85 (dd, J=8.4, $J_2$=4.8, 1H), 6.47 (s, 1H), 6.97 (m, 2H), 7.39 (dd, $J_1$=4.8, $J_2$=1.6, 1H), 7.62 (d, J=11.6, 1H), 8.47 (d, J=8.4, 1H). LCMS: single peak, 565 [M+H$^+$], calculated for $C_{24}H_{18}N_2O_8F_2S_2$: 564.

Figure 2:
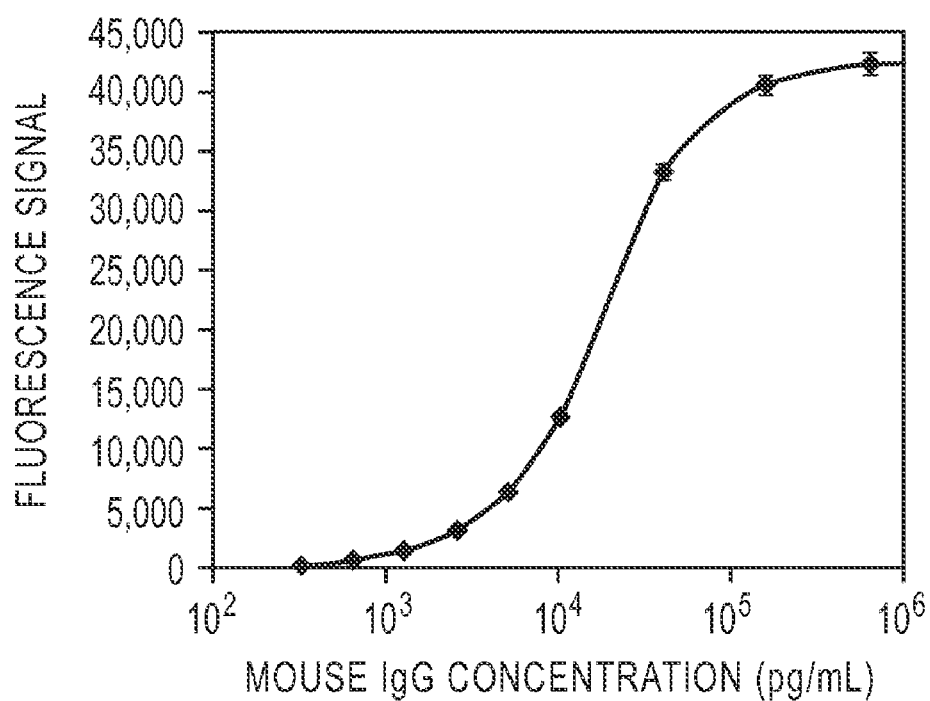
FIG. 2: Shows the dynamic range of Compound 108 in a direct ELISA format wherein streptavidin is detected with a primary antibody conjugated to a β-lactamase enzyme and subsequent cleavage of the Compound 108. The wells of a microplate were coated with a saturating amount of streptavidin. After incubation and washes, biotinylated IgG was applied to the wells at the stated concentrations (100 μl/well). Detection was achieved using 100 μl of a 10 μg/ml of a (β-lactamase-conjugated goat anti-mouse IgG secondary antibody in the presence of 1 μg of Compound 108 substrate (with appropriate washes between steps). Fluorescence was read at 60 minutes without the addition of the stop reagent (β-lactamase inhibitor). IgG was reliably detected in the range of 320 pg/ml to 640 ng/ml (over three orders of magnitude). Across the range of detection, the accuracy of the data obtained can be dramatically improved if curve fitting (e.g., Hill plot) is employed.

The fluorescence intensity versus time of β-lactamase substrate 41 after reaction with β-lactamase is shown in FIG. 1. The variation in fluorescence intensity at different concentrations of β-lactamase substrate 41 is also shown. A comparison of the fluorescence intensity versus time of β-lactamase substrate 41 alone and also after reaction with β-lactamase is shown in FIG. 2.

f) Preparation of (42)

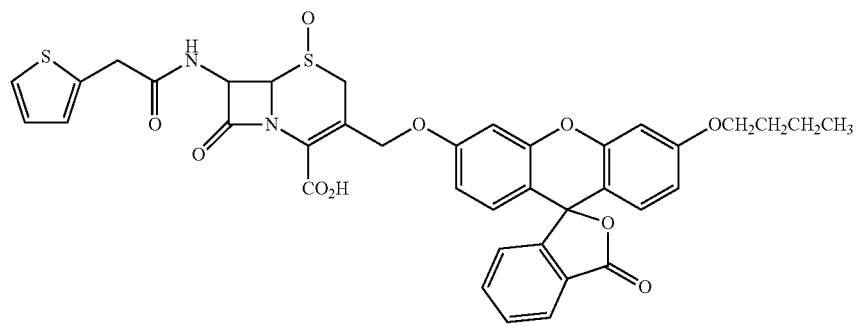

Compound 32 and 33 (0.015 g, 0.021 mmol) were dissolved in 1 mL of methylene chloride and the solution was cooled in an ice/water bath. m-Chloroperoxyacetic acid (77% in methylene chloride, 0.0046 g, 0.021 mmol) was added to the solution and the reaction mixture was stirred for 30 min at bath temperature. The resulting solution was loaded on prep. TLC plate, and developed using chloroform:methanol:acetic acid (50:7:0.3) as an eluent. The product band was separated and the product was dissolved in methanol. After evaporation and dissolution in chloroform, the solution was filtered and concentrated to yield a single product, 42, as a yellowish powder (0.008 g, 52%).

LCMS: single peak, 741 [M+H$^+$], calculated for $C_{38}H_{32}N_2O_{10}S_2$: 740.

g) Preparation of (43)

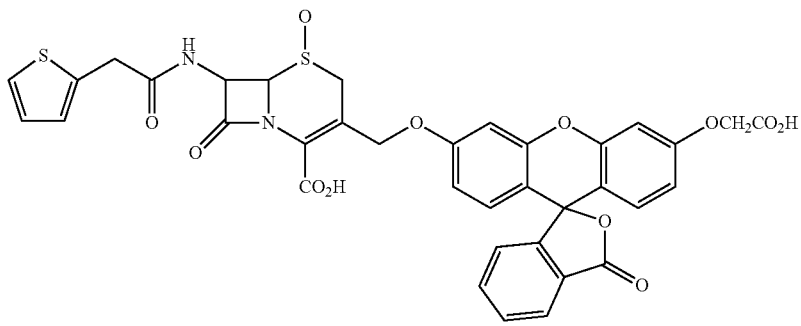

Compound 34 and 35 (0.231 g, 0.287 mmol) were dissolved in 5 mL of methylene chloride and the solution was cooled in an ice/water bath. m-Chloroperoxybenzoic acid (77% in 2 mL methylene chloride, 0.064 g, 0.285 mmol) was added to the solution and the reaction mixture was stirred for 20 min at rt and evaporated. The residue was re-dissolved in chloroform and the solution was loaded on a silica gel column, which was eluted with chloroform:ethyl acetate (5:1). The eluate was evaporated to yield a single product, 43, as a yellow glass (0.124 g, 53%).

Example 8

Preparation of i: Compounds 23, 25, and 34 a) 7β-(Phenoxyacetamido)-3-(((2-(3H-quinazoline-4-one-2-yl)-phenyl)oxy)methyl)-3-cephem-4-carboxylic acid (23)

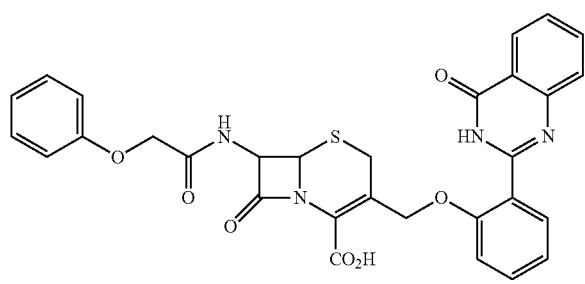

Compound 37 (0.05 g, 0.083 mmol) was dissolved in 2 mL of DMF. SnCl$_2$.2H$_2$O (0.047 g, 0.21 mmol) was added to the solution and the mixture was cooled in an ice/water bath. AcCl (0.21 mL, 2.95 mmol) was added to the solution and the mixture was stirred for 1 h at bath temperature. MeOH (2 mL) was added to the solution and the mixture was diluted with 10 mL of water. The product was extracted with ethyl acetate (5×10 mL). The combined extracts were washed with water (3×10 mL), brine (10 mL), and dried over sodium sulfate. After filtering, the solvent was removed in vacuo to yield 23 as a white powder (0.039 g, 80%).

LCMS: single peak, 585 [M+H$^+$], calculated for $C_{30}H_{24}N_4O_7S$: 584.

b) 7β-(2-(Thien-2-yl)acetamido)-3-(((2-(-3H-quinazoline-4-one-2-yl)-(phenyl)oxy)methyl)-3-cephem-4-carboxylic acid (25)

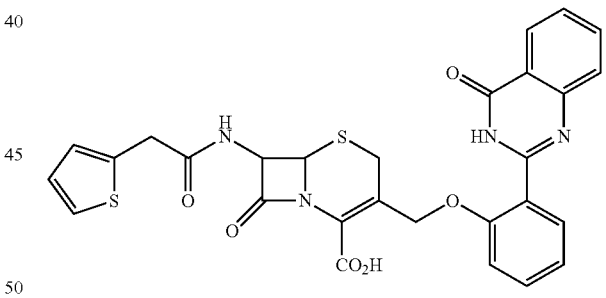

Compound 38 (0.10 g, 0.16 mmol) was dissolved in 4 mL of DMF. SnCl$_2$.2H$_2$O was added to the solution and the mixture was cooled in an ice/water bath. AcCl (0.4 mL, 5.62 mmol) was added to the solution and the mixture was stirred at bath temperature for 30 min, diluted with 10% HCl (50 mL) and extracted with ethyl acetate (4×30 mL). The combined extracts were washed with brine (30 mL), and dried over sodium sulfate. After filtering, the solvent was removed in vacuo. The residue was triturated with ethyl acetate. A precipitate formed which was filtered and evaporated in vacuo to yield 25 (0.09 g, 96%).

$^1$H NMR (δ, CD$_3$OD): 3.67 (s, 2H), 3.80 (AB, 2H), 5.08 (d, J=4.8, 1H), 5.13 (s, 2H), 5.75 (d, J=4.8, 1H), 6.90-7.90 (m, 10H), 8.27 (d, J=8.0, 1H). LCMS: single peak, 575 [M+H$^+$], calculated for C$_{28}$H$_{22}$N$_4$O$_6$S$_2$: 574.

Figure 3A:
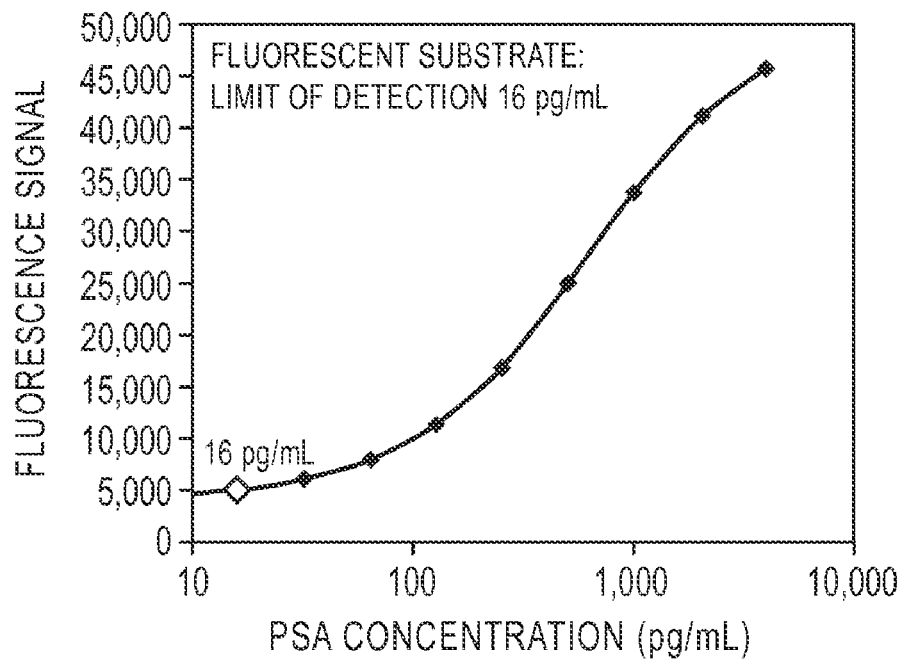
FIG. 3: Shows a comparison of a A) fluorescent assay using Compound 108 and a B) colimertic assay. For the fluorogenic assay, 100 μl/well of a 10 μg/ml solution of anti-prostate specific antigen (PSA) antibody was applied to microplate wells. After incubation and washes, a dilution series of purified PSA was applied, and detection was achieved using 100 μl of a 10 μg/ml of an anti-PSA primary antibody and 100 μl of a 10 μg/ml of a β-lactamase-conjugated secondary antibody in the presence of 1 μg Compound 108 substrate (with appropriate washes between steps). The Z-statistic[1] gives a lower limit of detection of PSA in this assay of 16 pg/ml. For the colorimetric assay, a commercially available kit for the detection of PSA in human serum or plasma was used according to the manufacturers instructions. The assay was performed using the PSA standards provided in the kit. The capture antibody was supplied preimmobilzed in the wells, and detection was achieved using an HRP-labeled detection antibody and tetramethyl benzidine (TMB) substrate. The reaction was stopped after 15 minutes using the stop solution provided in the kit and the absorbance was read at 450 nm. The Z-statistic gives a lower limit of detection of PSA in this assay of 250 pg/ml. See, Example 32.
Figure 3B:
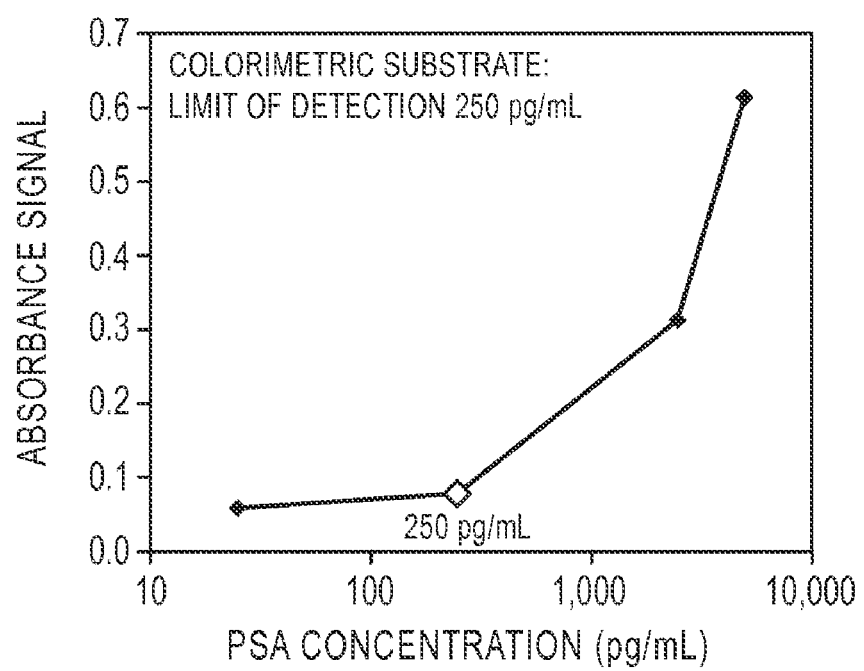

A comparison of the fluorescence intensity versus time of β-lactamase substrate 25 after reaction with β-lactamase is shown in FIG. 3.

c) Preparation of (34)

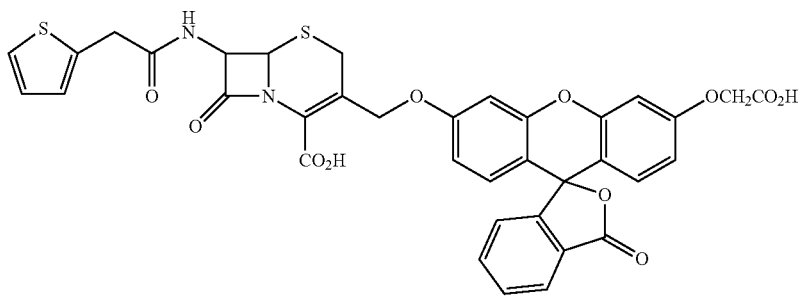

Compound 43 (0.027 g, 0.036 mmol) was dissolved in 2 mL of DMF. SnCl$_2$.2H$_2$O (0.020 g, 0.089 mmol) was added to the solution and the mixture was cooled in an ice/water bath. AcCl (0.090 mL, 1.26 mmol) was added to the solution and the mixture was stirred for 1 h at bath temperature. The reaction mixture was concentrated in vacuo to dryness and re-dissolved in chloroform:methanol:acetic acid (6:2:0.4). This solution was loaded onto a prep. TLC plate, which was developed in chloroform:methanol:acetic acid (6:2:0.4). The band containing the desired product was separated, and the product was dissolved in methanol. After evaporation of methanol, the residue was re-dissolved in chloroform, filtered and evaporated to yield 34 as a yellow powder (0.009 g, 34%).

LCMS: single peak, 725 [M–H$^+$], calculated for C$_{36}$H$_{26}$N$_2$O$_{11}$S$_2$: 726.

Example 9

Preparation of k (Compound 44)

A 0.1 M solution of clavulanic acid in anhydrous acetonitrile (20 mL) is treated with DIEA (1.2 eq) and allyl bromide (1.1 eq). The resulting reaction mixture is stirred overnight at rt, then evaporated and mixed with 30 mL 5% HCl, followed by extraction with ethyl acetate (3×30 mL). The extract is washed with brine (1×30 mL), dried over sodium sulfate, and concentrated. The crude product is purified by flash chromatography using methanol in chloroform to give ester Compound 44 as a colorless oil.

Example 10

Preparation of I (Compound 45)

To a 0.1 M solution of ester Compound 44 in 20 mL anhydrous THF is added 1.1 eq of triphenylphosphine and 1.1 eq of diethyl azodicarboxylate. After 30' 0.1M solution of 1.0 eq 4-methyl-7-hydroxycoumarin and 1.0 eq of DIEA is added. The resulting mixture is stirred overnight, then evaporated and mixed with 30 mL 5% HCl, followed by extraction with ethyl acetate (3×30 mL). The extract is washed with brine (1×30 mL), dried over sodium sulfate, and concentrated. The crude product is purified by flash chromatography using ethyl acetate in chloroform to give ester Compound 45 as a colorless oil.

Example 11

Preparation of m (Compound 46)

A 0.05 M solution of 45, triphenylphosphine (0.3 eq), and tetrakis(triphenylphosphine)palladium (0.1 eq) in anhydrous dichloromethane is treated dropwise with a 0.1 M solution of 1.1 eq sodium 2-ethylhexanoate in anhydrous ethyl acetate with stirring. The reaction mixture is stirred at rt for 4 h, and the resulting precipitate is collected by filtration and rinsed with ethyl acetate to afford fluorogenic substrate 46 as a colorless powder.

Example 12

Exemplary Synthetic Scheme for Preparing Fluorogenic Rhodol-Cephalosporins

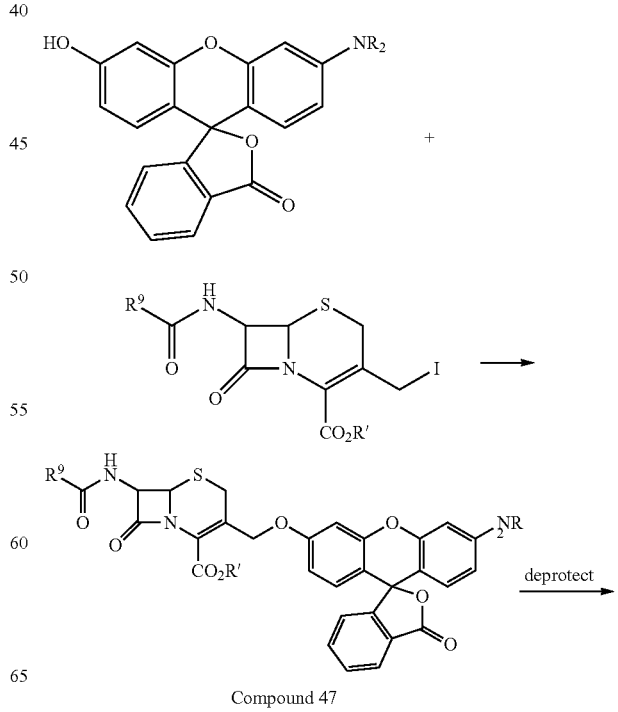

Compound 47

123
-continued

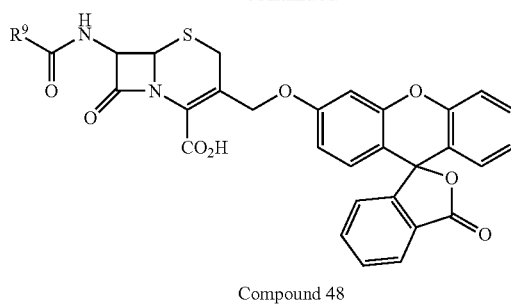

Compound 48

$R^9$ = any such $R^9$ group disclosed above
R = H, alkyl, heteroalkyl, aryl, heteroaryl, acyl
R' = a protecting group, for example, allyl, benzhydryl, or t-butyl

Example 13

Exemplary Synthetic Scheme for Preparing Fluorogenic Rhodamine-Cephalosporins

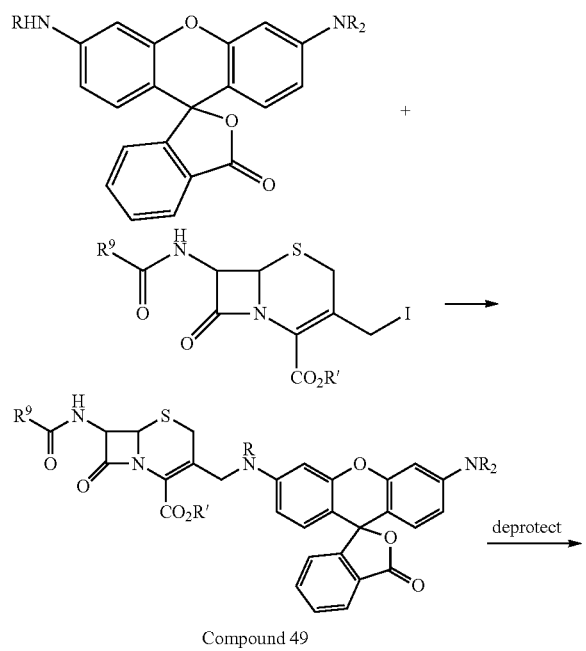

Compound 49

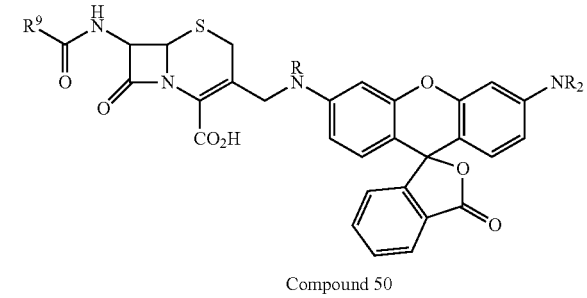

Compound 50

$R^9$ = any such $R^9$ group disclosed above
R = H, alkyl, heteroalkyl, aryl, heteroaryl, acyl
R' = a protecting group, for example, allyl, benzhydryl, or t-butyl

124

Example 14

Exemplary Synthetic Scheme for Preparation of Fluorogenic Rhodol Clavulanates

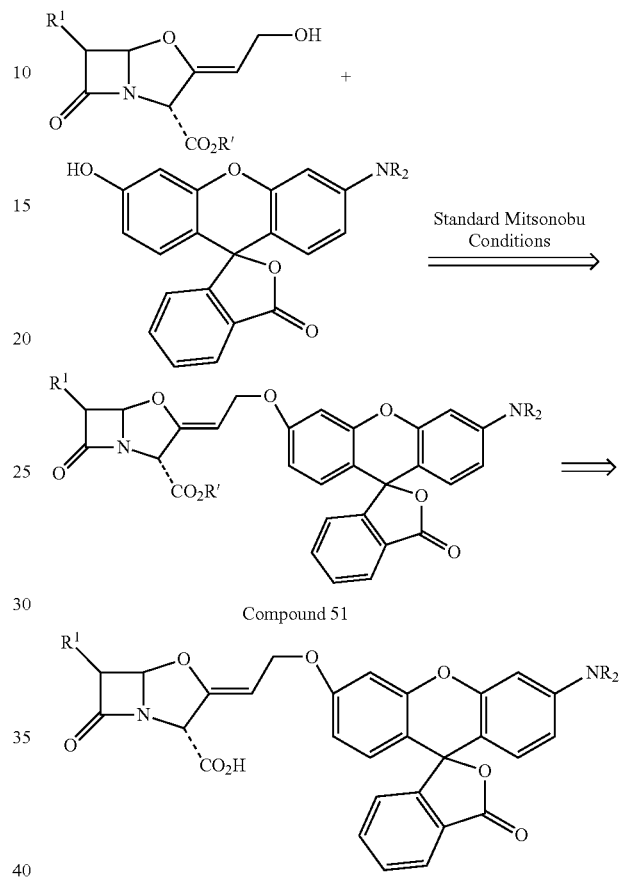

Compound 51

A fluorogenic rhodol-clavulanate
Compound 52

R = H, akyl, heteroalkyl, aryl, heteroaryl, acyl
$R^1$ = any $R^1$ as described above
R' = a protecting group, for example, allyl, benzhydryl, or t-butyl

Example 15

Exemplary Synthetic Scheme for Preparing Fluorogenic Rhodamine-Clavulanates

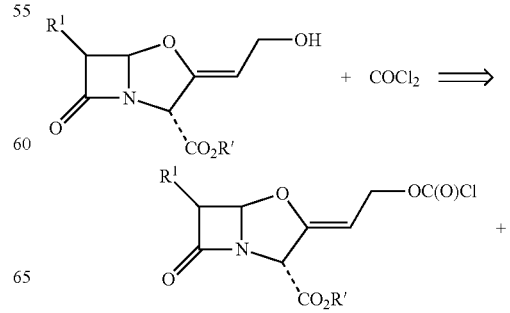

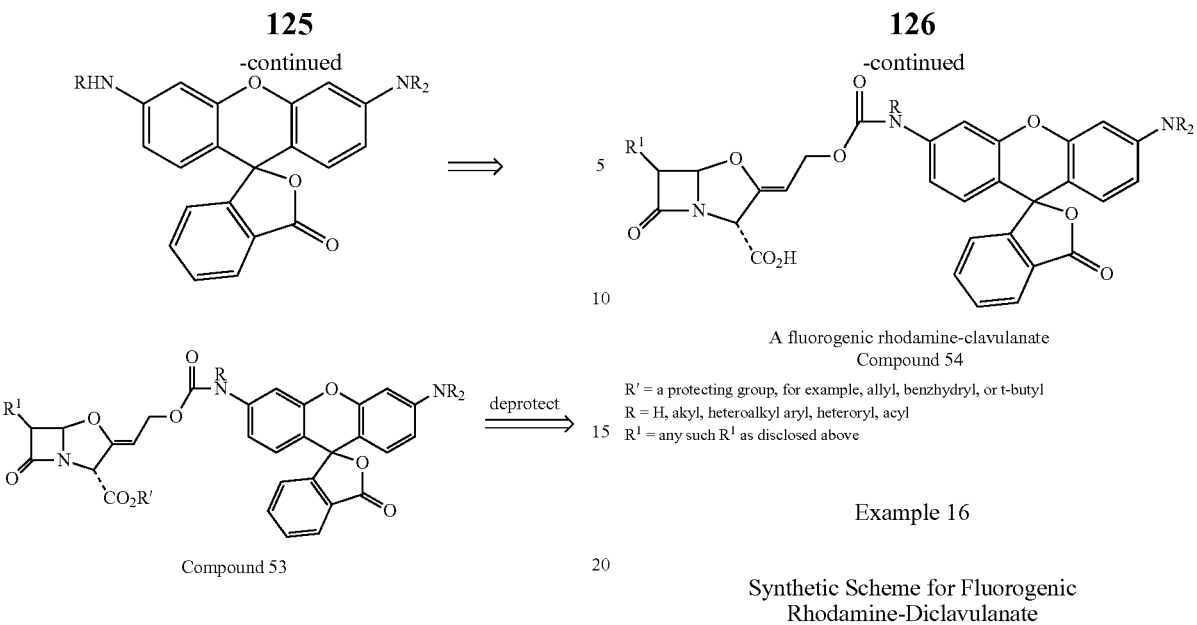

A fluorogenic rhodamine-clavulanate
Compound 54

R' = a protecting group, for example, allyl, benzhydryl, or t-butyl
R = H, akyl, heteroalkyl aryl, heteroryl, acyl
R¹ = any such R¹ as disclosed above Example 16

Synthetic Scheme for Fluorogenic Rhodamine-Diclavulanate

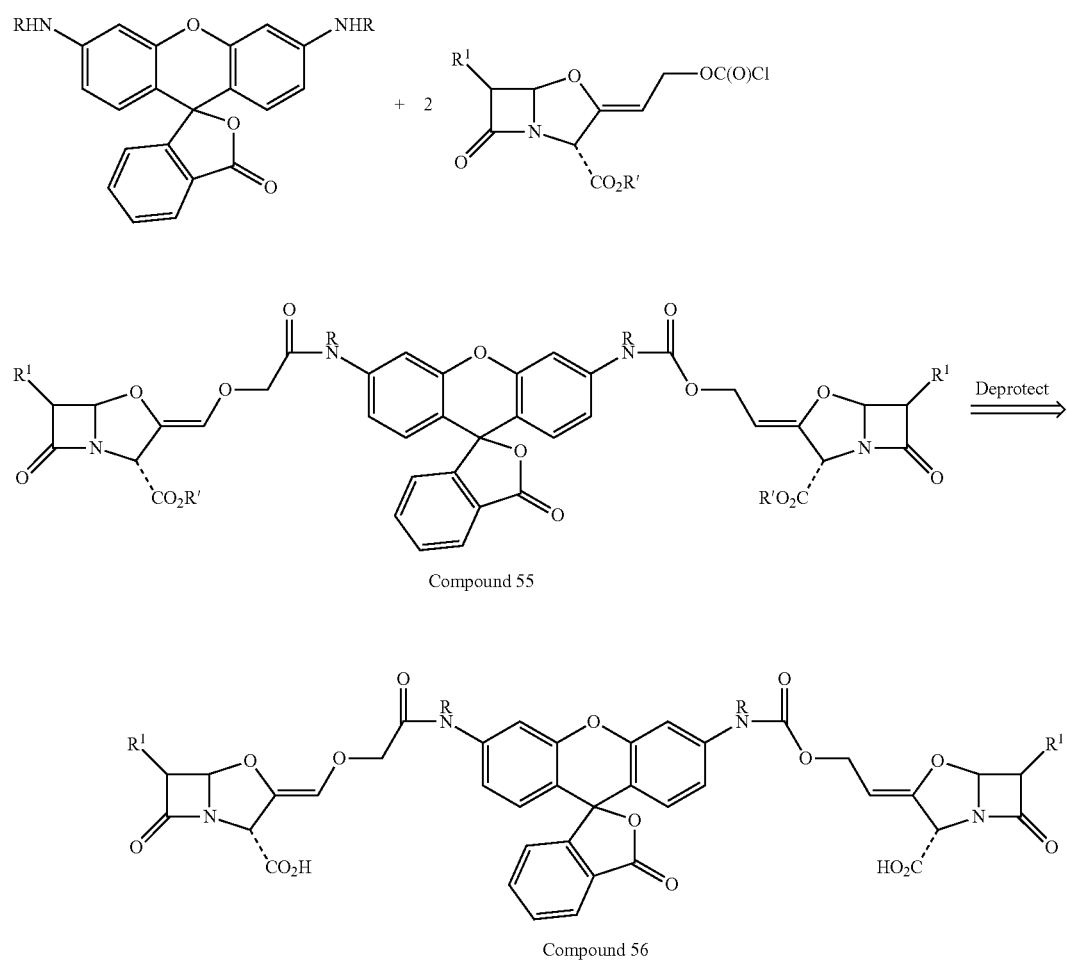

Compound 55

Compound 56

R' = a protecting group, for example, allyl, benzhydryl, or t-butyl
R = H, akyl, heteroalkyl, aryl, heteroryl, acyl
R¹ = any such R¹ disclosed above

Example 17
Exemplary Synthetic Schemes for Colorogenic Nitrophenol-Clavulanates
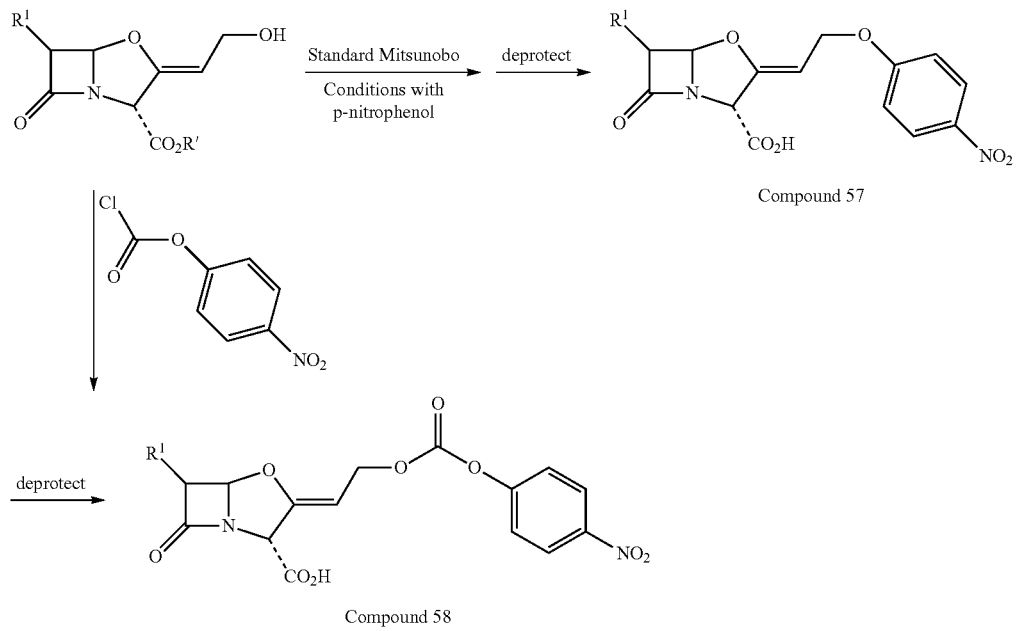
R' = a protecting group, for example, allyl, benzhydryl, or t-butyl
R¹ = any R¹ group disclosed above
Example 18
Exemplary Synthetic Scheme for a Fluorogenic Coumarin-Benzopyranone
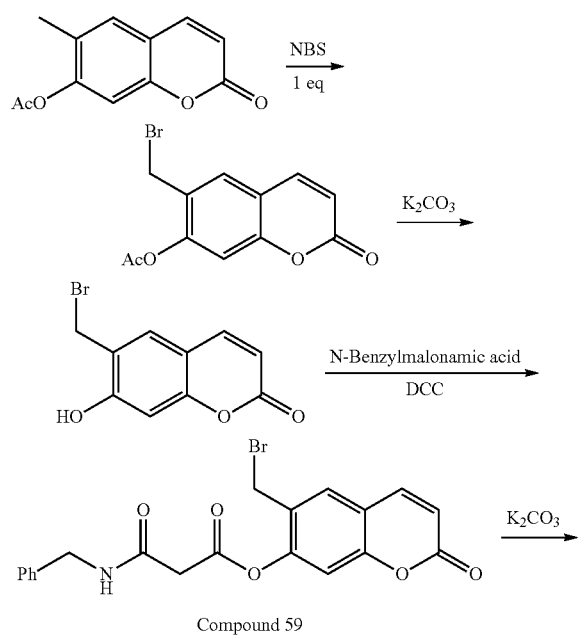
-continued
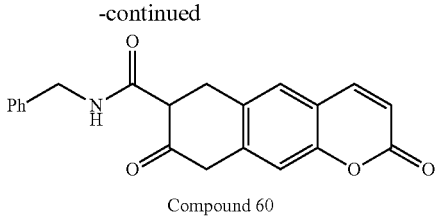
Example 19
Exemplary Synthetic Scheme for a Fluorogenic Coumarin-Benzofuranone
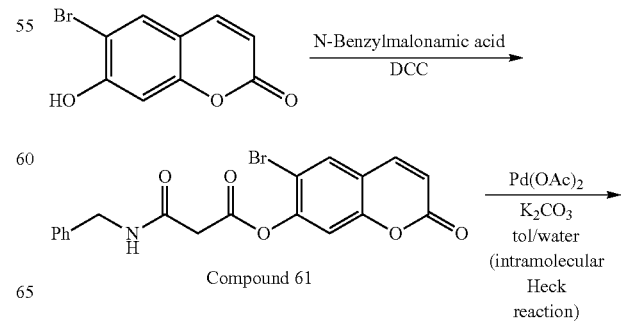

-continued

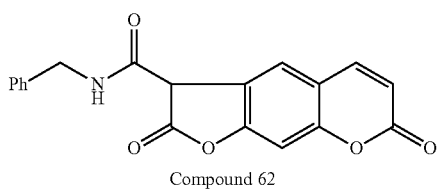

Compound 62

G = a bond
Preparation of N-benzylmalonamic acid is described in Cabaret et al., *Biochemistry* 2003, 42: 6719-25.

The Heck reaction employs a source of palladium (0) [Pd(0)] catalyst and a base. Examples of commercially available Pd(0) sources include palladium tetrakis triphenylphosphine (Pd(Ph$_3$)$_4$); palladium acetate (Pd(OAc)$_2$); Tris(dibenzylideneacetone) dipalladium (0) (C$_6$H$_5$CH=CHCOCH=CHC$_6$H$_5$)$_3$Pd$_2$); Tris(dibenzylideneacetone)dipalladium (0) chloroform adduct (C$_6$H$_5$CH=CHCOCH=CHC$_6$H$_5$)$_3$Pd$_2$.CHCl$_3$), and the like. Examples of suitable bases include weak bases, such as tertiary amine bases, for example triethylamine. Additional suitable bases include metal carbonates, such as potassium carbonate. Additives can optionally be included in the Heck reaction, such as additional ligands, for example phosphine ligands, salts, particularly silver (I) salts. General conditions for intramolecular Heck reactions are provided by Link and Overman, In Metal Catalyzed Cross-coupling Reactions, Diederich, F., Ed.; Wiley-VCH: New York, 1998, pp. 231-269; and by Gibson and Middleton, *Contemp. Org. Synth.* 1996, 3, 447-471.

Example 20

Exemplary Synthetic Scheme for a Fluorogenic Coumarin-Phenaceturate

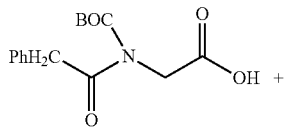

Preparation in Cabaret et al., Bioorganic & Medicinal Chemistry 1994, 2: 757-71.

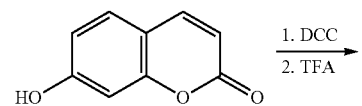

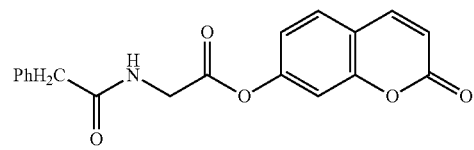

Compound 63

Example 21

Exemplary Synthetic Scheme for a Fluorogenic Coumarin-Malonamate

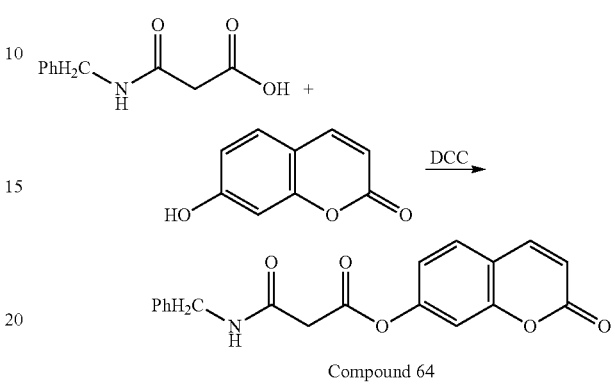

Compound 64

Example 22

Exemplary Synthetic Scheme for a Fluorogenic Coumarin-Benzopyranone

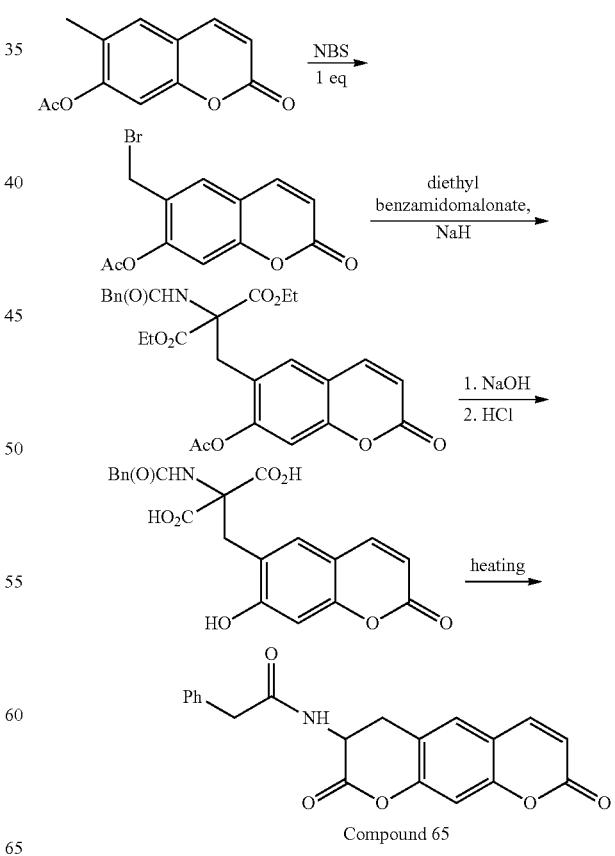

Compound 65

Example 23

Exemplary Synthetic Scheme for a Fluorogenic Coumarin-Benzofurnone

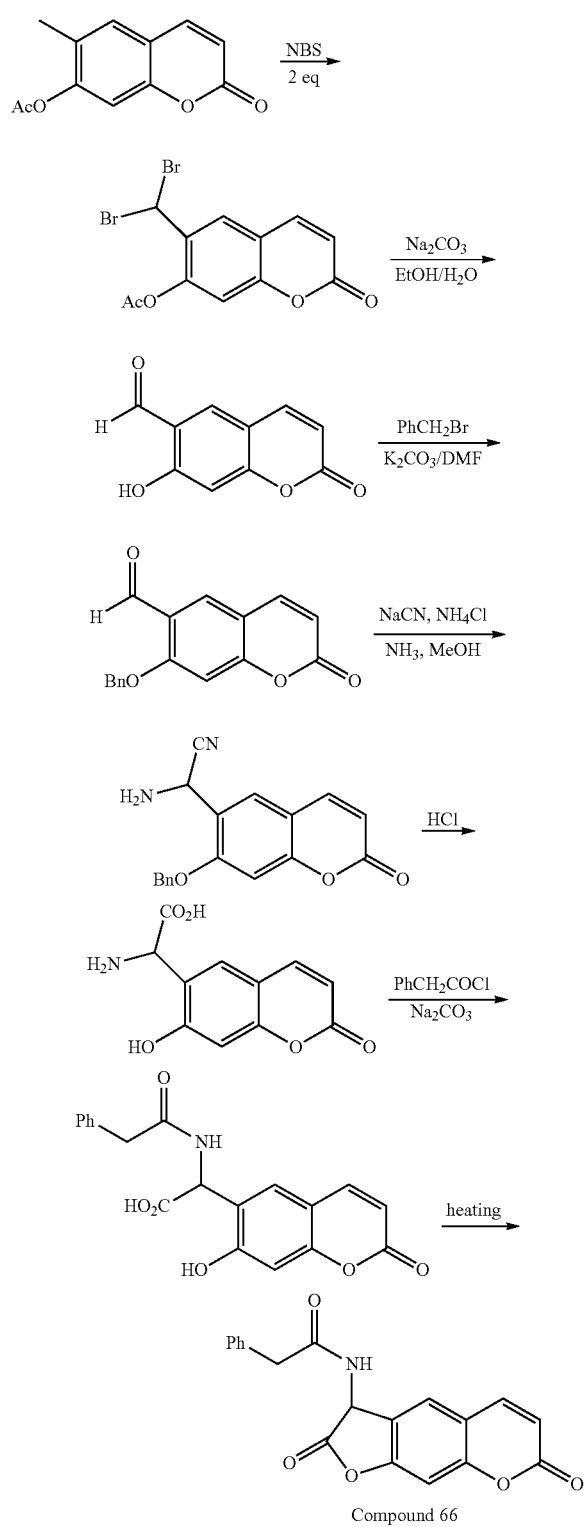

Compound 66

Example 24

Synthesis of the Peg-β-Lactamse Substrate Lacking a C2 Linker

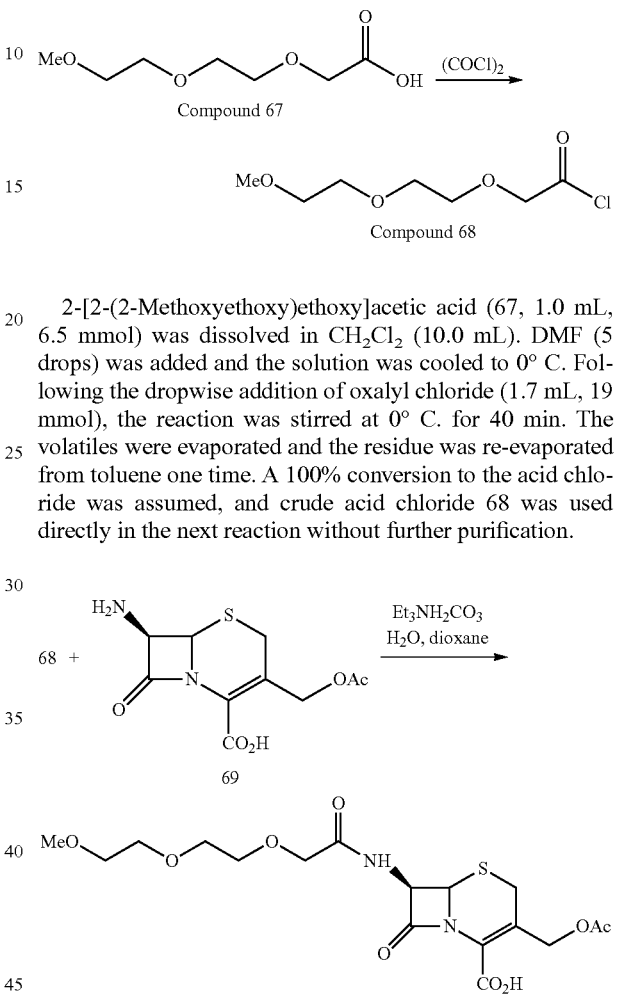

2-[2-(2-Methoxyethoxy)ethoxy]acetic acid (67, 1.0 mL, 6.5 mmol) was dissolved in $CH_2Cl_2$ (10.0 mL). DMF (5 drops) was added and the solution was cooled to 0° C. Following the dropwise addition of oxalyl chloride (1.7 mL, 19 mmol), the reaction was stirred at 0° C. for 40 min. The volatiles were evaporated and the residue was re-evaporated from toluene one time. A 100% conversion to the acid chloride was assumed, and crude acid chloride 68 was used directly in the next reaction without further purification.

7-Aminocephalosporanic acid (69, 0.44 g, 1.6 mmol) was dissolved in a 1.0 M, pH 8.5 solution of triethylammonium bicarbonate buffer (13 mL). Dioxane (10 mL) was added. Acid chloride 68 (3.2 mmol) was dissolved in dioxane (2.0 mL) and added dropwise to the 7-aminocephalosporanic acid solution. The initial clear, pale yellow solution turned white and cloudy as the acid chloride was added. After 10 min at room temperature, the white, cloudy solution was concentrated to half volume and acidified to a pH of 2 with 1 N HCl. The solution was extracted with EtOAc (15×30 mL); the EtOAc layer was checked by TLC for the presence of product. Saturated NaCl was added to the aqueous layer, and the layer was extracted with EtOAc (7×15 mL). The combined organic layers were dried over $Na_2SO_4$, filtered and concentrated. The residue was purified using column chromatography ($SiO_2$, 6:2:0.1, $CHCl_3$/MeOH/AcOH) to afford product 70 (0.69 g, 99%) as a clear, pale yellow oil. $R_f$=0.38 (6:2:0.05, $CHCl_3$/MeOH/AcOH).

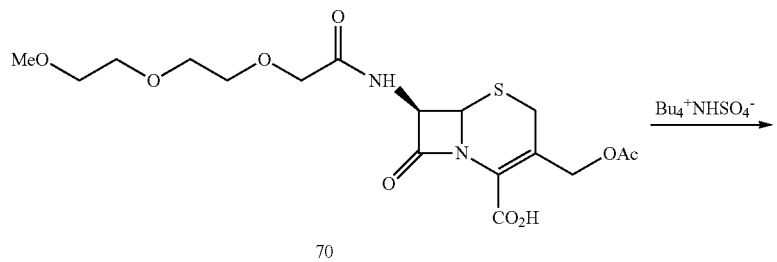

70

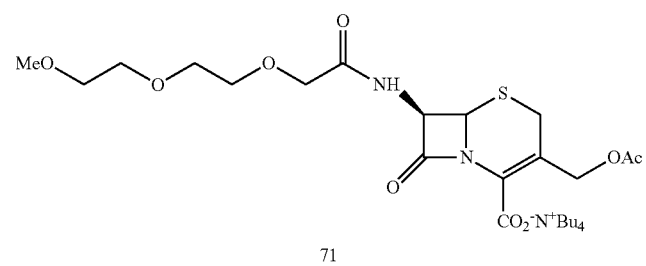

71

Intermediate 70 (1.1 g, 2.6 mmol) was dissolved in water (15 mL) and the pH was adjusted to 7.2 using saturated sodium bicarbonate. In a second flask, tetrabutylammonium bisulfate (0.90 g, 2.6 mmol) was dissolved in water (15 mL) and adjusted to a pH of 7.0 using saturated sodium bicarbonate. The two solutions were combined and the product was extracted with $CH_2Cl_2$ (15×150 mL). The combined organic solutions were dried over $Na_2SO_4$, then decanted. The solution was concentrated and 71 (1.6 g, 89%), a clear, brown oil, was used directly in the next step without further purification.

Tetrabutylammonium salt 71 (0.37 g, 0.55 mmol) was dissolved in acetonitrile (4.0 mL). Allyl bromide (0.47 mL, 5.5 mmol) was added and the solution was stirred overnight at room temperature. Following concentration of the solution, the residue was dissolved in EtOAc (50 mL), and washed sequentially with 1 N HCl (20 mL) and saturated NaCl (20 mL). The organic layer was dried over $Na_2SO_4$, decanted and concentrated. The residue was purified using column chromatography ($SiO_2$, 100% EtOAc) to afford product 72 (0.14 g, 59%) as a viscous, pale yellow oil. $R_f$=0.41 (100% EtOAc);

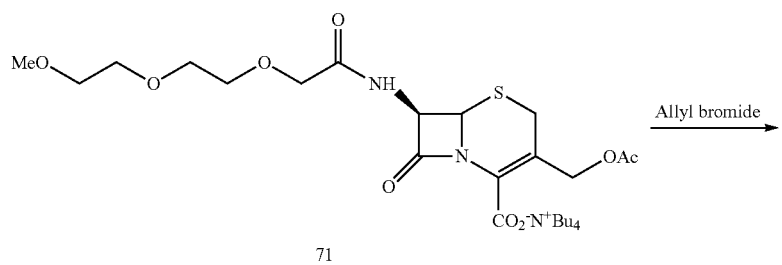

71

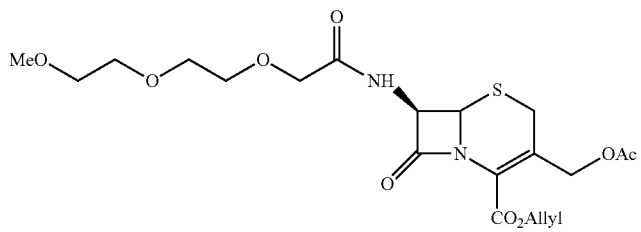

72

MS (ESI+) m/e 413.3 (M-CH$_3$CO$_2$H, C$_{18}$H$_{25}$N$_2$O$_7$S requires 413.47).

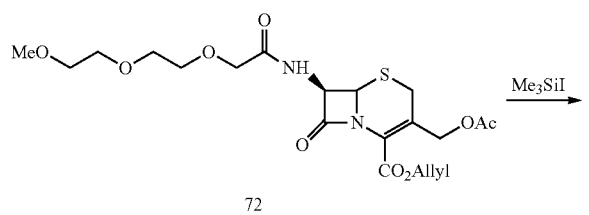

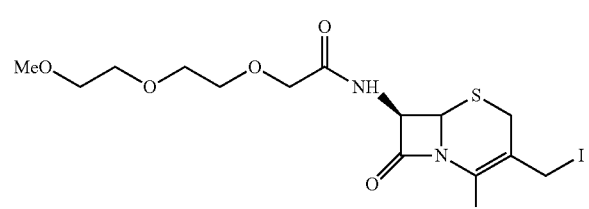

Intermediate 72 (0.25 g, 0.53 mmol) was dissolved in CH$_2$Cl$_2$ (3.0 mL) and cooled to 0° C. TMSI (0.16 mL, 1.2 mmol) was added. The reaction was stirred at 0° C. for 10 min, and then removed from the ice bath and stirred for 40 min at room temperature. Following complete consumption of the starting material, the reaction solution was diluted with EtOAc (65 mL), extracted with ice cold 5% sodium sulfite (2×25 mL) and rinsed with saturated NaCl (1×25 mL). The pale yellow organic layer was dried over Na$_2$SO$_4$, decanted and concentrated to provide crude 73 (0.18 g, 61%) that was used directly in the next reaction without further purification. R$_f$=0.50 (100% EtOAc).

Phenol 74 (0.22 g, 0.20 mmol) was suspended in DMF (5.0 mL). A 25% MeONa solution (0.11 mL, 0.48 mmol) was added and the reaction was stirred and sonicated for 15 min at room temperature. Intermediately 73 (0.25 g, 0.47 mmol) was added as a solution in DMF (3 mL) and the reaction was stirred for 1.5 h at room temperature. The solution was then diluted with 5% HCl (80 mL), and the product was extracted with EtOAc (4×50 mL). The combined extracts (which contained a white solid) was washed with water (3×30 mL), saturated NaCl (1×30 mL) and dried over Na$_2$SO$_4$. Following evaporation, the residue was mixed with CHCl$_3$ (100 mL) and stirred for 10 min, filtered and evaporated to give the product as a yellow glass. The residue was purified using column chromatography (SiO$_2$, 1:1, CHCl$_3$/EtOAc) to afford product 75 (0.13 g, 39%). MS (ESI+) m/e 719.2 (M$^+$, C$_{32}$H$_{32}$Cl$_2$N$_4$O$_9$S requires 719.59).

Preparation of Phenol 4

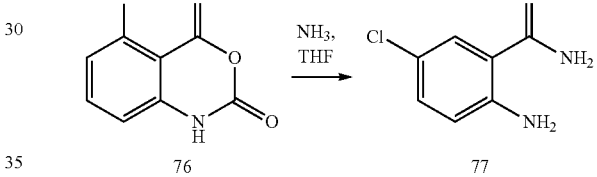

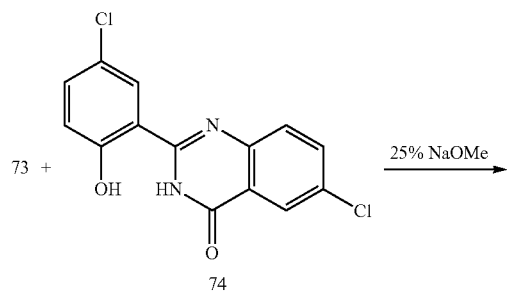

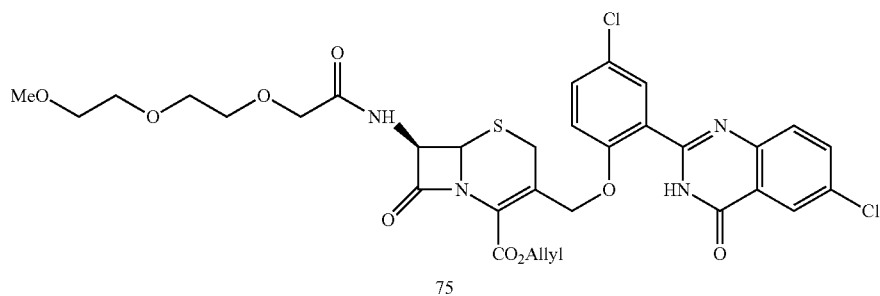

5-Chloroisatoic anhydride (76, 50.0 g, 250 mol) was suspended in anhydrous THF (660 mL). The mixture was cooled to 0° C. and dry ammonia was bubbled through the mixture for 2 h. The ice bath was removed, and the mixture warmed to room temperature. Stirring continued overnight at room temperature. The volatiles were removed in vacuo, and the residue was suspended in a 3:1 solution of water to saturated sodium bicarbonate and stirred for 30 min. The white precipitate which formed was filtered. The filtrate was back-extracted with EtOAc (3×200 mL) and the combined extracts were rinsed with brine (1×100 mL) and then dried over Na$_2$SO$_4$. The solution was concentrated. The solids were checked for purity, and when verified that they were of equal purity, combined to afford 77 as a white solid (39 g, 91%).

5-Chloroanthranilamide (77, 670 mg, 3.9 mmol) and 5-chlorosalicylaldehyde (78, 620 mg, 4.0 mmol) were added to EtOH (10 mL). p-Toluenesulfonic acid monohydrate (20 mg, 0.11 mmol) was added to the reaction mixture and the solution was refluxed 1 h. The reaction solution was cooled to 5° C. and added 2,3-dichloro-5,6-dicyano-1,4-benzoquinone (DDQ, 0.90 g, 4.0 mmol). The solution was stirred for 1 h at 5° C. A white precipitate formed, and was subsequently filtered. The precipitate was rinsed with cold EtOH (3×10 mL). Phenol 74 was obtained as a white solid (1.0 g, 83%).

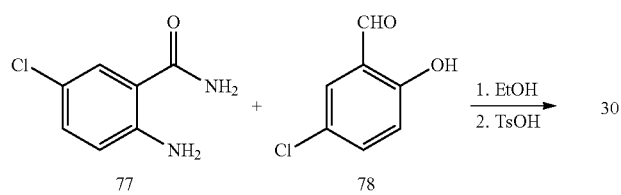

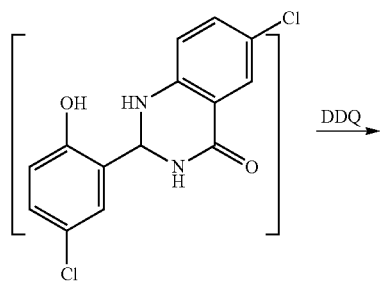

79
not isolated

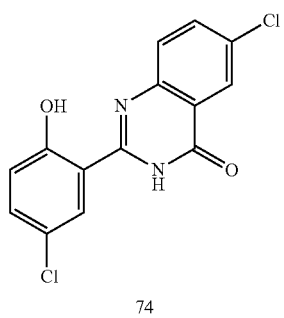

74

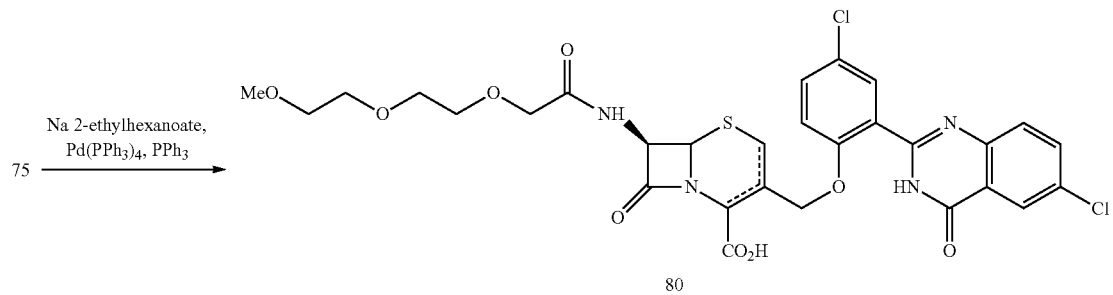

80

The allyl ester 75 (0.13 g, 0.18 mmol) was dissolved in CH$_2$Cl$_2$ (3 mL). Triphenylphosphine (5 mg, 0.02 mmol) and tetrakis(triphenylphosphine) palladium(0) (4 mg, 0.004 mmol) were added followed by the addition of sodium 2-ethylhexanoate (32 mg, 0.19 mmol) in EtOAc (2 mL). The reaction mixture was stirred for 1 h at room temperature. Acetic acid (0.1 mL) was added and the solution was evaporated to dryness. The residue was washed with hexanes (2×20 mL), and then the solid was mixed with 5% HCl (20 mL). The product was extracted with EtOAc (3×30 mL) and the combined extracts were washed with brine (20 mL), dried over Na$_2$SO$_4$ and evaporated to provide 80 (0.12 g, 99%). 2 isomers, R$_f$=0.38 and 0.50 (6:2:0.1, CHCl$_3$/MeOH/AcOH.

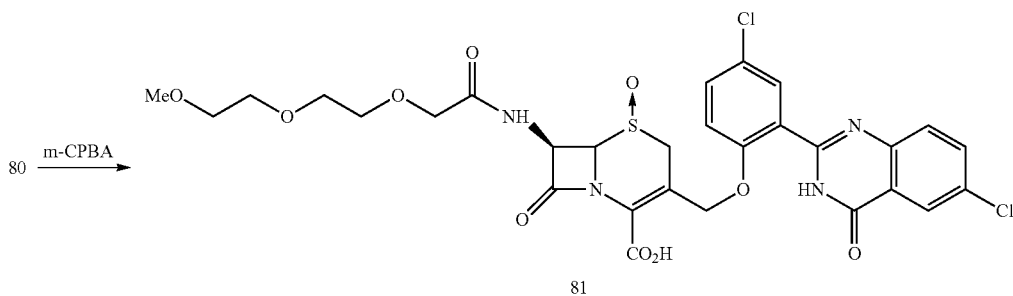

Intermediately 80 (0.12 g, 0.18 mmol) was dissolved in $CH_2Cl_2$ (30 mL) and the solution was filtered through celite. Following concentration to 4 mL, the solution was cooled in an ice/water bath. m-CPBA (77% solid, 44 mg, 0.20 mmol) in $CH_2Cl_2$ (1 mL) was added. After stirring at 5° C. for 40 min, a white precipitate was observed. The mixture was centrifuged and the supernant was removed. The solid was washed with fresh $CH_2Cl_2$ (4 mL) and centrifuged again. After removing the supernant, 81 was obtained as a yellow powder (38 mg, 30%). MS (ESI+) m/e 695.0 ($M^+$, $C_{29}H_{28}Cl_2N_4O_{10}S$ requires 695.52).

Example 25

Synthesis of the Peg-β-Lactamse Substrate Containing a C2 Linker

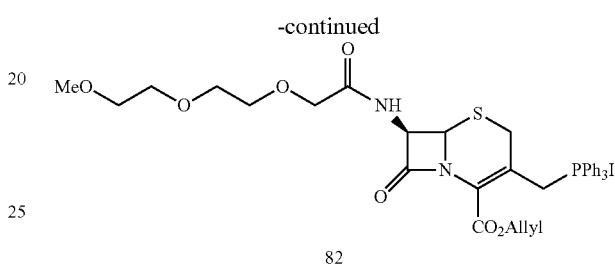

Intermediately 73 (0.15 g, 0.28 mmol) was dissolved in EtOAc (1.0 mL) at room temperature. A solution of triphenylphospine (73 mg, 0.28 mmol) in EtOAc (0.5 mL) was added and the reaction solution was stirred at room temperature for 2.5 h. The initial clear, orange solution turned cloudy as the triphenylphosphine was added and a sticky orange precipitate was observed. The solution was decanted and the filtrate obtained was resubjected to stirring at room temperature. After 1 h, the solution was decanted again and the solids obtained were combined. The decanted solution was concentrated to a few milliliters and let to sit at room temperature for another 30 min. After that time, the solution was again decanted. The combined orange precipitates, 82, (0.12 g, 52%) obtained were used without purification in the next reaction.

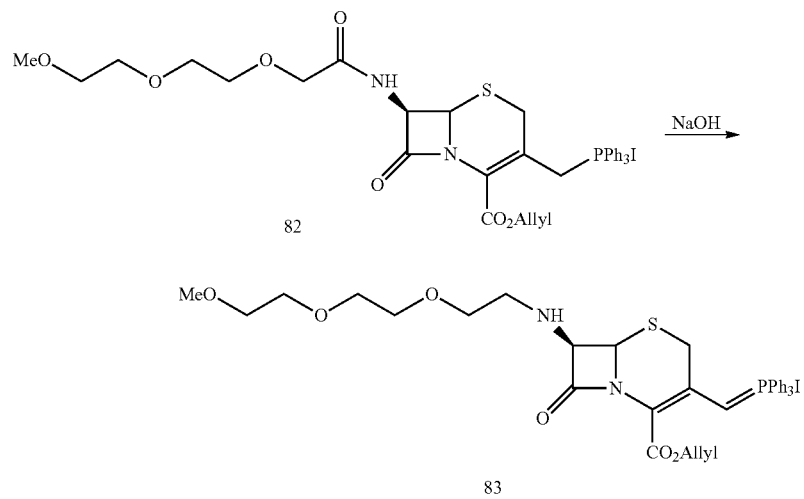

Compound 82 (0.081 g, 0.10 mmol) was dissolved in CH$_2$Cl$_2$ (2.6 mL). An aqueous solution of 1 N NaOH (0.9 mL) was added and the solution was stirred vigorously at room temperature for 40 min. The organic solution was separated from the aqueous solution. The aqueous layer was back-extracted with CH$_2$Cl$_2$ (5×10 mL). The organic layer was dried over MgSO$_4$, decanted and concentrated to a few mLs. A 100% conversion was assumed and intermediate 83 was used without further purification in the next reaction.

To a solution of 83 (0.10 mmol) was added a solution of aldehyde 84 (45 mg, 0.13 mmol) in CH$_2$Cl$_2$ (2.6 mL); the mixture was stirred overnight at room temperature. The solvent was removed via evaporation, and the residue was purified using column chromatography (SiO$_2$, 5:1, CHCl$_3$/EtOAc, followed by rinsing with 100% EtOAc which eluted the pure product) to afford 85 (17 mg, 23%) as a yellow solid. R$_f$=0.25 (6:1:0.05, CHCl$_3$/MeOH/AcOH); MS (ESI+) m/e 745.8 (M$^+$, C$_{34}$H$_{34}$Cl$_2$N$_4$O$_9$S requires 745.6).

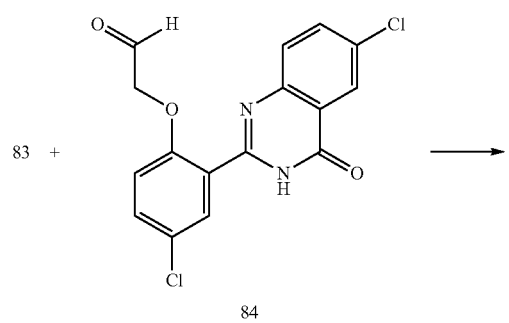

83 +

84

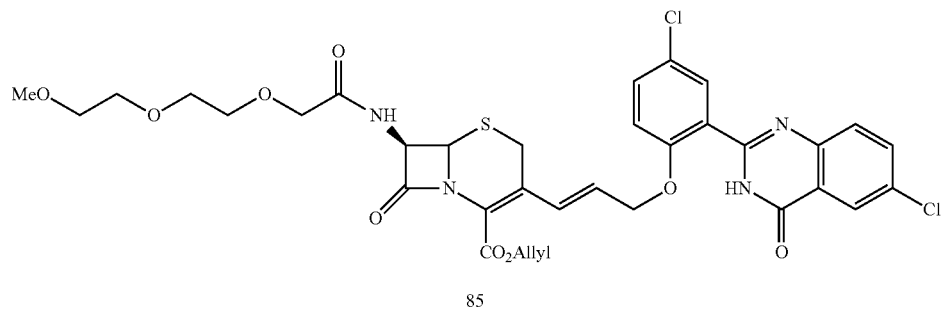

85

Preparation of Aldehyde 84

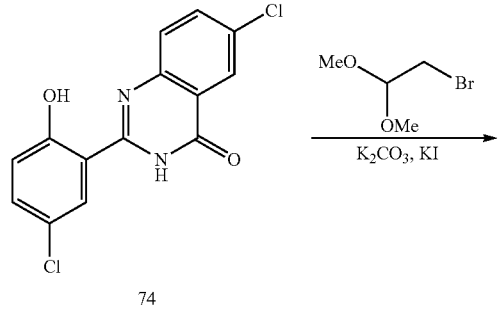

74

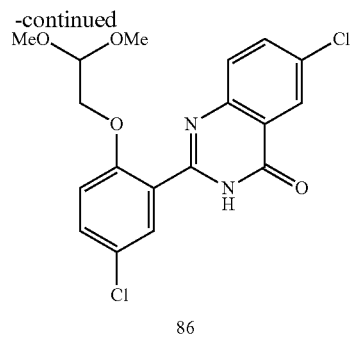

86

Phenol 74 (1.0 g, 3.3 mmol) was dissolved in DMF (75 mL) and bromoacetaldehyde dimethyl acetal (1.9 mL, 16 mmol), potassium carbonate (2.3 g, 16 mmol) and potassium iodide (0.5 g, 3.0 mmol) were added. The reaction was refluxed at 95° C. for 5 days. The reaction solution was removed from the oil bath and allowed to cool to room temperature. The solution was partitioned between EtOAc (300 mL) and water (100 mL). The aqueous layer was then re-extracted with EtOAc (2×250 mL) and the combined organic layers were dried over $Na_2SO_4$, decanted and concentrated. The residue was purified using column chromatography ($SiO_2$, loaded with 100% $CHCl_3$, eluted with 6:1 $CHCl_3$/EtOAc) to afford 86 (0.25 g, 20%) as an orange solid. $R_f$=0.27 (1:1, $CHCl_3$/EtOAc); MS (ESI+) m/e 395.2 (M+, $C_{18}H_{16}Cl_2N_2O_4$ requires 395.24).

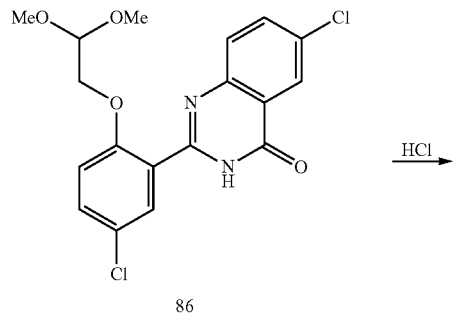

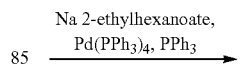

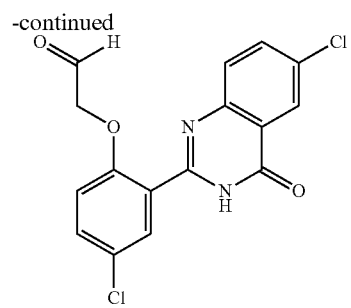

To a solution of 86 (0.28 g, 0.70 mmol) in dioxane (11 mL) was added concentrated HCl (3.5 mL). After stirring the reaction at room temperature for 20 min, the solution was diluted with water (200 mL) and extracted with EtOAc (3×100 mL). The combined organic layers were rinsed with water (1×200 mL), saturated sodium bicarbonate (1×200 mL) and brine (1×200 mL). After drying over $Na_2SO_4$, the solution was decanted and concentrated. Aldehyde 84 (a yellow solid, 0.19 g, 76%), was used directly in the next reaction without further purification. $R_f$=0.29 (100% EtOAc).

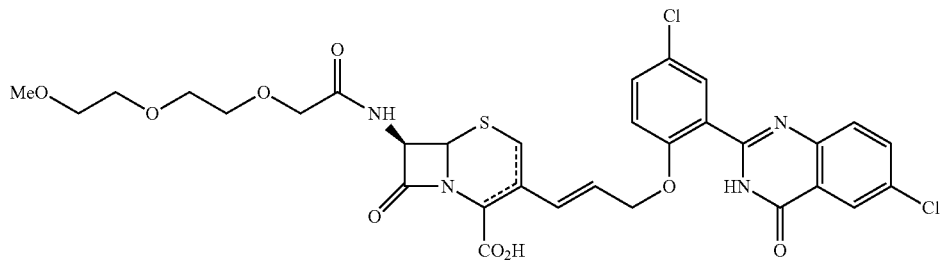

Allyl ester 85 (0.11 g, 0.15 mmol) was dissolved in dry $CH_2Cl_2$ (1.2 mL). Triphenylphosphine (4.6 mg, 0.02 mmol), tetrakis(triphenylphosphine) palladium(0) (3.4 mg, 0.003 mmol) were added. Sodium 2-ethylhexanoate (0.024 g, 0.15 mmol) was dissolved in EtOAc (0.5 mL) and added to the reaction solution. After stirring at room temperature 7 h, the solution was quenched with AcOH (7.0 mL), evaporated and then re-evaporated from toluene twice. The solid was washed with hexanes multiple times, then dissolved in EtOAc and rinsed with 1% HCl. The organic layer was separated and the aqueous layer was back-extracted with EtOAc (5 times). The combined organics were rinse with saturated NaCl and dried over $Na_2SO_4$. The resulting yellow solution was concentrated and 87 (an orange solid, 43 mg, 41%) was used directly in the next reaction without further purification. $R_f$=0.37 (6:1:0.05, $CHCl_3$/MeOH/AcOH); MS (ESI+) m/e 704.97 (M+, $C_{31}H_{29}Cl_2N_4O_9S$ requires 704.55).

87 →(m-CPBA)

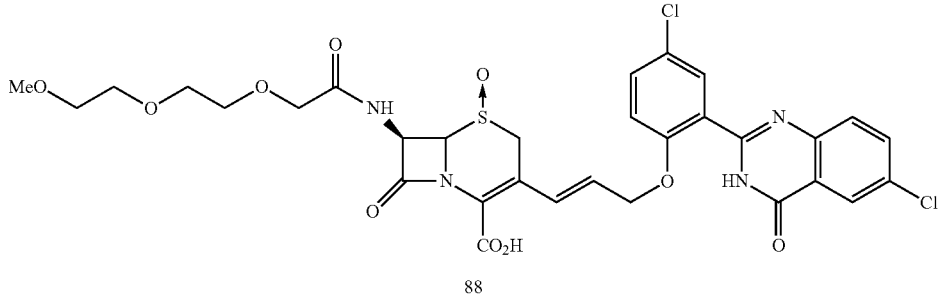

88

Acid 87 (43 mg, 0.061 mmol) was dissolved in CH$_2$Cl$_2$ (3.0 mL) and cooled to 0° C. m-Chloroperbenzoic acid (m-CPBA, 10 mg, 0.061 mmol) was dissolved in CH$_2$Cl$_2$ (0.5 mL) and added to the solution. The orange solution was stirred at 0° C. for 2 h and a white precipitate was observed. The solution was centrifuged and the solution decanted to provide the product as a white-yellow solid. The resulting reaction solution and crude product were further purified by HPLC (Xterra MS C8, internal diameter 2.1 mm, eluent 20-60% CH$_3$CN, 10 mM NH$_4$OAc, pH 4.7, flow rate of 0.2 mL/min) to provide the 88 ($t_R$=14.0 min, 7 mg, 16%). MS (ESI+) m/e 721.7 (M$^+$, C$_{31}$H$_{30}$Cl$_2$N$_4$O$_{10}$S requires 721.56).

Example 26

Preparation of o,o'-Di-{3-[2-carboxy-5,8-dioxo-7-(2-thiophen-2-yl-acetylamino)-5λ$^4$-thia-1-aza-bicyclo[4.2.0]oct-2-en-3-yl]-allyl}-2',7'-dichlorofluorescein (Compound 100).

2-(2,7-Dichloro-3,6-dihydroxy-9H-xanthen-9-yl)-benzoic acid (Compound 89).

2',7'-Dichlorofluorescein (2.0 g, 5.0 mmol) was dissolved in 80 mL of THF, containing 2 mL of acetic acid. Zn (powder, 8.0 g, 122 mmol) was added portionwise (0.5 g with ~15 min intervals) to the solution of 2',7'-Dichlorofluorescein. After all amount of Zn was added the reaction mixture was stirred overnight. All solids have been filtered off, washed with THF and evaporated. The residue was re-dissolved in ethyl acetate (120 mL) and washed with water (2×30 mL), brine (30 mL), dried over sodium sulfate and evaporated. The crude product (~2.0 g, oil) was used for the next step without further purification.

2-[3,6-Bis-(2,2-dimethoxy-ethoxy)-2,7-dichloro-9H-xanthen-9-yl]-benzoic acid 2,2-dimethoxy-ethyl ester (Compound 90)

Phenol 89 (~5 mmol of the crude product) was dissolved in 80 mL of DMF. Powdered K$_2$CO$_3$ (6.9 g, 50 mmol) was added to the solution followed by BrCH$_2$CH(OMe)$_2$ (8.8 mL, 75 mmol). The reaction mixture was stirred at ~120° C. for 6 hrs, then concentrated in vacuum. The residue was mixed with 100 mL of water and extracted with ethyl acetate (100 mL, then 2×30 mL). The combined extracts were washed with water (30 mL), brine (30 mL), dried over sodium sulfate and evaporated. The crude product was re-dissolved in chloroform and loaded on silica gel column (packed in 100:3 chloroform-ethyl acetate). The column was eluted with 100:3 chloroform-ethyl acetate mixture. Pure fractions containing ester 90 were combined and evaporated to give desired product (2.62 g, 79%) as viscous oil which solidified later.

2-[3,6-Bis-(2,2-dimethoxy-ethoxy)-2,7-dichloro-9H-xanthen-9-yl]-benzoic acid (Compound 91)

Ester 90 (2.62 g, 3.93 mmol) was dissolved in 260 mL of dioxane. 80 mL of water and 40 mL 1M KOH was added to the solution and the mixture was stirred overnight at RT. The reaction mixture was concentrated in vacuum to the volume ~150 mL and acidified with 10% HCl. The product was extracted with ethyl acetate (2×70 mL). The combined extracts were washed with water (3×30 mL), brine (30 mL), dried over sodium sulfate and evaporated to give acid 91 as a yellow solid (2.27 g, quant.). The material was used for the next step without any purification o,o'-Di-(2,2-dimethoxyethyl)-2',7'-dichlorofluorescein (Compound 92)

Carboxylic acid 91 (2.35 g, 4.06 mmol) was dissolved in 100 mL of chloroform. The solution was diluted with 100 mL of methanol and then tetrachloro-1,4-benzoquinone (1.99 g, 8.09 mmol) was added to the solution. The reaction mixture was stirred under reflux for 7 hrs and concentrated in vacuum. The crude product was loaded on silica gel column (packed in 100:1 chloroform-ethyl acetate mixture) as a suspension in chloroform. The column was eluted with 50:2 chloroform-ethyl acetate mixture. Fractions containing substituted fluorescein 92 were combined and evaporated to give 92 as a yellow solid (2.0 g. 85%).

o,o'-Di-(2-oxoethyl)-2',7'-dichlorofluorescein (Compound 93)

Protected aldehyde 92 (0.30 g, 0.52 mmol) was dissolved 10 mL of dioxane. Conc. HCl (3 mL) was added and the mixture was stirred for 40 min at RT. Then it was diluted with 80 mL of water and the product was extracted with ethyl acetate (4×30 mL). The combined extracts were washed with water (30 mL), brine (30 mL), dried over sodium sulfate and evaporated. The residue was re-dissolved in ethyl acetate and loaded on silica gel column (packed in ethyl acetate). The column was eluted with ethyl acetate. Pure fractions containing the product were combined and solvent was evaporated to give aldehyde 93 as a yellow glass (0.26 g, quant.).

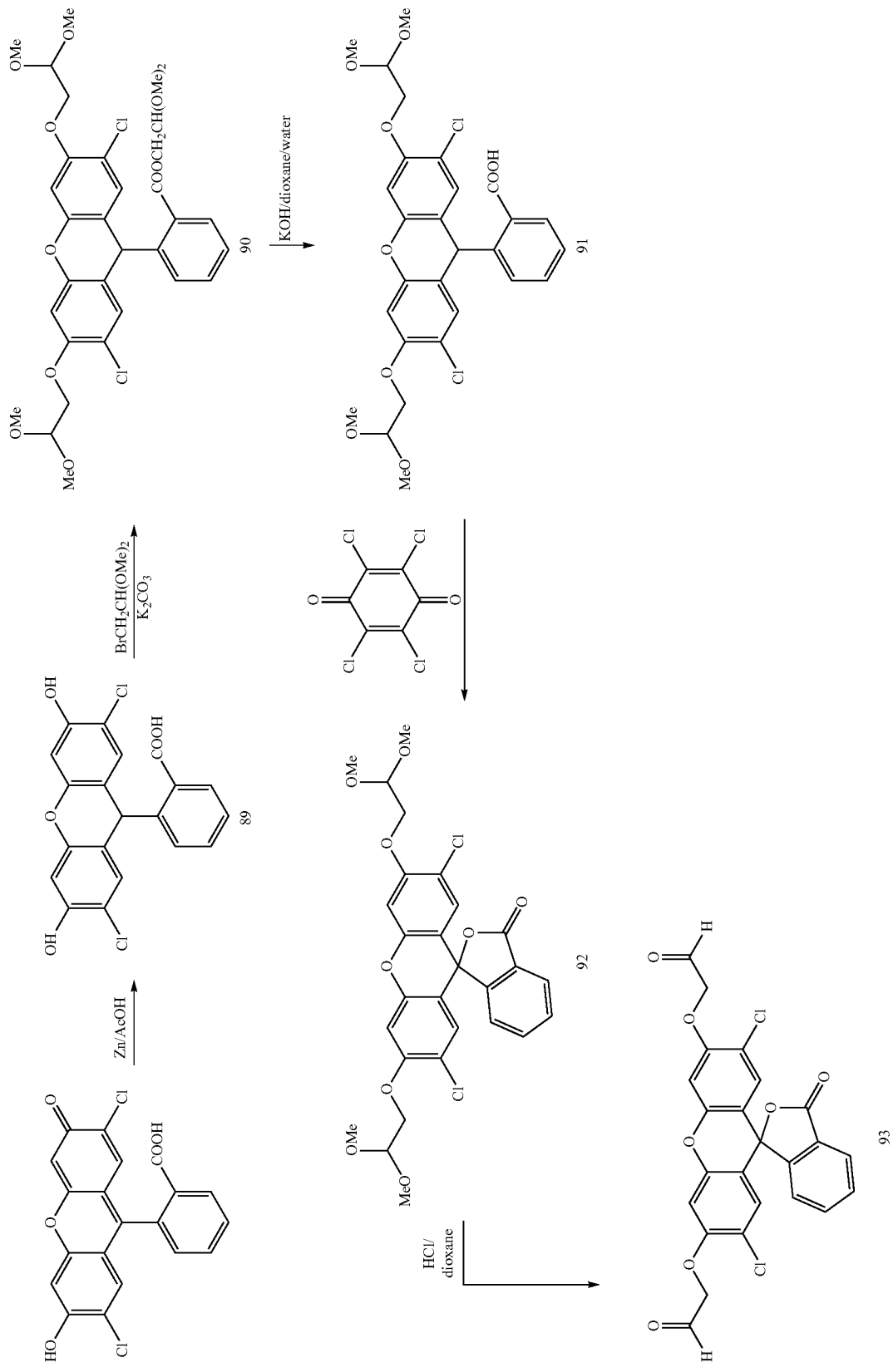

3-Acetoxymethyl-8-oxo-7-(2-thiophen-2-yl-acetylamino)-5-thia-1-aza-bicyclo[4.2.0]oct-2-ene-2-carboxylic acid allyl ester (Compound 95)

Tetrabutylammonium hydrogensulfate (7.40 g, 21.8 mmol) was dissolved in 50 mL of water and pH of solution was adjusted to 7.0 using conc. NaHCO$_3$. Cephalothune sodium salt 94 (9.12 g, 21.8 mmol) was added to the solution and tetrabutylammonium salt was extracted with methylene chloride (6×60 mL+8×30 mL). The combined extracts were dried over sodium sulfate and concentrated in vacuum. The residue was re-dissolved in acetonitrile (400 mL) and then allyl bromide (18.8 mL, 218 mmol) was added to the solution. The reaction mixture was stirred overnight at RT and evaporated. The residue was re-dissolved in ethyl acetate (400 mL) and washed with 1% HCl (2×50 mL), water (50 mL), brine (50 mL) and dry over sodium sulfate to give allyl ester 95 as a white solid (9.55 g, quant.).

3-Iodomethyl-8-oxo-7-(2-thiophen-2-yl-acetylamino)-5-thia-1-aza-bicyclo[4.2.0]oct-2-ene-2-carboxylicacid allyl ester (Compound 96)

Acetate 95 (3.00 g, 6.88 mmol) was dissolved in 15 mL of dry methylene chloride and solution was cooled using ice/water bath. Trimethylsilyl iodide was added to the solution and reaction mixture was stirred for ~20 min on ice/water bath and then ~40 min at RT. The solution was diluted with 120 mL of ethyl acetate and washed with 10% Na$_2$S$_2$O$_3$ solution (2×40 mL), sat. NaHCO$_3$ solution (2×40 mL), brine (40 mL) and dried over sodium sulfate. The crude product was re-dissolved in chloroform and loaded on silica gel column (packed in chloroform). The column was eluted with 6:1 chloroform-EtOAc mixture. Pure fractions containing product were combined and the solvent was evaporated to give iodide 96 as a yellow solid (2.69 g, 77%).

[2-Allyloxycarbonyl-8-oxo-7-(2-thiophen-2-yl-acetylamino)-5-thia-1-aza-bicyclo[4.2.0]oct-2-en-3-ylmethyl]-triphenyl-phosphonium iodide (Compound 97).

Iodide 96 (2.69 g, 5.34 mmol) was dissolved in 15 mL of ethyl acetate. Triphenylphosphine (1.68 g, 6.40 mmol) was added as a solution in 6 mL of ethyl acetate. The resulting mixture was stirred for 35 min at RT. Yellow precipitate was collected on fritted glass funnel, washed with ethyl acetate (3×10 mL) and dried in vacuum to give phosphonium salt 97 as a yellow powder (2.82 g, 69%).

o,o'-Di-{3-[2-allyloxycarbonyl-8-oxo-7-(2-thiophen-2-yl-acetylamino)-5-thia-1-aza-bicyclo[4.2.0]oct-2-en-3-yl]-allyl}-2',7'-dichlorofluorescein (Compound 98)

Phosphonium salt 97 (0.57 g, 0.744 mmol) was dissolved in 40 mL of methylene chloride. 1M KOH (7.4 mL, 7.4 mmol) was adde to the solution and the mixture was stirred for 30 min at RT. Organic layer was separated, dried over magnesium sulfate and filtered. The resulting solution was added to the flask containing freshly prepared aldehyde 93 (0.120 g, 0.248 mmol). The reaction mixture was stirred overnight at RT and then concentrated in vacuum. The crude product was dissolved in chloroform and loaded on silica gel column (packed in chloroform). The column was eluted with 3:1 chloroform-EtOAc mixture. Fractions containing pure product were combined and evaporated to obtain 98 as yellow foam (0.100 g, 11%).

o,o'-Di-{3-[2-carbxy-8-oxo-7-(2-thiophen-2-yl-acetylamino)-5-thia-1-aza-bicyclo[4.2.0]oct-2-en-3-yl]-allyl}-2',7'-dichlorofluorescein (Compound 99)

Allyl ester 98 (0.050 g, 0.041 mmol) was dissolved in 2 mL of methylene chloride. Triphenylphosphine (0.0026 g, 0.0.0099 mmol) and tetrakis(triphenylphosphine)palladium (0) (0.0019 g, 0.0016 mmol) were added to solution followed by adding of sodium 2-ethylhexanoate (0.015 g, 0.090 mmol) dissolved in 15 mL of EtOAc. The reaction mixture was stirred for 40 min at RT and then acetic acid (0.2 mL) was added. The reaction mixture was concentrated in vacuum and re-evaporated from toluene. The residue was washed with hexanes (2×30 mL) and dried in vacuum. The resulting solid was mixed with 10 mL of 1% HCl and extracted with ethyl acetate (4×20 mL). The organic solution was washed with brine (30 mL), dried over sodium sulfate and evaporated to give acid 99 as a brown glass (0.05 g, quant.).

o,o'-Di-(3-(2-carboxy-5,8-dioxo-7-(2-thiophen-2-yl-acetylamino)-5$\lambda^4$-thia-1-aza-bicyclo[4.2.0]oct-2-en-3-yl)-allyl-2',7'-dichlorofluorescein (Compound 100)

Acid 99 (0.05 g, 0.044 mmol) was sonicated with 3 mL of methylene chloride and filtered. The solution was cooled using ice/water bath. m-Chloroperoxybenzoic acid (77% pure, 0.022 g, 0.098 mmol) was added as a solution in 1 mL of methylene chloride. The resulting mixture was stirred for 30 min in ice/water bath and then put on centrifuge for 15 min. Supernatant was discarded and centrifugation was repeated twice with fresh 2 mL of methylene chloride. Solid was dried in vacuum and then washed with 0.5 mL of methanol. The mixture was put on centrifuge for 10 min, supernatant was discarded. Repeated two times with 0.5 mL of methanol. After that, solid was dried in vacuum to give sulfoxide 100 as yellow powder (0.008 g, 16%).

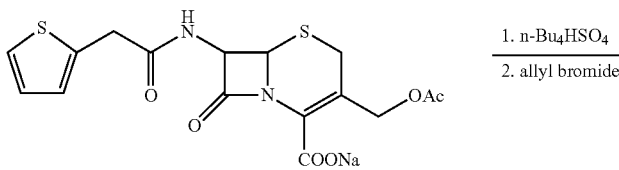

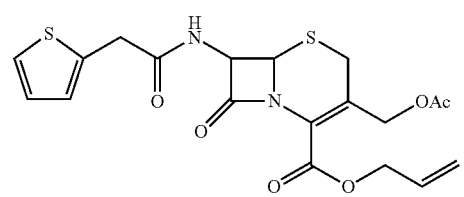

151
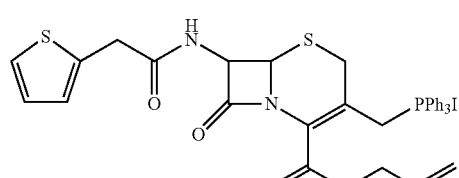
97
152
-continued
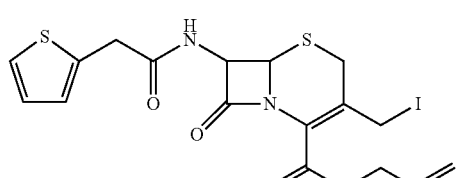
96
PPh₃
6/NaOH
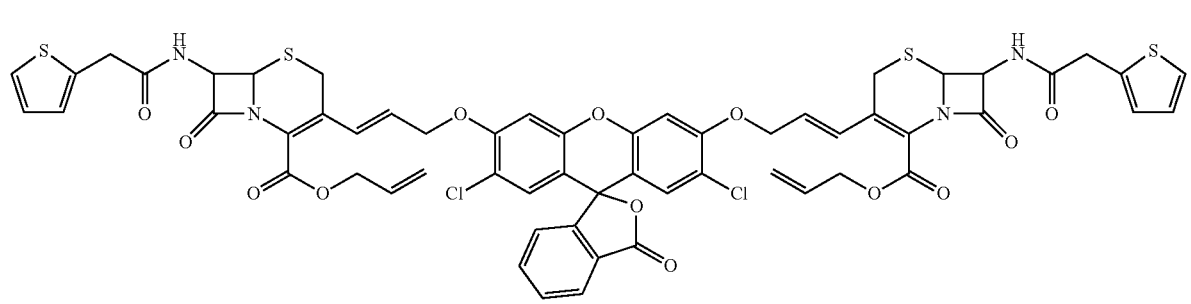
98
PPh₃/Pd(PPh₃)₂/
sodium 2-ethylhexanoate
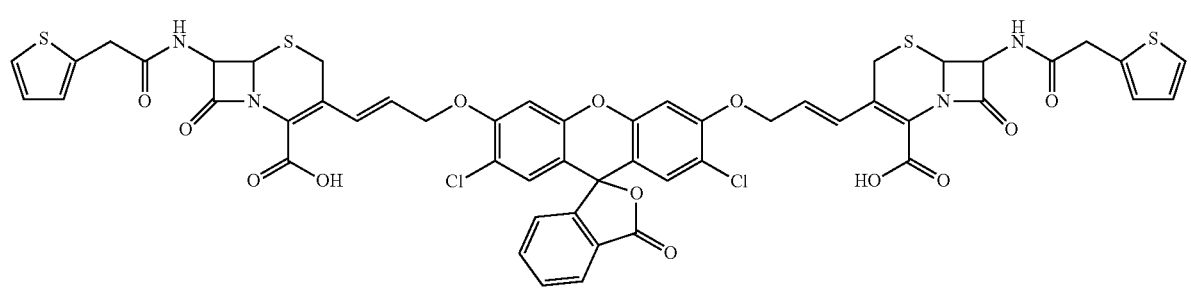
99
m-C₆H₄CO₃H
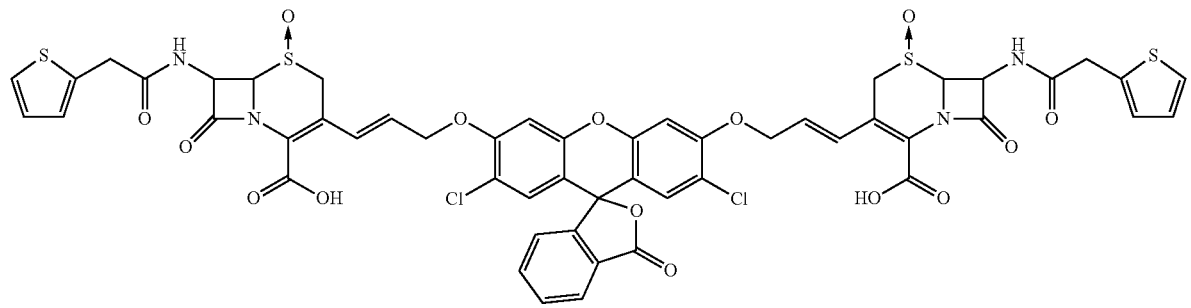
100

Example 27

Preparation of o,o'-Di-{3-[2-carboxy-5,8-dioxo-7-(2-thiophen-2-yl-acetylamino)-5λ$^4$-thia-1-aza-bicyclo[4.2.0]oct-2-en-3-yl]-allyl}-2',7'-difluorofluorescein (Compound 108)

2-(2,7-difluoro-3,6-dihydroxy-9H-xanthen-9-yl)-benzoic acid (Compound 101)

2',7'-Difluoroscein (4.0 g, 10.9 mmol) was suspended in 330 mL of THF containing 10 mL of acetic acid. Zinc powder (30 g, 460 mmol) was added to the suspension portionwise during 4 hrs at RT with vigorous stirring under nitrogen. Zinc was filtered off using glass fritted funnel, washed with THF (4×30 mL). Combined washings and solution were evaporated. The residue was mixed with 150 mL of 5% HCl, the product was extracted with EtOAc (4×40 mL). The combined extracts were washed with water (30 mL), brine (30 mL), dried over sodium sulfate and evaporate to give acid 101 (yellow oil, about 7 g). It was used for the next step without further purification.

2-[3,6-Bis-(2,2-dimethoxy-ethoxy)-2,7-difluoro-9H-xanthen-9-yl]-benzoic acid 2,2-dimethoxy-ethyl ester (Compound 102)

Acid 101 (all material prepared in the previous step, ~10.9 mmol) was dissolved in 150 mL of DMF. Powdered $K_2CO_3$ (25 g, 180 mmol) was added to the solution followed by adding of bromoacetaldehyde dimethyl acetal (33.3. mL, 283 mmol). The reaction mixture was stirred overnight at 110° C. DMF solution was removed from the flask (leaving insoluble material in the flask) and evaporated. The residue was mixed with 150 mL of water and combined with the solid left in the flask. The product was extracted with ethyl acetate (4×45 mL), combined extracts were washed with water (4×30 mL), brine (30 mL), dried over sodium sulfate and evaporated in vacuum. The residue was dissolved in chloroform, loaded on silica gel column (packed in 100:3 chloroform-EtOAc mixture). The column was eluted with 100:3 chloroform-EtOAc mixture. Pure fractions containing the product were combined and evaporated to give ester 102 as a clear oil, solidified later to form white solid (4.54 g, 66%).

2-[3,6-Bis-(2,2-dimethoxy-ethoxy)-2,7-difluoro-9H-xanthen-9-yl]-benzoic acid (Compound 103)

Ester 102 (4.54 g, 7.12 mmol) was dissolved in 470 mL of 1,4-dioxane. Water (144 mL) and 1M KOH (72 mL) were added to the solution. The reaction mixture was stirred overnight at RT and then concentrated in vacuum to ~200 mL. 5% HCl (~100 mL) was added and, the product was extracted with EtOAc (4×50 mL). The combined extracts were washed with water (3×30 mL), brine (40 mL), dried over sodium sulfate and evaporate to give acid 103 as a white solid (3.918 g, quant.).

o,o'-Di-(2,2-dimethoxyethyl)-2',7'-difluorofluorescein (Compound 104)

Acid 103 (3.92 g, 7.18 mmol) was dissolved in 100 mL of chloroform and 80 mL of methanol. p-Chloranil (3.53 g, 14.4 mmol) was added to solution and the mixture was stirred under reflux for ~6 hrs. Solvents were removed in vacuum, the residue was suspended in chloroform and loaded on silica gel column (packed in 100:1 chloroform-EtOAc mixture). The column was eluted with 25:1 chloroform-EtOAc mixture, fractions containing the product were combined and evaporated in vacuum. The residue was re-purified on silica gel column (packed in chloroform) using first chloroform and then 50:1 chloroform-EtOAc mixture to remove impurities. The product was eluted with 25:1 chloroform-EtOAc. Pure fractions were combined and solution evaporated to give pure 104 as a white solid (3.86 g, 98%).

o,o'-Di-(2-oxoethyl)-2',7'-difluorofluorescein (Compound 105)

Protected aldehyde 104 (0.50 g, 0.92 mmol) was dissolved in 20 mL of dioxane. Conc. HCl (6 mL) was added and the mixture was vigorously stirred for 40 min at RT. Then it was diluted with 150 mL of water, and the product was extracted with EtOAc (40, 3×30 mL). The combined extracts were washed with water (4×30 mL), brine (30 mL), dried over sodium sulfate and evaporated. The residue was dissolved in EtOAc and loaded on silica gel column (packed in EtOAc). The column was eluted with EtOAc. Pure fractions were combined and the solvent was evaporated to give aldehyde 105 as a clear glass (0.436 g, quant.).

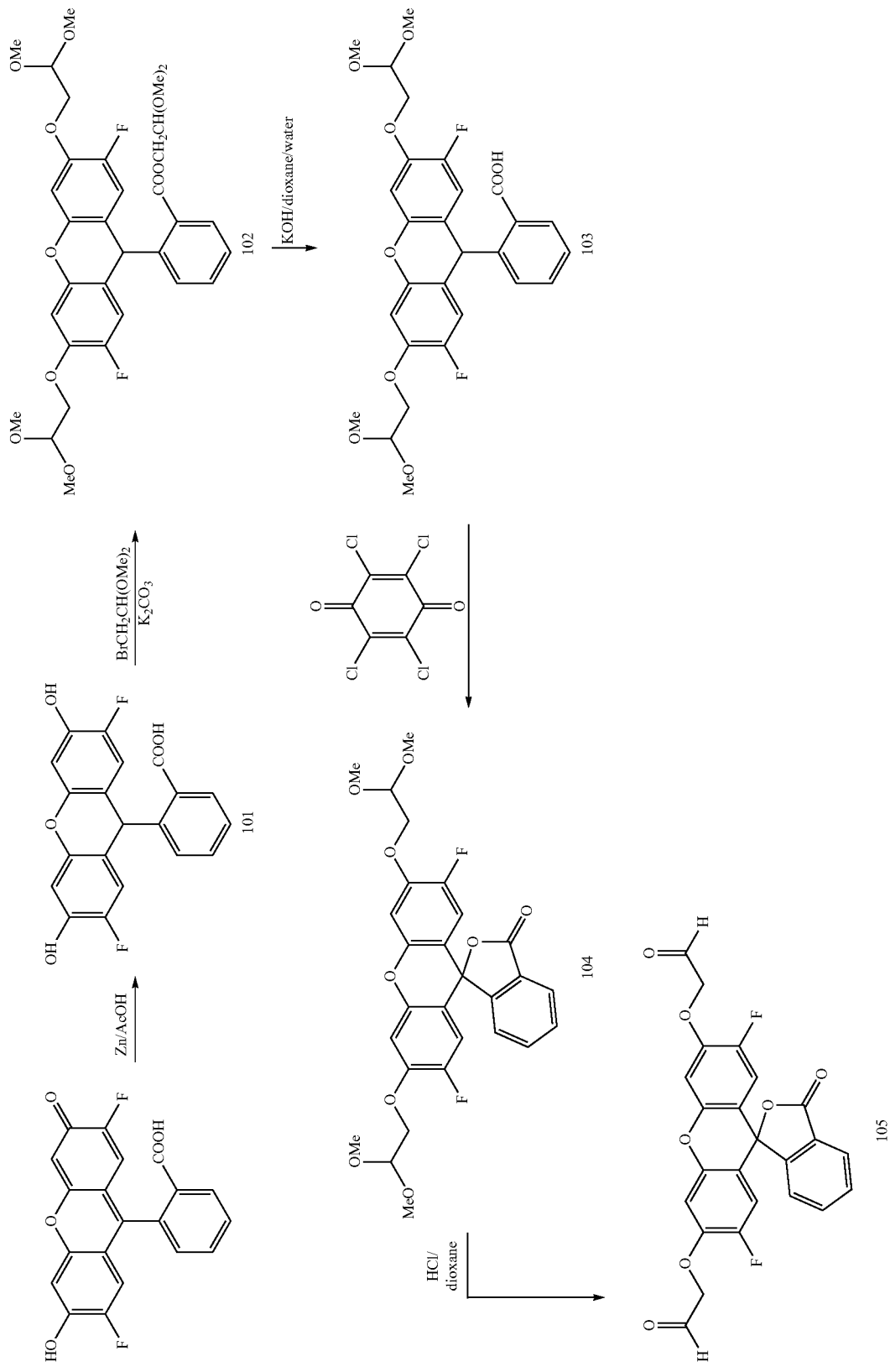

o,o'-Di-{3-[2-allyloxycarbonyl-8-oxo-7-(2-thiophen-2-yl-acetylamino)-5-thia-1-aza-bicyclo[4.2.0]oct-2-en-3-yl]-allyl}-2',7'-difluorofluorescein (Compound 106)

Phosphonium salt 97 (2.82 g, 3.68 mmol) was dissolved in 80 mL of methylene chloride. 1M NaOH (41 mL, 41 mmol) was added to the solution and reaction mixture was stirred for 30 min at RT. Organic layer was separated, dried over magnesium sulfate and filtered. The resulting solution was added to the flask containing freshly prepared aldehyde 105 (0.616 g, 1.36 mmol). The reaction mixture was stirred overnight at RT and then concentrated in vacuum. The crude product was dissolved in chloroform and loaded on silica gel column (packed in chloroform). The column was eluted with 3:1 chloroform-EtOAc mixture. Fractions containing pure product were combined and evaporated to obtain 106 as yellow foam (0.807 g, 50%).

o,o'-Di-{3-[2-carboxy-8-oxo-7-(2-thiophen-2-yl-acetylamino)-5-thia-1-aza-bicyclo[4.2.0]oct-2-en-3-yl]-allyl}-2',7'-difluorofluorescein (Compound 107)

Allyl ester 106 (0.775 g, 0.661 mmol) was dissolved in 26 mL of dry methylene chloride. Triphenylphosphine (0.042 g, 0.16 mmol) and tetrakis(triphenylphosphine)palladium(0) (0.030 g, 0.026 mmol) were added to solution followed by adding of sodium 2-ethylhexanoate (0.243 g, 1.46 mmol) dissolved in 15 mL of EtOAc. The reaction mixture was stirred for 40 min at RT and then acetic acid (1 mL) was added. The reaction mixture was concentrated in vacuum and re-evaporated from toluene. The residue was washed with hexanes (2×30 mL) and dried in vacuum. The resulting solid was mixed with 80 mL of 1% HCl and extracted with ethyl acetate (2×40 mL). All insoluble in ethyl acetate/1% HCl brown material was dissolved in 10:1 ethyl acetate-methanol mixture and solution combined with EtOAc extracts. The organic solution was washed with brine (30 mL), dried over sodium sulfate and evaporated to give acid 107 as a brown glass (0.755 g, quant).

o,o'-Di-(3-(2-carboxy-5,8-dioxo-7-(2-thiophen-2-yl-acetylamino)-5$\lambda^4$-thia-1-aza-bicyclo[4.2.0]oct-2-en-3-yl)-allyl-2',7'-difluorofluorescein (Compound 108)

Acid 107 (0.755 g, 0.690 mmol) was sonicated with 100 mL of methylene chloride and filtered. The solution was concentrated at 30° C. until fine precipitate start to form and then cooled using ice/water bath. m-Chloroperoxybenzoic acid (77% pure, 0.341 g, 1.52 mmol) was added as a solution in 5 mL of methylene chloride. The resulting mixture was stirred for 30 min in ice/water bath and then put on centrifuge for 15 min. Supernatant was discarded and centrifugation was repeated twice with fresh 8 mL of methylene chloride. Solid was dried in vacuum and then washed with 2 mL of methanol. The mixture was put on centrifuge for 10 min, supernatant was discarded. Repeated two times with 2 mL of methanol. After that solid was dried in vacuum to give sulfoxide 108 as a yellow powder (0.219 g, 28%).

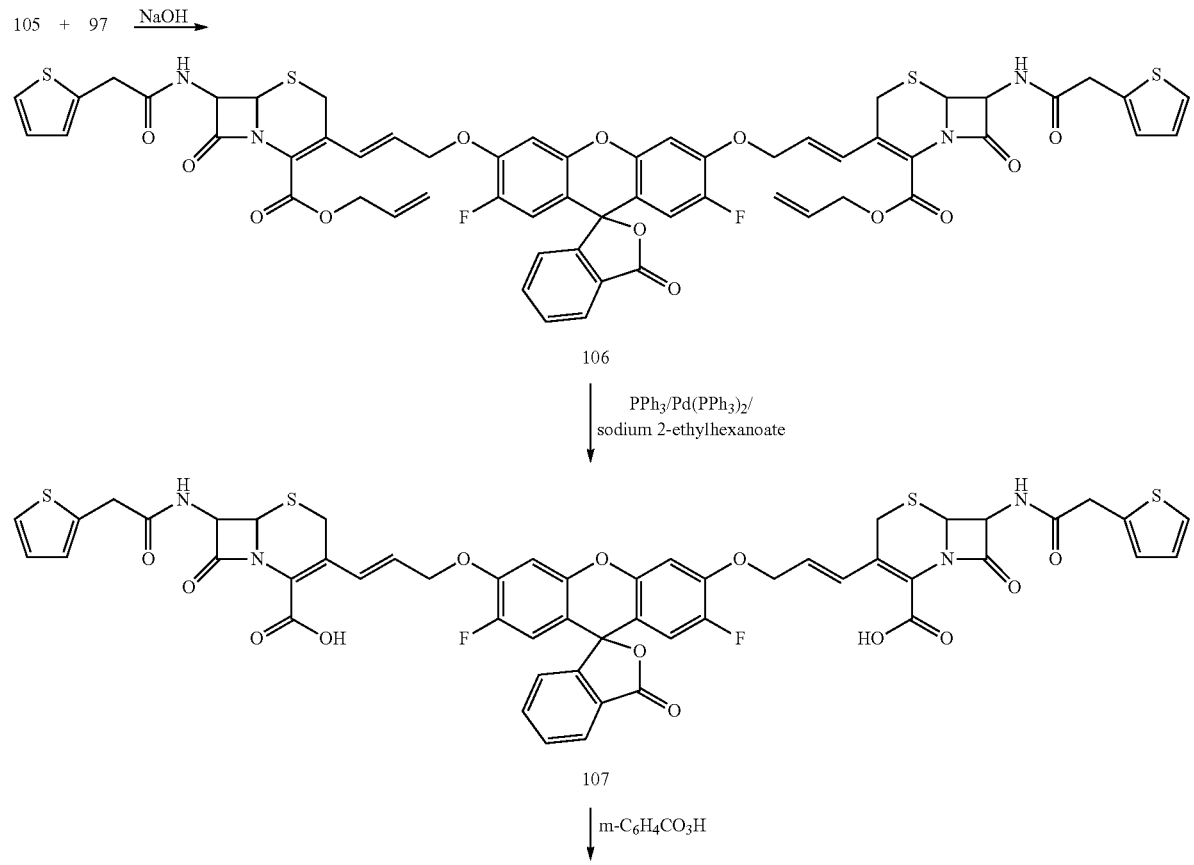

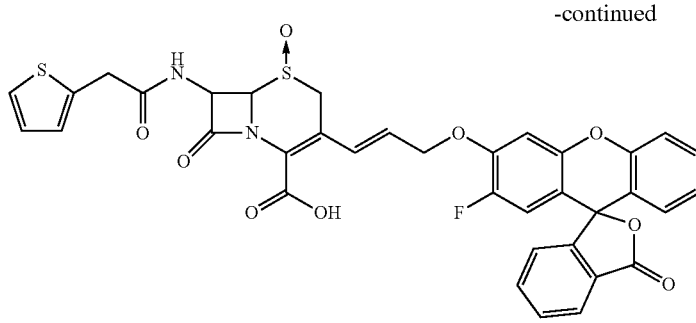
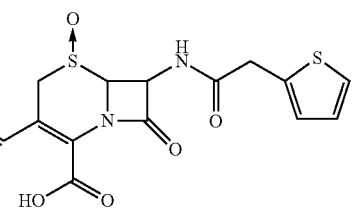

108

Example 28

7-[3-(4,4-Difluoro-5,7-dimethyl-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid 117.

4-(4-dimethylaminophenylazophenyl) 4-aminophenyl disulfide (Compound 109)

4-Aminodisulfide (1.03 g, 4.03 mmol) was dissolved in 100 mL of methanol and 6.5 mL of acetic acid. The solution was cooled down to 0° C. using ice/salt bath. Conc. $H_2SO_4$ (0.05 mL) was added to the solution followed by dropwise addition of $NaNO_2$ (0.61 g, 8.8 mmol) dissolved in 10 mL of water keeping the temperature of reaction mixture in 0° C.-+5° C. interval. The resulting solution was stirred for 1 h at 0° C. The solution of N,N-dimethylaminoaniline (0.911 mL, 7.19 mmol) in 5 mL of methanol was added to reaction mixture followed by adding of sodium acetate (25.0 g, 184 mmol) in 60 mL of water. The reaction mixture was allowed to warm to RT, and then it was stirred overnight. The mixture was diluted with 200 mL of water and filtered using glass fritted funnel. Clear solution was discarded, all insoluble material (including solid collected on the funnel and the brown gummy material in the flask) was dissolved in chloroform (~150 mL), washed with water (30 mL), brine (30 mL), dried over sodium sulfate and evaporated. The crude material was re-dissolved in chloroform and loaded on silica gel column (packed in chloroform). The column was eluted first with chloroform to separated disulfide 110 (minor component), then with 5% ethyl acetate in chloroform to separate amine 109 (major component, 1.04 g, 22%) as an orange solid.

4-(4-Dimethylamino-phenylazo)-phenyl disulfide (Compound 110)

Amine 109 (1.04 g, 2.73 mmol) was dissolved in the mixture of methanol (30 mL) and dioxane (30 mL) and the solution was cooled using ice/water bath. $NaBH_4$ (1.03 g, 27.2 mmol) was added and the reaction mixture was stirred for 15 min under nitrogen. Then 170 mL of 12% acetic acid was added and the products were extracted with ethyl acetate (4×30 mL). The combined extracts were washed with water (3×30 mL), brine (30 mL), dried over sodium sulfate and evaporated. The residue was dissolved in chloroform and loaded on silica gel column (packed in chloroform). The column was eluted with chloroform to remove mixture of two products: thiophenol 111 and disulfide 110 (TLC solvent: 3:1 hexanes-EtOAc). Chloroform was evaporated and the residue was re-dissolved in 80 mL of ethyl acetate and 40 mL of chloroform. Iodine (0.10 g, 0.39 mmol) was added to the solution to oxidize 111 to disulfide 110. If reaction is not complete (control by TLC) after 5 min, more iodine (~0.05 g) needs to be added. Sat. $NaHCO_3$ (50 mL) was added to reaction mixture and organic solution was separated. Water solution containing insoluble product was extracted with chloroform until all insoluble material dissolved in chloroform. The combined organic solutions were washed with brine (40 mL), dried over sodium sulfate and evaporated to give crude disulfide 110. It was combined with disulfide obtained as the minor product in the first step and the resulting material was washed with hexanes (2×30 mL), dissolved in chloroform and loaded on silica gel column (packed in chloroform). The column was eluted with chloroform, pure fractions combined and solvent was evaporated to give disulfide 110 as an orange solid (0.684 g, 49%).

4-(4-Dimethylamino-phenylazo)-benzenethiol (Compound 111)

Disulfide 110 (0.326 g, 0.637 mmol) was suspended in methanol (10 mL) and dioxane (10 mL) mixture. $NaBH_4$ (0.313 g, 8.27 mmol) was added to the suspension and the reaction mixture was stirred for 15 min at RT under nitrogen. Dark red solution was diluted with 100 mL of 5% acetic acid and the product was extracted with ethyl acetate (3×40 mL). The combined extracts were washed with water (3×30 mL), brine (30 mL), dried over sodium sulfate and evaporated to give thiol 111 as orange solid (0.269 g, 82%). The product was used for the next step without further purification.

7-Amino-3-[4-(4-dimethylamino-phenylazo)-phenyl-sulfanylmethyl]-8-oxo-5-thia-1-aza-bicyclo[4.2.0] oct-2-ene-2-carboxylic acid benzhydryl ester (Compound 113)

Hydrochloride 112 (Otsuka Chemical, 0.422 g, 0.935 mmol) was mixed with 100 mL of sat. $NaHCO_3$. Free amine was extracted with ethyl acetate (5×30 mL). The combined extracts were washed with brine (30 mL), dried over sodium sulfate and evaporated. The residue was dissolved in 30 mL of chloroform then thiol 111 was added followed by adding of i-Pr$_2$NEt (0.182 mL, 1.05 mmol). Reaction mixture was stirred for 1.5 hrs at RT, then diluted with 50 mL of chloroform and washed with 5% acetic acid (2×30 mL), water (2×30 mL), brine (30 mL), dried over sodium sulfate and evaporated. The residue was re-evaporated from toluene (20 mL), dissolved in chloroform and loaded on silica gel column (packed in chloroform). The column was eluted with 3:1 chloroform-EtOAc mixture. Pure fractions were combined and evaporated to give amine 113 (red foam, 0.320 g, 54%).

7-[3-(4,4-Difluoro-5,7-dimethyl-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid benzhydril ester (Compound 116)

BODIPY acid 114 (Molecular Probes, 0.100 g, 0.342 mmol) was dissolved in dry methylene chloride (10 mL) containing 3 drops of DMF. Oxalyl chloride (0.082 mL, 0.94 mmol) was added to the solution and the reaction mixture was stirred for 15 min at RT. Then solution was concentrated in vacuum at 30° C. and the residue was re-evaporated from toluene to give acid chloride 115 as an orange gum (~0.11 g). The resulting material was dissolved in 6 mL of methylene chloride and the solution was added dropwise to the solution of amine 113 (0.198 g, 0.311 mmol) in 10 mL of methylene chloride containing N,N-diisopropyl ethyl amine (0.163 mL, 0.937 mmol). The reaction mixture was stirred for 15 min at RT then diluted with 100 mL of methylene chloride and washed with 3% acetic acid (2×30 mL), water (30 mL), sat. NaHCO$_3$ (2×30 mL), dried over sodium sulfate and evaporated. The residue was dissolved in chloroform and loaded on silica gel column (packed in chloroform). The column was eluted with 100:2 chloroform-ethyl acetate to 100:6 chloroform-ethyl acetate mixture. All fractions containing desired material (TLC hexanes-ethyl acetate 1:1) were combined and evaporated. The residue was re-dissolved in ~3 mL of chloroform and precipitated from the solution with 6 mL of methanol. The resulting solid was re-crystallized from 4:3 chloroform-methanol mixture to give amid 116 as orange solid (0.164 g, 58%).

7-[3-(4,4-Difluoro-5,7-dimethyl-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid (Compound 117)

Ester 116 (0.164 g, 0.180 mmol) and thioanisol (4.9 mL, 41.7 mmol) were dissolved in 150 mL of methylene chloride. The solution was cooled using ice/water bath and then cooled trifluoroacetic acid (25 mL, 324 mmol) was added to the solution. The reaction mixture was stirred for 15 min on ice/water bath, mixed with 150 mL of icy cooled water and shaken. Water solution was removed and extracted with methylene chloride (2×30 mL). Combined organic solutions were washed with water (8×40 mL, until pH 7 of the last water extract). Then it was washed with brine (40 mL), dried over sodium sulfate and evaporated. The crude product was dissolved in chloroform and loaded on silica gel column packed in chloroform). The column was eluted first with chloroform to remove thioanisole, then with 10:1:0.05 chloroform-methanol-acetic acid. Fractions containing desired material were combined and evaporated. The residue was re-evaporated from toluene and dried in vacuum to give acid 117 as black powder (0.096 g, 72%).

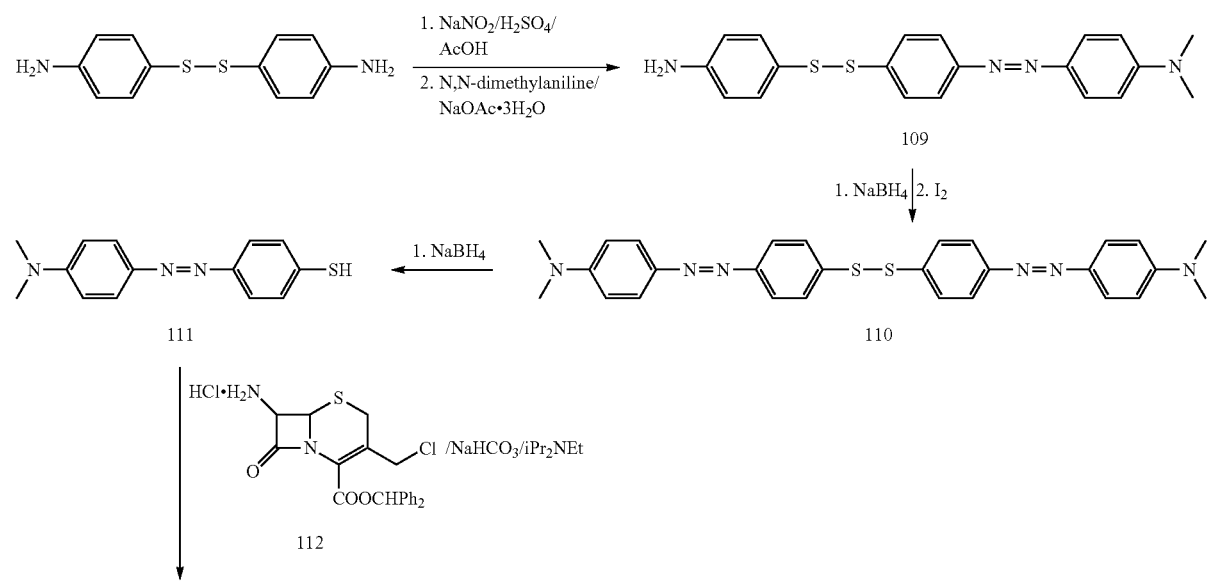

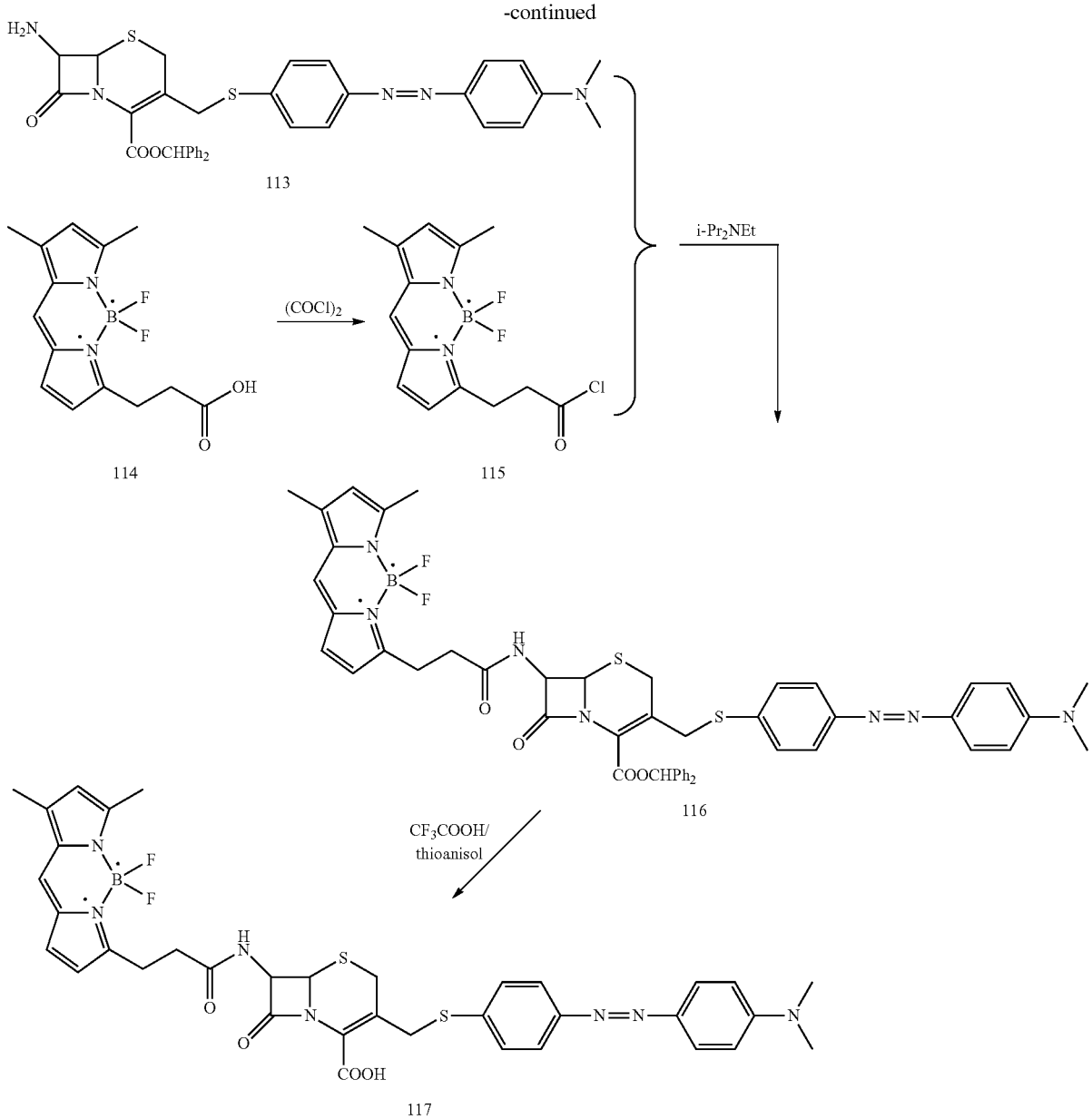

Example 29

7-[3-(4,4-Difluoro-5-(2-pyrrolyl)-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid 120

7-[3-(4,4-Difluoro-5-(2-pyrrolyl)-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid benzhydril ester (Compound 119)

5-(2-pyrrolyl)-BODIPY acid 118 (0.052 g, 0.158 mmol) and amine 113 (0.100 g, 0.157 mmol) were dissolved in 3 mL of acetonitrile. EDC (0.030 g, 0.156 mmol) was added to the solution and reaction mixture was stirred overnight at RT. Then the reaction mixture was diluted with chloroform (80 mL), washed with 3% acetic acid (2×30 mL), water (4×30 mL), brine (30 mL) and dried over sodium sulfate. The solution was evaporated, the residue was re-dissolved in chloroform and loaded on silica gel column (packed in chloroform). The column was eluted with 15:1 chloroform-ethyl acetate mixture. Pure fractions were combined and evaporated to give amide 119 as a black gum (0.093 g, 62%).

7-[3-(4,4-Difluoro-5-(2-pyrrolyl)-4-bora-3a,4a-diaza-s-indacen-3-yl)-propionylamino]-3-[4-(4-dimethylamino-phenylazo)-phenylsulfanylmethyl]-8-oxo-5-thia-1-aza-bicyclo[4.2.0]oct-2-ene-2-carboxylic acid (Compound 120)

Ester 119 (0.093 g, 0.098 mmol) and thioanisol (3.0 mL, 25.5 mmol) were dissolved in 90 mL of methylene chloride. The solution was cooled using ice/water bath and then cooled trifluoroacetic acid (30 mL, 389 mmol) was added to the solution. The reaction mixture was stirred for 15 min on ice/water bath, mixed with 150 mL of icy cooled water and shaken. Water solution was removed and extracted with methylene chloride (2×30 mL). Combined organic solutions were washed with water (8×40 mL, until pH 7 of the last water extract). Then it was washed with brine (40 mL), dried over sodium sulfate and evaporated. The crude product was dissolved in chloroform and loaded on silica gel column packed in chloroform). The column was eluted first with chloroform to remove thioanisole, then with 10:1:0.05 chloroform-methanol-acetic acid. Pure fractions containing desired material were combined and evaporated. The residue was re-evaporated from toluene and dried in vacuum to give acid 120 as black powder (0.025 g, 33%).

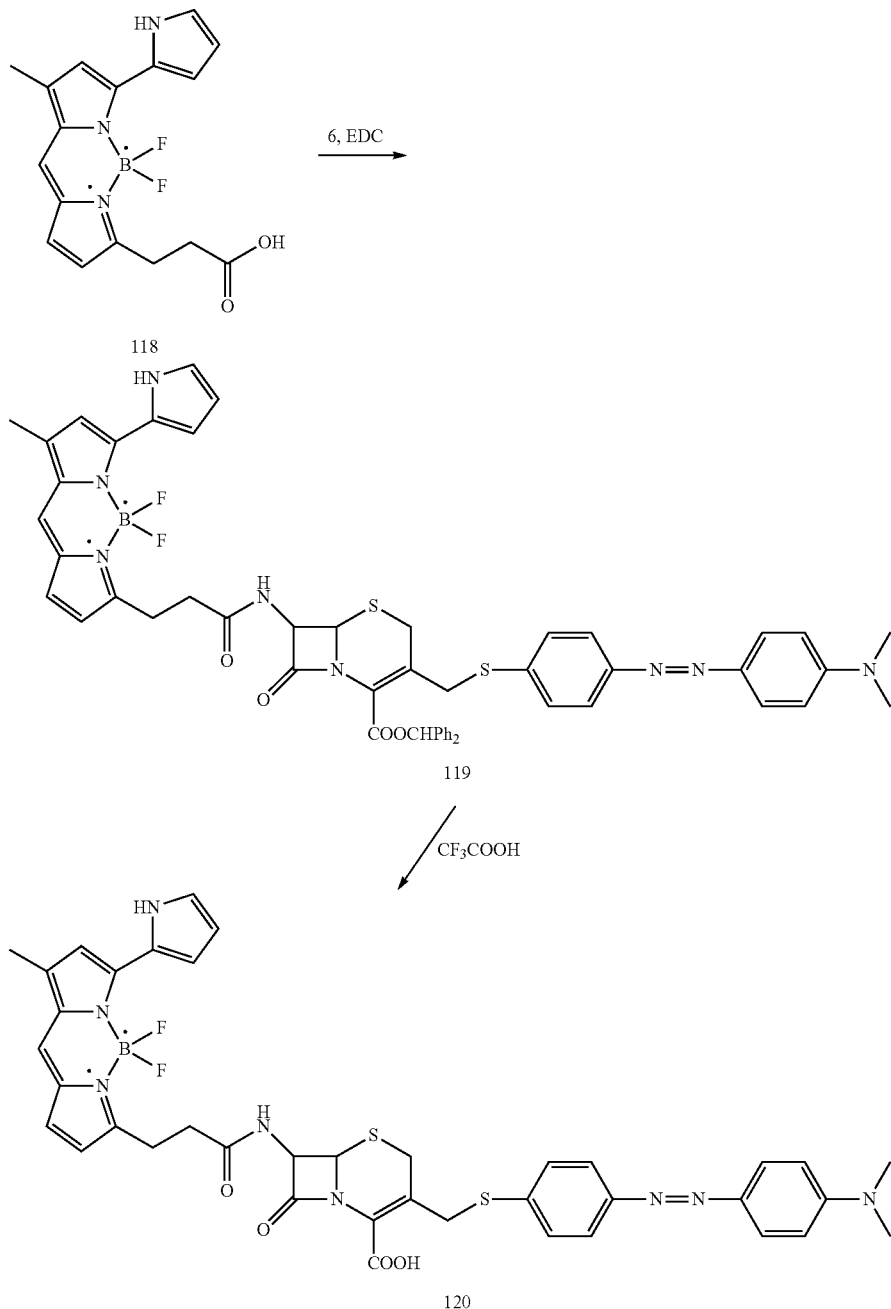

Example 30

Preparation of Compound 123

DDAO-hexanoic acid 121 (0.064 g, 0.157 mmol) and amine 113 (0.10 g, 0.157 mmol) were dissolved in 10 mL of acetonitrile. EDC (0.030 g, 0.156 mmol) was added to the solution and the reaction mixture was stirred overnight at RT. Then the mixture was diluted with 100 mL of chloroform, washed with water (30 mL), brine (30 mL), dried over sodium sulfate and evaporated. The residue was dissolved in chloroform and loaded on silica gel column (packed in chloroform). The column was eluted with 1:1 chloroform-ethyl acetate. The desired product and unreacted amine 113 came out together. Fractions containing both compounds were combined and evaporated. The residue was re-dissolved in 80 mL of ethyl acetate and amine 113 was washed out using 10% HCl (4×30 mL). The organic solution was washed with brine (30 mL), dried over sodium sulfate and evaporated to give amide 122 as a black powder (0.023 g, 14%).

Ester 122 (0.023 g, 0.022 mmol) and thioanisol (1.0 mL, 8.5 mmol) were dissolved in 30 mL of methylene chloride. The solution was cooled using ice/water bath and then cooled trifluoroacetic acid (6 mL, 65 mmol) was added to the solution. The reaction mixture was stirred for 15 min on ice/water bath, and then diluted with 80 mL of methylene chloride. Then it was washed with icy cooled water (6×30 mL, until pH of the last extract is neutral), brine (30 mL), dried over sodium sulfate and evaporated. The crude product was dissolved in chloroform and loaded on silica gel column packed in chloroform). The column was eluted first with chloroform to remove thioanisole, then with 10:1:0.05 chloroform-methanol-acetic acid. Pure fractions containing desired material were combined and evaporated. The residue was re-evaporated from toluene and dried in vacuum to give acid 123 as black powder (0.0062 g, 36%).

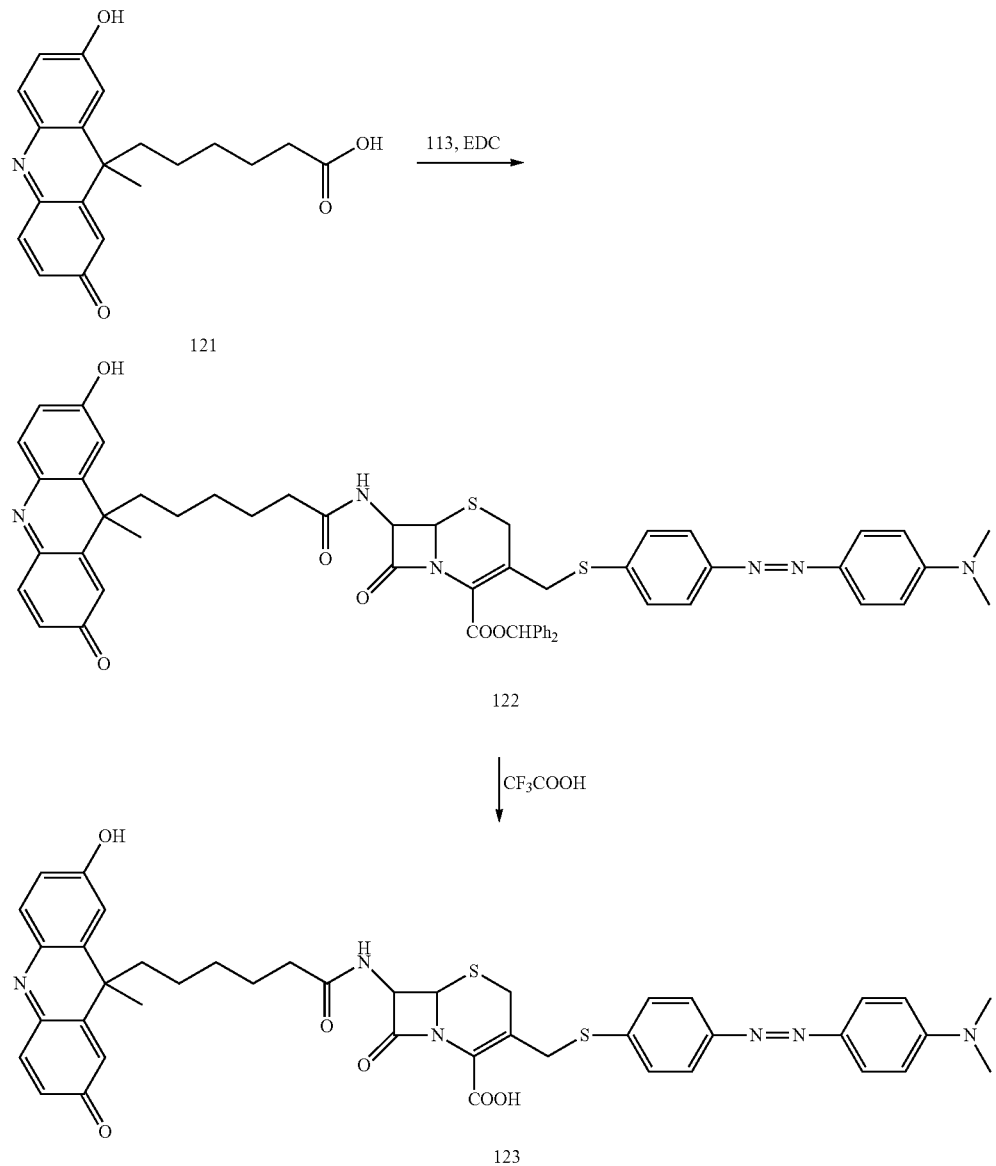

Example 31

Preparation of Compound 128

4-Nitroresorcinol (1.39 g, 10.0 mmol) was combined with 2,6-dihydroxybenzoic acid (1.69 g, 11.0 mmol). Conc. $H_2SO_4$ was added and the mixture was stirred at 70° C. for 1 hr. Then it was cooled down to RT and diluted with icy cooled water (300 mL). The product was extracted with ethyl acetate (15×200 mL). The combined extracts were evaporated and the residue was dissolved in 15% MeOH in chloroform, loaded on silica gel column (packed in chloroform). The column was eluted with chloroform, then with 10 to 15% methanol in chloroform and finally with 15 to 30% methanol+1% acetic acid in chloroform. Clean fractions were combined and evaporated to give carboxylic acid 124 as a dark brown solid (0.321 g, 19%).

Carboxylic acid 124 (0.119 g, 0.463 mmol) was dissolved in 8 mL of pyridine. The solution was cooled using ice/water bath. SE trifluoroacetate (1.2 g, 5.68 mmol) was added to the solution and the mixture was stirred for 30 min. The solution was diluted with ethyl acetate (120 mL), washed with 5% acetic acid (6×30 mL), water (4×30 mL), brine (30 mL), dried over sodium sulfate and evaporated to give SE ester 125 as a brown solid (0.103 g, 63%).

SE ester 125 (0.103 g, 0.291 mmol) was dissolved in 10 mL of dioxane. β-Alanine (0.260 g, 2.92 mmol) was dissolved 5 mL of water containing 5.8 mL of 1M $Et_3NH_2CO_3$. Two solutions were mixed and the resulting mixture was stirred overnight at RT. The reaction mixture was diluted with 80 mL of 2% HCl and the product was extracted with ethyl acetate (5×30 mL). The combined extracts were washed with water (3×30 mL), brine (30 mL), dried over sodium sulfate and evaporated to give carboxylic acid 126 as a brown solid (0.072 g, 75%).

Carboxylic acid 126 (0.068 g, 0.207 mmol) was suspended in 5 mL acetonitrile and 2 mL of DMF. Amine 113 (0.126 g, 0.198 mmol) was added to this suspension followed by adding EDC (0.040 g, 0.209 mmol). The resulting mixture was stirred overnight at RT. The mixture was diluted with water (80 mL) and the product was extracted with ethyl acetate (3×30 mL). The combined extract was washed with water (3×30 mL), brine (30 mL), dried over sodium sulfate and evaporated. The crude product was dissolved in chloroform and loaded on preparative TLC plate. The plate was developed in 2:1 ethyl acetate-chloroform mixture. The red quenched band was separated from the plate and the compound was washed from silica gel using chloroform-ethyl acetate 1:1 mixture. The solution was evaporated to give desired amide 127 (0.038 g, 20%).

Ester 127 (0.038 g, 0.040 mmol) and thioanisol (1.15 mL, 9.77 mmol) were dissolved in 36 mL of methylene chloride. The solution was cooled using ice/water bath and then cooled trifluoroacetic acid (11.5 mL, 124 mmol) was added to the solution. The reaction mixture was stirred for 15 min on ice/water bath, and then diluted with 80 mL of methylene chloride. Then it was washed with icy cooled water (6×30 mL, until pH of the last extract is neutral), brine (30 mL), dried over sodium sulfate and evaporated. The crude product was dissolved in chloroform and loaded on silica gel column packed in chloroform). The column was eluted first with chloroform to remove thioanisole, then with 10:1:0.05 chloroform-methanol-acetic acid. Pure fractions containing desired material were combined and evaporated. The residue was re-evaporated from toluene and dried in vacuum to give acid 128 as a black powder (0.013 g, 41%).

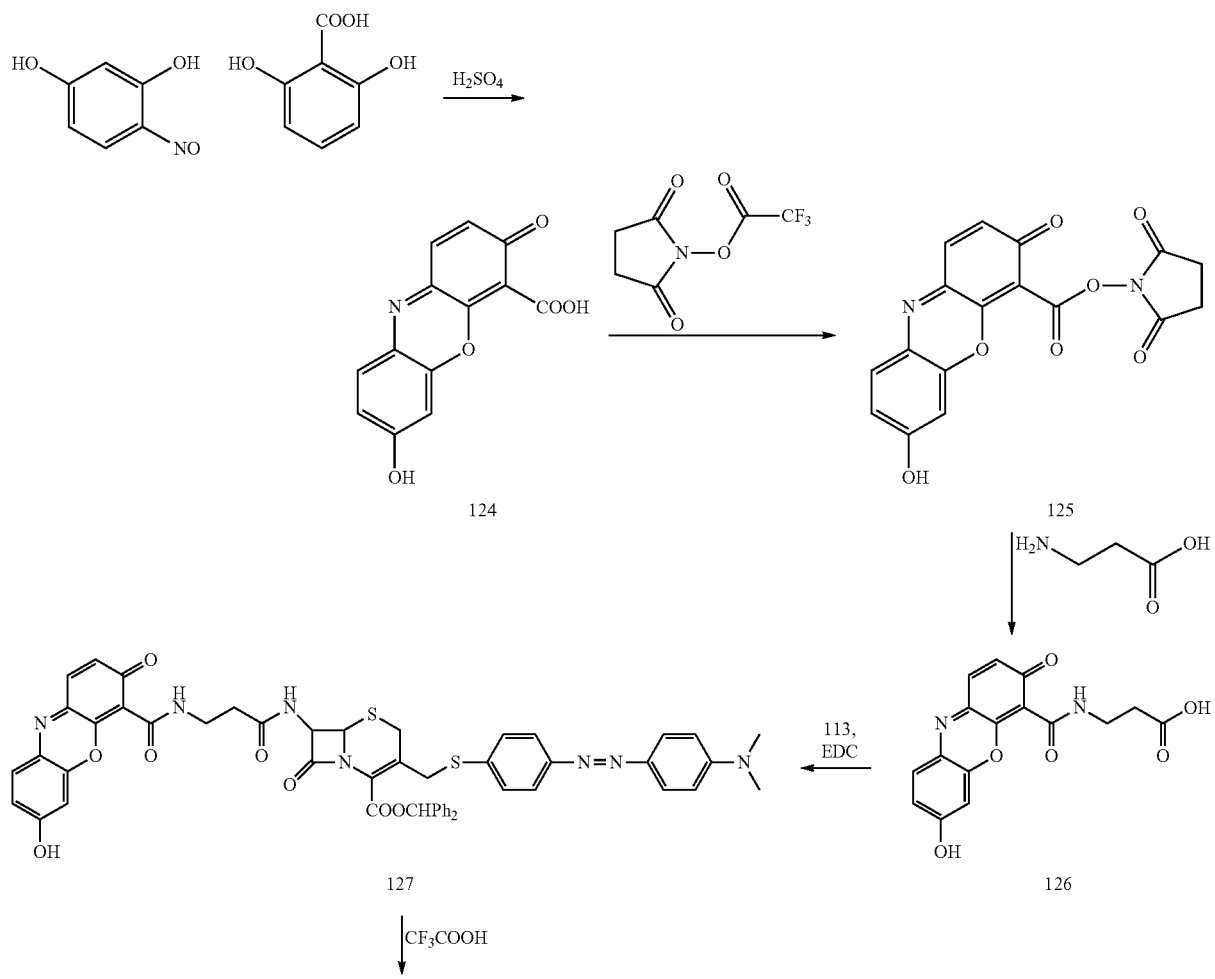

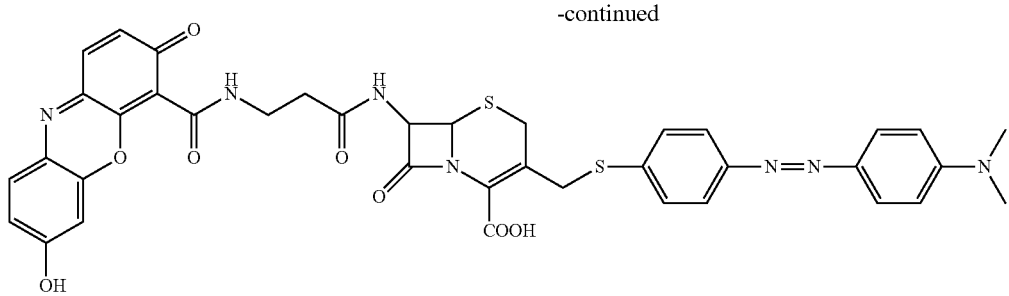

128

Example 32

Figure 6A:
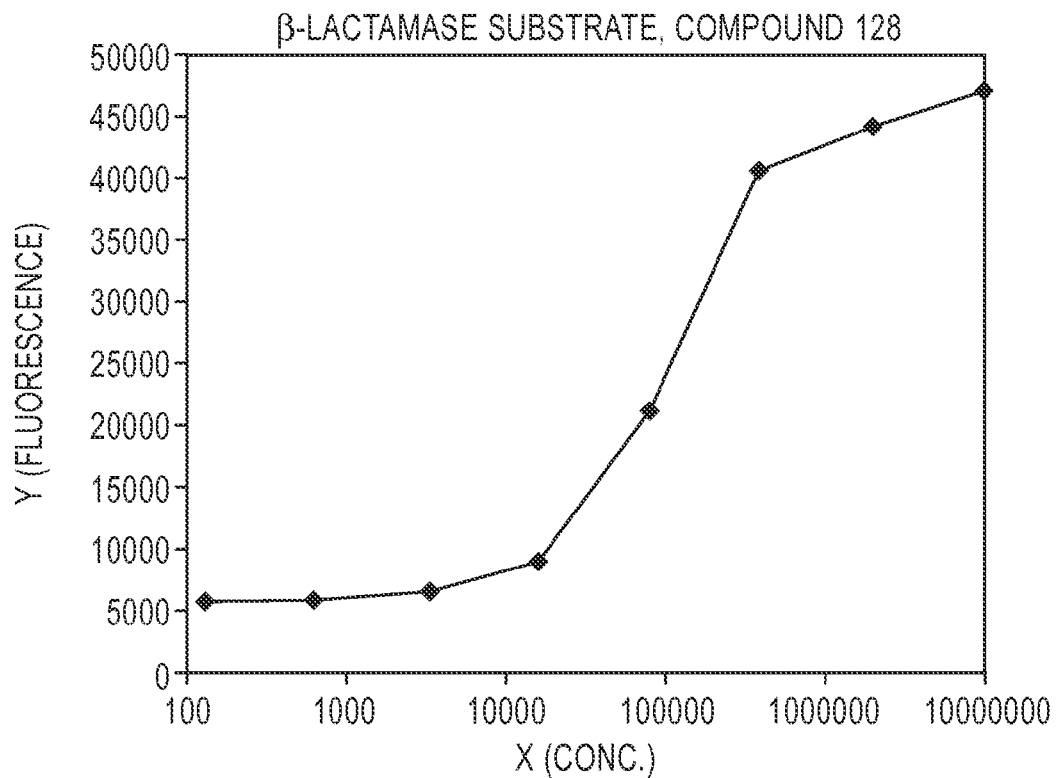
FIG. 6: Shows Fluorescence vs. TEM-1 concentration for A) Compound 128, the instrument gain was set to 59-60 and B) Compound 123, the instrument gain was set to 179-180. See, Example 32.
Figure 6B:
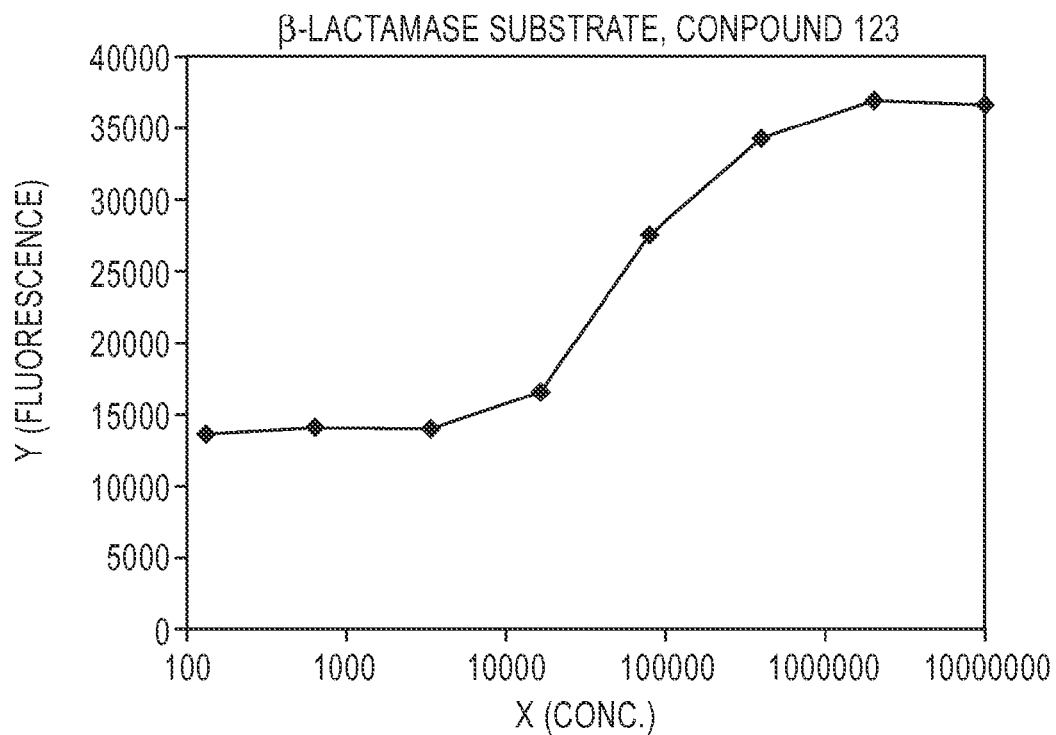

Development for ELISA Method Using β-Lactamase Enzyme Conjugated to a Detection Reagent and a β-Lacatamase Fluorogenic Substrate Screening Method:

Dilutions of TEM-1 or a TEM-1 enzyme/protein conjugate were prepared, with concentrations ranging from ~100 pg/mL to ~10 µg/mL total protein plus several negative controls (no TEM-1). Several replicates of each dilution were added to a 96-well plate. The substrate to be tested was prepared in water or pH 7.2 PBS at a concentration of ~10 µg/mL and immediately added to the TEM-1 dilutions and controls. The volume of substrate added was equivalent to the amount of TEM-1 solution present, so that enzyme and substrate final concentrations were half the initial concentrations. The plate was read at various time points after addition of substrate to the enzyme dilutions. Overall fluorescence (proportional to the instrument gain setting), variance of signal (for replicates), and monotonicity (more enzyme results in higher signal) were the primary screening criteria. This screening method also applies to other β-lactamase variants, such as p99. It can be used to test a new substrate's activity with an enzyme, or an enzyme's activity with a working substrate after the enzyme has been conjugated. See FIG. 6, which show examples of a substrate with high TEM-1 activity (FIG. 6A), and with very low TEM-1 activity (FIG. 6B).

A variety of substrates were tested including Compound 123, 128, 108, 100, 117 and 120

$K_m$ Determination:

Both $K_m$ and $V_{max}$ are parameters used to describe enzyme/substrate activity. While $K_m$ is constant regardless of enzyme or substrate concentration, $V_{max}$ is only constant for a given enzyme concentration. The Michaelis-Menten equation is used to derive both $V_{max}$ and $K_m$:

$$d[P]/dt = V_{max}[S]/(K_m+[S]) \quad (1)$$

[S] is substrate concentration, while [P] is product concentration. The reaction's initial velocity, $v_0$, is defined as $d[P]/dt$ at time zero. If we only look at the initial velocity, Equation 1 becomes:

$$v_0 = V_{max}[S]/(K_m+[S]) \quad (2)$$

Both the Lineweaver-Burk and Scatchard equations are simply linearizations of the Michaelis-Menten equation:

$$\text{Lineweaver-Burk Equation } 1/v_0 = K_m/V_{max} * 1/[S] + 1/V_{max} \quad (3)$$

$$\text{Scatchard Equation } v_0/[S] = (-1/K_m) * v_0 + V_{max}/K_m \quad (4)$$

Figure 7A:
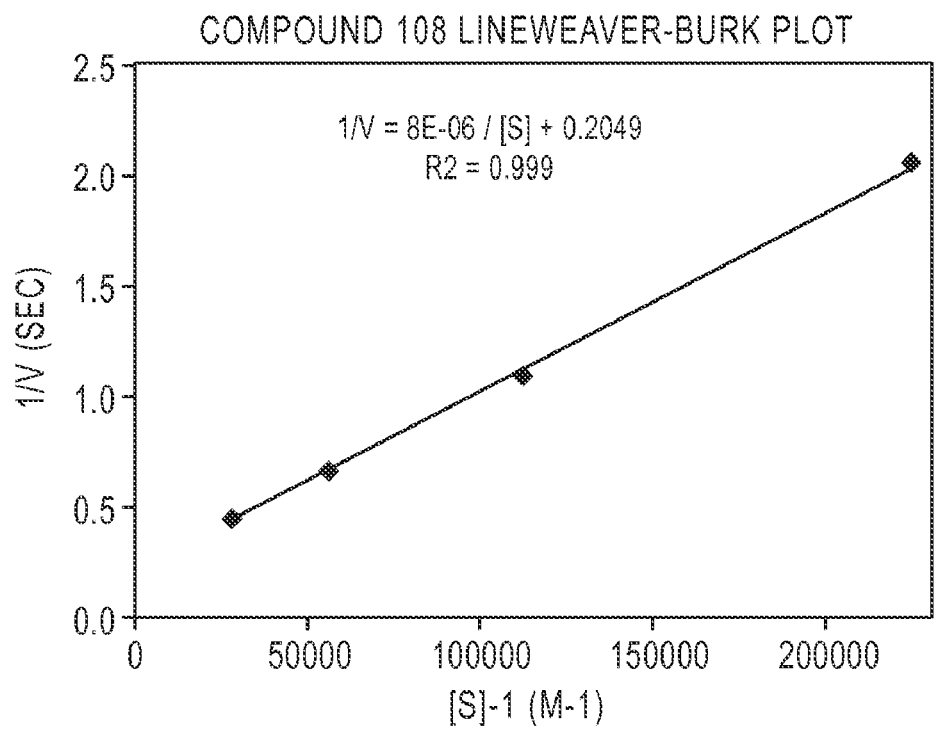
FIG. 7: Shows A) the Lineweaver-Burk plot for TEM-1 with Compound 108 and B) The Scatchard plot for TEM-1 with Compound 108. See, Example 32.
Figure 7B:
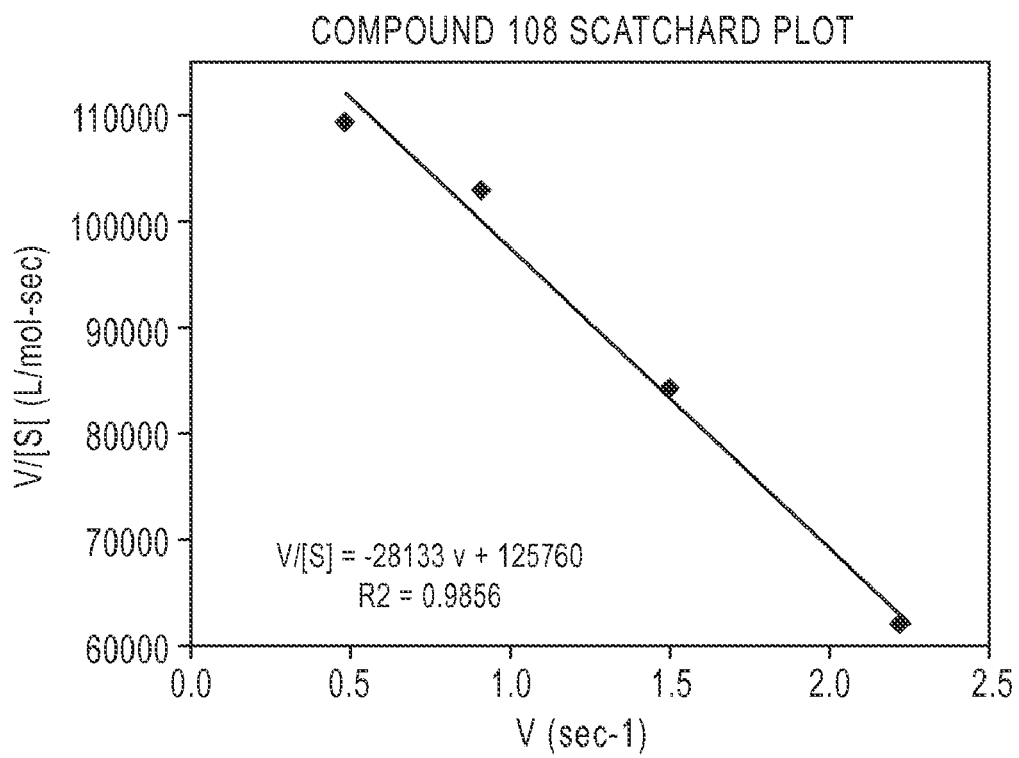
Figure 8:
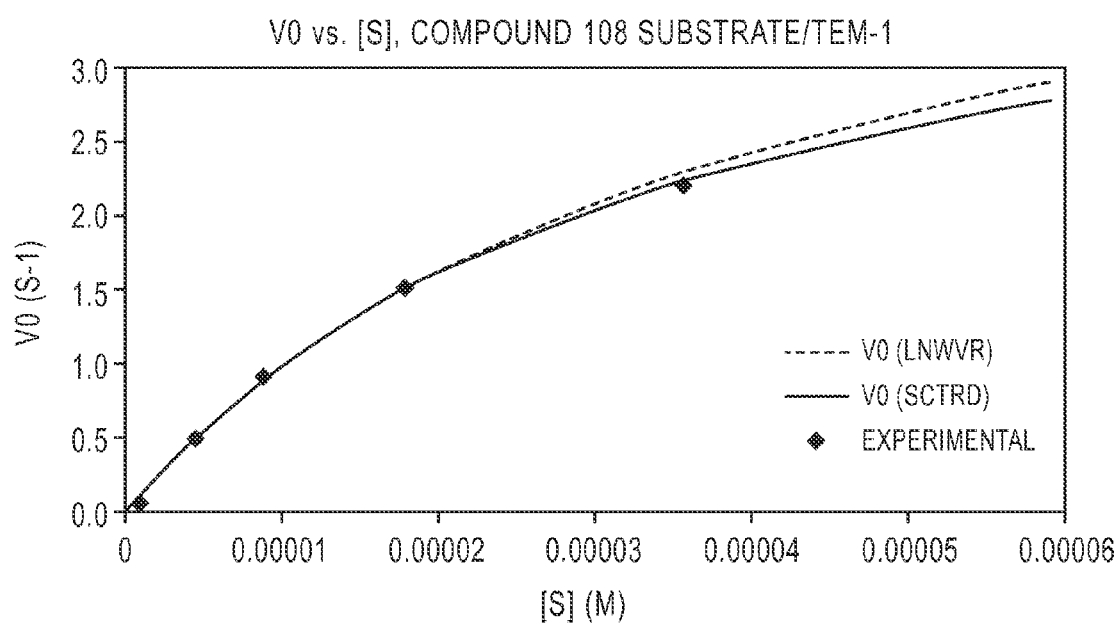
FIG. 8: Shows the Experimental and theoretical Michaelis-Menten curves.
Figure 9A:
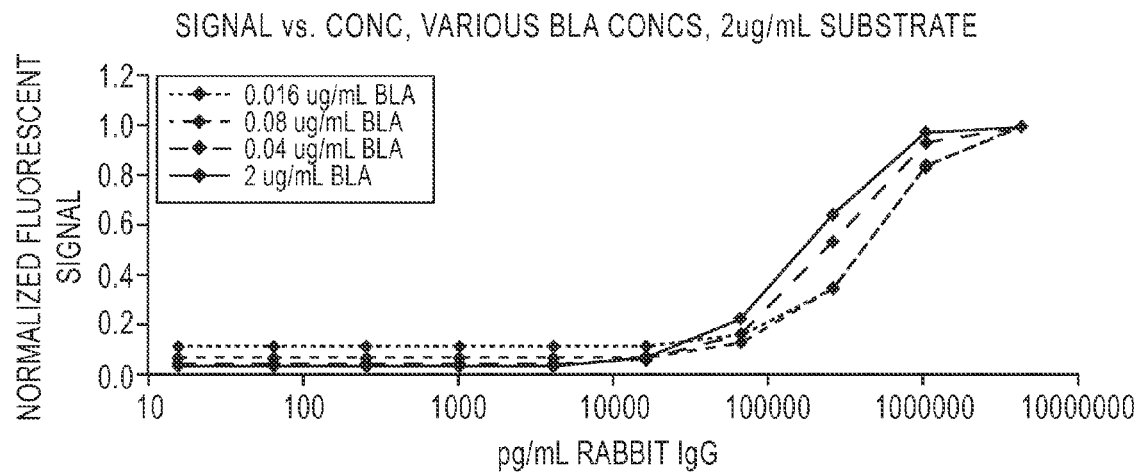
FIG. 9: Shows Signal vs. Concentration and Z vs. Concentration for various TEM-1 concentrations with 2 μg/mL (Figures A and B) or 0.5 μg/mL Fluorocillin substrate (Figures C and D). See, Example 32.
Figure 9B:
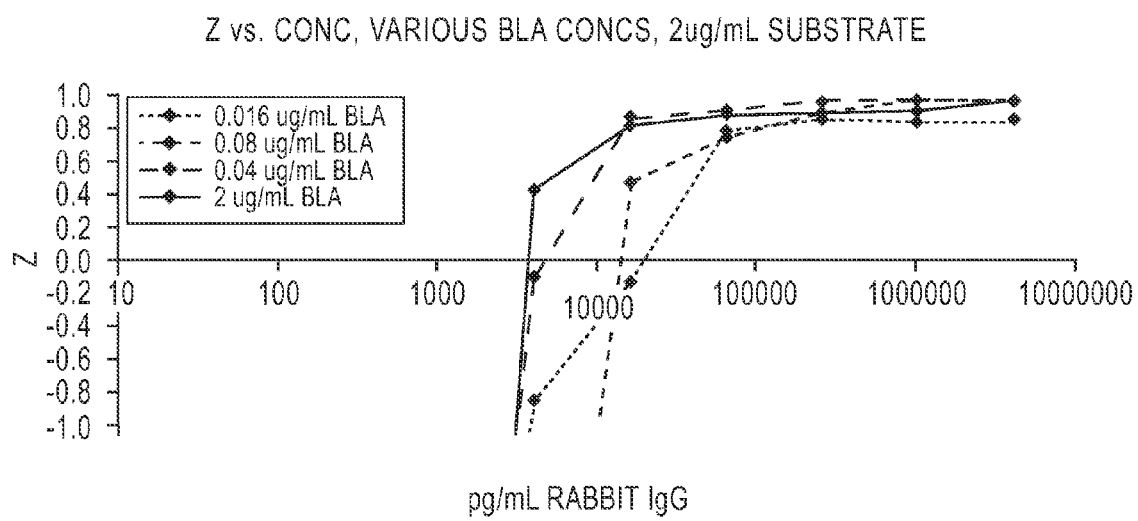
Figure 9C:
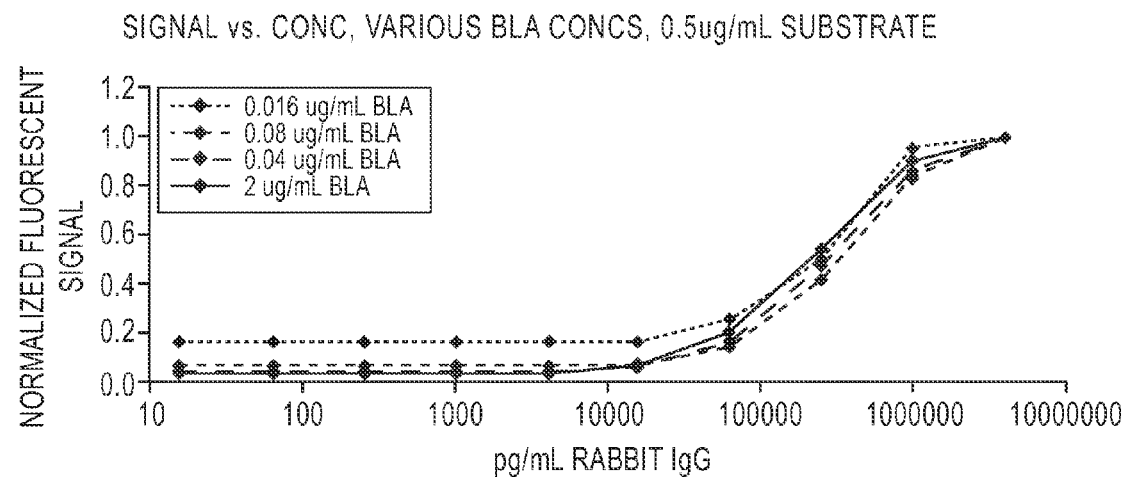
Figure 9D:
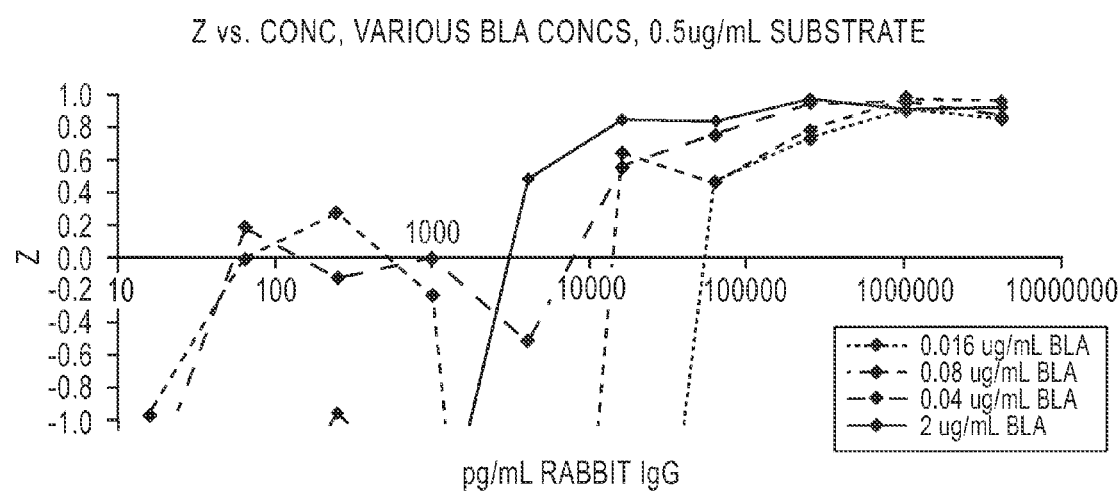

For determination of $K_m$ of the β-lactamase substrate with TEM-1, substrates ranging from 40 µg/mL to 5 µg/mL were added to microplate wells with a constant concentration of 5 nM TEM-1. The plate was read for the first 5 minutes with a Tecan Safire fluorescence plate reader using a constant gain setting. Relative Fluorescence Units (RFUs) were converted into moles of product produced using a standard curve of the substrate's fluorescent product. This standard curve was produced by adding an excess of TEM-1 (0.5 µM) to an equal volume of substrate, and incubating for more than 1 hour. Substrate standard concentrations ranged from ~16 nM to 2 µM. It was assumed the reaction went to completion. All enzyme and substrate solutions were prepared in PBS, pH 7.2. See, FIG. 7, which shows the Lineweaver-Burk and Scatchard plots for TEM-1 with the β-lactamase substrate, and FIG. 8 which plots the experimentally-determined values for $v_o$ along with theoretical curves based on the $K_m$ and $V_{max}$ values obtained from the Lineweaver-Burk and Scatchard plots:

The table below summarizes $K_m$ determinations for both methods.

TABLE 10

$K_m$ as determined from Lineweaver-Burk and Scatchard plots.

Figure 4:
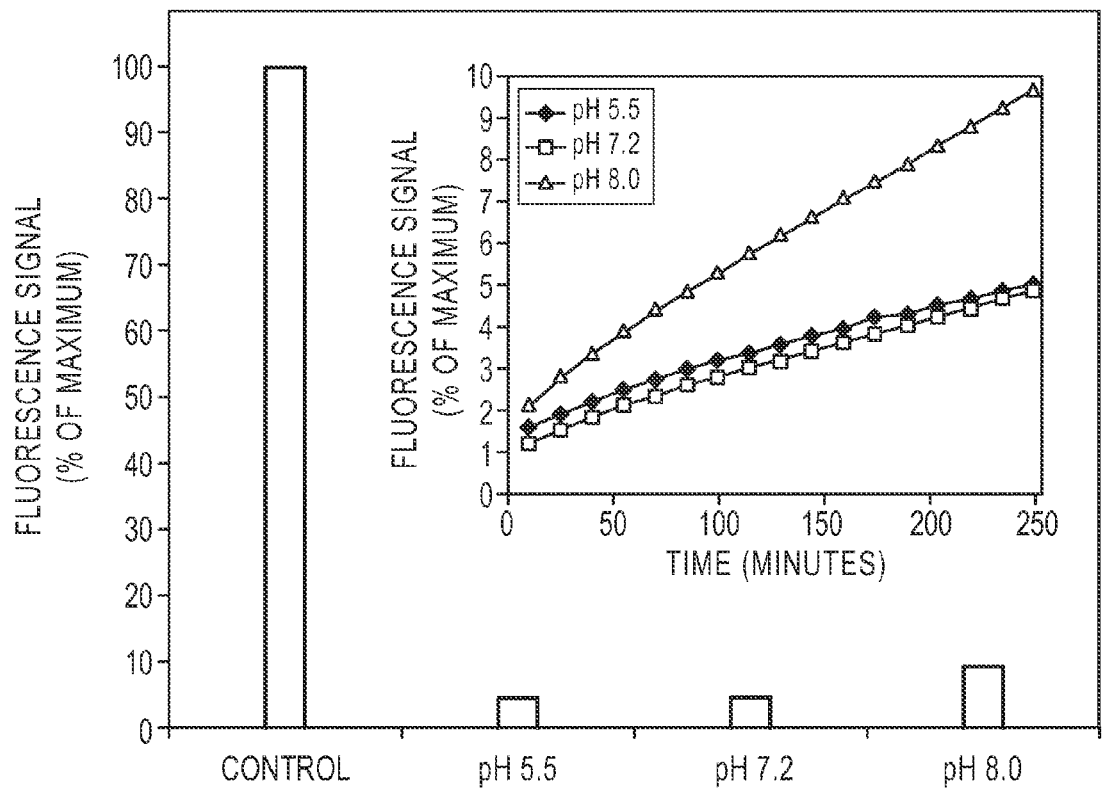
FIG. 4 Shows the background of Compound 108 over time in different buffers. Compound 108 was prepared at a concentration of 1 μg/ml in three different buffers: MES at pH 5.5, PBS at pH 7.2, and Tris at pH 8.0. The substrate solutions were applied to the wells of a microplate, the plate was protected from light, and fluorescence values were gathered at time points from 10-250 minutes. The bar graph shows the percentage of maximum signal given by each substrate solution after 250 minutes. The line graph (inset) shows the background signal given by each substrate solution as a function of time. Maximum signal was determined by the fluorescence value obtained when 10 μl of a 100 μg/ml solution of β-lactamase was added to control wells. Each point is the mean of 12 replicates. See, Example 32.
Figure 5:
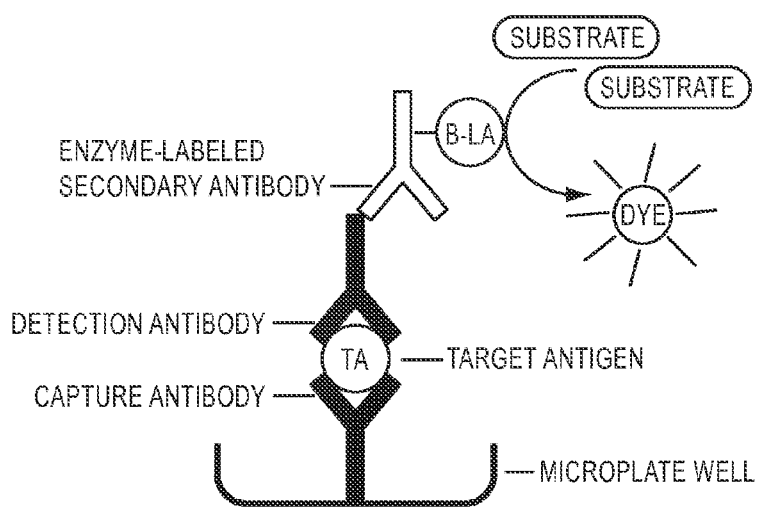
FIG. 5: Shows a schematic diagram of the sandwich ELISA method. The microplate is coated with a capture antibody that has reactivity to the target antigen but has no reactivity to the detection antibody or the enzyme-labeled secondary antibody. A solution containing the target antigen is applied to the plate. A portion of the target antigen is retained by the capture antibody, and nonbinding components of the solution are washed away. A solution containing the detection antibody is applied to the plate. The detection antibody is specific for the target antigen, and any detection antibody not bound to the target antigen is washed away. The B-LA-labeled secondary antibody binds to the detection antibody and cleaves the substrate, producing a fluorescent signal. The target antigen described in this assay is "sandwiched" between two antibodies, hence the name "sandwich ELISA." This is in contrast to direct-capture assays where the plate is coated with the target antigen. Sandwich ELISAs are generally more sensitive than direct-capture ELISAs because of the amplification of signal that arises from the presence of the capture antibody.

| model | equation | $K_m$ (variables) | $K_m$ (µM) difluoro sub. | $R^2$ (linear regression) |
|---|---|---|---|---|
| Scatchard | v/[S] = (-1/Km)*v + Vmax/Km | -1 slope | 36 | .986 |
| Lineweaver-Burk | 1/v = Km/Vmax* 1/[S] + 1/Vmax | -intercept slope | 40 | .999 | pH Range, Hydrolysis Rate:

Solutions of Compound 108 (1 µg/mL) were prepared in pH 5.5 MES, pH 7.2 PBS, and pH 8.0 Tris-HCl, then added to 16 wells of a 96-well plate. For each pH, high concentrations of TEM-1 were added to 4 wells to obtain a maximum signal (assuming complete cleavage of all substrate). The entire plate was read every 15 min. for 250 min. All fluorescent signals were averaged, then normalized to a percentage of the maximum fluorescence. The pH 5.5 MES and pH 7.2 PBS showed nearly identical hydrolysis rates, while the hydrolysis for pH 8.0 Tris-HCl was about double that rate. The Tris-HCl samples increased in fluorescence about 7.5% over 250 min., corresponding to complete hydrolysis after about 55 hrs. The MES and PBS samples increase in fluorescence about 3.25% over 250 min., corresponding to complete hydrolysis after about 128 hrs. These estimations assume a constant rate of hydrolysis. See FIG. 4, which shows the fluorescence at each pH (as a percentage of the maximum fluorescence at that pH) versus time due to hydrolysis as a function of time nad pH.
Optimization of TEM-1 and β-Lactamase Substrate Concentrations:

Optimal concentrations for use in ELISA-format assays was determined experimentally using a model sandwich ELISA to detect human Prostate Specific Antigen (PSA). For each sandwich ELISA, a Nunc Maxisorp 96-well plate was coated with a monoclonal mouse anti-PSA antibody, then blocked with BSA. A range of concentrations of a PSA standard was added to the plate, including negative controls (no PSA). The PSA standards were detected with a polyclonal rabbit anti-PSA antibody, then a secondary conjugate of goat anti-rabbit TEM-1. Plates were developed by addition of a β-lactamase substrate solution to drained wells, then measurement of fluorescence on the Tecan Safire fluorescence plate reader.

There were several criteria used to evaluate enzyme and substrate concentrations. a) The Z-factor, which indicates the lower limit of detection.
b) Monotonicity. That is, a higher concentration of the antigen (PSA) should produce a larger fluorescent signal.
c) Dynamic range; a broader range was more desirable.
d) Goodness of fit, in which the fluorescent signal vs. PSA concentration data set was fit with a four-parameter model, where the four parameters are designated as A, M, Q, and n:

$$\text{fluorescence} = A + [M^*(\text{concentration})^n]/[Q + (\text{concentration})^n] \quad (1)$$

After the parameters have been optimized to give the lowest residuals, we can solve for concentration:

$$\text{concentration} = \{Q^*[(\text{fluorescence} - A)/M]/[1 - (\text{fluorescence} - A)/M]\}^{1/n} \quad (2)$$

Figure 10A:
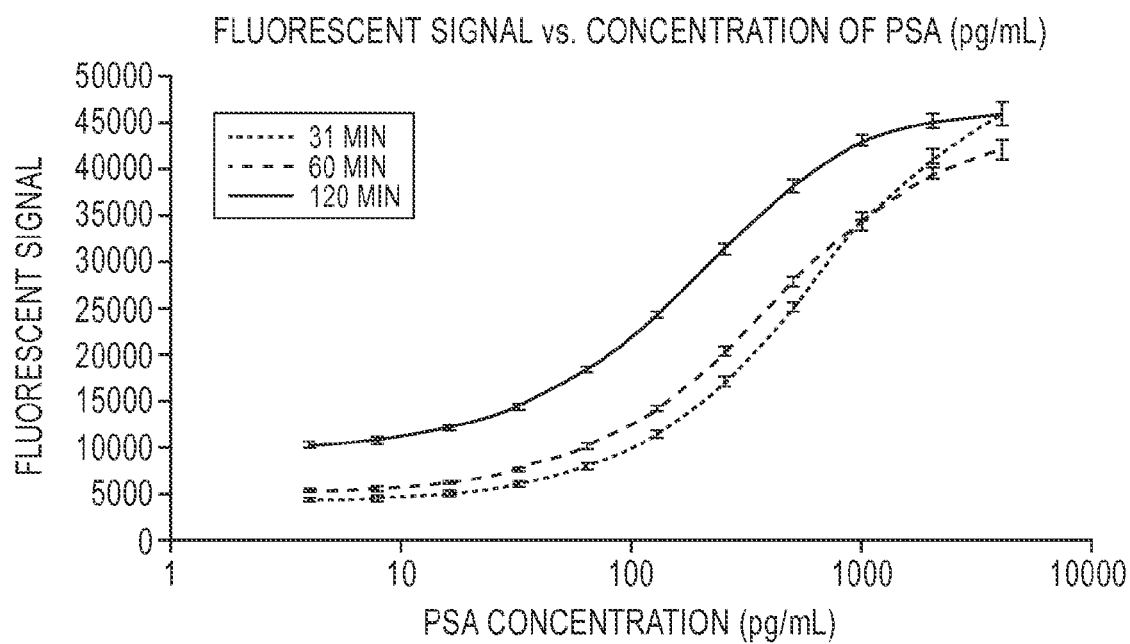
FIG. 10: Shows A) fluorescent signal and B) Z-factor vs. PSA concentration for a sandwich ELISA using optimized concentrations of TEM-1 conjugate and Compound 108. See, Example 32.
Figure 10B:
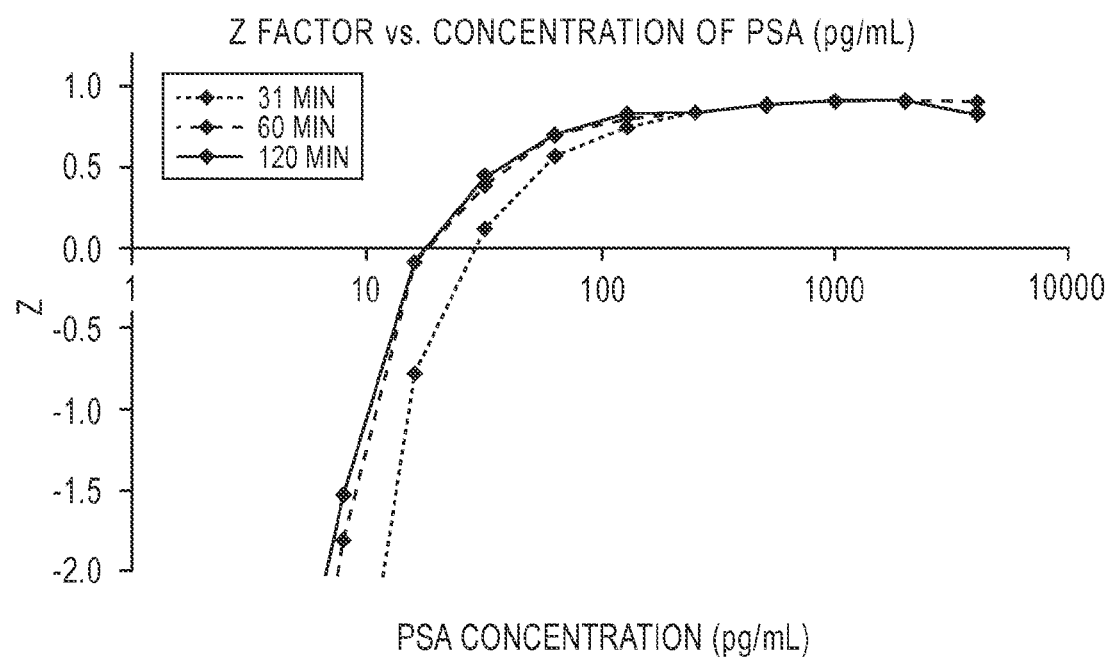
Figure 11:
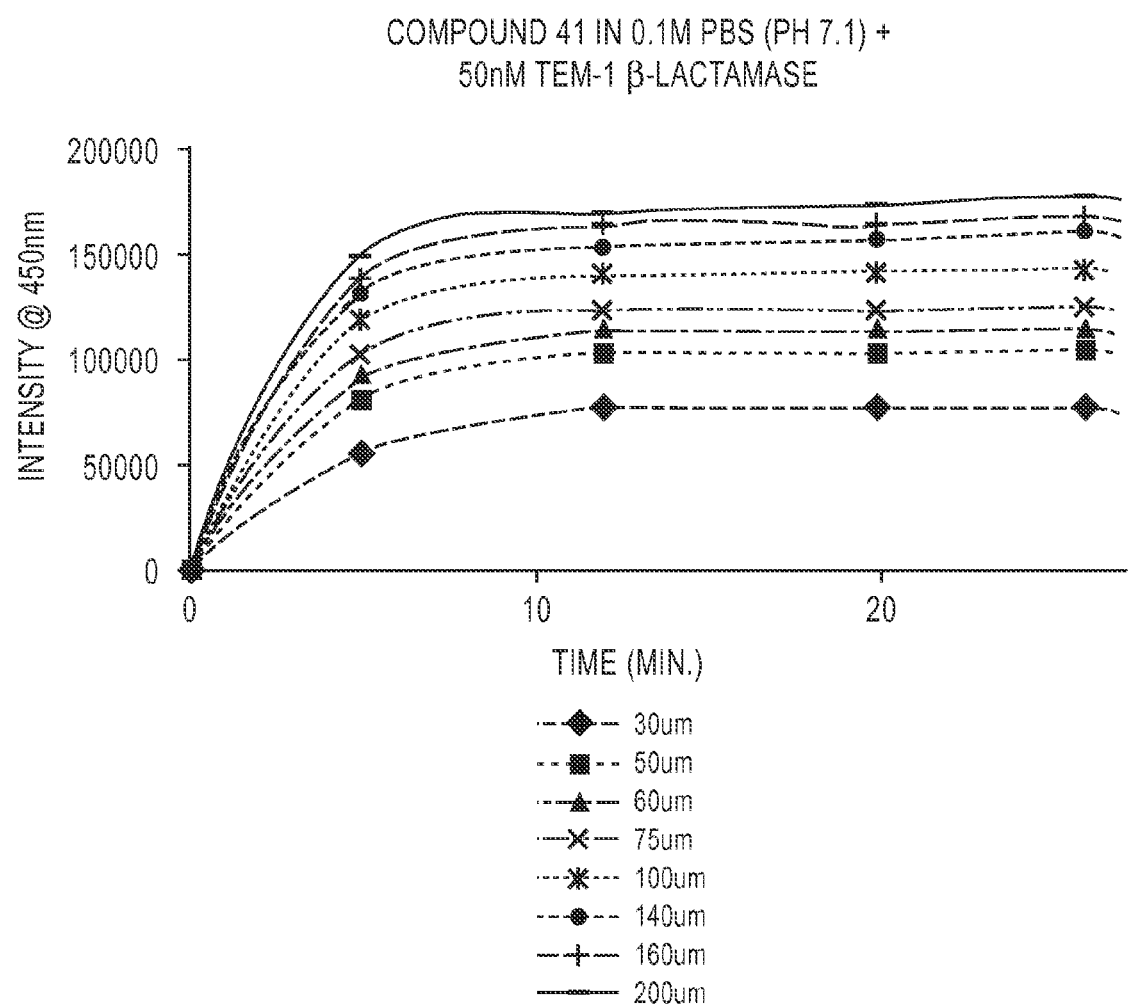
FIG. 11: is a comparison of the fluorescence intensity at 450 nm versus time of 7β-(2-(Thien-2-yl)acetamido)-3-((((6,8-difluoro)-4-methylumbelliferyl)-7-oxy)methyl)-3-cephem-4-carboxylic acid 1β-sulfoxide (Compound 41) after reaction with a β-lactamase (excitation at 360 nm). The variation in fluorescence intensity at different concentrations of the compound also is shown.
Figure 12:
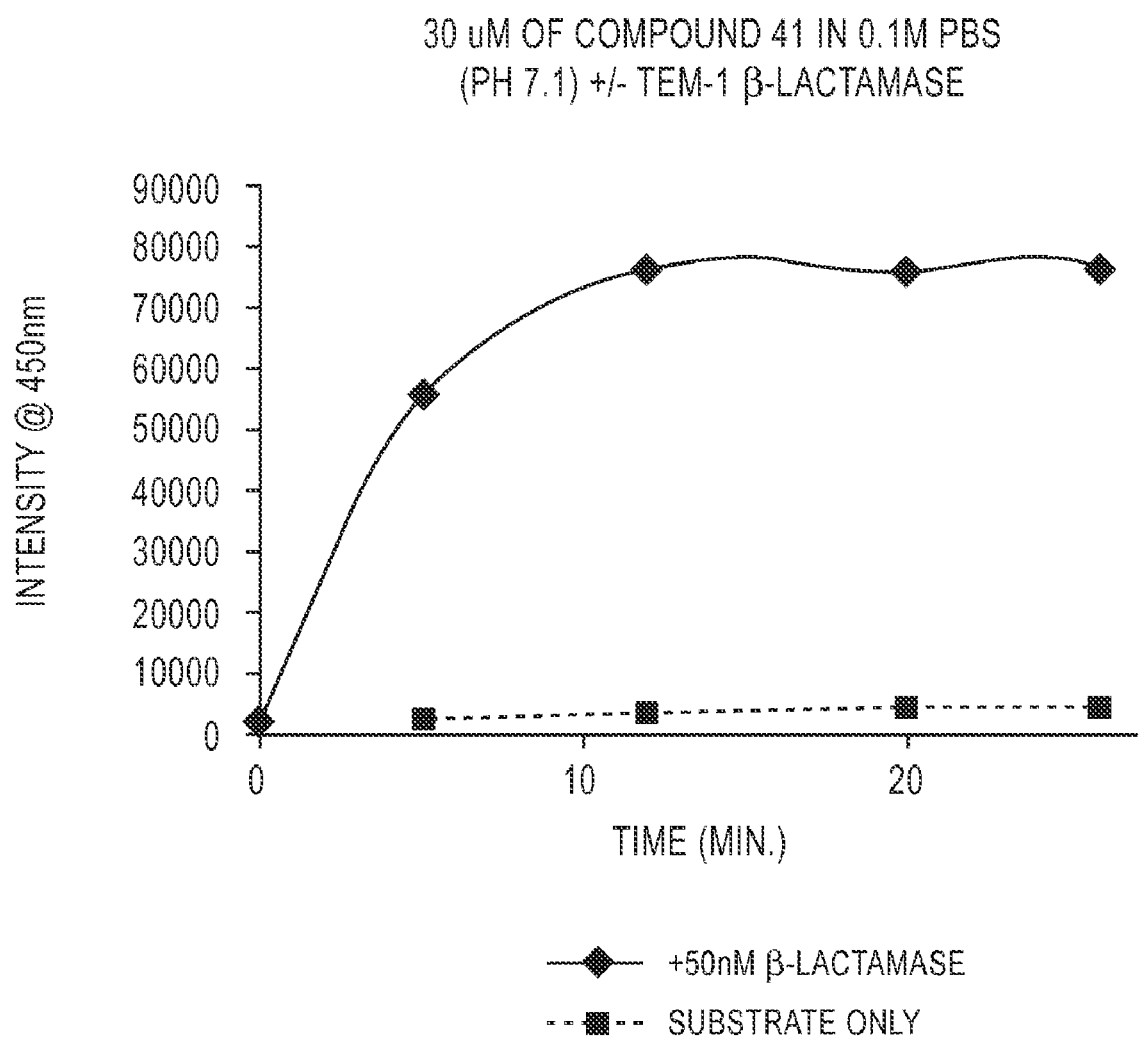
FIG. 12: is a comparison of the fluorescence intensity at 450 nm versus time of 7β-(2-(Thien-2-yl)acetamido)-3-((((6,8-difluoro)-4-methylumbelliferyl)-7-oxy)methyl)-3-cephem-4-carboxylic acid 1β-sulfoxide (Compound 41) after reaction with a β-lactamase (excitation at 360 nm). Fluorescence intensity caused by non-enzymatic hydrolysis of the compound also shown.
Figure 13:
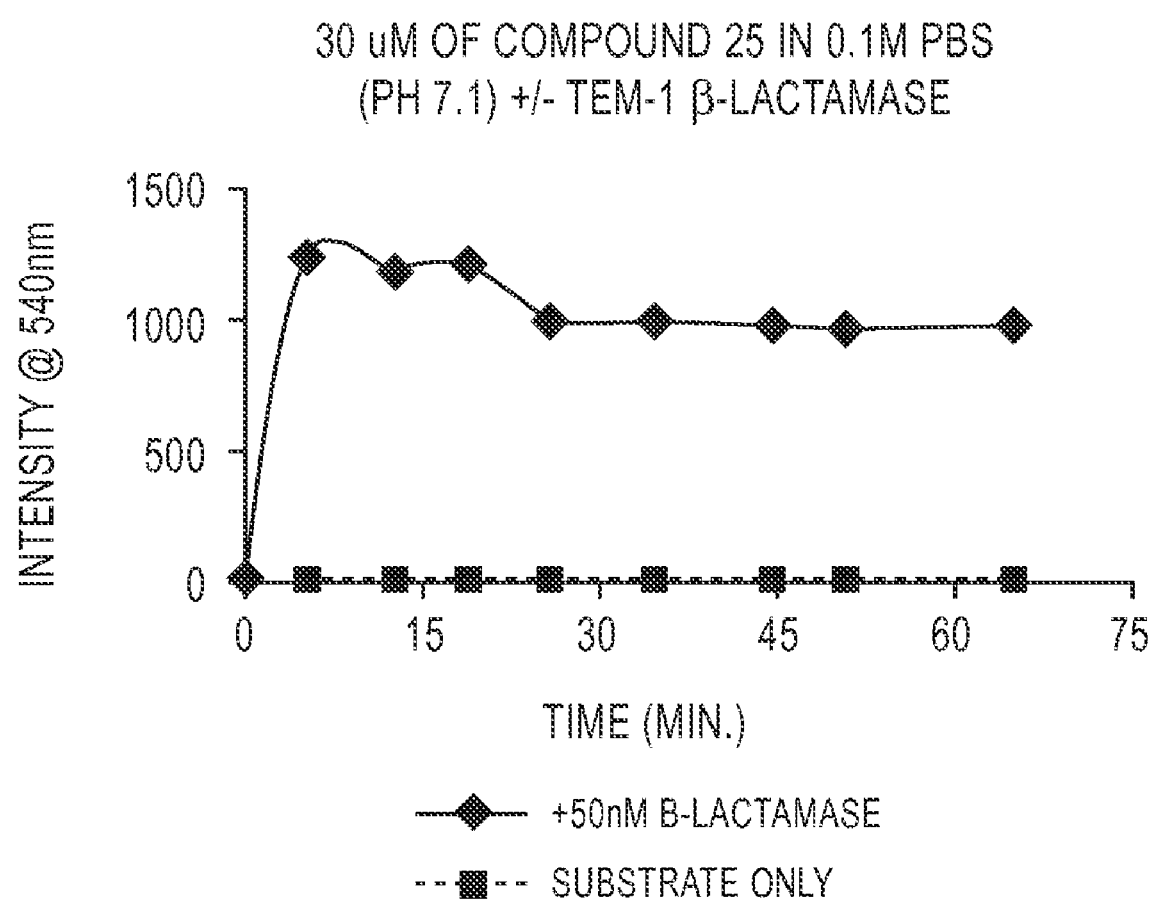
FIG. 13: is a comparison of the fluorescence intensity at 540 nm versus time of 7β-(2-(Thien-2-yl)acetamido)-3-(((2-(-3H-quinazoline-4-one-2-yl)-(phenyl)oxy)methyl)-3-cephem-4-carboxylic acid (Compound 25) after reaction with a β-lactamase (excitation at 360 nm). Fluorescence intensity caused by non-enzymatic hydrolysis of the substrate also is shown.

The known PSA concentration is compared with the concentration calculated from the signal and fit parameters. A close correlation between known and calculated concentration was desirable. Consistant results were obtained using TEM-1 concentrations ranging from 0.1-10 μg/mL and β-lactamase substrate concentrations ranging from 1-10 μg/mL. Furthermore, results did not deteriorate when the plate continued to incubate for up to 24 hrs for samples with low to moderate PSA concentrations. Sensitivity for higher PSA concentrations did deteriorate if the plate was incubated too long. By reading the plate early (15-30 min.) and later (up to 24 hrs later) better results were obtained for both the low- and high-ends of the PSA concentration range. See, FIG. 9 which shows normalized fluorescent signal and Z-factors for some of the enzyme and substrate concentrations tested. See, FIG. 10, which shows fluorescent signal and Z-factors vs. PSA concentration for an optimized assay.

Example 33

Fluorescence from Precipitating β-Lactamase Substrate 3.08 mg of Compound 38 was dissolved in 3 mL of methanol to give a stock solution of 2 mM. This was diluted 4-fold to give a working solution of 500 uM. 200 uL of Compound 38 was added to 100 mM phosphate, 150 mM NaCl (pH7.1) in a cuvette to give a final volume of 2 mL (50 μM final concentration of Compound 38). To another cuvette, TEM-1β-lactamase was added to give a final concentration of 250 nM, with a substrate concentration of 50 μM and final volume of 2 mL. Samples were excited @ 360 nm and spectra were plotted from 400-700 nm.

Example 34

Fluorescence from Precipitating β-Lactamase Substrate 4 mg of Compound 38 was dissolved in 2:1 $H_2O$:methanol to give a stock solution concentration of 2 mM. This was diluted 2-fold in methanol to give a working solution of 1 mM. 20 μL of 250 nM TEM-1 β-lactamase was added to the wells of a 96-well microplate. Appropriate volumes of substrate were added to the wells to give final concentrations of 0, 30, 50, 60, 75, 100, 140, 160 and 200 uM after diluting to 100 μL with 100 mM phosphate, 150 mM NaCl (pH7.1). The final β-lactamase concentration was 50 nM. Samples were excited @ 360 nm and fluorescence was measured @ 450 nm, signal was read @ 5, 13, 19, 26, 35, 45, 51 and 65 minutes. Maximum signal was attained after 5 minutes. The substrate exhibited at least a 90-fold enhancement upon reaction w/β-lactamase. The signal dropped at high concentrations of substrate presumably due to decreased solubility. Experiments were also done in the presence of 40% methanol, but no reaction occurred.

Example 35

Preparation of β-Lactamase Enzyme Conjugates (Strpetaviding and IgG)

SMCC Derivatization of Tem-1 Enzyme
After dialysis into pH 7.5 coupling buffer (0.1M NaPhos, 0.1M NaCl) the enzyme (5-10 mg/ml concentration) is modified with SMCC (succinimidyl maleimidomethyl cyclohexane carboxylate, at MR (molar ratio) 8 for 30 min (room temp). Unreacted SMCC is then removed by standard desalting chromatography over P30 or G50 resin.
DTT Reduction of IgG
IgG (concentration 5-10 mg/ml in pH 7.5 bfr) is reduced with 50 mM DTT (dithiothreitol) for 30 minutes at room temp. The reagent is then removed by desalting chromatography.
IgG-BLA Conjugation
Immediately after DTT treatment, the reduced IgG is mixed with SMCC-modified BLA (equimolar ratio) and allowed to react for 1-2 hrs at room temp or overnight at 4 degrees C. The IgG-BLA conjugate product is purified by size-exclusion chromatography (gel filtration) over P-100 resin.
SPDP/DTT Modification of Streptavidin
Streptavidin (5-10 mg/ml in pH 7.5 bfr) is reacted with SPDP (succinimidylpyridyl dithiopropionate) at MR 8 for 30 minutes at room temp, then the reagent is removed by desalting chromatography. This material is then treated with 50 mM DTT for 30 min (RT), and purified by desalting chromatography.
Streptavidin-BLA Conjugation
SPDP-modified/DTT-reduced streptavidin is mixed with SMCC-modified BLA (equimolar ratio) and allowed to react for 1-2 hrs RT (or overnight at 4 degrees). The streptavidin-BLA conjugate product is purified by gel filtration over P-60 resin.

The preceding examples can be repeated with similar success by substituting the specifically described compounds of the preceding examples with those generically and specifically described in the foregoing description. One skilled in the art can easily ascertain the essential characteristics of the present invention, and without departing from the spirit and scope thereof, can make various changes and modifications of the invention to adapt to various usages and conditions. All patents and patent applications cited herein are hereby incorporated by reference in their entirety for all purposes.

What is claimed is:

1. A method for determining the presence or absence of β-lactamase enzyme in a sample, the method comprising:

a) contacting the sample with a β-lactamase substrate to form a contacted sample;

b) incubating the contacted sample for a sufficient amount of time for a β-lactamase enzyme in the contacted sample to cleave the β-lactamase substrate to form an incubated sample;

c) illuminating the incubated sample with an appropriate wavelength to obtain an illuminated sample; and d) observing the illuminated sample whereby the presence or absence of β-lactamase enzyme in the illuminated sample is determined wherein the β-lactamase substrate has a structure of one of the following formulae:

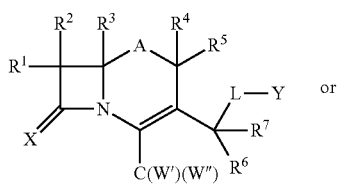 or

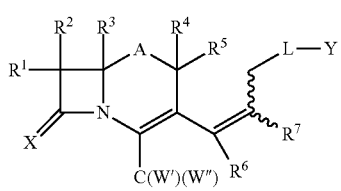

where $R_1$ is

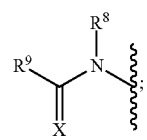

A is S, SO, or $SO_2$;

X is O;

L—Y is a thioether linked moiety formed by reaction with a quencher moiety having a structure of formula:

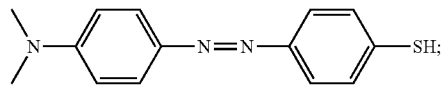

$R^2$ is hydrogen, alkyl, substituted alkyl, heteroalkyl, substituted heteroalkyl, aryl, substituted aryl, heteroaryl, substituted heteroaryl;

$R^3$ is hydrogen, alkyl, substituted alkyl, heteroalkyl, substituted heteroalkyl, aryl, substituted aryl, heteroaryl, substituted heteroaryl;

$R^4$ is hydrogen, alkyl, substituted alkyl, heteroalkyl, substituted heteroalkyl, aryl, substituted aryl, heteroaryl, substituted heteroaryl;

$R^5$ is hydrogen, alkyl, substituted alkyl, heteroalkyl, substituted heteroalkyl, aryl, substituted aryl, heteroaryl, substituted heteroaryl;

$R^6$ is hydrogen, alkyl, substituted alkyl, heteroalkyl, substituted heteroalkyl, aryl, substituted aryl, heteroaryl, substituted heteroaryl;

$R^7$ is hydrogen, alkyl, substituted alkyl, heteroalkyl, substituted heteroalkyl, aryl, substituted aryl, heteroaryl, substituted heteroaryl;

$R^8$ is hydrogen, alkyl, substituted alkyl, heteroalkyl, substituted heteroalkyl, aryl, substituted aryl, heteroaryl, substituted heteroaryl;

R⁹ is

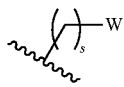

wherein W is a dye moiety;
s is an integer from 0 to 5;
W' is (=O);
W" is OR¹⁰, NHR¹¹, or halogen;
  wherein $R_{10}$ is hydrogen, alkyl, substituted alkyl, heteroalkyl, substituted heteroalkyl, aryl, substituted aryl, heteroaryl; or substituted heteroaryl; and,
  $R^{11}$ is hydrogen, substituted alkyl, heteroalkyl, substituted heteroalkyl, aryl, substituted aryl, heteroaryl; substituted heteroaryl or OR¹²; and $R^{12}$ is hydrogen, substituted or unsubstituted alkyl, and substituted or unsubstituted heteroalkyl or substituted or unsubstituted aryl or heteroaryl.

2. A method for determining the presence or absence of β-lactamase enzyme in a sample, the method comprising:
  a) contacting the sample with a β-lactamase substrate to form a contacted sample;
  b) incubating the contacted sample for a sufficient amount of time for a β-lactamase enzyme in the contacted sample to cleave the β-lactamase substrate to form an incubated sample;
  c) illuminating the incubated sample with an appropriate wavelength to obtain an illuminated sample; and
  d) observing the illuminated sample whereby the presence or absence of β-lactamase enzyme in the illuminated sample is determined, wherein the β-lactamase substrate has a structure of the formula:

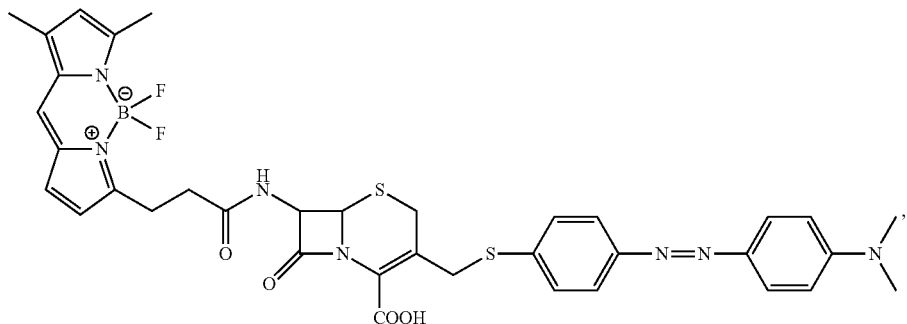

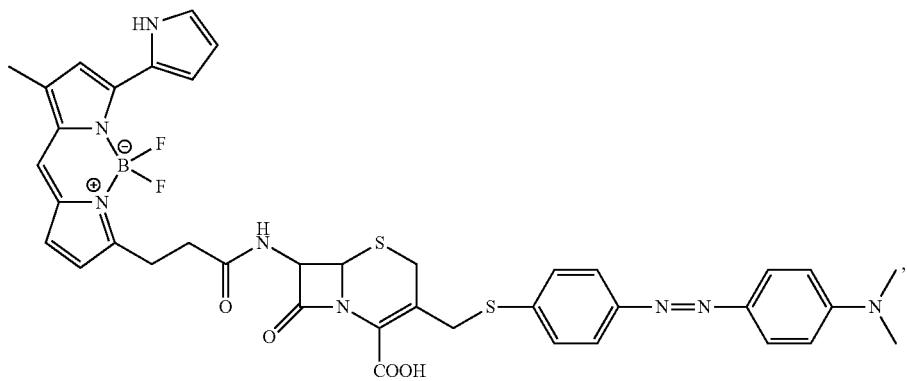

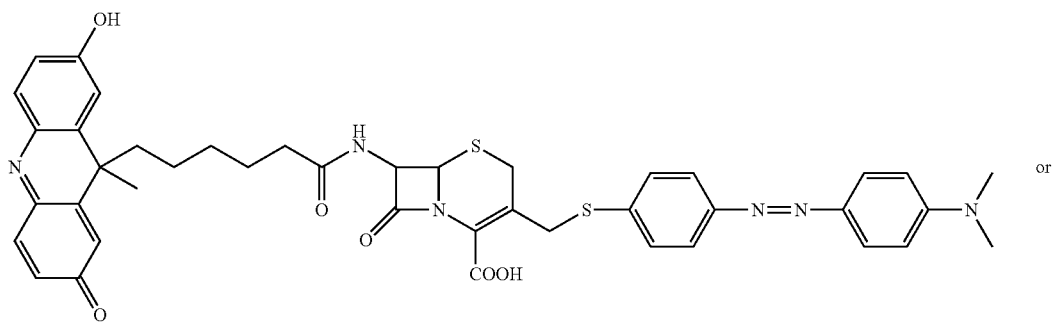

or

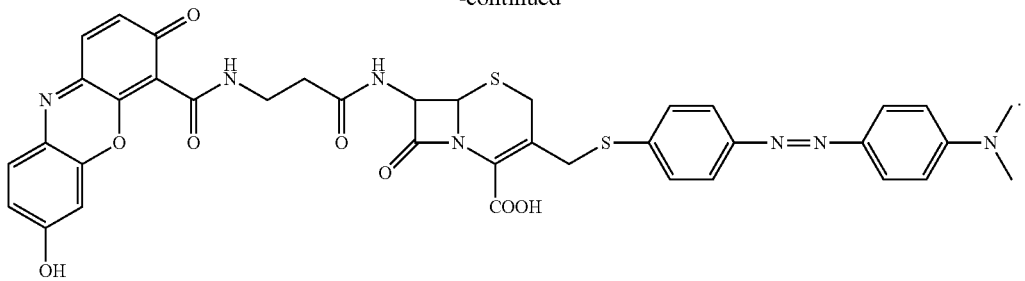

3. A method for determining the presence or absence of β-lactamase enzyme in a sample, the method comprising:
   a) contacting the sample with a β-lactamase substrate to form a contacted sample;
   b) incubating the contacted sample for a sufficient amount of time for a β-lactamase enzyme in the contacted sample to cleave the β-lactamase substrate to form an incubated sample;
   c) illuminating the incubated sample with an appropriate wavelength to obtain an illuminated sample; and
   d) observing the illuminated sample whereby the presence or absence of β-lactamase enzyme in the illuminated sample is determined, wherein the β-lactamase substrate has a structure of the formula:

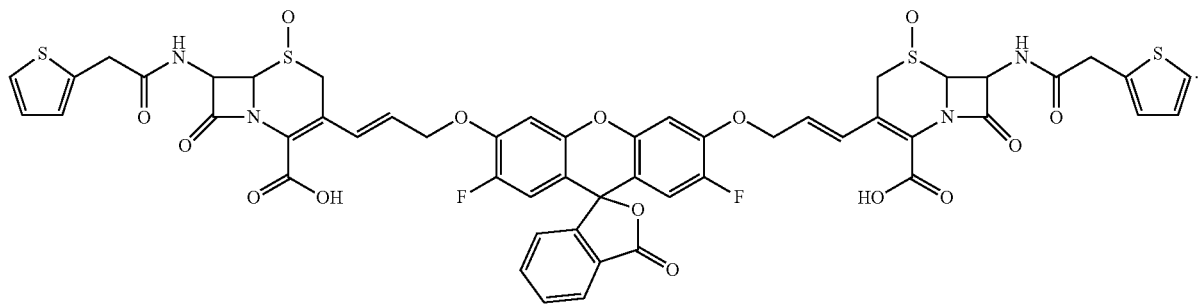

4. A method for determining the presence or absence of β-lactamase enzyme in a sample, the method comprising:
   a) contacting the sample with a β-lactamase substrate to form a contacted sample;
   b) incubating the contacted sample for a sufficient amount of time for a β-lactamase enzyme in the contacted sample to cleave the β-lactamase substrate to form an incubated sample;
   c) illuminating the incubated sample with an appropriate wavelength to obtain an illuminated sample; and
   d) observing the illuminated sample whereby the presence or absence of β-lactamase enzyme in the illuminated sample is determined, wherein the β-lactamase substrate has a structure of the formula:

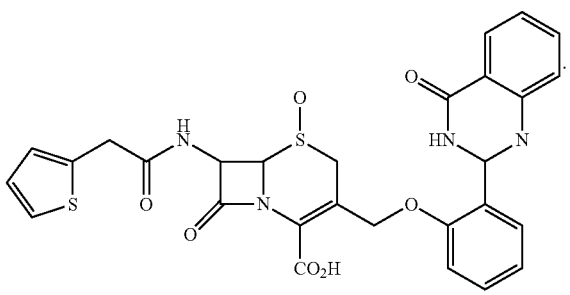

* * * * *

SEQUENCE LISTING

<160> NUMBER OF SEQ ID NOS: 116

<210> SEQ ID NO 1
<211> LENGTH: 265
<212> TYPE: PRT
<213> ORGANISM: Klebsiella pneumoniae

<400> SEQUENCE: 1

Met Gly His Pro Glu Thr Leu Val Lys Val Lys Asp Ala Glu Asp Gln
1               5                   10                  15

Leu Gly Ala Arg Val Gly Tyr Ile Glu Leu Asp Leu Asn Ser Gly Lys
            20                  25                  30

Ile Leu Glu Ser Phe Arg Pro Glu Arg Phe Pro Met Met Ser Thr
        35                  40                  45

Phe Lys Val Leu Leu Cys Gly Ala Val Leu Ser Arg Asp Asp Ala Gly
    50                  55                  60

Gln Glu Gln Leu Gly Arg Arg Ile His Tyr Ser Gln Asn Asp Leu Val
65                  70                  75                  80

Glu Tyr Ser Pro Val Thr Glu Lys His Leu Thr Asp Gly Met Thr Val
                85                  90                  95

Arg Glu Leu Cys Ser Ala Ala Ile Thr Met Ser Asp Asn Thr Ala Ala
            100                 105                 110

Asn Leu Leu Leu Thr Thr Ile Gly Gly Pro Lys Glu Leu Thr Ala Phe
        115                 120                 125

Leu His Asn Met Gly Asp His Val Thr Arg Leu Asp His Trp Glu Pro
    130                 135                 140

Glu Leu Asn Glu Ala Ile Pro Asn Asp Glu Arg Asp Thr Thr Met Pro
145                 150                 155                 160

Val Ala Met Ala Thr Thr Leu Arg Lys Leu Leu Thr Gly Glu Leu Leu
                165                 170                 175

Thr Leu Ala Ser Arg Gln Gln Leu Ile Asp Trp Met Glu Ala Asp Lys
            180                 185                 190

Val Ala Gly Pro Leu Leu Arg Ser Ala Leu Pro Ala Gly Trp Phe Ile
        195                 200                 205

Ala Asp Lys Ser Gly Ala Gly Glu Arg Gly Ser Arg Gly Ile Ile Ala
    210                 215                 220

Ala Leu Gly Pro Asp Gly Lys Pro Ser Arg Ile Val Val Ile Tyr Thr
225                 230                 235                 240

Thr Gly Ser Gln Ala Thr Met Asp Glu Arg Asn Arg Gln Ile Ala Glu
                245                 250                 255

Ile Gly Ala Ser Leu Ile Lys His Trp
            260                 265

<210> SEQ ID NO 2
<211> LENGTH: 5
<212> TYPE: DNA
<213> ORGANISM: Vaccinia virus

<400> SEQUENCE: 2 ycctt                                                                   5

<210> SEQ ID NO 3
<211> LENGTH: 7
<212> TYPE: DNA
<213> ORGANISM: Escherichia coli -continued

```
<400> SEQUENCE: 3 gcaactt                                                                    7

<210> SEQ ID NO 4
<211> LENGTH: 15
<212> TYPE: DNA
<213> ORGANISM: Bacteriophage lambda

<400> SEQUENCE: 4
gcttttttat actaa                                                          15

<210> SEQ ID NO 5
<211> LENGTH: 7
<212> TYPE: DNA
<213> ORGANISM: Bacteriophage lambda

<400> SEQUENCE: 5 tttatac                                                                    7

<210> SEQ ID NO 6
<211> LENGTH: 7
<212> TYPE: DNA
<213> ORGANISM: Bacteriophage lambda

<400> SEQUENCE: 6 tttatac                                                                    7

<210> SEQ ID NO 7
<211> LENGTH: 7
<212> TYPE: DNA
<213> ORGANISM: Bacteriophage lambda
<220> FEATURE:
<221> NAME/KEY: misc_feature
<222> LOCATION: (1)..(3)
<223> OTHER INFORMATION: n is a, c, g, or t

<400> SEQUENCE: 7 nnnatac                                                                    7

<210> SEQ ID NO 8
<211> LENGTH: 21
<212> TYPE: DNA
<213> ORGANISM: Bacteriophage lambda

<400> SEQUENCE: 8
caactttttt atacaaagtt g                                                   21

<210> SEQ ID NO 9
<211> LENGTH: 7
<212> TYPE: DNA
<213> ORGANISM: Bacteriophage lambda

<400> SEQUENCE: 9 gaaatac                                                                    7

<210> SEQ ID NO 10
<211> LENGTH: 7
<212> TYPE: DNA
<213> ORGANISM: Bacteriophage lambda

<400> SEQUENCE: 10 gatatac                                                                    7
```

-continued

```
<210> SEQ ID NO 11
<211> LENGTH: 7
<212> TYPE: DNA
<213> ORGANISM: Bacteriophage lambda

<400> SEQUENCE: 11 acaatac                                                                    7

<210> SEQ ID NO 12
<211> LENGTH: 7
<212> TYPE: DNA
<213> ORGANISM: Bacteriophage lambda

<400> SEQUENCE: 12 tgcatac                                                                    7

<210> SEQ ID NO 13
<211> LENGTH: 7
<212> TYPE: DNA
<213> ORGANISM: Bacteriophage lambda

<400> SEQUENCE: 13 aaaatac                                                                    7

<210> SEQ ID NO 14
<211> LENGTH: 7
<212> TYPE: DNA
<213> ORGANISM: Bacteriophage lambda

<400> SEQUENCE: 14 aacatac                                                                    7

<210> SEQ ID NO 15
<211> LENGTH: 7
<212> TYPE: DNA
<213> ORGANISM: Bacteriophage lambda

<400> SEQUENCE: 15 aagatac                                                                    7

<210> SEQ ID NO 16
<211> LENGTH: 7
<212> TYPE: DNA
<213> ORGANISM: Bacteriophage lambda

<400> SEQUENCE: 16 aatatac                                                                    7

<210> SEQ ID NO 17
<211> LENGTH: 7
<212> TYPE: DNA
<213> ORGANISM: Bacteriophage lambda

<400> SEQUENCE: 17 acaatac                                                                    7

<210> SEQ ID NO 18
<211> LENGTH: 7
<212> TYPE: DNA
<213> ORGANISM: Bacteriophage lambda

<400> SEQUENCE: 18 accatac                                                                    7
```

```
<210> SEQ ID NO 19
<211> LENGTH: 7
<212> TYPE: DNA
<213> ORGANISM: Bacteriophage lambda

<400> SEQUENCE: 19 acgatac                                                                    7

<210> SEQ ID NO 20
<211> LENGTH: 7
<212> TYPE: DNA
<213> ORGANISM: Bacteriophage lambda

<400> SEQUENCE: 20 actatac                                                                    7

<210> SEQ ID NO 21
<211> LENGTH: 7
<212> TYPE: DNA
<213> ORGANISM: Bacteriophage lambda

<400> SEQUENCE: 21 agaatac                                                                    7

<210> SEQ ID NO 22
<211> LENGTH: 7
<212> TYPE: DNA
<213> ORGANISM: Bacteriophage lambda

<400> SEQUENCE: 22 agcatac                                                                    7

<210> SEQ ID NO 23
<211> LENGTH: 7
<212> TYPE: DNA
<213> ORGANISM: Bacteriophage lambda

<400> SEQUENCE: 23 aggatac                                                                    7

<210> SEQ ID NO 24
<211> LENGTH: 7
<212> TYPE: DNA
<213> ORGANISM: Bacteriophage lambda

<400> SEQUENCE: 24 agtatac                                                                    7

<210> SEQ ID NO 25
<211> LENGTH: 7
<212> TYPE: DNA
<213> ORGANISM: Bacteriophage lambda

<400> SEQUENCE: 25 ataatac                                                                    7

<210> SEQ ID NO 26
<211> LENGTH: 7
<212> TYPE: DNA
<213> ORGANISM: Bacteriophage lambda

<400> SEQUENCE: 26 atcatac                                                                    7
```

```
<210> SEQ ID NO 27
<211> LENGTH: 7
<212> TYPE: DNA
<213> ORGANISM: Bacteriophage lambda

<400> SEQUENCE: 27 atgatac                                                                    7

<210> SEQ ID NO 28
<211> LENGTH: 7
<212> TYPE: DNA
<213> ORGANISM: Bacteriophage lambda

<400> SEQUENCE: 28 attatac                                                                    7

<210> SEQ ID NO 29
<211> LENGTH: 7
<212> TYPE: DNA
<213> ORGANISM: Bacteriophage lambda

<400> SEQUENCE: 29 caaatac                                                                    7

<210> SEQ ID NO 30
<211> LENGTH: 7
<212> TYPE: DNA
<213> ORGANISM: Bacteriophage lambda

<400> SEQUENCE: 30 cacatac                                                                    7

<210> SEQ ID NO 31
<211> LENGTH: 7
<212> TYPE: DNA
<213> ORGANISM: Bacteriophage lambda

<400> SEQUENCE: 31 cagatac                                                                    7

<210> SEQ ID NO 32
<211> LENGTH: 7
<212> TYPE: DNA
<213> ORGANISM: Bacteriophage lambda

<400> SEQUENCE: 32 catatac                                                                    7

<210> SEQ ID NO 33
<211> LENGTH: 7
<212> TYPE: DNA
<213> ORGANISM: Bacteriophage lambda

<400> SEQUENCE: 33 ccaatac                                                                    7

<210> SEQ ID NO 34
<211> LENGTH: 7
<212> TYPE: DNA
<213> ORGANISM: Bacteriophage lambda

<400> SEQUENCE: 34 cccatac                                                                    7
```

```
<210> SEQ ID NO 35
<211> LENGTH: 7
<212> TYPE: DNA
<213> ORGANISM: Bacteriophage lambda

<400> SEQUENCE: 35 ccgatac                                                                    7

<210> SEQ ID NO 36
<211> LENGTH: 7
<212> TYPE: DNA
<213> ORGANISM: Bacteriophage lambda

<400> SEQUENCE: 36 cctatac                                                                    7

<210> SEQ ID NO 37
<211> LENGTH: 7
<212> TYPE: DNA
<213> ORGANISM: Bacteriophage lambda

<400> SEQUENCE: 37 cgaatac                                                                    7

<210> SEQ ID NO 38
<211> LENGTH: 7
<212> TYPE: DNA
<213> ORGANISM: Bacteriophage lambda

<400> SEQUENCE: 38 cgcatac                                                                    7

<210> SEQ ID NO 39
<211> LENGTH: 7
<212> TYPE: DNA
<213> ORGANISM: Bacteriophage lambda

<400> SEQUENCE: 39 cggatac                                                                    7

<210> SEQ ID NO 40
<211> LENGTH: 7
<212> TYPE: DNA
<213> ORGANISM: Bacteriophage lambda

<400> SEQUENCE: 40 cggatac                                                                    7

<210> SEQ ID NO 41
<211> LENGTH: 7
<212> TYPE: DNA
<213> ORGANISM: Bacteriophage lambda

<400> SEQUENCE: 41 ctaatac                                                                    7

<210> SEQ ID NO 42
<211> LENGTH: 7
<212> TYPE: DNA
<213> ORGANISM: Bacteriophage lambda

<400> SEQUENCE: 42 ctcatac                                                                    7
```

```
<210> SEQ ID NO 43
<211> LENGTH: 7
<212> TYPE: DNA
<213> ORGANISM: Bacteriophage lambda

<400> SEQUENCE: 43 ctgatac                                                                      7

<210> SEQ ID NO 44
<211> LENGTH: 7
<212> TYPE: DNA
<213> ORGANISM: Bacteriophage lambda

<400> SEQUENCE: 44 cttatac                                                                      7

<210> SEQ ID NO 45
<211> LENGTH: 7
<212> TYPE: DNA
<213> ORGANISM: Bacteriophage lambda

<400> SEQUENCE: 45 gaaatac                                                                      7

<210> SEQ ID NO 46
<211> LENGTH: 7
<212> TYPE: DNA
<213> ORGANISM: Bacteriophage lambda

<400> SEQUENCE: 46 gacatac                                                                      7

<210> SEQ ID NO 47
<211> LENGTH: 7
<212> TYPE: DNA
<213> ORGANISM: Bacteriophage lambda

<400> SEQUENCE: 47 gacatac                                                                      7

<210> SEQ ID NO 48
<211> LENGTH: 7
<212> TYPE: DNA
<213> ORGANISM: Bacteriophage lambda

<400> SEQUENCE: 48 gatatac                                                                      7

<210> SEQ ID NO 49
<211> LENGTH: 7
<212> TYPE: DNA
<213> ORGANISM: Bacteriophage lambda

<400> SEQUENCE: 49 gcaatac                                                                      7

<210> SEQ ID NO 50
<211> LENGTH: 7
<212> TYPE: DNA
<213> ORGANISM: Bacteriophage lambda

<400> SEQUENCE: 50 gccatac                                                                      7
```

```
<210> SEQ ID NO 51
<211> LENGTH: 7
<212> TYPE: DNA
<213> ORGANISM: Bacteriophage lambda

<400> SEQUENCE: 51 gcgatac                                                                    7

<210> SEQ ID NO 52
<211> LENGTH: 7
<212> TYPE: DNA
<213> ORGANISM: Bacteriophage lambda

<400> SEQUENCE: 52 gctatac                                                                    7

<210> SEQ ID NO 53
<211> LENGTH: 7
<212> TYPE: DNA
<213> ORGANISM: Bacteriophage lambda

<400> SEQUENCE: 53 ggaatac                                                                    7

<210> SEQ ID NO 54
<211> LENGTH: 7
<212> TYPE: DNA
<213> ORGANISM: Bacteriophage lambda

<400> SEQUENCE: 54 ggcatac                                                                    7

<210> SEQ ID NO 55
<211> LENGTH: 7
<212> TYPE: DNA
<213> ORGANISM: Bacteriophage lambda

<400> SEQUENCE: 55 gggatac                                                                    7

<210> SEQ ID NO 56
<211> LENGTH: 7
<212> TYPE: DNA
<213> ORGANISM: Bacteriophage lambda

<400> SEQUENCE: 56 ggtatac                                                                    7

<210> SEQ ID NO 57
<211> LENGTH: 7
<212> TYPE: DNA
<213> ORGANISM: Bacteriophage lambda

<400> SEQUENCE: 57 gtaatac                                                                    7

<210> SEQ ID NO 58
<211> LENGTH: 7
<212> TYPE: DNA
<213> ORGANISM: Bacteriophage lambda

<400> SEQUENCE: 58 gtcatac                                                                    7
```

```
<210> SEQ ID NO 59
<211> LENGTH: 7
<212> TYPE: DNA
<213> ORGANISM: Bacteriophage lambda

<400> SEQUENCE: 59 gtgatac                                                                    7

<210> SEQ ID NO 60
<211> LENGTH: 7
<212> TYPE: DNA
<213> ORGANISM: Bacteriophage lambda

<400> SEQUENCE: 60 gttatac                                                                    7

<210> SEQ ID NO 61
<211> LENGTH: 7
<212> TYPE: DNA
<213> ORGANISM: Bacteriophage lambda

<400> SEQUENCE: 61 taaatac                                                                    7

<210> SEQ ID NO 62
<211> LENGTH: 7
<212> TYPE: DNA
<213> ORGANISM: Bacteriophage lambda

<400> SEQUENCE: 62 tacatac                                                                    7

<210> SEQ ID NO 63
<211> LENGTH: 7
<212> TYPE: DNA
<213> ORGANISM: Bacteriophage lambda

<400> SEQUENCE: 63 tagatac                                                                    7

<210> SEQ ID NO 64
<211> LENGTH: 7
<212> TYPE: DNA
<213> ORGANISM: Bacteriophage lambda

<400> SEQUENCE: 64 tatatac                                                                    7

<210> SEQ ID NO 65
<211> LENGTH: 7
<212> TYPE: DNA
<213> ORGANISM: Bacteriophage lambda

<400> SEQUENCE: 65 tcaatac                                                                    7

<210> SEQ ID NO 66
<211> LENGTH: 7
<212> TYPE: DNA
<213> ORGANISM: Bacteriophage lambda

<400> SEQUENCE: 66 tccatac                                                                    7
```

```
<210> SEQ ID NO 67
<211> LENGTH: 7
<212> TYPE: DNA
<213> ORGANISM: Bacteriophage lambda

<400> SEQUENCE: 67 tcgatac                                                                  7

<210> SEQ ID NO 68
<211> LENGTH: 7
<212> TYPE: DNA
<213> ORGANISM: Bacteriophage lambda

<400> SEQUENCE: 68 tctatac                                                                  7

<210> SEQ ID NO 69
<211> LENGTH: 7
<212> TYPE: DNA
<213> ORGANISM: Bacteriophage lambda

<400> SEQUENCE: 69 tgaatac                                                                  7

<210> SEQ ID NO 70
<211> LENGTH: 7
<212> TYPE: DNA
<213> ORGANISM: Bacteriophage lambda

<400> SEQUENCE: 70 tgcatac                                                                  7

<210> SEQ ID NO 71
<211> LENGTH: 7
<212> TYPE: DNA
<213> ORGANISM: Bacteriophage lambda

<400> SEQUENCE: 71 tggatac                                                                  7

<210> SEQ ID NO 72
<211> LENGTH: 7
<212> TYPE: DNA
<213> ORGANISM: Bacteriophage lambda

<400> SEQUENCE: 72 tgtatac                                                                  7

<210> SEQ ID NO 73
<211> LENGTH: 7
<212> TYPE: DNA
<213> ORGANISM: Bacteriophage lambda

<400> SEQUENCE: 73 ttaatac                                                                  7

<210> SEQ ID NO 74
<211> LENGTH: 7
<212> TYPE: DNA
<213> ORGANISM: Bacteriophage lambda

<400> SEQUENCE: 74 ttcatac                                                                  7
```

```
<210> SEQ ID NO 75
<211> LENGTH: 7
<212> TYPE: DNA
<213> ORGANISM: Bacteriophage lambda

<400> SEQUENCE: 75 ttgatac                                                                       7

<210> SEQ ID NO 76
<211> LENGTH: 7
<212> TYPE: DNA
<213> ORGANISM: Bacteriophage lambda

<400> SEQUENCE: 76 tttatac                                                                       7

<210> SEQ ID NO 77
<211> LENGTH: 25
<212> TYPE: DNA
<213> ORGANISM: Bacteriophage lambda

<400> SEQUENCE: 77
agcctgcttt tttgtacaaa cttgt                                                  25

<210> SEQ ID NO 78
<211> LENGTH: 233
<212> TYPE: DNA
<213> ORGANISM: Bacteriophage lambda

<400> SEQUENCE: 78
tacaggtcac taataccatc taagtagttg attcatagtg actggatatg ttgtgtttta           60
cagtattatg tagtctgttt tttatgcaaa atctaattta atatattgat atttatatca          120
ttttacgttt ctcgttcagc ttttttgtac aaagttggca ttataaaaaa gcattgctca          180
tcaatttgtt gcaacgaaca ggtcactatc agtcaaaata aaatcattat ttg                 233

<210> SEQ ID NO 79
<211> LENGTH: 100
<212> TYPE: DNA
<213> ORGANISM: Bacteriophage lambda

<400> SEQUENCE: 79
caaataatga ttttattttg actgatagtg acctgttcgt tgcaacaaat tgataagcaa           60
tgctttttta taatgccaac tttgtacaaa aaagcaggct                                100

<210> SEQ ID NO 80
<211> LENGTH: 125
<212> TYPE: DNA
<213> ORGANISM: Bacteriophage lambda

<400> SEQUENCE: 80
acaagtttgt acaaaaaagc tgaacgagaa acgtaaaatg atataaatat caatatatta           60
aattagattt tgcataaaaa acagactaca taatactgta aaacacaaca tatccagtca          120
ctatg                                                                      125

<210> SEQ ID NO 81
<211> LENGTH: 27
<212> TYPE: DNA
<213> ORGANISM: Bacteriophage lambda

<400> SEQUENCE: 81
agcctgcttt tttatactaa cttgagc                                               27
```

<210> SEQ ID NO 82
<211> LENGTH: 27
<212> TYPE: DNA
<213> ORGANISM: Bacteriophage lambda

<400> SEQUENCE: 82
gttcagcttt tttatactaa gttggca                                27

<210> SEQ ID NO 83
<211> LENGTH: 27
<212> TYPE: DNA
<213> ORGANISM: Bacteriophage lambda

<400> SEQUENCE: 83
agcctgcttt tttatactaa gttggca                                27

<210> SEQ ID NO 84
<211> LENGTH: 27
<212> TYPE: DNA
<213> ORGANISM: Bacteriophage lambda

<400> SEQUENCE: 84
gttcagcttt tttatactaa cttgagc                                27

<210> SEQ ID NO 85
<211> LENGTH: 25
<212> TYPE: DNA
<213> ORGANISM: Bacteriophage lambda

<400> SEQUENCE: 85
agcctgcttt tttgtacaaa cttgt                                  25

<210> SEQ ID NO 86
<211> LENGTH: 27
<212> TYPE: DNA
<213> ORGANISM: Bacteriophage lambda

<400> SEQUENCE: 86
gttcagcttt tttgtacaaa gttggca                                27

<210> SEQ ID NO 87
<211> LENGTH: 27
<212> TYPE: DNA
<213> ORGANISM: Bacteriophage lambda

<400> SEQUENCE: 87
agcctgcttt tttgtacaaa gttggca                                27

<210> SEQ ID NO 88
<211> LENGTH: 25
<212> TYPE: DNA
<213> ORGANISM: Bacteriophage lambda

<400> SEQUENCE: 88
gttcagcttt tttgtacaaa cttgt                                  25

<210> SEQ ID NO 89
<211> LENGTH: 25
<212> TYPE: DNA
<213> ORGANISM: Bacteriophage lambda

<400> SEQUENCE: 89
acccagcttt cttgtacaaa gtggt                                  25

<210> SEQ ID NO 90
<211> LENGTH: 27
<212> TYPE: DNA
<213> ORGANISM: Bacteriophage lambda

<400> SEQUENCE: 90
gttcagcttt cttgtacaaa gttggca                                27

<210> SEQ ID NO 91
<211> LENGTH: 27
<212> TYPE: DNA
<213> ORGANISM: Bacteriophage lambda

<400> SEQUENCE: 91
acccagcttt cttgtacaaa gttggca                                27

<210> SEQ ID NO 92
<211> LENGTH: 25
<212> TYPE: DNA
<213> ORGANISM: Bacteriophage lambda

<400> SEQUENCE: 92
gttcagcttt cttgtacaaa gtggt                                  25

<210> SEQ ID NO 93
<211> LENGTH: 22
<212> TYPE: DNA
<213> ORGANISM: Bacteriophage lambda

<400> SEQUENCE: 93
caactttatt atacaaagtt gt                                     22

<210> SEQ ID NO 94
<211> LENGTH: 27
<212> TYPE: DNA
<213> ORGANISM: Bacteriophage lambda

<400> SEQUENCE: 94
gttcaacttt attatacaaa gttggca                                27

<210> SEQ ID NO 95
<211> LENGTH: 24
<212> TYPE: DNA
<213> ORGANISM: Bacteriophage lambda

<400> SEQUENCE: 95
caactttatt atacaaagtt ggca                                   24

<210> SEQ ID NO 96
<211> LENGTH: 25
<212> TYPE: DNA
<213> ORGANISM: Bacteriophage lambda

<400> SEQUENCE: 96
gttcaacttt attatacaaa gttgt                                  25

<210> SEQ ID NO 97
<211> LENGTH: 22
<212> TYPE: DNA
<213> ORGANISM: Bacteriophage lambda

<400> SEQUENCE: 97
caacttttct atacaaagtt gt                                     22

```
<210> SEQ ID NO 98
<211> LENGTH: 27
<212> TYPE: DNA
<213> ORGANISM: Bacteriophage lambda

<400> SEQUENCE: 98
gttcaacttt tctatacaaa gttggca                                          27

<210> SEQ ID NO 99
<211> LENGTH: 24
<212> TYPE: DNA
<213> ORGANISM: Bacteriophage lambda

<400> SEQUENCE: 99
caacttttct atacaaagtt ggca                                             24

<210> SEQ ID NO 100
<211> LENGTH: 25
<212> TYPE: DNA
<213> ORGANISM: Bacteriophage lambda

<400> SEQUENCE: 100
gttcaacttt tctatacaaa gttgt                                            25

<210> SEQ ID NO 101
<211> LENGTH: 22
<212> TYPE: DNA
<213> ORGANISM: Bacteriophage lambda

<400> SEQUENCE: 101
caacttttgt atacaaagtt gt                                               22

<210> SEQ ID NO 102
<211> LENGTH: 27
<212> TYPE: DNA
<213> ORGANISM: Bacteriophage lambda

<400> SEQUENCE: 102
gttcaacttt tgtatacaaa gttggca                                          27

<210> SEQ ID NO 103
<211> LENGTH: 24
<212> TYPE: DNA
<213> ORGANISM: Bacteriophage lambda

<400> SEQUENCE: 103
caacttttgt atacaaagtt ggca                                             24

<210> SEQ ID NO 104
<211> LENGTH: 25
<212> TYPE: DNA
<213> ORGANISM: Bacteriophage lambda

<400> SEQUENCE: 104
gttcaacttt tgtatacaaa gttgt                                            25

<210> SEQ ID NO 105
<211> LENGTH: 22
<212> TYPE: DNA
<213> ORGANISM: Bacteriophage lambda

<400> SEQUENCE: 105
caactttttc gtacaaagtt gt                                               22
```

<210> SEQ ID NO 106
<211> LENGTH: 27
<212> TYPE: DNA
<213> ORGANISM: Bacteriophage lambda

<400> SEQUENCE: 106
gttcaacttt ttcgtacaaa gttggca                                    27

<210> SEQ ID NO 107
<211> LENGTH: 24
<212> TYPE: DNA
<213> ORGANISM: Bacteriophage lambda

<400> SEQUENCE: 107
caactttttc gtacaaagtt ggca                                       24

<210> SEQ ID NO 108
<211> LENGTH: 25
<212> TYPE: DNA
<213> ORGANISM: Bacteriophage lambda

<400> SEQUENCE: 108
gttcaacttt ttcgtacaaa gttgt                                      25

<210> SEQ ID NO 109
<211> LENGTH: 22
<212> TYPE: DNA
<213> ORGANISM: Bacteriophage lambda

<400> SEQUENCE: 109 caacttttg gtacaaagtt gt                                          22

<210> SEQ ID NO 110
<211> LENGTH: 27
<212> TYPE: DNA
<213> ORGANISM: Bacteriophage lambda

<400> SEQUENCE: 110
gttcaacttt ttggtacaaa gttggca                                    27

<210> SEQ ID NO 111
<211> LENGTH: 24
<212> TYPE: DNA
<213> ORGANISM: Bacteriophage lambda

<400> SEQUENCE: 111 caacttttg gtacaaagtt ggca                                        24

<210> SEQ ID NO 112
<211> LENGTH: 25
<212> TYPE: DNA
<213> ORGANISM: Bacteriophage lambda

<400> SEQUENCE: 112
gttcaacttt ttggtacaaa gttgt                                      25

<210> SEQ ID NO 113
<211> LENGTH: 22
<212> TYPE: DNA
<213> ORGANISM: Bacteriophage lambda

<400> SEQUENCE: 113
caacttttta atacaaagtt gt                                         22

```
<210> SEQ ID NO 114
<211> LENGTH: 27
<212> TYPE: DNA
<213> ORGANISM: Bacteriophage lambda

<400> SEQUENCE: 114
gttcaacttt ttaatacaaa gttggca                                        27

<210> SEQ ID NO 115
<211> LENGTH: 24
<212> TYPE: DNA
<213> ORGANISM: Bacteriophage lambda

<400> SEQUENCE: 115 caactttta atacaaagtt ggca                                            24

<210> SEQ ID NO 116
<211> LENGTH: 25
<212> TYPE: DNA
<213> ORGANISM: Bacteriophage lambda

<400> SEQUENCE: 116
gttcaacttt ttaatacaaa gttgt                                          25
```